US012202859B2

United States Patent
Houghton et al.

(10) Patent No.: US 12,202,859 B2
(45) Date of Patent: Jan. 21, 2025

(54) HEPATITIS C VIRUS E1/E2 HETERODIMERS AND METHODS OF PRODUCING SAME

(71) Applicant: The Governors of the University of Alberta, Edmonton (CA)

(72) Inventors: Michael Houghton, Danville, CA (US); Darren Hockman, Edmonton (CA); John L. Law, Edmonton (CA); Chao Chen, Edmonton (CA); Michael Logan, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 570 days.

(21) Appl. No.: 17/509,808

(22) Filed: Oct. 25, 2021

(65) Prior Publication Data

US 2022/0041661 A1    Feb. 10, 2022

Related U.S. Application Data

(63) Continuation of application No. 15/763,370, filed as application No. PCT/IB2016/056000 on Oct. 7, 2016, now Pat. No. 11,186,615.

(60) Provisional application No. 62/239,157, filed on Oct. 8, 2015, provisional application No. 62/337,212, filed on May 16, 2016.

(51) Int. Cl.
| | |
|---|---|
| *C07K 14/005* | (2006.01) |
| *A61K 39/00* | (2006.01) |
| *A61K 39/12* | (2006.01) |
| *A61K 39/29* | (2006.01) |
| *A61P 31/14* | (2006.01) |
| *C07K 1/22* | (2006.01) |
| *C07K 19/00* | (2006.01) |
| *C12N 7/00* | (2006.01) |
| *C12N 15/62* | (2006.01) |
| *C12P 21/02* | (2006.01) |

(52) U.S. Cl.
CPC ............ *C07K 14/005* (2013.01); *A61K 39/12* (2013.01); *A61K 39/29* (2013.01); *A61P 31/14* (2018.01); *C07K 1/22* (2013.01); *C07K 19/00* (2013.01); *C12N 7/00* (2013.01); *C12N 15/62* (2013.01); *C12P 21/02* (2013.01); *A61K 2039/54* (2013.01); *A61K 2039/55505* (2013.01); *A61K 2039/55572* (2013.01); *A61K 2039/575* (2013.01); *C07K 2319/30* (2013.01); *C07K 2319/50* (2013.01); *C12N 2770/24222* (2013.01); *C12N 2770/24234* (2013.01); *C12N 2770/28122* (2013.01)

(58) Field of Classification Search
None
See application file for complete search history.

(56) References Cited

U.S. PATENT DOCUMENTS

| | | |
|---|---|---|
| 8,007,805 B2 | 8/2011 | George et al. |
| 8,025,873 B2 | 9/2011 | George et al. |
| 8,029,803 B2 | 10/2011 | George et al. |
| 8,309,690 B2 | 11/2012 | Allan et al. |
| 8,465,745 B2 | 6/2013 | George et al. |
| 10,300,131 B2 | 5/2019 | Houghton et al. |
| 11,186,615 B2 | 11/2021 | Houghton et al. |
| 2004/0147721 A1 | 7/2004 | Valiante |
| 2006/0068421 A1 | 3/2006 | Gray |
| 2007/0065912 A1 | 3/2007 | Carson et al. |
| 2009/0092582 A1 | 4/2009 | Bogin et al. |
| 2011/0091495 A1 | 4/2011 | Marcotrigiano et al. |
| 2011/0129498 A1 | 6/2011 | Cortese et al. |
| 2011/0223185 A1 | 9/2011 | George et al. |
| 2012/0070435 A1 | 3/2012 | George et al. |
| 2012/0301465 A1 | 11/2012 | Dutartre et al. |
| 2013/0045205 A1 | 2/2013 | Mason et al. |
| 2014/0199763 A1 | 7/2014 | Dutartre et al. |
| 2015/0056233 A1* | 2/2015 | Marshall ............... A61K 45/06 530/396 |
| 2015/0368668 A1 | 12/2015 | Marcotrigiano et al. |

FOREIGN PATENT DOCUMENTS

| | | |
|---|---|---|
| CA | 2776195 A1 | 4/2011 |
| CA | 2986342 A1 | 1/2017 |
| CN | 102883734 A | 1/2013 |

(Continued)

OTHER PUBLICATIONS

Mazzocca A, Sciammetta SC, Carloni V, Cosmi L, Annunziato F, Harada T, Abrignani S, Pinzani M. Binding of hepatitis C virus envelope protein E2 to CD81 up-regulates matrix metalloproteinase-2 in human hepatic stellate cells. J Biol Chem. Mar. 25, 2005; 280(12):11329-39. (Year: 2005).*
Xiang ZH, Cai WJ, Zhao P, Kong LB, Ye LB, Wu ZH. Purification and application of bacterially expressed chimeric protein E1E2 of hepatitis C virus. Protein Expr Purif. Sep. 2006;49(1):95-101. (Year: 2006).*
Attwood; "The Babel of Bioinformatics"; Science; vol. 290, No. 5491, pp. 471-473 (Oct. 27, 2000).
Baker, et al.; "Protein Structure Predication and Structural Genomics"; Science; vol. 294, No. 5540, pp. 93-96 (Oct. 5, 2001).
Block, et al.; "Chronic hepatitis B: a wave of new therapies on the horizon"; Antiviral Res.; vol. 121, pp. 69-82 (Sep. 2015).

(Continued)

*Primary Examiner* — Michelle S Horning
(74) *Attorney, Agent, or Firm* — Bozicevic, Field & Francis LLP; Shweta Chandra

(57) ABSTRACT

The present disclosure provides affinity tagged heterodimeric polypeptides comprising a hepatitis C virus (HCV) E1 polypeptide and an HCV E2 polypeptide, where one or both of the E1 and E2 polypeptides comprises an affinity tag. The present disclosure provides a method of producing an affinity tagged E1/E2 heterodimer of the present disclosure. The present disclosure provides methods of producing untagged HCV E1/E2 heterodimers. The present disclosure provides HCV E1/E2 heterodimers, compositions comprising same, and methods of inducing an immune response to HCV.

15 Claims, 24 Drawing Sheets

Specification includes a Sequence Listing.

(56) References Cited

FOREIGN PATENT DOCUMENTS

| JP | 2015034165 | 2/2015 |
|---|---|---|
| WO | WO 2005/087813 A1 | 9/2005 |
| WO | WO 2009/131681 A2 | 10/2009 |
| WO | WO 2013/115926 A2 | 8/2013 |
| WO | WO 2013/173706 A3 | 11/2013 |
| WO | WO 2014/033441 A1 | 3/2014 |
| WO | WO 2014/060851 A2 | 4/2014 |
| WO | WO 2015/132619 A1 | 9/2015 |
| WO | WO 2017/006182 A1 | 1/2017 |

OTHER PUBLICATIONS

Chan-Fook, et al.; "Hepatitis C Virus Glycoprotein E2 Binding to CD81: The Role of E1E2 Cleavage and Protein Glycosylation in Bioactivity"; Virology; vol. 273, No. 1, pp. 60-66 (Jul. 20, 2000).

Fenouillet, et al.; "Contribution of redox status to hepatitis C virus E2 envelope protein function and antigenicity"; The Journal of Biological Chemistry; vol. 283, No. 39, pp. 26340-26348 (Sep. 26, 2008).

George, et al.; "Immune Responses to a Novel Chimigen® HCV Prophylactic/Therapeutic Vaccine"; Poster presented at: 18th International Congress HCV 2011, Seattle, Sep. 8-12, 2011. URL: http://www.akshayabio.com/pdf/Chimigen_HCV_Vaccine18th_International_Congress_HCV_2011 Seattle.pdf (Date of last access Dec. 10, 2019). Date Publication: Sep. 1, 2011 (1 page).

Ghose, et al.; "Binding capacity differences for antibodies and Fc-fusion proteins on protein A chromatographic materials"; Biotechnol Bioeng; vol. 96, No. 4, pp. 768-779 (Mar. 1, 2007).

Logan, et al.; "Native folding of a recombinant gpE1/gpE2 heterodimer vaccine antigen from a precursor protein fused with Fx IgG"; Journal of Virology; vol. 91, No. 1 (Jan. 2017).

Mirnurollahi, et al.; "Expression and Purification of HCV Core and Core-E1E2 Proteins in Different Bacterial Strains"; Iran J Biotechnol.; vol. 13, No. 3, pp. 57-62. (Sep. 2015).

Mirnurollahi, et al.; "Expression and Purification of HCV Core and Core-E1E2 Proteins in Different Bacterial Strains"; Iran J Biotech; vol. 13, No. 3, 6 pages (Sep. 2015).

Olaby, et al.; "Identification of a Novel Drug Lead That Inhibits HCV Infection and Cell-to-Cell Transmission by Targeting the HCV E2 Glycoprotein"; PLoS One; vol. 9, Issue 10, 20 pages (Oct. 2014).

PDB: 3S7G_A Aglycosylated human igg 1 fc fragment 2020; 2 pages (2020).

Sun, et al.; "Enhancement of immune response to a hepatitis C virus E2 DNA vaccine by an immunoglobulin Fc fusion tag"; J Med Virol; vol. 87, pp. 2090-2097 (Jun. 12, 2015).

Tasaki, et al.; "The N-End rule pathway"; Annual Review of Biochemistry; vol. 81, pp. 261-289 (Jul. 2012).

Whidby, et al.; "Blocking hepatitis C virus infection with recombinant form of envelope protein 2 ectodomain"; Journal of Virology; vol. 83, No. 21, pp. 11078-11089 (Nov. 2009).

Zhao, et al.; "A neutralization epitope in the hepatitis C virus E2 glycoprotein interacts with host entry factor CD81"; PLoS One; vol. 9, No. 1, 9 pages (Jan. 2014).

Zhao, et al.; "Several affinity tags commonly used in chromatographic purification"; J. Anal. Methods Chem.; vol. 2013, 8 pages (Dec. 2, 2013).

Cao et al., "Functional expression and characterization of the envelope glycoprotein E1E2 heterodimer of hepatitis C virus", PLoS Pathogens., May 22, 2019, 15(5):26 pages.

Cuypers et al., "Genetic Diversity and Selective Pressure in Hepatitis C Virus Genotypes 1-6: Significance for Direct-Acting Antiviral Treatment and Drug Resistance", Viruses, Sep. 2015, 7(9): 5018-5039.

Guest et al., "Design of a native-like secreted form of the hepatitis C virus E1E2 heterodimer", Proc Natl Acad Sci USA, Jan. 19, 2021, 118(3):11 pages.

Kimple et al., "Overview of Affinity Tags for Protein Purification", Curr Protoc Protein Sci., Aug. 2015, 73:26 pages.

Kowarsch et al., "Correlated Mutations: A Hallmark of Phenotypic Amino Acid Substitutions", PLoS Computational Biology, Sep. 2010, 6(9):13 pages.

Schlotthauer et al., "To Include or Occlude: Rational Engineering of HCV Vaccines for Humoral Immunity", Viruses, Apr. 30, 2021, 13(5):26 pages.

Smith et al., "Expanded classification of hepatitis C virus into 7 genotypes and 67 subtypes: updated criteria and genotype assignment web resource", Hepatology, Jan. 2014, 59(1):318-327.

\* cited by examiner

FIG. 5A
GenBank 3S7G_A
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtkng
241 vsltclvkgf ypsdiavewe snggpennyk ttppmldsdg sfflyskltv dksrwqqgnv
301 fscsvmheal hnhytqksls lspgk
```

GenBank AAW65947
*Homo sapiens* IgG3 Fc (amino acids 19-246)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 5B

GenBank AAA52770
*Homo sapiens* IgD Fc (amino acids 162-383)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkattfcf vvgsdlkdah ltwevagkvp tggveeglle rhsngsqsqh sritlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank 0308221A
*Homo sapiens* IgM Fc
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 5C

GenBank P01876
*Homo sapiens* IgA Fc (amino acids 120-353)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprislh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvltc largfspkdv lvrwlqgsqe lprekyltwa srqepsqgtt tfavtsilrv
301 aaedwkkgdt fscmvghealL plaftqktid rlagkpthvn vsvvmaevdg tcy
```

GenBank 1F6A_B
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk cksnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 10A
Protein A

```
  1 mkkkniysir klgvgiasvt lgtllisggv tpaanaaqhd eaqqnafyqv lnmpnlnadq
 61 rngfiqslkd dpsqsanvlg eaqklndsqa pkadaqqnnf nkdqqsafye ilnmpnlnea
121 qrngfiqslk ddpsqstnvl geakklnesq apkadnnfnk eqqnafyeil nmpnlneeqr
181 ngfiqslkdd psqsanllse akklnesqap kadnkfnkeq qnafyei
```

FIG. 10B
Protein G

```
  1 mekekkvkyf lrksafglas vsaaflvgst vfavdspied tpiirnggel tnllgnsett
 61 lalrneesat adltaaavad tvaaaaaena gaaaweaaaa adalakakad alkefnkygv
121 sdyyknlinn aktvegvkdl qaqvvesakk ariseatdgl sdflksqtpa edtvksiela
181 eakvlanrel dkygvsdyyk nlinnaktve gvkalideil aalpktdtyk lilngktlkg
241 qttteavdaa taekvfkqya ndngvdgewt yddatktftv tekpevidap eltpavttyk
301 lvingktlkg etttkavdae taekafkqya ndngvdgvwt yddatktftv temvtevpgd
361 aptepekpea siplvpltpa tpiakddakk ddtkkedakk peakkedakk aetlpttgeg
421 snpfftaaal avmagagala vaskrked
```

FIG. 10C
Protein L

```
  1 mkinkkllma alagaivvgg ganayaaeed ntdnnlsmde isdayfdyhg dvsdsvdpve
 61 eeidealaka laeaketakk hidslnhlse takklakndi dsattinain divaradvme
121 rktaekeeae klaaaketak khidelkhla dktkelakrd idsattinai ndivaradvm
181 erktaekeea eklaaaketa kkhidelkhl adktkelakr didsattida indivaradv
241 merklseket pepeeevtik anlifadgst qnaefkgtfa kavsdayaya dalkkdngey
301 tvdvadkglt lnikfagkke kpeepkeevt ikvnlifadg ktqtaefkgt feeatakaya
361 yadllakeng eytadledgg ntinikfagk etpetpeepk eevtikvnli fadgkiqtae
421 fkgtfeeata kayayanlla kengeytadl edggntinik fagketpetp eepkeevtik
481 vnlifadgkt qtaefkgtfe eataeayrya dllakvngey tadledggyt inikfagkeq
541 pgenpgitid ewllknakee aikelkeagi tsdlyfslin kaktvegvea lkneilkaha
601 geetpelkdg yatyeeaeaa akealknddv nnayeivqga dgryyyvlki evadeeepge
661 dtpevqegya tyeeaeaaak ealkedkvnn ayevvqgadg ryyyvlkied kedeqpgeep
721 genpgitide wllknakeda ikelkeagis sdiyfdaink aktvegveal kneilkahae
781 kpgenpgiti dewllknake aaikelkeag itaeylfnli nkaktvegve slkneilkah
841 aekpgenpgi tidewllkna kedaikelke agitsdiyfd ainkaktieg vealkneilk
901 ahkkdeepgk kpgedkkped kkpgedkkpe dkkpgedkkp edkkpgktdk dspnkkkkak
961 lpkagseaei ltlaaaalst aagayvslkk rk
```

HEPATITIS C VIRUS E1/E2 HETERODIMERS AND METHODS OF PRODUCING SAME

CROSS-REFERENCE

This application claims the benefit of U.S. Provisional Patent Application No. 62/239,157, filed Oct. 8, 2015, and U.S. Provisional Patent Application No. 62/337,212, filed May 16, 2016, which applications are incorporated herein by reference in their entirety.

INTRODUCTION

Hepatitis C virus (HCV) is a blood-borne pathogen that is estimated to infect 150-200 million people worldwide. Infection by HCV may be non-symptomatic, and can be cleared by patients, sometimes without medical intervention. However, the majority of patients develop a chronic HCV infection, which may lead to liver inflammation, scarring, and even to liver failure or liver cancer. In the United States alone, over 3 million people have a chronic infection.

The HCV virion contains a positive-sense single stranded RNA genome of about 9.5 kb. The genome encodes a single polyprotein of 3,010 to 3,030 amino acids. The structural proteins comprise a core protein forming the viral nucleocapsid and two envelope glycoproteins, E1 and E2.

There is a need in the art for compositions and methods for inducing immune responses to HCV.

SUMMARY

The present disclosure provides a method to facilitate large-scale purification of the hepatitis C virus (HCV) E1E2 glycoprotein heterodimer using affinity purification tags, for example the human fragment crystallizable region (Fc region) of immunoglobulins (human or from other species) fused to the N-terminus of E2. Following affinity purification of the E1E2 heterodimer complex (for example, using Protein A or Protein G or Protein L affinity columns), the Fc domain can be removed from the E1E2 complex by digestion with a suitable protease at a proteolytic cleavage site placed downstream of the Fc domain. Ordinarily, the large scale purification of E1E2 is challenging which limits its use as a HCV vaccine in humans. The present disclosure addresses this challenge. The present disclosure also provides various affinity purification-tagged heterodimeric polypeptides comprising an HCV E1 polypeptide and an HCV E2 polypeptide, where one or both of the E1 and E2 polypeptides comprises an affinity purification tag. The present disclosure provides a method of producing an affinity tagged E1/E2 heterodimer of the present disclosure. The present disclosure provides methods of producing untagged HCV E1/E2 heterodimers. The present disclosure also provides HCV E1/E2 heterodimers, compositions comprising the HCV E1/E2 heterodimers, and methods of inducing an immune response to HCV; where the HCV E1/E2 heterodimers comprise a variant HCV E1 polypeptide or a variant HCV E2 polypeptide, the variant E1 or E2 polypeptide comprising from 1 to 6 amino acids from a proteolytically cleavable linker.

The present disclosure provides an affinity tagged heterodimeric polypeptide comprising: a) a hepatitis C virus (HCV) E1 polypeptide; and b) an HCV E2 polypeptide, wherein at least one of the HCV E1 and HCV E2 polypeptides is a fusion polypeptide comprising an affinity tag polypeptide. In some cases, the affinity tagged heterodimeric polypeptide comprises a proteolytically cleavable linker interposed between the affinity tag polypeptide and the HCV E1 or HCV E2 polypeptide. In some cases, a) the proteolytically cleavable linker comprises the sequence LEVLFQGP (SEQ ID NO:1), wherein cleavage occurs between the glutamine and the glycine; b) the proteolytically cleavable linker comprises the sequence ENLYFQS (SEQ ID NO:2), wherein cleavage occurs between the glutamine and the serine; c) the proteolytically cleavable linker comprises the sequence DDDDK (SEQ ID NO:3), wherein cleavage occurs immediately C-terminal to the lysine residue; or d) the proteolytically cleavable linker comprises the sequence LVPR (SEQ ID NO:4) (e.g., where the proteolytically cleavable linker comprises the sequence LVPRGS (SEQ ID NO:5)). In some cases, the affinity tag is an immunoglobulin (Ig) Fc polypeptide, Protein A, Protein G, a hybrid Protein A-Protein G polypeptide, a Protein L polypeptide, a polypeptide comprising a poly(histidine) tract, an immunoglobulin light chain, or glutathione-S-transferase. In some cases, the affinity tagged heterodimeric polypeptide comprises: a) an HCV E1-affinity tag fusion polypeptide comprising an HCV E1 polypeptide and an affinity tag polypeptide; and b) an HCV E2 polypeptide. In some cases, the affinity tagged heterodimeric polypeptide comprises: a) an HCV E1-Fc fusion polypeptide comprising an HCV E1 polypeptide and an Ig Fc polypeptide; and b) an HCV E2 polypeptide. In some cases, the HCV E1-Fc fusion polypeptide comprises, in order from N-terminus to C-terminus: i) the HCV E1 polypeptide; and ii) the Ig Fc polypeptide. In some cases, the HCV E1-Fc fusion polypeptide comprises, in order from N-terminus to C-terminus: i) the Ig Fc polypeptide; and ii) the HCV E1 polypeptide. In some cases, the affinity tagged heterodimeric polypeptide comprises: a) an HCV E2-affinity tag fusion polypeptide comprising an HCV E2 polypeptide and an affinity tag polypeptide; and b) an HCV E1 polypeptide. In some cases, the affinity tagged heterodimeric polypeptide comprises: a) an HCV E2-Fc fusion polypeptide comprising an HCV E2 polypeptide and an Ig Fc polypeptide; and b) an HCV E1 polypeptide. In some cases, the HCV E2-Fc fusion polypeptide comprises, in order from N-terminus to C-terminus: i) the HCV E2 polypeptide; and ii) the Ig Fc polypeptide. In some cases, the HCV E2-Fc fusion polypeptide comprises, in order from N-terminus to C-terminus: i) the Ig Fc polypeptide; and ii) the HCV E2 polypeptide. In some cases, the affinity tagged heterodimeric polypeptide comprises: a) an HCV E1-affinity tag fusion polypeptide comprising an HCV E1 polypeptide and an affinity tag polypeptide; and b) an HCV E2-affinity tag fusion polypeptide comprising an HCV E2 polypeptide and an affinity tag polypeptide. In some cases, the affinity tagged heterodimeric polypeptide comprises: a) an HCV E1-Fc fusion polypeptide comprising an HCV E1 polypeptide and an Ig Fc polypeptide; and b) an HCV E2-Fc fusion polypeptide comprising an HCV E2 polypeptide and an Ig Fc polypeptide. In some cases, a) the HCV E1-Fc fusion polypeptide comprises, in order from N-terminus to C-terminus: i) the HCV E1 polypeptide; and ii) the Ig Fc polypeptide; and b) the HCV E2-Fc fusion polypeptide comprises, in order from N-terminus to C-terminus: i) the HCV E2 polypeptide; and ii) the Ig Fc polypeptide. In some cases: a) the HCV E1-Fc fusion polypeptide comprises, in order from N-terminus to C-terminus: i) the Ig Fc polypeptide; and ii) the HCV E1 polypeptide; and b) the HCV E2-Fc fusion polypeptide comprises, in order from N-terminus to C-terminus: i) the Ig Fc polypeptide; and ii) the HCV E2 polypeptide. In some cases, the HCV E2 polypeptide comprises an amino acid sequence having at least 20% amino acid sequence identity to an E2 polypeptide depicted in one of FIG. 1A-1C, FIG. 2A-2C, FIG. 3A-3C, and FIG. 4A-4B. In some cases, the HCV E1 polypeptide comprises an amino acid sequence having at least 20% amino acid sequence identity to an E1 polypeptide depicted in FIG. 1A-1C, FIG. 2A-2C, FIG. 3A-3C, and FIG. 4A-4B. In some cases, the Ig Fc polypeptide comprises an amino acid sequence having at least 85% amino acid sequence identity to an amino acid sequence depicted in FIG. 5A-5C. In some cases, an affinity tagged heterodimeric polypeptide of comprising an affinity tagged HCV E2 polypeptide, wherein the HCV E2-affinity tag fusion polypeptide comprises, in order from N-terminus to C-terminus: i) from 2 to 15 amino acids of the N-terminus of an HCV E2 polypeptide; ii) the affinity tag polypeptide, iii) a proteolytically cleavable linker; and iv) an HCV E2 polypeptide. In some cases, the from 2 to 15 amino acids of the N-terminus of an HCV E2 polypeptide is a dipeptide selected from QT, ET, HT, GT, TT, RH, NT, AY, VI, and ST. In some cases: a) the proteolytically cleavable linker comprises the sequence LEVLFQGP (SEQ ID NO:1), wherein cleavage occurs between the glutamine and the glycine; b) the proteolytically cleavable linker comprises the sequence ENLYFQS (SEQ ID NO:2), wherein cleavage occurs between the glutamine and the serine; c) the proteolytically cleavable linker comprises the sequence DDDDK (SEQ ID NO:3), wherein cleavage occurs immediately C-terminal to the lysine residue; or d) the proteolytically cleavable linker comprises the sequence LVPR (SEQ ID NO:4) (e.g., where the proteolytically cleavable linker comprises the sequence LVPRGS (SEQ ID NO:5)). In some cases, the HCV E2 polypeptide and the HCV E1 polypeptide are of the same genotype. In some cases, the HCV E2 polypeptide and the HCV E1 polypeptide are of different genotypes. In some cases, the HCV E2 polypeptide is of genotype 1, 2, 3, or 7. In some cases, the HCV E1 polypeptide is of genotype 1, 2, 3, or 7.

The present disclosure provides a composition comprising: a) a heterodimeric polypeptide as described above or elsewhere herein; and b) a buffer. The composition can include a protease inhibitor.

The present disclosure provides a nucleic acid comprising: a) a first nucleotide sequence encoding a hepatitis C virus (HCV) E1 polypeptide; and b) a second nucleotide sequence encoding an HCV E2 polypeptide, wherein at least one of the HCV E1 and HCV E2 polypeptides is a fusion polypeptide comprising an affinity tag polypeptide. In some cases, the nucleic acid comprises a nucleotide sequence encoding a polyprotein comprising, in order from N-terminus to C-terminus: a) an HCV E1 polypeptide; and b) an HCV E2-affinity tag fusion polypeptide comprising, in order from N-terminus to C-terminus: i) an affinity tag polypeptide; ii) a proteolytically cleavable linker; and iii) an HCV E2 polypeptide. In some cases, a nucleotide sequence encoding from 2 amino acids to 15 amino acids from the N-terminus of an HCV E2 polypeptide is interposed between the HCV E1 polypeptide and the affinity tag polypeptide such that a wild-type signal protease E1/E2 junction cleavage site is generated between the HCV E1 polypeptide and the affinity tag polypeptide. In some cases, the nucleic acid comprises a nucleotide sequence encoding a polyprotein comprising, in order from N-terminus to C-terminus: a) an HCV E1 polypeptide; and b) an HCV E2-affinity tag fusion polypeptide comprising, in order from N-terminus to C-terminus: i) an HCV E2 polypeptide; ii) a proteolytically cleavable linker; and iii) an affinity tag polypeptide. In some cases, the nucleic acid comprises a nucleotide sequence encoding a polyprotein comprising, in order from N-terminus to C-terminus: a) an HCV E1-affinity tag fusion polypeptide comprising, in order from N-terminus to C-terminus: i) an affinity tag polypeptide; ii) a proteolytically cleavable linker; and iii) an HCV E1 polypeptide; and b) an HCV E2 polypeptide. In some cases, the nucleic acid comprises a nucleotide sequence encoding a polyprotein comprising, in order from N-terminus to C-terminus: a) an HCV E1-affinity tag fusion polypeptide comprising, in order from N-terminus to C-terminus: i) an HCV E1 polypeptide; ii) a proteolytically cleavable linker; and iii) an affinity tag polypeptide; and b) an HCV E2 polypeptide. In some cases, a nucleotide sequence encoding a signal peptide is interposed between the affinity tag polypeptide and the HCV E2 polypeptide such that signal protease cleavage site is generated between the affinity tag polypeptide and the HCV E2 polypeptide. In some cases, the nucleic acid comprises a nucleotide sequence encoding a polyprotein comprising, in order from N-terminus to C-terminus: a) an HCV E1-affinity tag fusion polypeptide comprising, in order from N-terminus to C-terminus: i) an affinity tag polypeptide; ii) a proteolytically cleavable linker; and iii) an HCV E1 polypeptide; and b) an HCV E2-affinity tag fusion polypeptide comprising, in order from N-terminus to C-terminus: i) an affinity tag polypeptide; ii) a proteolytically cleavable linker; and iii) an HCV E2 polypeptide. In some cases, a nucleotide sequence encoding from 2 amino acids to 15 amino acids from the N-terminus of an HCV E2 polypeptide is interposed between the HCV E1 polypeptide and the affinity tag polypeptide such that a wild-type signal protease E1/E2 junction cleavage site is generated between the HCV E1 polypeptide and the affinity tag polypeptide. In some cases, the nucleic acid comprises a nucleotide sequence encoding a polyprotein comprising, in order from N-terminus to C-terminus: a) an HCV E1-affinity tag fusion polypeptide comprising, in order from N-terminus to C-terminus: i) an HCV E1 polypeptide; ii) a proteolytically cleavable linker; and iii) an affinity tag polypeptide; and b) an HCV E2-affinity tag fusion polypeptide comprising, in order from N-terminus to C-terminus: i) an HCV E2 polypeptide; ii) a proteolytically cleavable linker; and iii) an affinity tag polypeptide. In some cases, a nucleotide sequence encoding a signal peptide is interposed between the affinity tag polypeptide and the HCV E2 polypeptide such that a signal protease cleavage site is generated between the affinity tag polypeptide and the HCV E2 polypeptide. In some cases, the nucleotide sequence encoding the polyprotein is operably linked to a promoter. In some cases, the affinity tag polypeptide is an Ig Fc polypeptide. In some cases, the Ig Fc polypeptide comprises an amino acid sequence having at least 85% amino acid sequence identity to an amino acid sequence depicted in FIG. 5A-5C. In some cases, the from 2 to 15 amino acids of the N-terminus of an HCV E2 polypeptide is a dipeptide selected from QT, ET, HT, GT, TT, RH, NT, AY, VI, and ST. In some cases, a) the proteolytically cleavable linker comprises the sequence LEVLFQGP (SEQ ID NO:1), wherein cleavage occurs between the glutamine and the glycine; b) the proteolytically cleavable linker comprises the sequence ENLYFQS (SEQ ID NO:2, wherein cleavage occurs between the glutamine and the serine; c) the proteolytically cleavable linker comprises the sequence DDDDK (SEQ ID NO:3), wherein cleavage occurs immediately C-terminal to the lysine residue; or d) the proteolytically cleavable linker comprises the sequence LVPR (SEQ ID NO:4) (e.g., where the proteolytically cleavable linker comprises the sequence LVPRGS (SEQ ID NO:5)). In some cases, the HCV E2 polypeptide comprises an amino acid sequence having at least 20% amino acid sequence identity to an E2 polypeptide depicted in one of FIG. 1A-1C, FIG. 2A-2C, FIG. 3A-3C, and FIG. 4A-4B. In some cases, the HCV E1 polypeptide comprises an amino acid sequence having at least 20% amino acid sequence identity to an E1 polypeptide depicted in FIG. 1A-1C, FIG. 2A-2C, FIG. 3A-3C, and FIG. 4A-4B.

The present disclosure provides a recombinant expression vector comprising a nucleic acid as described above, or elsewhere herein. The present disclosure provides a genetically modified in vitro host cell comprising a nucleic acid as described above, or elsewhere herein. The present disclosure provides a genetically modified in vitro host cell comprising a recombinant expression vector as described above, or elsewhere herein. In some cases, the host cell is a eukaryotic cell. In some cases, the host cell is a mammalian cell.

The present disclosure provides a method of making an affinity tagged heterodimeric polypeptide as described above, or elsewhere herein, the method comprising: a) culturing a genetically modified host cell as described above, or elsewhere herein, under conditions such that the affinity tagged HCV E1-E2 heterodimer is produced in the cell; and b) lysing the cell to generate a cell lysate comprising the affinity tagged HCV E1-E2 heterodimer.

The present disclosure provides a method of producing an HCV E1/E2 heterodimer, the method comprising: a) contacting a lysate of the genetically modified host cell as described above, or elsewhere herein, with an affinity tag-binding polypeptide immobilized on an insoluble support, wherein the affinity tagged HCV E1-E2 heterodimer present in the lysate binds to the immobilized affinity tag-binding polypeptide, generating an immobilized affinity tagged HCV E1-E2 heterodimer; b) contacting the immobilized HCV E1-E2 heterodimer with a protease that cleaves the proteolytically cleavable linker present in the immobilized affinity tagged HCV E1-E2 heterodimer, thereby releasing the HCV E1-E2 heterodimer from the affinity tag; and c) collecting the released HCV E1-E2 heterodimer. In some cases, the released HCV E1-E2 he excipient. In some cases, the pharmaceutically acceptable excipient comprises an adjuvant. In some cases, the adjuvant is MF59; alum; poly(DL-lactide co-glycolide); a CpG oligonucleotide; keyhole limpet hemocyanin; or a suspension of liposomes comprising 3'-O-desacyl-4'-monophosphoryl lipid A (MPL) and Quillaja saponaria 21 (QS21).

The present disclosure provides a heterodimeric polypeptide comprising: a) an HCV E1 polypeptide; and b) a modified E2 polypeptide comprising, in order from N-terminus to C-terminus: i) an HCV E2 polypeptide; and ii) from 1 to 6 heterologous amino acids, wherein the from 1 to 6 heterologous amino acids are N-terminal to a site of proteolytic cleavage in a proteolytically cleavable linker. The present disclosure provides a heterodimeric polypeptide comprising: a) an HCV E2 polypeptide; and b) a modified E1 polypeptide comprising, in order from N-terminus to C-terminus: i) an HCV E1 polypeptide; and ii) from 1 to 6 heterologous amino acids, wherein the from 1 to 6 heterologous amino acids are N-terminal to a site of proteolytic cleavage in a proteolytically cleavable linker. In some cases, the from 1 to 6 heterologous amino acids are DDDDK (SEQ ID NO:3). In some cases, the from 1 to 6 heterologous amino acids are LEVLFQ (SEQ ID NO:7). In some cases, the from 1 to 6 heterologous amino acids are ENLYFQ (SEQ ID NO:8). In some cases, the from 1 to 6 heterologous amino acids are LVPR (SEQ ID NO:4). The present disclosure provides a composition comprising: a) the heterodimeric polypeptide; and b) a pharmaceutically acceptable excipient. In some cases, the pharmaceutically acceptable excipient comprises an adjuvant. In some cases, the adjuvant is MF59; alum; poly(DL-lactide co-glycolide); a CpG oligonucleotide; keyhole limpet hemocyanin; or a suspension of liposomes comprising 3'-O-desacyl-4'-monophosphoryl lipid A (MPL) and Quillaja saponaria 21 (QS21).

The present disclosure provides a method of inducing an immune response in an individual to an HCV polypeptide, the method comprising administering to the individual an effective amount of a heterodimeric polypeptide as described above or elsewhere herein, or a composition comprising a heterodimeric polypeptide, as described above or elsewhere herein. In some cases, said administering is by intramuscular administration. In some cases, said administering is by subcutaneous administration.

BRIEF DESCRIPTION OF THE DRAWINGS

FIG. 1A-1C provide an amino acid sequence alignment of examples of the core-E1-E2 coding regions of a HCV genotype 1 virus, specifically representative HCV 1A, 1B and 1C genotypes. Genbank database sequences for the coding region core-E1-E2 were aligned using Geneious software v5.6.4. Numbering of amino acids is according to strain NP_671941 (H77). Consensus: SEQ ID NO:46; AVI1a129: SEQ ID NO:47; NP_671491 (H77): SEQ ID NO:48; EU155269: SEQ ID NO:49; EU781810: SEQ ID NO:50; EU781771: SEQ ID NO:51; AB520610: SEQ ID NO:52; EU781752: SEQ ID NO:53; EU781759: SEQ ID NO:54; EF407439: SEQ ID NO:55; EF407427: SEQ ID NO:56; EU362905: SEQ ID NO:57; EF407413: SEQ ID NO:58; EU781808: SEQ ID NO:59; EU781790: SEQ ID NO:60; AJ238799 (Con1): SEQ ID NO:61; AAK97744: SEQ ID NO:62; AF139594: SEQ ID NO:63; AF176573: SEQ ID NO:64; BAA19625: SEQ ID NO:65; BAA25076: SEQ ID NO:66; BAC54896: SEQ ID NO:67; BAD91386: SEQ ID NO:68; BAF46764: SEQ ID NO:69; BAG30950: SEQ ID NO:70; CAB41951: SEQ ID NO:71; AAK95832: SEQ ID NO:72; AAT69968: SEQ ID NO:73; and BAA03581: SEQ ID NO:74.

FIG. 2A-2C provide an alignment of amino acid sequences of the core-E1-E2 coding region of representative HCV 2A and HCV2B subtypes. Genbank database sequences for the coding region core-E1-E2 were aligned using Geneious software v5.6.4. The amino acid numbering depicted is in accordance to the common HCV strains: AB047639 (JFH1) and HPCJ8G-J8 (J8) for HCV2A and HCV2B, respectively. Consensus: SEQ ID NO:75; AB047639 (JFH1): SEQ ID NO:76; AB047645: SEQ ID NO:77; AF169005: SEQ ID NO:79; AF238482: SEQ ID NO:78; AY746460: SEQ ID NO:80; HPCPOLP: SEQ ID NO:81; NC_009823: SEQ ID NO:82; HPCJ8G HC-J8: SEQ ID NO:83; AB030907: SEQ ID NO:86; AY232730: SEQ ID NO:84; AY232747: SEQ ID NO:85; and DQ430817: SEQ ID NO:87.

FIG. 3A-3C provide an amino acid sequence alignment of the core-E1-E2 coding region for representative HCV 3A, 3B and 3K genotypes. Genbank database sequences for the coding region core-E1-E2 were aligned using Geneious software v5.6.4. Consensus: SEQ ID NO:88; AVI3a177: SEQ ID NO:89; ADF97232(S52): SEQ ID NO:90; YP_0014696: SEQ ID NO:91; CAA54244: SEQ ID NO:92; AAC03058: SEQ ID NO:93; AAY29642: SEQ ID NO:94; ABD85062: SEQ ID NO:95; ABD85063: SEQ ID NO:96; ABD97104: SEQ ID NO:97; BAA06044: SEQ ID NO:98; BAA08372: SEQ ID NO:99; and BAA09890: SEQ ID NO:100.

FIG. 5A-5C provide amino acid sequences of immunoglobulin Fc regions. 3S7G_A: SEQ ID NO:102; AAN76044: SEQ ID NO:103; AAW65947: SEQ ID NO:104; AAA52770: SEQ ID NO:105; 0308221A: SEQ ID NO:106; P01876: SEQ ID NO:107; 1F6A_B: SEQ ID NO:108 and P01861: SEQ ID NO:109.

FIG. 10A-10C provide amino acid sequences of Protein A (SEQ ID NO:121), Protein G (SEQ ID NO:122), and Protein L (SEQ ID NO:123) polypeptides.

FIG. 11A depicts the proteolytically cleavable linker LEVLFQGP (SEQ ID NO:1).

DEFINITIONS

Figure 4A:
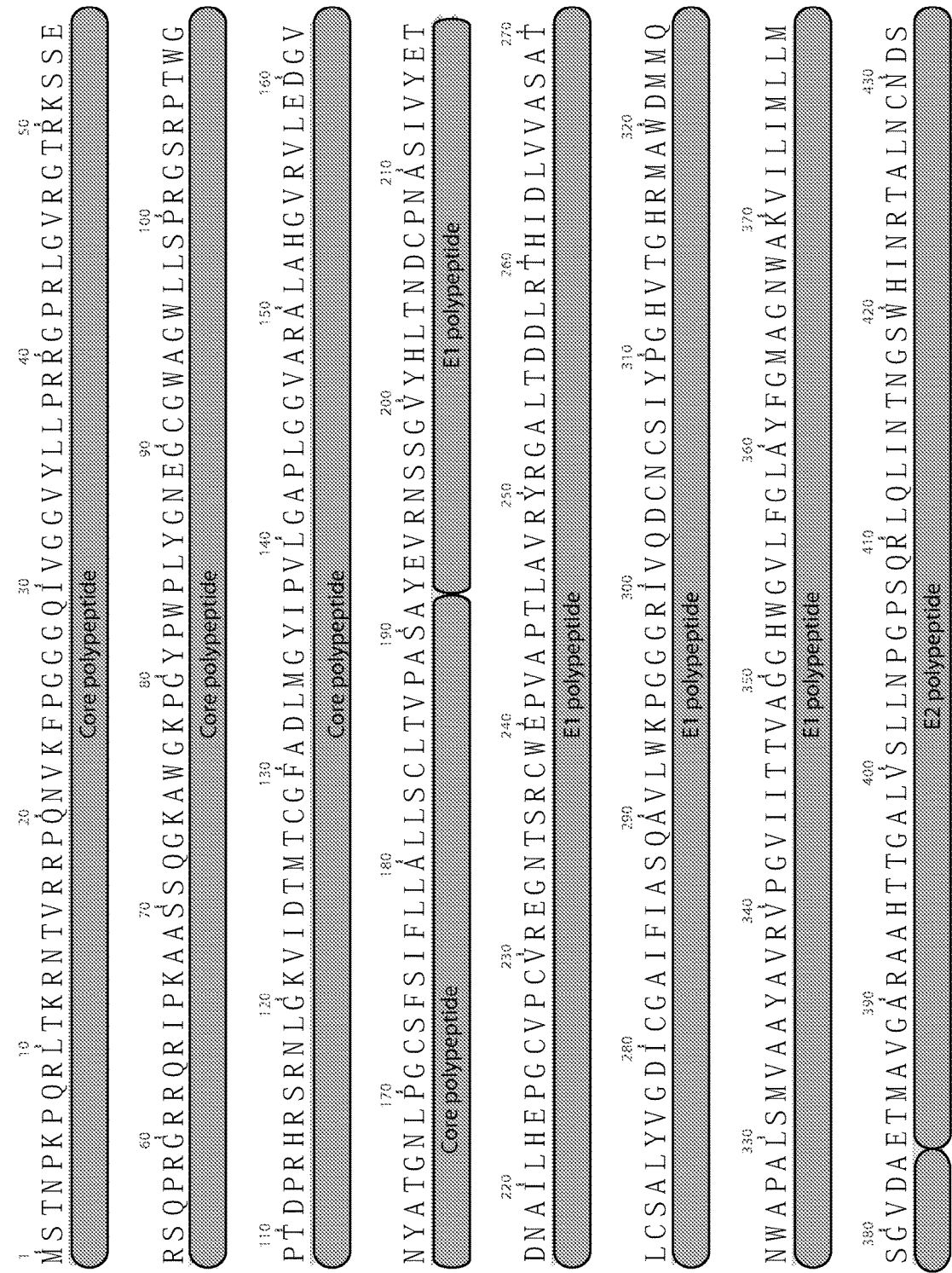
FIG. 4A-4B provide an amino acid sequence of the core-E1-E2 coding region for HCV genotype 7a. Amino acid sequence for the coding region core-E1-E2 of genotype 7a (isolate QC69; Genbank: ABN05226.1; SEQ ID NO:101) is shown according to the numbering scheme of the reference strain, NP_671941 (H77).

The term "hepatitis C virus" ("HCV"), as used herein, refers to any one of a number of different genotypes and isolates of hepatitis C virus. Thus, "HCV" encompasses any of a number of genotypes, subtypes, or quasispecies, of HCV, including, e.g., genotype 1, 2, 3, 4, 6, 7, etc. and subtypes (e.g., 1a, 1b, 2a, 2b, 3a, 4a, 4c, etc.), and quasispecies. Representative HCV genotypes and isolates include: the "Chiron" isolate HCV-1, H77, J6, Con1, isolate 1, BK, EC1, EC10, HC-J2, HC-J5; HC-J6, HC-J7, HC-J8, HC-JT, HCT18, HCT27, HCV-476, HCV-KF, "Hunan", "Japanese", "Taiwan", TH, type 1, type 1a, H77 type 1b, type 1c, type 1d, type 1e, type 1f, type 10, type 2, type 2a, type 2b, type 2c, type 2d, type 2f, type 3, type 3a, type 3b, type 3g, type 4, type 4a, type 4c, type 4d, type 4f, type 4h, type 4k, type 5, type 5a, type 6 and type 6a.

The terms "individual," "host," "subject," and "patient" are used interchangeably herein, and refer to a mammal, including, but not limited to, non-human primates (e.g., simians), equines (e.g., horses), and humans.

As used herein, the term "isolated," in reference to a polypeptide, refers to a polypeptide that is in an environment different from that in which the polypeptide naturally occurs. An isolated polypeptide can be purified. By "purified" is meant a compound of interest (e.g., a polypeptide) has been separated from components that accompany it in nature. "Purified" can also be used to refer to a polypeptide separated from components that can accompany it during production of the polypeptide (e.g., during synthesis in vitro, etc.). In some embodiments, a polypeptide (or a mixture of polypeptides) is substantially pure when the polypeptide (or mixture of polypeptides) is at least 60% or at least 75% by weight free from organic molecules with which it is naturally associated or with which it is associated during production. In some embodiments, the polypeptide is from 30% to 60% pure. In some embodiments, the polypeptide (or mixture of polypeptides) is at least 60%, at least 75%, at least 80%, at least 85%, at least 90%, at least 95%, or at least 99%, by weight, pure. For example, in some cases, an E1 polypeptide, an E1-Fc polypeptide, an E2 polypeptide, or an E2-Fc polypeptide (or a heterodimer comprising such polypeptides) is substantially pure when the E1, E1-Fc, E2, or E2-Fc polypeptide (or a heterodimer of such polypeptides) is at least 60% or at least 75% by weight free from organic molecules with which the polypeptide(s) is naturally associated or with which it is associated during production.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. In some cases, a polynucleotide is RNA. In some cases, a polynucleotide is DNA. A "polynucleotide" includes a nucleic acid that is incorporated into a viral vector or a bacterial vector.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes glycosylated polypeptides.

The term "heterologous" refers to two components that are defined by structures derived from different sources. For example, where "heterologous" is used in the context of a polypeptide, where the polypeptide includes operably linked amino acid sequences that can be derived from one or more different polypeptides, e.g., amino acid sequences that are not operably linked to the polypeptide in nature.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a HCV E1" includes a plurality of such polypeptides and reference to "the affinity tagged HCV E1/E2 heterodimer" includes reference to one or more affinity tagged HCV E1/E2 heterodimers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides affinity tagged heterodimeric polypeptides comprising a hepatitis C virus (HCV) E1 polypeptide and an HCV E2 polypeptide, where one or both of the E1 and E2 polypeptides comprises an affinity purification tag that facilitates commercial, scaled-up purification and production of the E1E2 heterodimer for delivery of the HCV E1/E2 heterodimer as a vaccine. The present disclosure provides a method of producing an affinity-tagged E1/E2 heterodimer of the present disclosure. The present disclosure provides a method of producing an (untagged) HCV E1/E2 heterodimer suitable for use as a vaccine.

Affinity Tagged HCV E1/E2 Heterodimers

The present disclosure provides a method to facilitate large-scale purification of the E1E2 glycoprotein heterodimer using affinity purification tags such as the human Fc immunoglobulin domain fused to the N-terminus of E2, for example. Following purification of the E1E2 heterodimer complex, the human Fc domain can be removed from the E1E2 complex by digestion with a suitable protease at a proteolytic cleavage site placed downstream of the Fc domain. Ordinarily, the large scale purification of E1E2 is very challenging and severely limits its use as a HCV vaccine in humans. The present disclosure provides a method to address this challenge, and to produce HCV E1/E2 heterodimer suitable for use as a vaccine. The present disclosure also provides: a) an HCV E1-affinity tag fusion polypeptide and an HCV E2 polypeptide; b) an HCV E1 polypeptide and an HCV E2-affinity tag fusion polypeptide; or c) an HCV E1-affinity tag fusion polypeptide and an HCV E2-affinity tag fusion polypeptide. The affinity tag portion of an HCV E1-affinity tag fusion polypeptide can be at the N-terminus of the HCV E1 polypeptide, or at the C-terminus of the HCV E1 polypeptide. Likewise, the affinity tag portion of an HCV E2-affinity tag fusion polypeptide can be at the N-terminus of the HCV E2 polypeptide, or at the C-terminus of the HCV E2 polypeptide.

Suitable affinity tags (also referred to herein as "affinity purification tags") include immunoglobulin (Ig) Fc polypeptides, Protein A, Protein G, Protein L, a hybrid Protein A-Protein G polypeptide, a polypeptide comprising a poly (histidine) tract, an immunoglobulin light chain, and glutathione-S-transferase (GST). Purification can be achieved using Protein A-immobilized columns or Protein G-immobilized columns (in the case of Ig-tagged E1E2); Protein L-immobilized columns (in the case of Ig light chain-tagged E1E2); Ig-immobilized columns (in the case of Protein A- or Protein G-tagged E1E2); Ni-columns (in the case of His-tagged E1E2); or Glutathione-immobilized columns (in the case of Glutathione-S-transferase-tagged E1E2), as examples.

The present disclosure provides heterodimeric polypeptides comprising: a) an HCV E1-Fc fusion polypeptide and an HCV E2 polypeptide; b) an HCV E1 polypeptide and an HCV E2-Fc fusion polypeptide; or c) an HCV E1-Fc fusion polypeptide and an HCV E2-Fc fusion polypeptide. The Fc portion of an HCV E1-Fc fusion polypeptide can be at the N-terminus of the HCV E1 polypeptide, or at the C-terminus of the HCV E2 polypeptide. Likewise, the Fc portion of an HCV E2-Fc fusion polypeptide can be at the N-terminus of the HCV E2 polypeptide, or at the C-terminus of the HCV E2 polypeptide.

The HCV E1 and E2 polypeptides in an affinity tagged HCV E1/E2 heterodimer of the present disclosure can be of the same HCV genotype, or can be of different HCV genotypes.

Figure 4B:
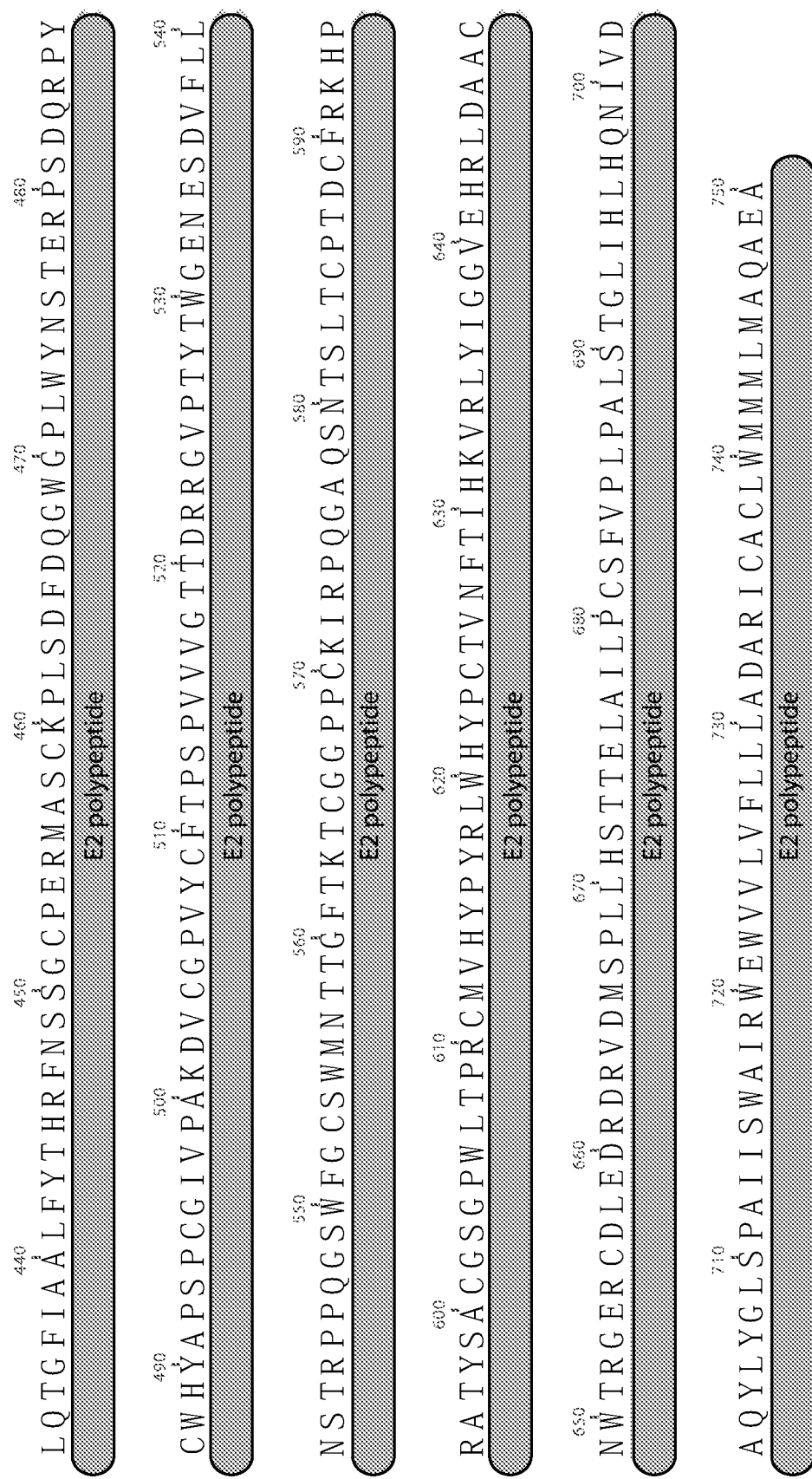

In some cases, the HCV E1 and E2 polypeptides in an affinity tagged HCV E1/E2 heterodimer of the present disclosure are genotype 1 HCV E1 and E2 polypeptides. In some cases, the HCV E1 and E2 polypeptides in an affinity tagged HCV E1/E2 heterodimer of the present disclosure are genotype 2 HCV E1 and E2 polypeptides. In some cases, the HCV E1 and E2 polypeptides in an affinity tagged HCV E1/E2 heterodimer of the present disclosure are genotype 3 HCV E1 and E2 polypeptides. In some cases, the HCV E1 and E2 polypeptides in an affinity tagged HCV E1/E2 heterodimer of the present disclosure are genotype 4 HCV E1 and E2 polypeptides. In some cases, the HCV E1 and E2 polypeptides in an affinity tagged HCV E1/E2 heterodimer of the present disclosure are genotype 5 HCV E1 and E2 polypeptides. In some cases, the HCV E1 and E2 polypeptides in an affinity tagged HCV E1/E2 heterodimer of the present disclosure are genotype 6 HCV E1 and E2 polypeptides. In some cases, the HCV E1 and E2 polypeptides in an affinity tagged HCV E1/E2 heterodimer of the present disclosure are genotype 7 HCV E1 and E2 polypeptides.

The HCV E1 and E2 polypeptides in an affinity tagged HCV E1/E2 heterodimer of the present disclosure are in some embodiments full-length HCV E1 and E2 polypeptides. The HCV E1 and E2 polypeptides in an affinity tagged HCV E1/E2 heterodimer of the present disclosure are in some embodiments full-length HCV E1 and E2 polypeptides and, other than the affinity tag (Ig Fc polypeptide) and an optional linker, do not include any heterologous polypeptides.

In some cases, an affinity tag can replace the N-terminal 20 to 50 amino acids of an HCV E2 polypeptide. For example, in some cases, an affinity tag can replace the N-terminal 20 amino acids (aa) to 25 aa, from 25 aa to 30 aa, from 30 aa to 35 aa, from 35 aa to 40 aa, or from 40 aa to 50 aa, of an HCV E2 polypeptide. For example, in some cases, an affinity tag can replace the N-terminal 30 amino acids of an HCV E2 polypeptide.

E2 Polypeptides

An E2 polypeptide suitable for inclusion in an affinity tagged HCV E1/E2 heterodimer of the present disclosure can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. In some cases, an HCV E2 polypeptide suitable for inclusion in an E1/E2 heterodimer of the present disclosure is an HCV E2 ectodomain polypeptide. In some cases, an HCV E2 polypeptide suitable for inclusion in an affinity tagged HCV E1/E2 heterodimer of the present disclosure is a full-length HCV E2 polypeptide.

Figure 1A:
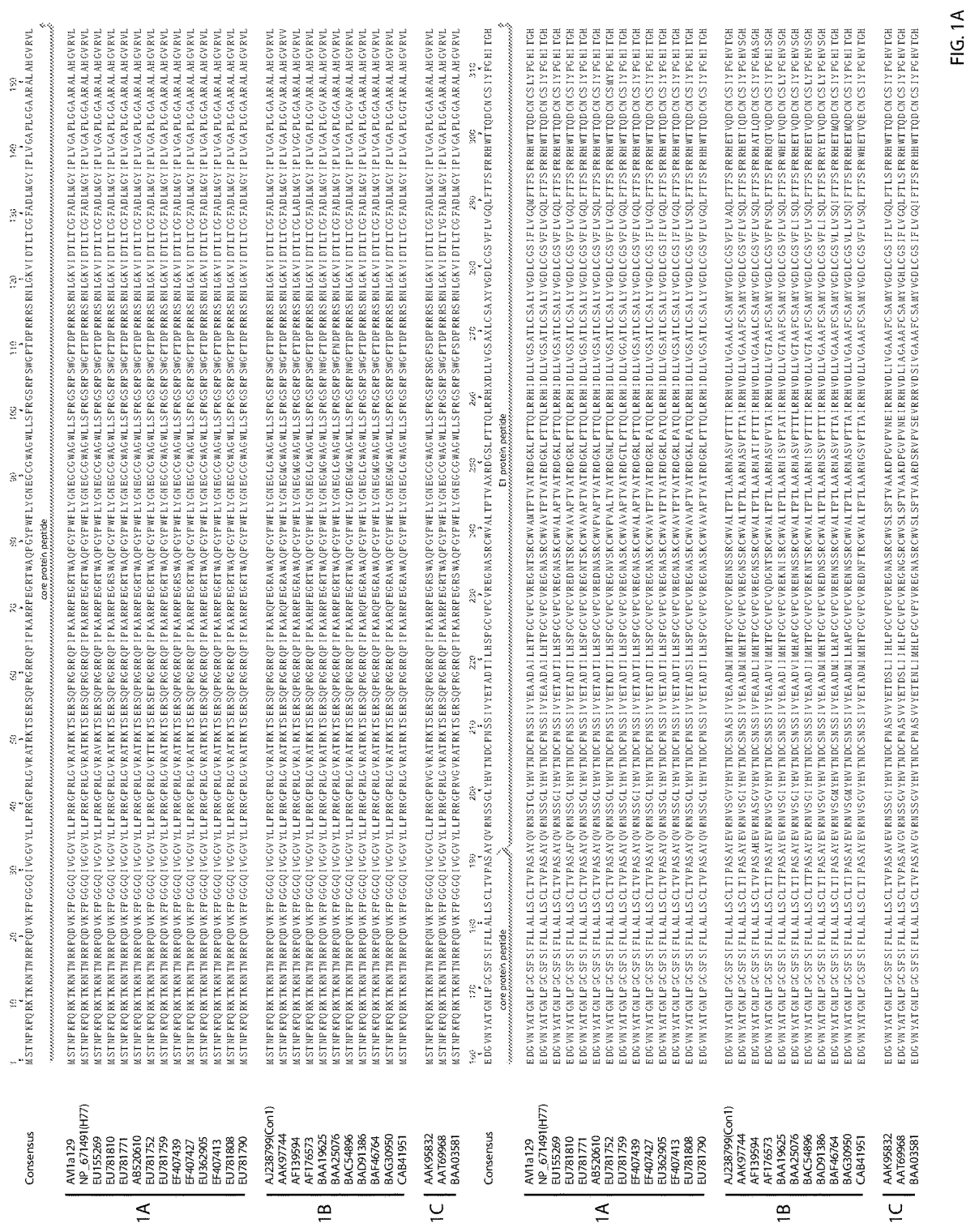

In FIG. 1A-AC, the amino acid sequence of E2 is amino acid 384 to amino acid 746. In FIG. 2A-2B, the amino acid sequence of E2 is amino acid 384 to amino acid 751. In FIG. 3A-3C, the amino acid sequence of E2 is amino acid 385 to amino acid 754. In FIG. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

Figure 1B:
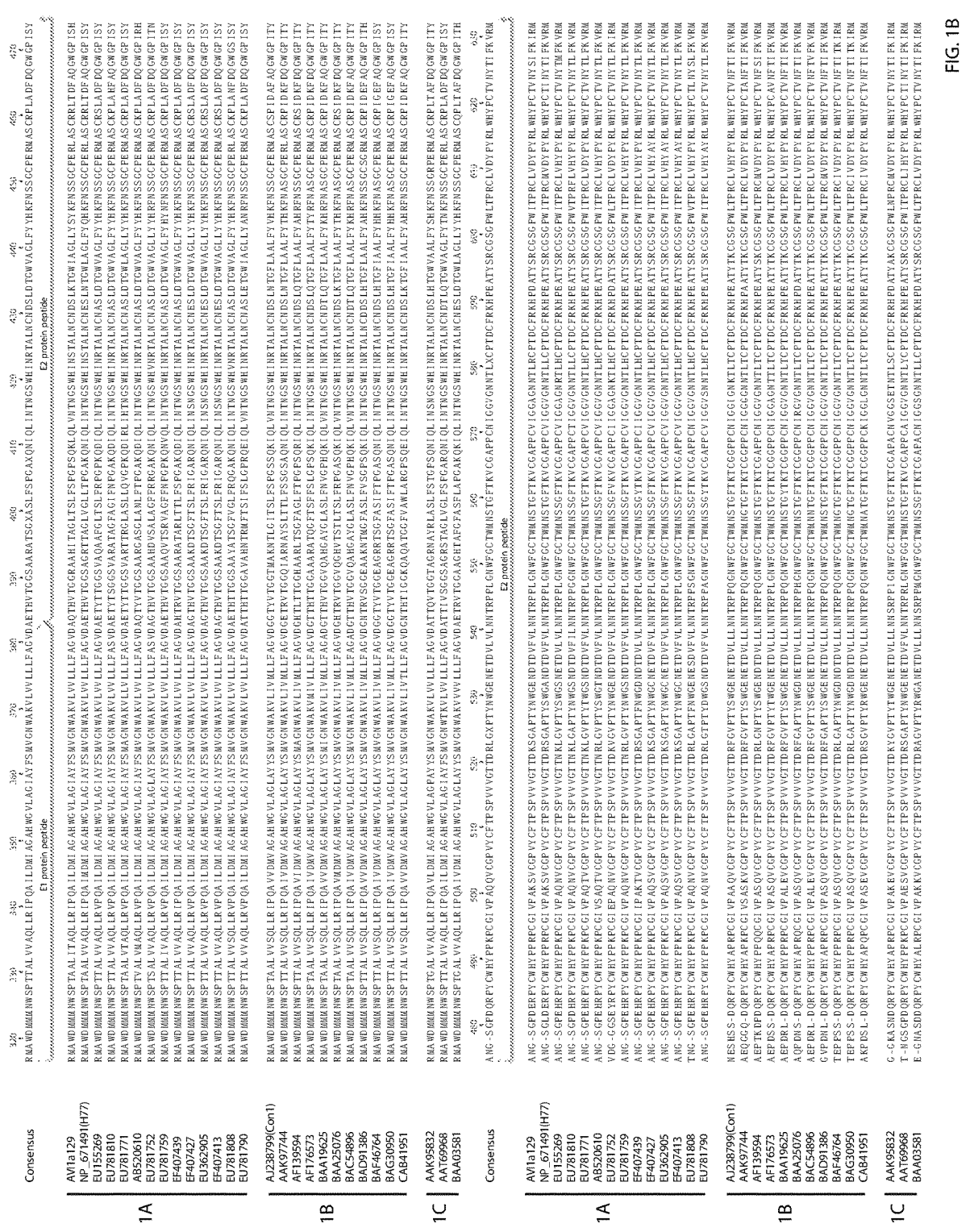
Figure 1C:
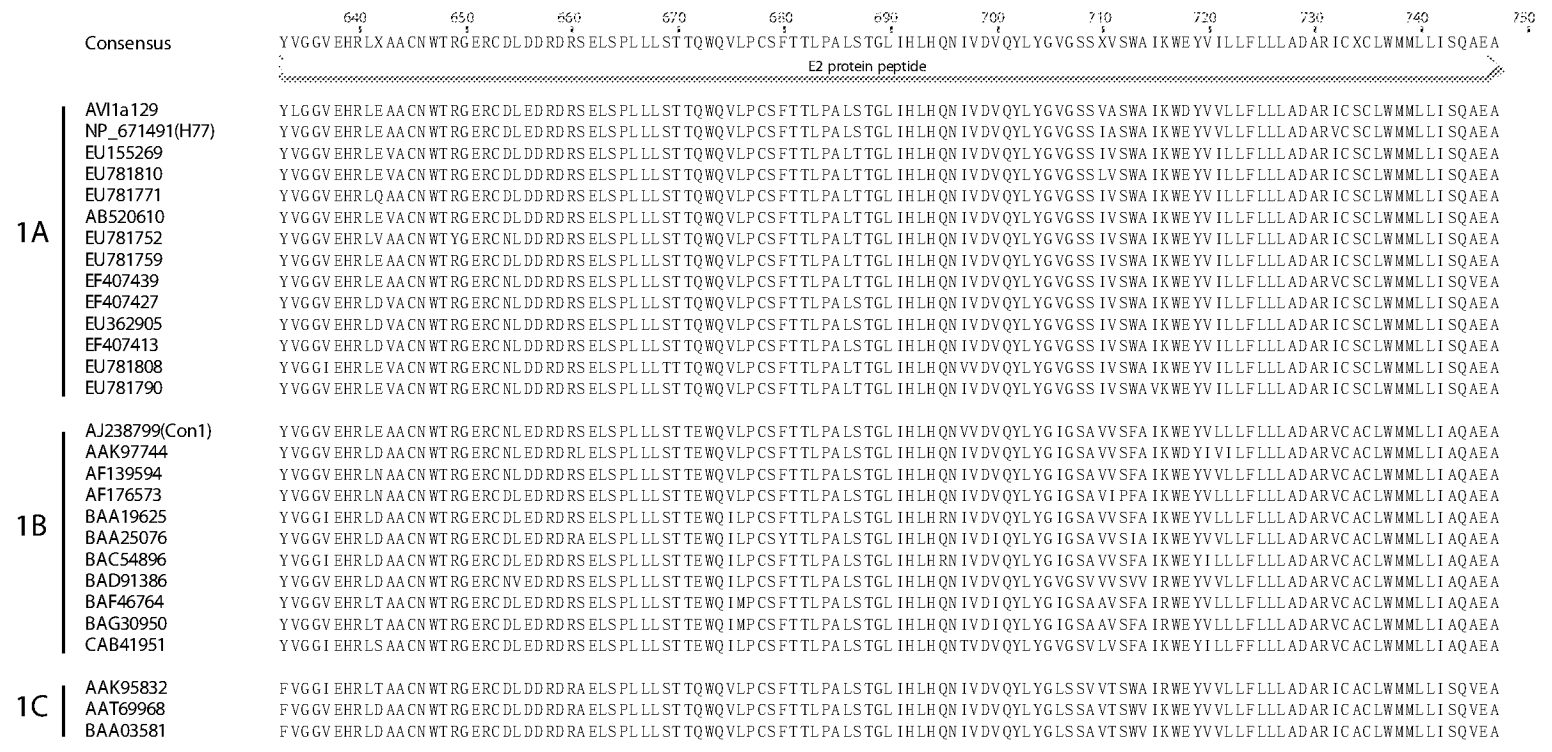

In some cases, a E2 polypeptide suitable for inclusion in an affinity tagged HCV E1/E2 heterodimer of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIG. 1A-1C. See, e.g., U.S. Pat. No. 6,521,423.

An E2 polypeptide suitable for inclusion in an affinity tagged HCV E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 1A-1C, FIG. 2A-2C, FIG. 3A-3C, or FIG. 4A-4B. An E2 polypeptide suitable for inclusion in an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, or at least about 75%, amino acid sequence identity to an amino acid sequence of an E2 polypeptide depicted in FIG. 1A-1C, FIG. 2A-2C, FIG. 3A-3C, or FIG. 4A-4B.

An E2 polypeptide suitable for inclusion in an affinity tagged HCV E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIG. 1A-1C. For example, an E2 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIG. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIG. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIG. 1A-1C.

Figure 2A:
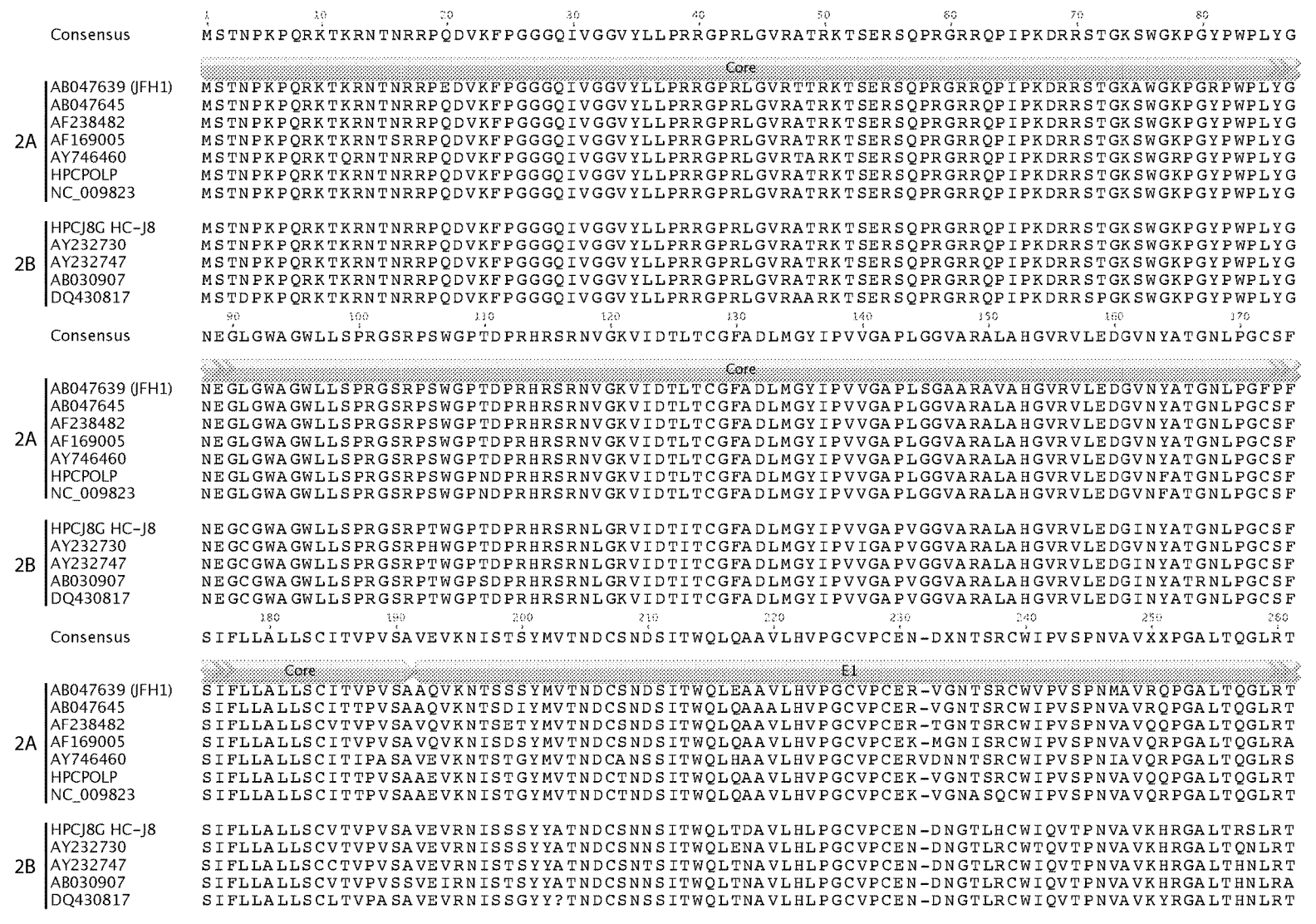
Figure 2B:
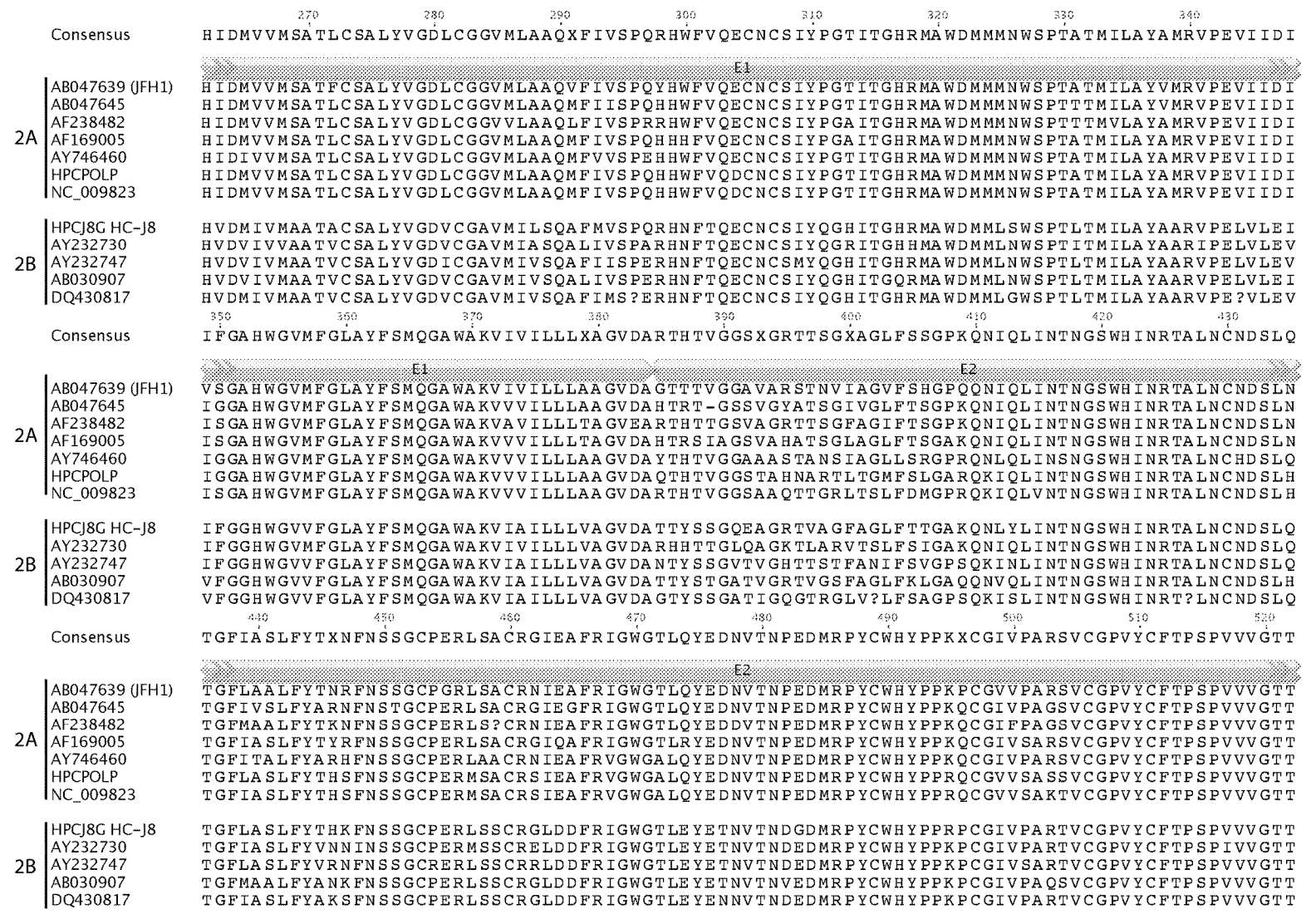
Figure 2C:
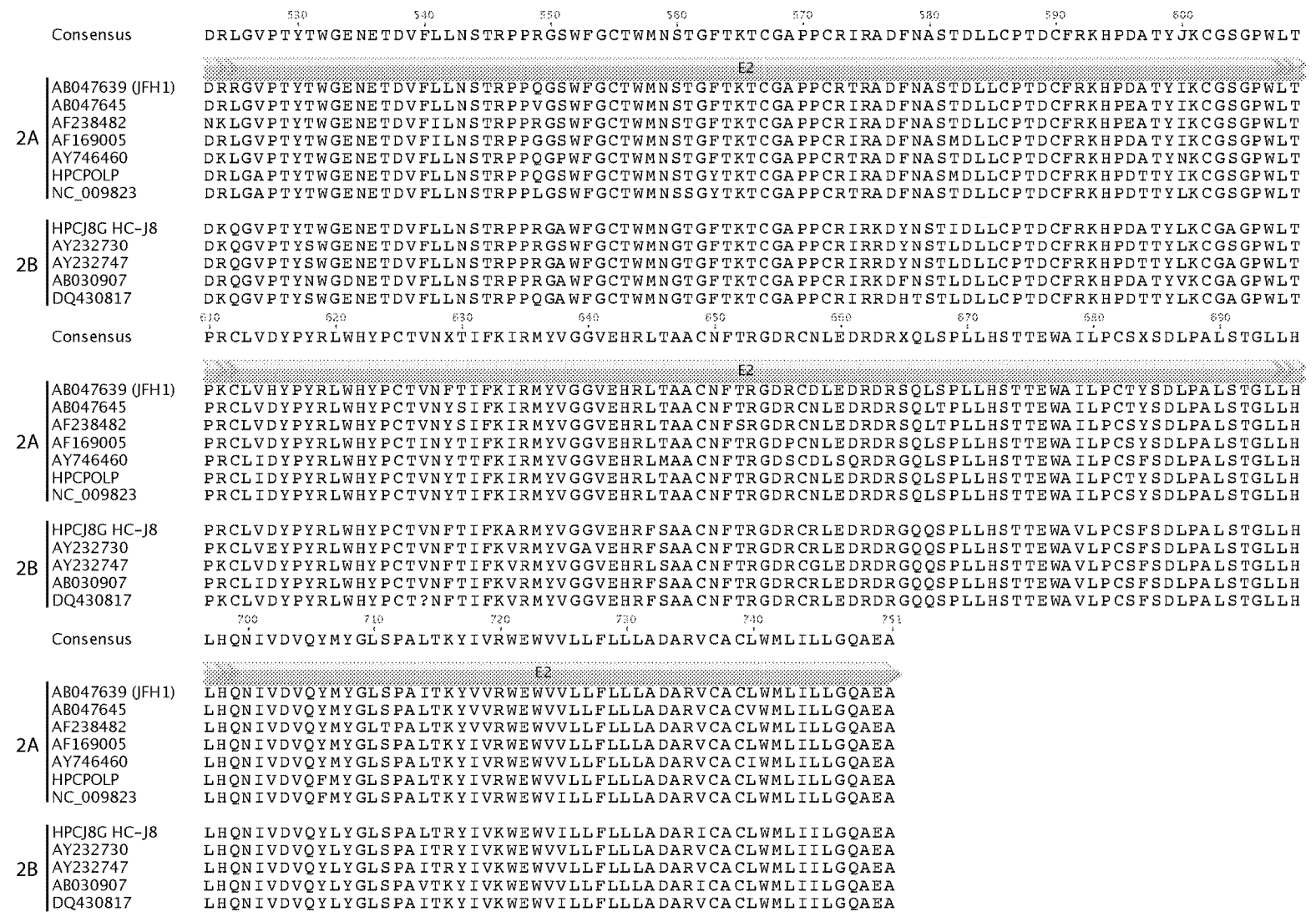

An E2 polypeptide suitable for inclusion in an affinity tagged HCV E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 2A-2C. For example, an E2 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of an amino acid sequence depicted in FIG. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIG. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIG. 2A-2C.

Figure 3B:
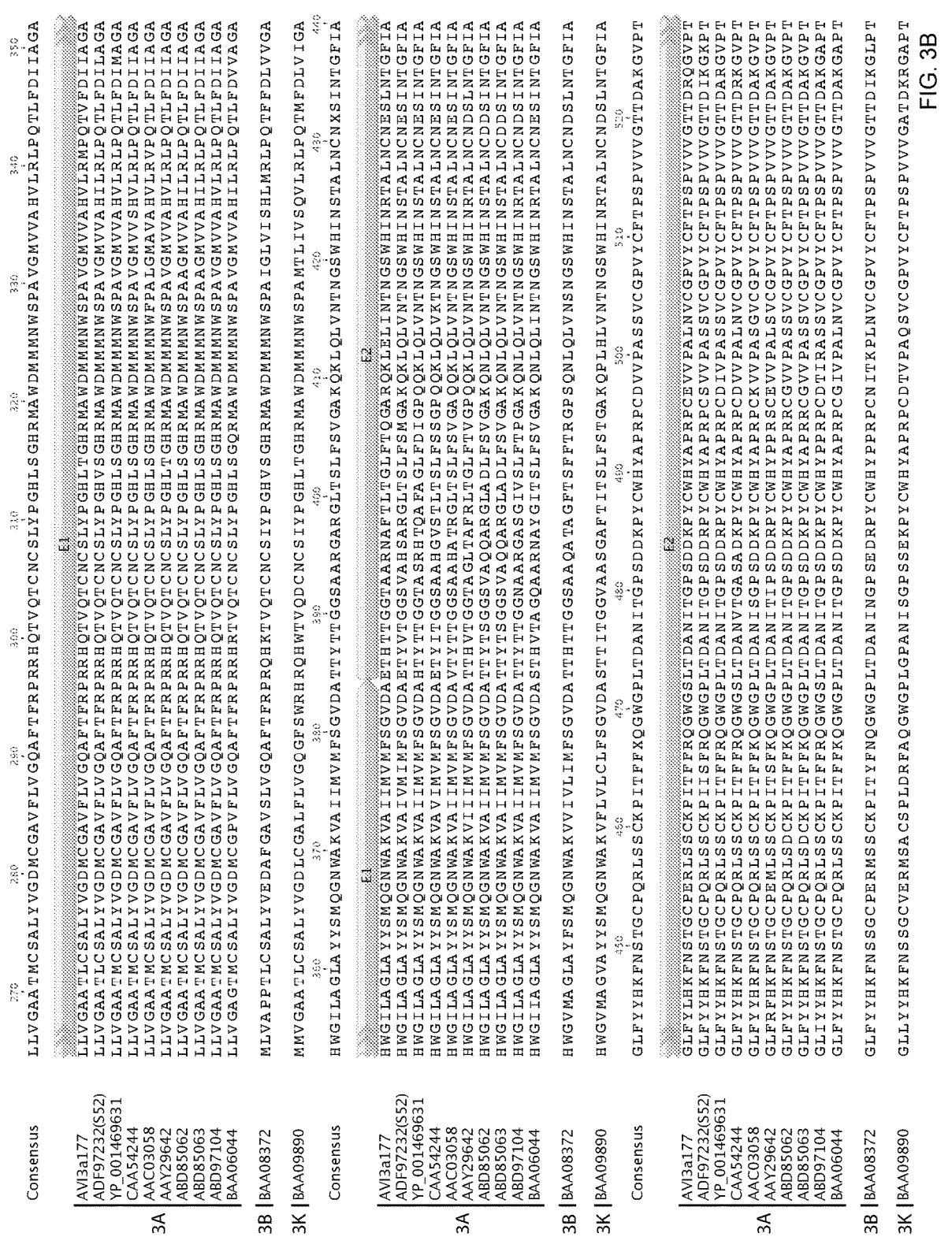
Figure 3C:
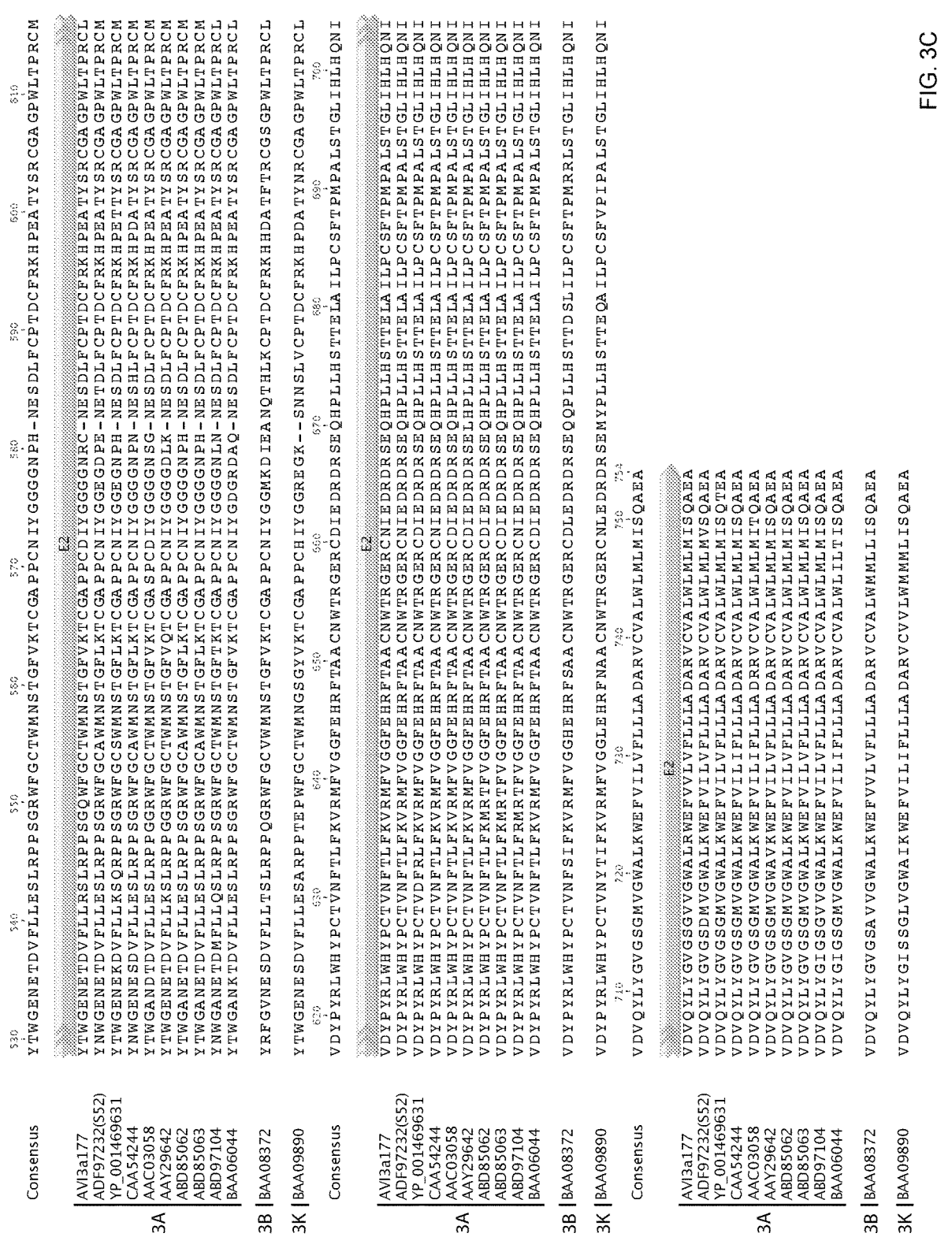

An E2 polypeptide suitable for inclusion in an affinity tagged HCV E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIG. 3A-3C. For example, an E2 polypeptide of genotype 3A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIG. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIG. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIG. 3A-3C.

An E2 polypeptide suitable for inclusion in an affinity tagged HCV E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIG. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIG. 4A-4B.

E1 Polypeptides

An HCV E1 polypeptide suitable for inclusion in an affinity tagged HCV E1/E2 heterodimer of the present disclosure can have a length of from about 150 amino acids (aa) to about 175 aa, from about 175 aa to about 195 aa, from about 131 aa to about 175 aa, or from about 175 aa to about 193 aa. In some cases, an HCV E1 polypeptide suitable for inclusion in an E1/E2 heterodimer of the present disclosure is an HCV E1 ectodomain polypeptide. In some cases, an HCV E1 polypeptide suitable for inclusion in an E1/E2 heterodimer of the present disclosure is a full-length HCV E1 polypeptide.

In FIG. 1A-1C, the amino acid sequence of E1 is amino acid 192 to amino acid 383. In FIG. 2A-2C, the amino acid sequence of E1 is amino acid 192 to amino acid 383. In FIG. 3A-3C, the amino acid sequence of E1 is amino acid 192 to amino acid 384. In FIG. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 1A-1C, FIG. 2A-2C, FIG. 3A-3C, or FIG. 4A-4B.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIG. 1A-1C. For example, an E1 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIG. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIG. 1A-1C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIG. 2A-2C. For example, an E1 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIG. 2A-2C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIG. 3A-3C. For example, an E1 polypeptide of genotype 3A, 3B, or 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino 192-384 of an amino acid sequence of an amino acid sequence identified as 3A, 3B, or 3K, respectively, as depicted in FIG. 3A-3C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIG. 4A-4B.

Affinity Tags

Suitable affinity tags (also referred to herein as "affinity purification tags") include immunoglobulin (Ig) Fc polypeptides, Protein A, Protein G, Protein L, a hybrid Protein A-Protein G polypeptide, a polypeptide comprising a poly (histidine) tract, an immunoglobulin light chain, and glutathione-S-transferase (GST).

Fc Polypeptides

Various Ig Fc polypeptides are suitable for inclusion in an affinity tagged HCV E1/E2 heterodimer of the present disclosure. The Fc region (Fc polypeptide) can be a human IgG1 Fc, a human IgG2 Fc, a human IgG3 Fc, a human IgG4 Fc, etc. The Fc polypeptide can be an Fc polypeptide from a non-human species.

In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIG. 5A-5C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 5A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 5A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 5A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 5A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 5A.

In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG4 Fc polypeptide depicted in FIG. 5C; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 100-327 of the human IgG4 Fc polypeptide depicted in FIG. 5C.

Protein A

In some cases, the affinity tag polypeptide included in an affinity tagged HCV E1/E2 heterodimer of the present disclosure is a Protein A polypeptide. A suitable Protein A polypeptide can comprises an amino acid sequence having at least 50%, at least 60%, at least 70%, at least 80%, at least 85%, at least 90%, at least 95%, at least 98%, or 100%, amino acid sequence identity to amino acids 27 to 227 the Protein A amino acid sequence depicted in FIG. 10A; and can have a length of from 150 to 200 amino acids. A suitable Protein A polypeptide can comprises an amino acid sequence having at least 50%, at least 60%, at least 70%, at least 80%, at least 85%, at least 90%, at least 95%, at least 98%, or 100%, amino acid sequence identity to amino acids 27 to 227 the Protein A amino acid sequence depicted in FIG. 10A; and can have a length of 200 amino acids.

Protein G

In some cases, the affinity tag polypeptide included in an affinity tagged HCV E1/E2 heterodimer of the present disclosure is a Protein G polypeptide. A suitable Protein G polypeptide can comprises an amino acid sequence having at least 50%, at least 60%, at least 70%, at least 80%, at least 85%, at least 90%, at least 95%, at least 98%, or 100%, amino acid sequence identity to amino acids 37-448 the Protein G amino acid sequence depicted in FIG. 10B; and can have a length of from 350 amino acids to 411 amino acids.

Protein L

Protein L binds antibody kappa light chains, single chain variable fragments (scFv), and Fab fragments. A suitable Protein L polypeptide can comprises an amino acid sequence having at least 50%, at least 60%, at least 70%, at least 80%, at least 85%, at least 90%, at least 95%, at least 98%, or 100%, amino acid sequence identity to amino acids 25-992 of the Protein L amino acid sequence depicted in FIG. 10C. A suitable Protein L polypeptide can comprises an amino acid sequence having at least 50%, at least 60%, at least 70%, at least 80%, at least 85%, at least 90%, at least 95%, at least 98%, or 100%, amino acid sequence identity to amino acids 25-992 of the Protein L amino acid sequence depicted in FIG. 10C; and can have a length of from 800 amino acids to 968 amino acids.

Polypeptides Comprising a Poly(Histidine) Tract

In some cases, the affinity tag polypeptide included in an affinity tagged HCV E1/E2 heterodimer of the present disclosure is a polypeptide that comprises a poly(histidine) tract. A suitable poly(histidine) tract-containing polypeptide can have a length of from about 25 amino acids to about 500 amino acids, e.g., from about 25 amino acids (aa) to 30 aa, from 30 aa to 35 aa, from 35 aa to 40 aa, from 40 aa to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 aa to 400 aa, from 400 aa to 450 aa, or 450 aa to 500 aa. The poly(histidine) tract can be from 4 to 20 consecutive histidines, e.g., from 4 to 6 consecutive histidines, from 6 to 10 consecutive histidines, from 10 to 15 consecutive histidines, or from 15 to 20 consecutive histidines. For example, a suitable affinity tag polypeptide can have a length of about 50 amino acids, and can include a (His)$_6$ histidine tract.

Light Chain

In some cases, the affinity tag polypeptide included in an affinity tagged HCV E1/E2 heterodimer of the present disclosure is an immunoglobulin light chain, or an Ig light chain-containing polypeptide. For example, an Ig light chain-containing polypeptide can be a single chain variable fragment (scFv), an Fab fragment, or any other Ig light chain-containing polypeptide. In some cases, the Ig light chain-containing polypeptide comprises an Ig kappa light chain, e.g., a human Ig kappa light chain. Ig light chain amino acid sequences are known in the art.

Linkers

In some cases, a linker can be interposed between the affinity tag (e.g., Ig Fc) and the HCV E1 or HCV E2 polypeptide. The linker peptide may have any of a variety of amino acid sequences. A linker can be a peptide of between about 6 and about 40 amino acids in length, or between about 6 and about 25 amino acids in length. These linkers can be produced by using synthetic, linker-encoding oligo-nucleotides to couple the proteins. Peptide linkers allowing a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly, Ala, or Ser) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO:9) and $(GGGS)_n$ (SEQ ID NO:10), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited to, GGSG (SEQ ID NO:11), GGSGG (SEQ ID NO:12), GSGSG (SEQ ID NO:13), GSGGG (SEQ ID NO:14), GGGSG (SEQ ID NO:15), GSSSG (SEQ ID NO:16), and the like. The ordinarily skilled artisan will recognize that design of a peptide conjugated to any elements described above can include linkers that are all or partially flexible, such that the linker can include a flexible linker as well as one or more portions that confer less flexible structure.

E1-Fc Fusion/E2 Heterodimers

In some cases, an affinity tagged HCV E1/E2 heterodimer of the present disclosure comprises: a) an HCV E1-Fc fusion polypeptide; and b) an HCV E2 polypeptide.

The Fc polypeptide can be attached, directly or via a linker, to the carboxyl terminus (C terminus) of an HCV E1 polypeptide. In other words, in some cases, the HCV E1-Fc fusion polypeptide comprises, in order from N-terminus to C-terminus: i) an HCV E1 polypeptide; and ii) an Ig Fc polypeptide. In some case, the HCV E1-Fc fusion polypeptide comprises, in order from N-terminus to C-terminus: i) an HCV E1 polypeptide; ii) a linker; and iii) an Ig Fc polypeptide.

The Fc polypeptide can be attached, directly or via a linker, to the amino terminus (N terminus) of the HCV E1 polypeptide. In other words, in some cases, the HCV E1-Fc fusion polypeptide comprises, in order from N-terminus to C-terminus: i) an Ig Fc polypeptide; and ii) an HCV E1 polypeptide. In some cases, the HCV E1-Fc fusion polypeptide comprises, in order from N-terminus to C-terminus: i) an Ig Fc polypeptide; ii) a linker; and iii) an HCV E1 polypeptide

E1/E2-Fc Fusion Heterodimers

In some cases, an affinity tagged HCV E1/E2 heterodimer of the present disclosure comprises: a) an HCV E2-Fc fusion polypeptide; and b) an HCV E1 polypeptide.

The Fc polypeptide can be attached, directly or via a linker, to the C-terminus of an HCV E2 polypeptide. In other words, in some cases, the HCV E2-Fc fusion polypeptide comprises, in order from N-terminus to C-terminus: i) an HCV E2 polypeptide; and ii) an Ig Fc polypeptide. In some cases, the HCV E2-Fc fusion polypeptide comprises, in order from N-terminus to C-terminus: i) an HCV E2 polypeptide; ii) a linker; and iii) an Ig Fc polypeptide.

The Fc polypeptide can be attached, directly or via a linker, to N-terminus of the HCV E2 polypeptide. In other words, in some cases, the HCV E2-Fc fusion polypeptide comprises, in order from N-terminus to C-terminus: i) an Ig Fc polypeptide; and ii) an HCV E2 polypeptide. In some cases, the HCV E2-Fc fusion polypeptide comprises, in order from N-terminus to C-terminus: i) an Ig Fc polypeptide; ii) a linker; and iii) an HCV E2 polypeptide.

E1-Fc Fusion/E2-Fc Fusion Heterodimers

In some cases, an affinity tagged HCV E1/E2 heterodimer of the present disclosure comprises: a) an HCV E1-Fc fusion polypeptide; and b) an HCV E2-Fc fusion polypeptide.

In some cases, an affinity tagged HCV E1/E2 heterodimer of the present disclosure comprises: a) an HCV E1-Fc fusion polypeptide, where the HCV E1-Fc fusion polypeptide comprises, in order from N-terminus to C-terminus: i) an HCV E1 polypeptide; and ii) an Fc polypeptide; and b) an HCV E2-Fc fusion polypeptide, where the HCV E2-Fc fusion polypeptide comprises, in order from N-terminus to C-terminus: i) an HCV E2 polypeptide; and ii) an Fc polypeptide.

In some cases, an affinity tagged HCV E1/E2 heterodimer of the present disclosure comprises: a) an HCV E1-Fc fusion polypeptide, where the HCV E1-Fc fusion polypeptide comprises, in order from N-terminus to C-terminus: i) an Fc polypeptide; and ii) an HCV E1 polypeptide; and b) an HCV E2-Fc fusion polypeptide, where the HCV E2-Fc fusion polypeptide comprises, in order from N-terminus to C-terminus: i) an Fc polypeptide; and ii) an HCV E2 polypeptide.

Proteolytically Cleavable Linker

The affinity tag present in an affinity tagged HCV E1/E2 heterodimer of the present disclosure is cleaved off during purification, to generate an HCV E1/E2 heterodimer that does not include the affinity tag. To achieve this aim, a proteolytically cleavable linker can be positioned between an affinity tag and an HCV E1 and/or HCV E2 polypeptide.

Thus, in some cases, an affinity tagged HCV E1/E2 heterodimer of the present disclosure comprises an affinity tagged HCV E1 polypeptide, where the affinity tagged E1 polypeptide comprises, in order from N-terminus to C-terminus: i) an affinity tag (e.g., an Fc polypeptide); ii) a proteolytically cleavable linker; and ii) an HCV E1 polypeptide.

In some cases, an affinity tagged HCV E1/E2 heterodimer of the present disclosure comprises an affinity tagged HCV E2 polypeptide, where the affinity tagged E2 polypeptide comprises, in order from N-terminus to C-terminus: i) an affinity tag (e.g., an Fc polypeptide); ii) a proteolytically cleavable linker; and ii) an HCV E2 polypeptide.

In some cases, an affinity tagged HCV E1/E2 heterodimer of the present disclosure comprises an affinity tagged HCV E1 polypeptide and an affinity tagged HCV E2 polypeptide, where the affinity tagged E1 polypeptide comprises, in order from N-terminus to C-terminus: i) an affinity tag (e.g., an Fc polypeptide); ii) a proteolytically cleavable linker; and ii) an HCV E1 polypeptide; and where the affinity tagged E2 polypeptide comprises, in order from N-terminus to C-terminus: i) an affinity tag (e.g., an Fc polypeptide); ii) a proteolytically cleavable linker; and ii) an HCV E2 polypeptide.

The proteolytically cleavable linker can include a protease recognition sequence recognized by a protease selected from the group consisting of alanine carboxypeptidase, Armillaria mellea astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

For example, the proteolytically cleavable linker can comprise a matrix metalloproteinase (MMP) cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO:17) or Pro-Leu/Gln-Gly-Met-Thr (SEQ ID NO:18). Another example of a protease cleavage site is a plasminogen activator cleavage site, e.g., a uPA or a tissue plasminogen activator (tPA) cleavage site. Another example of a suitable protease cleavage site is a prolactin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYFQS (SEQ ID NO:2), where the protease cleaves between the glutamine and the serine. Another example of a protease cleavage site that can be included in a proteolytically cleavable linker is an enterokinase cleavage site, e.g., DDDDK (SEQ ID NO:3), where cleavage occurs after the lysine residue. Another example of a protease cleavage site that can be included in a proteolytically cleavable linker is a thrombin cleavage site, e.g., LVPR (SEQ ID NO:4) (e.g., where the proteolytically cleavable linker comprises the sequence LVPRGS (SEQ ID NO:5)). Additional suitable linkers comprising protease cleavage sites include linkers comprising one or more of the following amino acid sequences: LEVLFQGP (SEQ ID NO:1), cleaved by PreScission protease (a fusion protein comprising human rhinovirus 3C protease and glutathione-S-transferase; Walker et al. (1994) *Biotechnol.* 12:601); a thrombin cleavage site, e.g., CGLVPAGSGP (SEQ ID NO:19); SLLKSRMVPNFN (SEQ ID NO:20) or SLLIARRMPNFN (SEQ ID NO:21), cleaved by cathepsin B; SKLVQASASGVN (SEQ ID NO:22) or SSYLKASDAPDN (SEQ ID NO:23), cleaved by an Epstein-Barr virus protease; RPKPQQFFGLMN (SEQ ID NO:24) cleaved by MMP-3 (stromelysin); SLRPLA-LWRSFN (SEQ ID NO:25) cleaved by MMP-7 (matrilysin); SPQGIAGQRNFN (SEQ ID NO:26) cleaved by MMP-9;

DVDERDVRGFASFL SEQ ID NO:27) cleaved by a thermolysin-like MMP; SLPLGLWAPNFN (SEQ ID NO:28) cleaved by matrix metalloproteinase 2(MMP-2); SLLIFR-SWANFN (SEQ ID NO:29) cleaved by cathespin L; SGV-VIATVIVIT (SEQ ID NO:30) cleaved by cathepsin D; SLGPQGIWGQFN (SEQ ID NO:31) cleaved by matrix metalloproteinase 1 (MMP-1); KKSPGRVVGGSV (SEQ ID NO:32) cleaved by urokinase-type plasminogen activator; PQGLLGAPGILG (SEQ ID NO:33) cleaved by membrane type 1 matrixmetalloproteinase (MT-MMP); HGPEGLRVGFYESDVMGRGHARLVHVEEPHT (SEQ ID NO:34) cleaved by stromelysin 3 (or MMP-11), thermolysin, fibroblast collagenase and stromelysin-1; GPQGLAGQRGIV (SEQ ID NO:35) cleaved by matrix metalloproteinase 13 (collagenase-3); GGSGQRGRKALE (SEQ ID NO:36) cleaved by tissue-type plasminogen activator(tPA); SLSALLSSDIFN (SEQ ID NO:37) cleaved by human prostate-specific antigen; SLPRFKIIGGFN (SEQ ID NO:38) cleaved by kallikrein (hK3); SLLGIAVPGNFN (SEQ ID NO:39) cleaved by neutrophil elastase; and FFKNIVTPRTPP (SEQ ID NO:40) cleaved by calpain (calcium activated neutral protease).

E1-E2 Junctions

During processing of a wild-type HCV E1-E2 polyprotein in a eukaryotic (e.g., mammalian) cell, endogenous proteases cleave the E1 protein from the E2 protein; the endogenous proteases recognize the E1-E2 junction and cleave at the junction. During synthesis and processing of an affinity tagged HCV E1/E2 heterodimer of the present disclosure from a polyprotein precursor in a mammalian cell, the wild-type E1-E2 junction can be recapitulated, such that amino acids (e.g., from 2 to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa)) from the N-terminus of E2 are repeated at the N-terminus of the affinity tag, as depicted in FIG. 6A. In some cases, 2 amino acids from the N-terminus of an HCV E2 polypeptide are positioned at the N-terminus of the affinity tag. In some cases, the dipeptide QT, ET, HT, GT, TT, RH, NT, AY, VI, or ST is positioned at the N-terminus of the affinity tag. Depending on the genotype and specific isolate of E1E2, duplication of the first two amino acids of E2 may result in an undesirable amino acid created at the N-terminus of E2 following processing by signal peptidase (SP) (FIG. 6A). Such amino acids at the amino terminus include asparagine (N), glutamine (Q) or cysteine (C). Such amino acids can target the protein for proteasome-mediated degradation via the N-end rule pathway (reviewed in: Tasaki T et al. 2012. Annu Rev Biochem 81 261-289). In this case, an alternative amino acid could be selected according to either the consensus sequence for the particular genotype or a particular genotype subclass would be selected.

Thus, in some cases, an affinity tagged HCV E1/E2 heterodimer of the present disclosure comprises an affinity tagged HCV E2 polypeptide that comprises, in order from N-terminus to C-terminus: i) from 2 to 15 amino acids (e.g., 2 amino acids (aa), 3 aa, 4 aa, 5 aa, 6 aa, 7 aa, 8 aa, 9 aa, 10 aa, 11 aa, 12 aa, 13 aa, 14 aa, or 15 aa) of the N-terminus of an E2 polypeptide; ii) an affinity tag polypeptide; iii) a proteolytically cleavable linker; and iv) an HCV E2 polypeptide.

For example, in some cases, an affinity tagged HCV E1/E2 heterodimer of the present disclosure comprises an affinity tagged HCV E2 polypeptide that comprises, in order from N-terminus to C-terminus: i) ET (Glu-Thr); ii) an affinity tag polypeptide; iii) a proteolytically cleavable linker; and iv) an HCV E2 polypeptide.

As another example, in some cases, an affinity tagged HCV E1/E2 heterodimer of the present disclosure comprises an affinity tagged HCV E2 polypeptide that comprises, in order from N-terminus to C-terminus: i) GT (Gly-Thr); ii) an affinity tag polypeptide; iii) a proteolytically cleavable linker; and iv) an HCV E2 polypeptide.

As another example, in some cases, an affinity tagged HCV E1/E2 heterodimer of the present disclosure comprises an affinity tagged HCV E2 polypeptide that comprises, in order from N-terminus to C-terminus: i) TT (Thr-Thr); ii) an affinity tag polypeptide; iii) a proteolytically cleavable linker; and iv) an HCV E2 polypeptide.

As another example, in some cases, an affinity tagged HCV E1/E2 heterodimer of the present disclosure comprises an affinity tagged HCV E2 polypeptide that comprises, in order from N-terminus to C-terminus: i) a QT, ET, HT, GT, TT, RH, NT, AY, VI, or ST dipeptide; ii) an affinity tag polypeptide; iii) the cleavable linker LEVLFQGP (SEQ ID NO:1); and iv) an HCV E2 polypeptide.

As another example, in some cases, an affinity tagged HCV E1/E2 heterodimer of the present disclosure comprises an affinity tagged HCV E2 polypeptide that comprises, in order from N-terminus to C-terminus: i) a QT, ET, HT, GT, TT, RH, NT, AY, VI, or ST dipeptide; ii) an Ig Fc polypeptide; iii) the cleavable linker LEVLFQGP (SEQ ID NO:1); and iv) an HCV E2 polypeptide.

Nucleic Acids, Recombinant Expression Vectors, and Host Cells

The present disclosure provides nucleic acids comprising nucleotide sequences encoding an affinity tagged HCV E1/E2 heterodimer of the present disclosure, and recombinant expression vectors comprising the nucleic acids. Thus, the present disclosure provides recombinant expression vectors comprising nucleotide sequences encoding an affinity tagged HCV E1/E2 heterodimer of the present disclosure. The present disclosure provides host cells genetically modified with a nucleic acid or a recombinant expression vector of the present disclosure.

In some cases, a nucleic acid of the present disclosure comprises a nucleotide sequence encoding: a) an HCV E1 polypeptide of an affinity tagged HCV E1/E2 heterodimer of the present disclosure; b) an HCV E1-affinity tag fusion polypeptide of an affinity tagged HCV E1/E2 heterodimer of the present disclosure; c) an HCV E2 polypeptide of an affinity tagged HCV E1/E2 heterodimer of the present disclosure; d) an HCV E2-affinity tag fusion polypeptide of an affinity tagged HCV E1/E2 heterodimer of the present disclosure; or e) an affinity tagged HCV E1/E2 heterodimer of the present disclosure (e.g., where both polypeptides of the heterodimer are encoded in a single nucleic acid). Thus, in some cases, a nucleic acid of the present disclosure comprises a nucleotide sequence encoding one polypeptide chain of an affinity tagged HCV E1/E2 heterodimer of the present disclosure.

In some cases, a nucleic acid of the present disclosure comprises a nucleotide sequence encoding: a) an HCV E1 polypeptide of an affinity tagged HCV E1/E2 heterodimer of the present disclosure; b) an HCV E1-Fc fusion polypeptide of an affinity tagged HCV E1/E2 heterodimer of the present disclosure; c) an HCV E2 polypeptide of an affinity tagged HCV E1/E2 heterodimer of the present disclosure; d) an HCV E2-Fc fusion polypeptide of an affinity tagged HCV E1/E2 heterodimer of the present disclosure; or e) an affinity tagged HCV E1/E2 heterodimer of the present disclosure (e.g., where both polypeptides of the heterodimer are encoded in a single nucleic acid). Thus, in some cases, a nucleic acid of the present disclosure comprises a nucleotide sequence encoding one polypeptide chain of an affinity tagged HCV E1/E2 heterodimer of the present disclosure.

Where a nucleic acid of the present disclosure comprises a nucleotide sequence encoding one polypeptide chain of an affinity tagged HCV E1/E2 heterodimer of the present disclosure, the nucleotide sequence can be operably linked to a promoter, e.g., a promoter that is functional in a eukaryotic cell. In other instances, a nucleic acid of the present disclosure comprises a nucleotide sequence encoding both polypeptide chains of an affinity tagged HCV E1/E2 heterodimer of the present disclosure; the nucleotide sequence can be operably linked to a promoter, e.g., a promoter that is functional in a eukaryotic cell.

The present disclosure provides a composition comprising: a) a first nucleic acid comprising a nucleotide sequence encoding an HCV E1 polypeptide; and b) a second nucleic acid comprising a nucleotide sequence encoding an HCV E2 polypeptide, where at least one of the HCV E1 and HCV E2 polypeptides is a fusion polypeptide comprising an affinity tag polypeptide. The present disclosure provides a composition comprising: a) a first nucleic acid comprising a nucleotide sequence encoding an HCV E1 polypeptide; and b) a second nucleic acid comprising a nucleotide sequence encoding an HCV E2 polypeptide, where at least one of the HCV E1 and HCV E2 polypeptides is a fusion polypeptide comprising an Ig Fc polypeptide.

Where a nucleic acid of the present disclosure comprises a nucleotide sequence encoding both polypeptide chains of an HCV E1/E2 heterodimer of the present disclosure, the nucleotide sequence can be operably linked to a promoter, e.g., a promoter that is functional in a eukaryotic cell. Where a nucleic acid of the present disclosure comprises a nucleotide sequence encoding both polypeptide chains of an HCV E1/E2 heterodimer of the present disclosure, the nucleic acid can comprise a first nucleotide sequence encoding an HCV E1 polypeptide, and a second nucleotide sequence encoding an HCV E2 polypeptide, where one or both of the E1 and E2 polypeptides is a fusion polypeptide comprising an Fc polypeptide. In some cases, the first nucleotide sequence and the second nucleotide sequence are separated by an internal ribosome entry site (IRES). In some cases, the first nucleotide sequence and the second nucleotide sequence are separated by a ribosomal skipping sequence (e.g., a nucleotide sequence encoding a 2A peptide (e.g., VKQTLNFDLLKLAGDVESNPGP (SEQ ID NO:41); see, e.g., Radcliffe and Mitrophanous (2004) *Gene Therapy* 11:1673).

In some cases, a nucleic acid of the present disclosure is inserted into an expression vector, to generate a recombinant expression vector. Thus, the present disclosure provides a recombinant expression vector comprising a nucleic acid comprising a nucleotide sequence encoding: a) an HCV E1 polypeptide of an affinity tagged HCV E1/E2 heterodimer of the present disclosure; b) an HCV E1-Fc fusion polypeptide of an affinity tagged HCV E1/E2 heterodimer of the present disclosure; c) an HCV E2 polypeptide of an affinity tagged HCV E1/E2 heterodimer of the present disclosure; d) an HCV E2-Fc fusion polypeptide of an affinity tagged HCV E1/E2 heterodimer of the present disclosure; or e) an affinity tagged HCV E1/E2 heterodimer of the present disclosure (e.g., where both polypeptides of the heterodimer are encoded in a single nucleic acid).

In some cases, the nucleotide sequence encoding a) an HCV E1 polypeptide of an affinity tagged HCV E1/E2 heterodimer of the present disclosure; b) an HCV E1-Fc fusion polypeptide of an affinity tagged HCV E1/E2 heterodimer of the present disclosure; c) an HCV E2 polypeptide of an affinity tagged HCV E1/E2 heterodimer of the present disclosure; d) an HCV E2-Fc fusion polypeptide of an affinity tagged HCV E1/E2 heterodimer of the present disclosure; or e) an affinity tagged HCV E1/E2 heterodimer of the present disclosure is operably linked to a transcriptional control element, e.g., a promoter, such as a promoter functional in a eukaryotic cell.

In some cases, a recombinant expression vector of the present disclosure comprises a nucleotide sequence encoding only one polypeptide chain of an affinity tagged HCV E1/E2 heterodimer of the present disclosure. The present disclosure provides a composition comprising: a) a first recombinant expression vector comprising a nucleotide sequence encoding an HCV E1 polypeptide; and b) a second recombinant expression vector comprising a nucleotide sequence encoding an HCV E2 polypeptide, where at least one of the HCV E1 and HCV E2 polypeptides is a fusion polypeptide comprising an Ig Fc polypeptide. The nucleotide sequence encoding the first polypeptide chain (HCV E1 polypeptide or HCV E1-Fc fusion polypeptide) or the second polypeptide chain (HCV E2 polypeptide or HCV E2-Fc fusion polypeptide) can be operably linked to a promoter, e.g., a promoter functional in a eukaryotic host cell.

In some cases, a recombinant expression vector of the present disclosure comprises a nucleotide sequence encoding both polypeptide chains of an affinity tagged HCV E1/E2 heterodimer of the present disclosure. In some instances, the nucleotide sequence is operably linked to a promoter, e.g., a promoter that is functional in a eukaryotic cell. Where a recombinant expression vector of the present disclosure comprises a nucleotide sequence encoding both polypeptide chains of an affinity tagged HCV E1/E2 heterodimer of the present disclosure, the recombinant expression vector can comprise a first nucleotide sequence encoding an HCV E1 polypeptide, and a second nucleotide sequence encoding an HCV E2 polypeptide, where one or both of the E1 and E2 polypeptides is a fusion polypeptide comprising an affinity tag (e.g., an Ig Fc polypeptide). In some cases, the first nucleotide sequence and the second nucleotide sequence are separated by an internal ribosome entry site (IRES). In some cases, the first nucleotide sequence and the second nucleotide sequence are separated by a ribosomal skipping sequence (e.g., a nucleotide sequence encoding a 2A peptide (e.g., VKQTLNFDLLKLAGDVESNPGP (SEQ ID NO:41); see, e.g., Radcliffe and Mitrophanous (2004) *Gene Therapy* 11:1673).

The present disclosure provide a nucleic acid comprising a nucleotide sequence encoding an affinity tagged HCV E1/E2 heterodimer of the present disclosure, where the affinity tagged HCV E1/E2 heterodimer comprises: i) an E1 polypeptide and an E2-affinity tag fusion polypeptide; ii) an E2-affinity tag fusion polypeptide and an E1 polypeptide; or iii) an E1-affinity tag fusion polypeptide and an E2-affinity tag fusion polypeptide. In some cases, a nucleotide sequence encoding a proteolytically cleavable linker is interposed between the nucleotide sequence encoding the HCV E1 or the HCV E2 polypeptide and the affinity tag.

The proteolytically cleavable linker can include a protease recognition sequence recognized by a protease selected from the group consisting of alanine carboxypeptidase, Armillaria mellea astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

For example, the proteolytically cleavable linker can comprise a matrix metalloproteinase (MMP) cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO:17) or Pro-Leu/Gln-Gly-Met-Thr (SEQ ID NO:18). Another example of a protease cleavage site is a plasminogen activator cleavage site, e.g., a uPA or a tissue plasminogen activator (tPA) cleavage site. Another example of a suitable protease cleavage site is a prolactin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYFQS (SEQ ID NO:2), where the protease cleaves between the glutamine and the serine. Another example of a protease cleavage site that can be included in a proteolytically cleavable linker is an enterokinase cleavage site, e.g., DDDDK (SEQ ID NO:3), where cleavage occurs after the lysine residue. Another example of a protease cleavage site that can be included in a proteolytically cleavable linker is a thrombin cleavage site, e.g., LVPR (SEQ ID NO:4) (e.g., where the proteolytically cleavable linker comprises the sequence LVPRGS (SEQ ID NO:5)). Additional suitable linkers comprising protease cleavage sites include linkers comprising one or more of the following amino acid sequences: LEVLFQGP (SEQ ID NO:1), cleaved by PreScission protease (a fusion protein comprising human rhinovirus 3C protease and glutathione-S-transferase; Walker et al. (1994) *Biotechnol.* 12:601); a thrombin cleavage site, e.g., CGLVPAGSGP (SEQ ID NO:19); SLLKSRMVPNFN (SEQ ID NO:20) or SLLIARRMPNFN (SEQ ID NO:21), cleaved by cathepsin B; SKLVQASASGVN (SEQ ID NO:22) or SSYLKASDAPDN (SEQ ID NO:23), cleaved by an Epstein-Barr virus protease; RPKPQQFFGLMN (SEQ ID NO:24) cleaved by MMP-3 (stromelysin); SLRPLA-LWRSFN (SEQ ID NO:25) cleaved by MMP-7 (matrilysin); SPQGIAGQRNFN (SEQ ID NO:26) cleaved by MMP-9; DVDERDVRGFASFL SEQ ID NO:27) cleaved by a thermolysin-like MMP; SLPLGLWAPNFN (SEQ ID NO:28) cleaved by matrix metalloproteinase 2(MMP-2); SLLIFR-SWANFN (SEQ ID NO:29) cleaved by cathespin L; SGV-VIATVIVIT (SEQ ID NO:30) cleaved by cathepsin D; SLGPQGIWGQFN (SEQ ID NO:31) cleaved by matrix metalloproteinase 1(MMP-1); KKSPGRVVGGSV (SEQ ID NO:32) cleaved by urokinase-type plasminogen activator; PQGLLGAPGILG (SEQ ID NO:33) cleaved by membrane type 1 matrixmetalloproteinase (MT-MMP); HGPEGLRVGFYESDVMGRGHARLVHVEEPHT (SEQ ID NO:34) cleaved by stromelysin 3 (or MMP-11), thermolysin, fibroblast collagenase and stromelysin-1; GPQGLAGQRGIV (SEQ ID NO:35) cleaved by matrix metalloproteinase 13 (collagenase-3); GGSGQRGRKALE (SEQ ID NO:36) cleaved by tissue-type plasminogen activator(tPA); SLSALLSSDIFN (SEQ ID NO:37) cleaved by human prostate-specific antigen; SLPRFKIIGGFN (SEQ ID NO:38) cleaved by kallikrein (hK3); SLLGIAVPGNFN (SEQ ID NO:39) cleaved by neutrophil elastase; and FFKNIVTPRTPP (SEQ ID NO:40) cleaved by calpain (calcium activated neutral protease).

As noted above, a nucleic acid encoding one or both polypeptides of an affinity tagged HCV E1/E2 heterodimer of the present disclosure can be present in an expression vector. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, human immunodeficiency virus (HIV)-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as *E. coli*, mammalian cells, insect cells, or yeast cells). Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623).

The present disclosure provides genetically modified host cells, where the genetically modified host cells are genetically modified with a nucleic acid(s) or recombinant expression vector(s) of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MRC4 fibroblast cells, and the like.

Methods for introduction of nucleic acids into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated.

1) Nucleic Acid Encoding an HCV E1-Affinity Tag-E2 Polyprotein to Produce an Affinity Tagged HCV E1/E2 Heterodimer Comprising an HCV E2-Affinity Tag Fusion Polypeptide (N-Terminal Affinity Tagged E2) and an HCV E1 Polypeptide In some cases, a nucleic acid of the present disclosure comprises a nucleotide sequence encoding a polyprotein comprising, in order from N-terminus to C-terminus: i) an HCV E1 polypeptide; and ii) an HCV E2-affinity tag fusion polypeptide, where the HCV E2-affinity tag fusion polypeptide comprises, in order from N-terminus to C-terminus: i) an affinity tag polypeptide; and ii) an HCV E2 polypeptide. Upon expression in a suitable host cell, an affinity tagged HCV E1/E2 heterodimer is produced, where the affinity tagged HCV E1/E2 heterodimer comprises an HCV E1 polypeptide and an HCV E2-affinity tag fusion polypeptide. The HCV E2-affinity tag fusion polypeptide so produced comprises, in order from N-terminus to C-terminus: i) an affinity tag polypeptide; and ii) an HCV E2 polypeptide.

In some cases, a nucleic acid of the present disclosure comprises a nucleotide sequence encoding a polyprotein comprising, in order from N-terminus to C-terminus: i) an HCV E1 polypeptide; and ii) an HCV E2-affinity tag fusion polypeptide, where the HCV E2-affinity tag fusion polypeptide comprises, in order from N-terminus to C-terminus: i) an affinity tag polypeptide; ii) a proteolytically cleavable linker; and iii) an HCV E2 polypeptide. Upon expression in a suitable host cell, an affinity tagged HCV E1/E2 heterodimer is produced, where the affinity tagged HCV E1/E2 heterodimer comprises an HCV E1 polypeptide and an HCV E2-affinity tag fusion polypeptide. The HCV E2-affinity tag fusion polypeptide so produced comprises, in order from N-terminus to C-terminus: i) an affinity tag polypeptide; ii) a proteolytically cleavable linker; and iii) an HCV E2 polypeptide.

In some cases, a nucleic acid of the present disclosure comprises a nucleotide sequence encoding a polyprotein comprising, in order from N-terminus to C-terminus: i) an HCV E1 polypeptide; ii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iii) an affinity tag; iv) a proteolytically cleavable linker; and v) an HCV E2 polypeptide. In some cases, the nucleotide sequence encoding the polyprotein is operably linked to a transcription control element, e.g., a promoter that is functional in a eukaryotic cell. Suitable promoters include, e.g., a CMV promoter, an SV40 promoter, and the like, as described above. In some cases, the nucleic acid is present in an expression vector (e.g., a lentivirus vector; an adenoassociated virus vector; an adenovirus vector; a retroviral vector; a non-viral vector; etc.). In some cases, the affinity tag is an Ig Fc polypeptide. In other cases, the affinity tag is Protein A, Protein G, a polypeptide comprising a poly(histidine) tract, or a GST polypeptide. Suitable proteolytically cleavable linkers are described above. Upon expression in a suitable host cell, an affinity tagged HCV E1/E2 heterodimer is produced, where the affinity tagged HCV E1/E2 heterodimer comprises an HCV E1 polypeptide and an HCV E2-affinity tag fusion polypeptide. The HCV E2-affinity tag fusion polypeptide so produced comprises, in order from N-terminus to C-terminus: i) an affinity tag polypeptide; and an HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iii) an affinity tag; iv) a proteolytically cleavable linker; and v) an HCV E2 polypeptide. In some cases, the polyprotein comprises a signal peptide. Thus, for example, in some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iv) an affinity tag; v) a proteolytically cleavable linker; and vi) an HCV E2 polypeptide. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the affinity tag is an Ig Fc polypeptide. In other cases, the affinity tag is Protein A, Protein G, a polypeptide comprising a poly(histidine) tract, or a GST polypeptide. In some cases, the amino acids from the N-terminus of an HCV E2 polypeptide are a QT, ET, HT, GT, TT, RH, NT, AY, VI, or ST dipeptide.

Suitable signal peptides include, e.g., a tissue plasminogen activator (tPA) signal peptide; a prolactin signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKRGLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iii) an affinity tag; iv) a proteolytically cleavable linker; and v) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iv) an affinity tag; v) a proteolytically cleavable linker; and vi) an HCV E2 polypeptide. In some cases, the nucleic acid is present in an expression vector (e.g., a lentivirus vector; an adenoassociated virus vector; an adenovirus vector; a retroviral vector; a non-viral vector; etc.). In some cases, the affinity tag is an Ig Fc polypeptide. In other cases, the affinity tag is Protein A, Protein G, a polypeptide comprising a poly(histidine) tract, or a GST polypeptide. In some cases, the amino acids from the N-terminus of an HCV E2 polypeptide are a QT, ET, HT, GT, TT, RH, NT, AY, VI, or ST dipeptide.

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iii) an Ig Fc polypeptide; iv) a proteolytically cleavable linker; and v) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iv) an Ig Fc polypeptide; v) a proteolytically cleavable linker; and vi) an HCV E2 polypeptide. In some cases, the nucleic acid is present in an expression vector (e.g., a lentivirus vector; an adenoassociated virus vector; an adenovirus vector; a retroviral vector; a non-viral vector; etc.). In some cases, the amino acids from the N-terminus of an HCV E2 polypeptide are a QT, ET, HT, GT, TT, RH, NT, AY, VI, or ST dipeptide.

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) an ET (Glu-Thr) dipeptide from the N-terminus of an HCV E2 polypeptide; iii) an Ig Fc polypeptide; iv) a proteolytically cleavable linker; and v) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) an ET (Glu-Thr) dipeptide from the N-terminus of an HCV E2 polypeptide; iv) an Ig Fc polypeptide; v) a proteolytically cleavable linker; and vi) an HCV E2 polypeptide. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) a GT (Gly-Thr) dipeptide from the N-terminus of an HCV E2 polypeptide; iii) an Ig Fc polypeptide; iv) a proteolytically cleavable linker; and v) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) a GT (Gly-Thr) dipeptide from the N-terminus of an HCV E2 polypeptide; iv) an Ig Fc polypeptide; v) a proteolytically cleavable linker; and vi) an HCV E2 polypeptide. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) a TT (Thr-Thr) dipeptide from the N-terminus of an HCV E2 polypeptide; iii) an Ig Fc polypeptide; iv) a proteolytically cleavable linker; and v) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) a TT (Thr-Thr) dipeptide from the N-terminus of an HCV E2 polypeptide; iv) an Ig Fc polypeptide; v) a proteolytically cleavable linker; and vi) an HCV E2 polypeptide. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iii) an Ig Fc polypeptide; iv) a proteolytically cleavable linker comprising the amino acid sequence LEVLFQGP (SEQ ID NO:1); and v) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iv) an Ig Fc polypeptide; v) a proteolytically cleavable linker comprising the amino acid sequence LEVLFQGP (SEQ ID NO:1); and vi) an HCV E2 polypeptide. In some cases, the nucleic acid is present in an expression vector (e.g., a lentivirus vector; an adenoassociated virus vector; an adenovirus vector; a retroviral vector; a non-viral vector; etc.). In some cases, the amino acids from the N-terminus of an HCV E2 polypeptide are a QT, ET, HT, GT, TT, RH, NT, AY, VI, or ST dipeptide.

In some cases, a nucleic acid of the present disclosure comprises, in order from 5' to 3' and in operable linkage: a) a promoter; b) a nucleotide sequence encoding a polyprotein comprising, in order from N-terminus to C-terminus: i) a signal peptide having the amino acid sequence MDAMKR-GLCCVLLLCGAVFVSPS (SEQ ID NO:6); ii) an HCV E1 polypeptide; iii) the dipeptide QT or ET; iv) an Ig Fc polypeptide; v) a proteolytically cleavable linker having the amino acid sequence LEVLFQGP (SEQ ID NO:1); and vi) an HCV E2 polypeptide. In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide having the amino acid sequence MDAMKRGLCCVLLLCGAVFVSPS (SEQ ID NO:6); ii) an HCV E1 polypeptide; iii) the dipeptide QT or ET; iv) an Ig Fc polypeptide; v) a proteolytically cleavable linker having the amino acid sequence LEVLFQGP (SEQ ID NO:1); and vi) an HCV E2 polypeptide.

Figure 7:
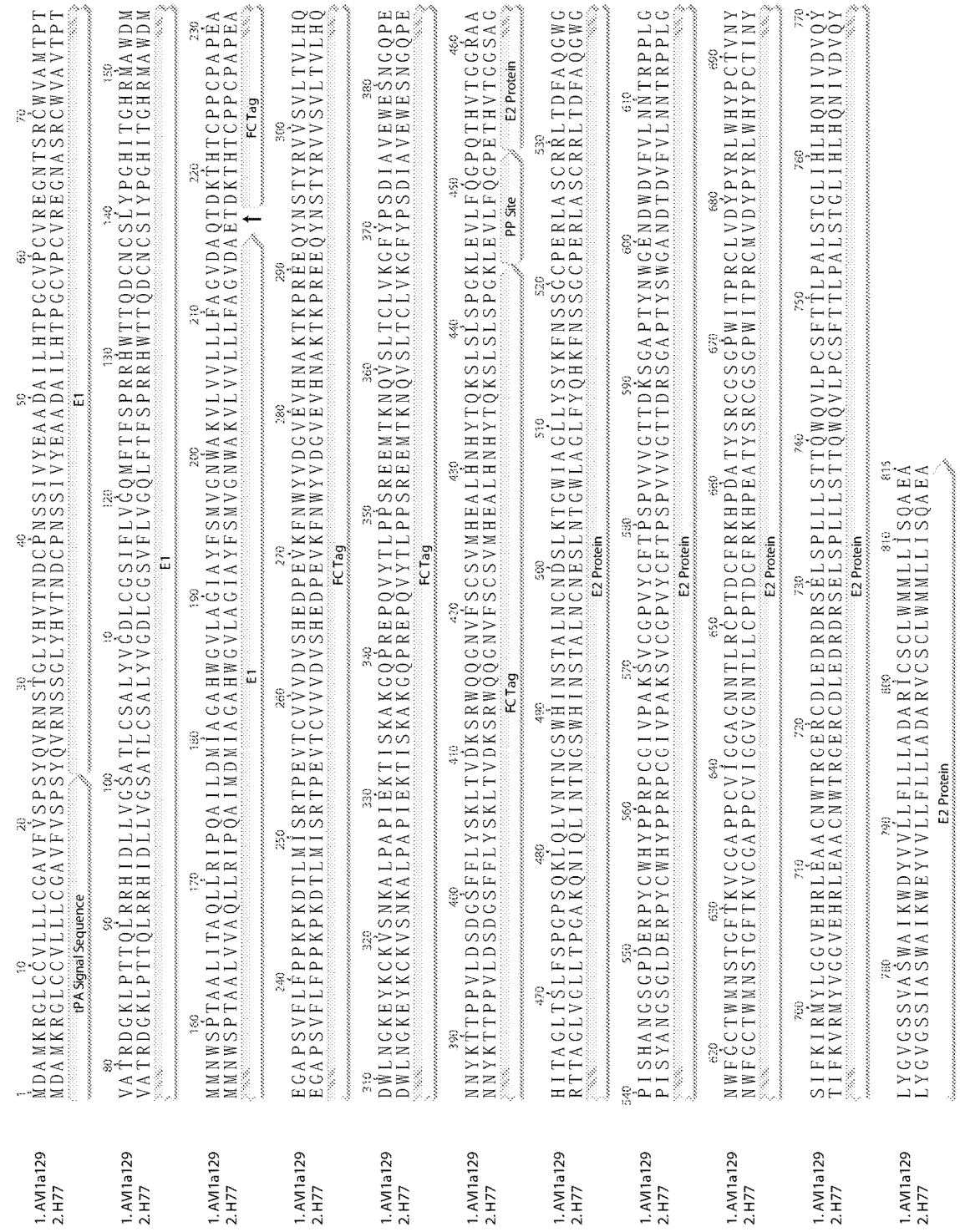
FIG. 7 provides an amino acid sequence alignment of Fc-tagged E1-E2 polyprotein of H77 (SEQ ID NO:118) and Alberta isolate Avi1a129 (SEQ ID NO:117).
Figure 8:
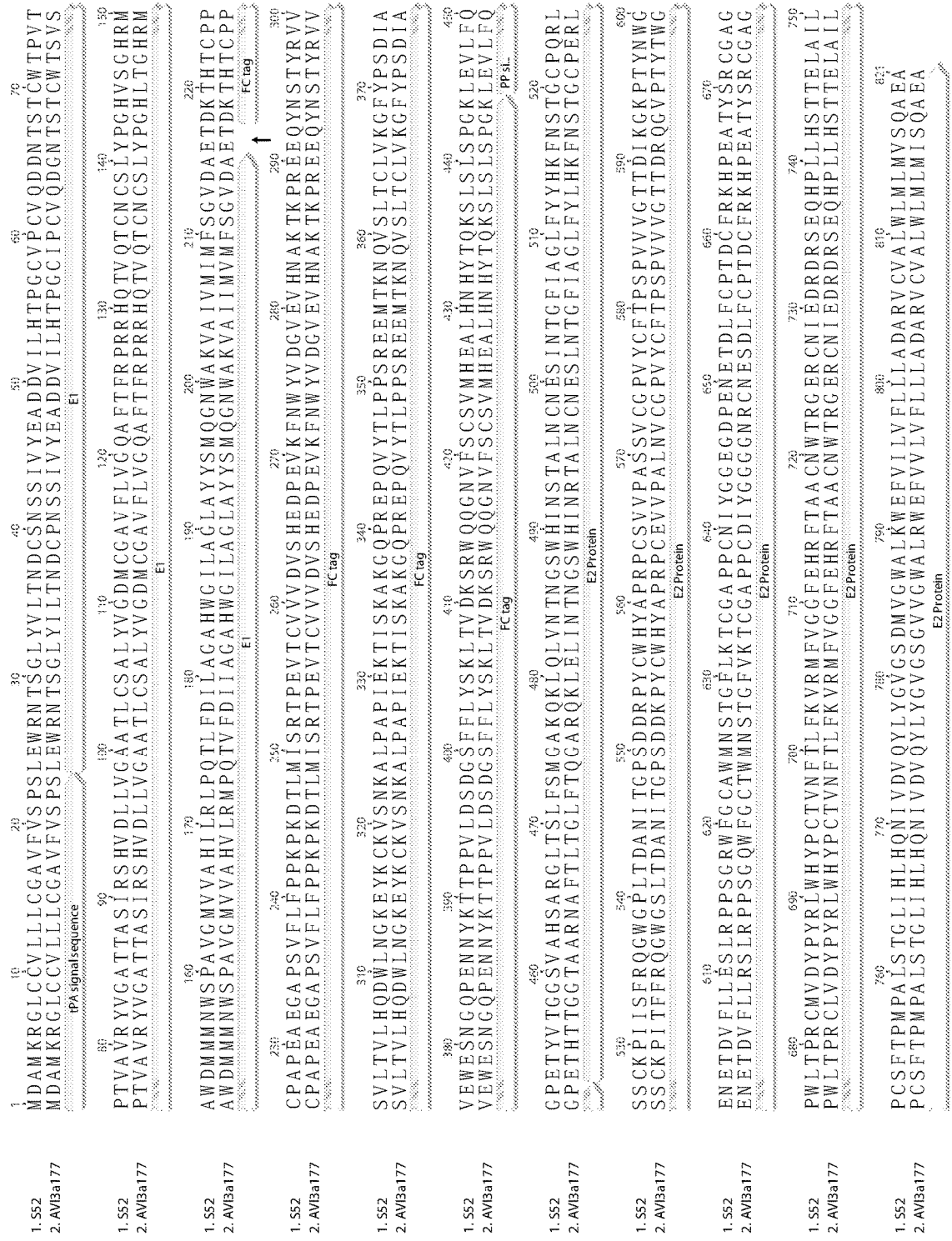
FIG. 8 provides an amino acid sequence alignment of Fc-tagged E1-E2 polyprotein of S52 (SEQ ID NO:119) and Alberta isolate Avi3a177 (SEQ ID NO:120).

In some cases, a nucleic acid of the present disclosure comprises, in order from 5' to 3' and in operable linkage and in operable linkage, a) a promoter; and b) a nucleotide sequence encoding an amino acid sequence having at least 80%, at least 85%, at least 90%, at least 95%, at least 98%, at least 99%, or 100%, amino acid sequence identity to an amino acid sequence depicted in FIG. 7 or FIG. 8.

2) Nucleic Acid Encoding an HCV E1-E2-Affinity Tag Polyprotein to Produce an Affinity Tagged HCV E1/E2 Heterodimer Comprising an HCV E2-Affinity Tag Fusion Polypeptide (C-Terminal Affinity Tagged E2) and an HCV E1 Polypeptide In some cases, a nucleic acid of the present disclosure comprises a nucleotide sequence encoding a polyprotein comprising, in order from N-terminus to C-terminus: i) an HCV E1 polypeptide; and ii) an HCV E2-affinity tag fusion polypeptide, where the HCV E2-affinity tag fusion polypeptide comprises, in order from N-terminus to C-terminus: i) an HCV E2 polypeptide; and ii) an affinity tag polypeptide. Upon expression in a suitable host cell, an affinity tagged HCV E1/E2 heterodimer is produced, where the affinity tagged HCV E1/E2 heterodimer comprises an HCV E1 polypeptide and an HCV E2-affinity tag fusion polypeptide. The HCV E2-affinity tag fusion polypeptide so produced comprises, in order from N-terminus to C-terminus: i) an HCV E2 polypeptide; and ii) an affinity tag polypeptide.

In some cases, a nucleic acid of the present disclosure comprises a nucleotide sequence encoding a polyprotein comprising, in order from N-terminus to C-terminus: i) an HCV E1 polypeptide; ii) an HCV E2 polypeptide; iii) a proteolytically cleavable linker; and iv) an affinity tag polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) an HCV E2 polypeptide; iii) a proteolytically cleavable linker; and iv) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) an HCV E2 polypeptide; iv) a proteolytically cleavable linker; and v) an affinity tag polypeptide.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) J. Mol. Biol. 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKR-GLCCVLLLCGAVFVSPSQEIHARFRRGARS (SEQ ID NO:42). In some cases, a suitable signal peptide comprises the amino acid sequence MDAMKR-GLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) an HCV E2 polypeptide; iii) a proteolytically cleavable linker; and iv) an affinity tag polypeptide. In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) an HCV E2 polypeptide; iv) a proteolytically cleavable linker; and v) an affinity tag polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) an HCV E2 polypeptide; iii) a proteolytically cleavable linker; and iv) an Ig Fc polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) an HCV E2 polypeptide; iv) a proteolytically cleavable linker; and v) an Ig Fc polypeptide.

3) Nucleic Acid Encoding an HCV E1-Affinity Tag-E2 Polyprotein to Produce an Affinity Tagged HCV E1/E2 Heterodimer Comprising an HCV E1-Affinity Tag Fusion Polypeptide (N-Terminal Affinity Tagged E1) and an HCV E2 Polypeptide In some cases, a nucleic acid of the present disclosure comprises a nucleotide sequence encoding a polyprotein comprising, in order from N-terminus to C-terminus: i) an HCV E1-affinity tag fusion polypeptide; and iii) an HCV E2 polypeptide, where the HCV E1-affinity tag fusion polypeptide comprises, in order from N-terminus to C-terminus: i) an affinity tag polypeptide; and ii) an HCV E1 polypeptide. Upon expression in a suitable host cell, an affinity tagged HCV E1/E2 heterodimer is produced, where the affinity tagged HCV E1/E2 heterodimer comprises an affinity tagged HCV E1 polypeptide and an HCV E2 polypeptide. The HCV E1-affinity tag fusion polypeptide so produced comprises, in order from N-terminus to C-terminus: i) an affinity tag polypeptide; and ii) an HCV E1 polypeptide.

In some cases, a nucleic acid of the present disclosure comprises a nucleotide sequence encoding a polyprotein comprising, in order from N-terminus to C-terminus: i) an affinity tag polypeptide; ii) a proteolytically cleavable linker; iii) an HCV E1 polypeptide; and iv) an HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an affinity tag polypeptide; ii) a proteolytically cleavable linker; iii) an HCV E1 polypeptide; and iv) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an affinity tag polypeptide; iii) a proteolytically cleavable linker; iv) an HCV E1 polypeptide; and v) an HCV E2 polypeptide.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKRGLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an affinity tag polypeptide; ii) a proteolytically cleavable linker; iii) an HCV E1 polypeptide; and iv) an HCV E2 polypeptide. In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an affinity tag polypeptide; iii) a proteolytically cleavable linker; iv) an HCV E1 polypeptide; and v) an HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an Ig Fc polypeptide; ii) a proteolytically cleavable linker; iii) an HCV E1 polypeptide; and iv) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an Ig Fc polypeptide; iii) a proteolytically cleavable linker; iv) an HCV E1 polypeptide; and v) an HCV E2 polypeptide.

4) Nucleic Acid Encoding an HCV E1-Affinity Tag-E2 Polyprotein to Produce an Affinity Tagged HCV E1/E2 Heterodimer Comprising an HCV E1-Affinity Tag Fusion Polypeptide (C-Terminal Affinity Tagged E1) and an HCV E2 Polypeptide In some cases, a nucleic acid of the present disclosure comprises a nucleotide sequence encoding a polyprotein comprising, in order from N-terminus to C-terminus: i) an HCV E1-affinity tag fusion polypeptide; and iii) an HCV E2 polypeptide, where the HCV E1-affinity tag fusion polypeptide comprises, in order from N-terminus to C-terminus: i) an HCV E1 polypeptide; and ii) an affinity tag polypeptide. Upon expression in a suitable host cell, an affinity tagged HCV E1/E2 heterodimer is produced, where the affinity tagged HCV E1/E2 heterodimer comprises an affinity tagged HCV E1 polypeptide and an HCV E2 polypeptide. The HCV E1-affinity tag fusion polypeptide so produced comprises, in order from N-terminus to C-terminus: i) an HCV E1 polypeptide; and ii) an affinity tag polypeptide.

In some cases, a nucleic acid of the present disclosure comprises a nucleotide sequence encoding a polyprotein comprising, in order from N-terminus to C-terminus: i) an HCV E1 polypeptide; ii) a proteolytically cleavable linker; iii) an affinity tag polypeptide; and iv) an HCV E2 polypeptide. In some cases, a signal peptide comprising a signalase cleavage site is interposed between the affinity tag polypeptide and the HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an affinity tag polypeptide; and iv) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) a proteolytically cleavable linker; iii) an affinity tag polypeptide; and v) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an affinity tag polypeptide; iv) a signal peptide comprising a signalase cleavage site; and v) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) a proteolytically cleavable linker; iv) an affinity tag polypeptide; v) a signal peptide comprising a signalase cleavage site; and vi) an HCV E2 polypeptide.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKRGLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) a proteolytically cleavable linker; iii) an affinity tag polypeptide; and iv) an HCV E2 polypeptide. In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) a proteolytically cleavable linker; iv) an affinity tag polypeptide; and v) an HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an Fc polypeptide; and iv) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) a proteolytically cleavable linker; iv) an Fc polypeptide; and v) an HCV E2 polypeptide.

Where the nucleotide sequence encodes two signal peptides, in some cases, the two signal peptides are two different signal peptides.

5) Nucleic Acid Encoding an HCV E1-Affinity Tag-HCV E2-Affinity Tag Polyprotein to Produce an Affinity Tagged HCV E1/E2 Heterodimer Comprising an HCV E1-Affinity Tag Fusion Polypeptide (N-Terminal Affinity Tagged E1) and an HCV E2-Affinity Tag Fusion Polypeptide (N-Terminal Affinity Tagged E2)

In some cases, a nucleic acid of the present disclosure comprises a nucleotide sequence encoding a polyprotein comprising, in order from N-terminus to C-terminus: i) an HCV E1-affinity tag fusion polypeptide; and iii) an HCV E2-affinity tag fusion polypeptide, where the HCV E1-affinity tag fusion polypeptide comprises, in order from N-terminus to C-terminus: i) an affinity tag polypeptide; and ii) an HCV E1 polypeptide, and where the HCV E2-affinity tag fusion polypeptide comprises, in order from N-terminus to C-terminus: i) an affinity tag polypeptide; and ii) an HCV E2 polypeptide. Upon expression in a suitable host cell, an affinity tagged HCV E1/E2 heterodimer is produced, where the affinity tagged HCV E1/E2 heterodimer comprises an affinity tagged HCV E2 polypeptide and an affinity tagged HCV E2 polypeptide. The HCV E1-affinity tag fusion polypeptide so produced comprises, in order from N-terminus to C-terminus: i) an affinity tag polypeptide; and ii) an HCV E1 polypeptide. The HCV E2-affinity tag fusion polypeptide so produced comprises, in order from N-terminus to C-terminus: i) an affinity tag polypeptide; and ii) an HCV E2 polypeptide.

In some cases, a nucleic acid of the present disclosure comprises a nucleotide sequence encoding a polyprotein comprising, in order from N-terminus to C-terminus: i) an affinity tag polypeptide; ii) a proteolytically cleavable linker; iii) an HCV E1 polypeptide; iv) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; iv) an affinity tag; v) a proteolytically cleavable linker; and vi) an HCV E2 polypeptide. In some cases, the nucleotide sequence encoding the polyprotein is operably linked to a transcription control element, e.g., a promoter that is functional in a eukaryotic cell. Suitable promoters include, e.g., a CMV promoter, an SV40 promoter, and the like, as described above. In some cases, the nucleic acid is present in an expression vector (e.g., a lentivirus vector; an adenoassociated virus vector; an adenovirus vector; a retroviral vector; a non-viral vector; etc.). In some cases, the affinity tag is an Ig Fc polypeptide. In other cases, the affinity tag is Protein A, Protein G, a polypeptide comprising a poly(histidine) tract, or a GST polypeptide. Suitable proteolytically cleavable linkers are described above. Upon expression in a suitable host cell, an affinity tagged HCV E1/E2 heterodimer is produced, where the affinity tagged HCV E1/E2 heterodimer comprises an HCV E1-affinity tag fusion polypeptide and an HCV E2-affinity tag fusion polypeptide. The HCV E2-affinity tag fusion polypeptide so produced comprises, in order from N-terminus to C-terminus: i) an affinity tag polypeptide; and an HCV E2 polypeptide. The HCV E1-affinity tag fusion polypeptide so produced comprises, in order from N-terminus to C-terminus: i) an affinity tag polypeptide; and an HCV E1 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an affinity tag polypeptide; ii) a proteolytically cleavable linker; iii) an HCV E1 polypeptide; iv) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; v) an affinity tag polypeptide; vi) a proteolytically cleavable linker; and vii) an HCV E2 polypeptide. In some cases, the polyprotein comprises a signal peptide. Thus, for example, in some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an affinity tag polypeptide; iii) a proteolytically cleavable linker; iv) an HCV E1 polypeptide; v) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; vi) an affinity tag; vii) a proteolytically cleavable linker; and viii) an HCV E2 polypeptide. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the affinity tag is an Ig Fc polypeptide. In other cases, the affinity tag is Protein A, Protein G, a polypeptide comprising a poly(histidine) tract, or a GST polypeptide. In some cases, the amino acids from the N-terminus of an HCV E2 polypeptide are a QT, ET, HT, GT, TT, RH, NT, AY, VI, or ST dipeptide.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKR-GLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an affinity tag polypeptide; ii) a proteolytically cleavable linker; iii) an HCV E1 polypeptide; iv) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; v) an affinity tag; vi) a proteolytically cleavable linker; and vii) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an affinity tag polypeptide; ii) a proteolytically cleavable linker; iii) an HCV E1 polypeptide; iv) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; v) an affinity tag; vi) a proteolytically cleavable linker; and vii) an HCV E2 polypeptide. In some cases, the nucleic acid is present in an expression vector (e.g., a lentivirus vector; an adenoassociated virus vector; an adenovirus vector; a retroviral vector; a non-viral vector; etc.). In some cases, the affinity tag is an Ig Fc polypeptide. In other cases, the affinity tag is Protein A, Protein G, a polypeptide comprising a poly(histidine) tract, or a GST polypeptide. In some cases, the amino acids from the N-terminus of an HCV E2 polypeptide are a QT, ET, HT, GT, TT, RH, NT, AY, VI, or ST dipeptide.

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an Ig Fc polypeptide; ii) a proteolytically cleavable linker; iii) an HCV E1 polypeptide; iv) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; v) an Ig Fc polypeptide; vi) a proteolytically cleavable linker; and vii) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an Ig Fc polypeptide; iii) a proteolytically cleavable linker; iv) an HCV E1 polypeptide; v) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; vi) an Ig Fc polypeptide; vii) a proteolytically cleavable linker; and viii) an HCV E2 polypeptide. In some cases, the nucleic acid is present in an expression vector (e.g., a lentivirus vector; an adenoassociated virus vector; an adenovirus vector; a retroviral vector; a non-viral vector; etc.). In some cases, the amino acids from the N-terminus of an HCV E2 polypeptide are a QT, ET, HT, GT, TT, RH, NT, AY, VI, or ST dipeptide.

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an Ig Fc polypeptide; ii) a proteolytically cleavable linker; iii) an HCV E1 polypeptide; iv) an ET (Glu-Thr) dipeptide from the N-terminus of an HCV E2 polypeptide; v) an Ig Fc polypeptide; vi) a proteolytically cleavable linker; and vii) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an Ig Fc polypeptide; iii) a proteolytically cleavable linker; iv) an HCV E1 polypeptide; v) an ET (Glu-Thr) dipeptide from the N-terminus of an HCV E2 polypeptide; vi) an Ig Fc polypeptide; vii) a proteolytically cleavable linker; and viii) an HCV E2 polypeptide. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an Ig Fc polypeptide; ii) a proteolytically cleavable linker; iii) an HCV E1 polypeptide; iv) a GT (Gly-Thr) dipeptide from the N-terminus of an HCV E2 polypeptide; v) an Ig Fc polypeptide; vi) a proteolytically cleavable linker; and vii) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an Ig Fc polypeptide; iii) a proteolytically cleavable linker; iv) an HCV E1 polypeptide; v) a GT (Gly-Thr) dipeptide from the N-terminus of an HCV E2 polypeptide; vi) an Ig Fc polypeptide; vii) a proteolytically cleavable linker; and viii) an HCV E2 polypeptide. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an Ig Fc polypeptide; ii) a proteolytically cleavable linker; iii) an HCV E1 polypeptide; iv) a TT (Thr-Thr) dipeptide from the N-terminus of an HCV E2 polypeptide; v) an Ig Fc polypeptide; vi) a proteolytically cleavable linker; and vii) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an Ig Fc polypeptide; iii) a proteolytically cleavable linker; iv) an HCV E1 polypeptide; v) a TT (Thr-Thr) dipeptide from the N-terminus of an HCV E2 polypeptide; vi) an Ig Fc polypeptide; vii) a proteolytically cleavable linker; and viii) an HCV E2 polypeptide. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an Ig Fc polypeptide; ii) a proteolytically cleavable linker; iii) an HCV E1 polypeptide; iv) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; v) an Ig Fc polypeptide; vi) a proteolytically cleavable linker comprising the amino acid sequence LEVLFQGP (SEQ ID NO:1); and vii) an HCV E2 polypeptide. In some cases, the polyprotein comprises a signal peptide. Thus, for example, in some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an Ig Fc polypeptide; iii) a proteolytically cleavable linker; iv) an HCV E1 polypeptide; v) from 2 amino acids to 15 amino acids (aa) (e.g., 2 aa, 3 aa, 4 aa, 5 aa, 6 aa, 7 aa, 8 aa, 9 aa, 10 aa, 11 aa, 12 aa, 13 aa, 14 aa, or 15 aa) from the N-terminus of an HCV E2 polypeptide; vi) an Ig Fc polypeptide; vi) a proteolytically cleavable linker comprising the amino acid sequence LEVLFQGP (SEQ ID NO:1); and viii) an HCV E2 polypeptide. In some cases, the nucleic acid is present in an expression vector (e.g., a lentivirus vector; an adenoassociated virus vector; an adenovirus vector; a retroviral vector; a non-viral vector; etc.). In some cases, the amino acids from the N-terminus of an HCV E2 polypeptide are a QT, ET, HT, GT, TT, RH, NT, AY, VI, or ST dipeptide.

6) Nucleic Acid Encoding an HCV E1-Affinity Tag-HCV E2-Affinity Tag Polyprotein to Produce an Affinity Tagged HCV E1/E2 Heterodimer Comprising an HCV E1-Affinity Tag Fusion Polypeptide (C-Terminal Affinity Tagged E1) and an HCV E2-Affinity Tag Fusion Polypeptide (C-Terminal Affinity Tagged E2)

In some cases, a nucleic acid of the present disclosure comprises a nucleotide sequence encoding a polyprotein comprising, in order from N-terminus to C-terminus: i) an HCV E1-affinity tag fusion polypeptide; and iii) an HCV E2-affinity tag fusion polypeptide, where the HCV E1-affinity tag fusion polypeptide comprises, in order from N-terminus to C-terminus: i) an HCV E1 polypeptide; and ii) an affinity tag polypeptide; and where the HCV E2-affinity tag fusion polypeptide comprises, in order from N-terminus to C-terminus: i) an HCV E2 polypeptide; and ii) an affinity tag polypeptide. Upon expression in a suitable host cell, an affinity tagged HCV E1/E2 heterodimer is produced, where the affinity tagged HCV E1/E2 heterodimer comprises an affinity tagged HCV E2 polypeptide and an affinity tagged HCV E2 polypeptide. The HCV E1-affinity tag fusion polypeptide so produced comprises, in order from N-terminus to C-terminus: i) an HCV E1 polypeptide; and ii) an affinity tag polypeptide. The HCV E2-affinity tag fusion polypeptide so produced comprises, in order from N-terminus to C-terminus: i) an HCV E2 polypeptide; and ii) an affinity tag polypeptide.

In some cases, a nucleic acid of the present disclosure comprises a nucleotide sequence encoding a polyprotein comprising, in order from N-terminus to C-terminus: i) an HCV E1 polypeptide; ii) a proteolytically cleavable linker; iii) an affinity tag polypeptide; iv) an HCV E2 polypeptide; v) a proteolytically cleavable linker; and vi) an affinity tag polypeptide. In some cases, a signal peptide comprising a signalase cleavage site is interposed between the affinity tag polypeptide and the HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an affinity tag polypeptide; iv) an HCV E2 polypeptide; v) a proteolytically cleavable linker; and vi) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) a proteolytically cleavable linker; iv) an affinity tag polypeptide; v) an HCV E2 polypeptide; vi) a proteolytically cleavable linker; and vii) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an affinity tag polypeptide; iv) a signal peptide comprising a signalase cleavage site; v) an HCV E2 polypeptide; vi) a proteolytically cleavable linker; and vii) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) a proteolytically cleavable linker; iv) an affinity tag polypeptide; v) a signal peptide comprising a signalase cleavage site; vi) an HCV E2 polypeptide; vii) a proteolytically cleavable linker; and viii) an affinity tag polypeptide.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKRGLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an HCV E1 polypeptide; ii) a proteolytically cleavable linker; iii) an affinity tag polypeptide; iv) an HCV E2 polypeptide; v) a proteolytically cleavable linker; and vi) an affinity tag polypeptide. In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an HCV E1 polypeptide; iii) a proteolytically cleavable linker; iv) an affinity tag polypeptide; v) an HCV E2 polypeptide; vi) a proteolytically cleavable linker; and vii) an affinity tag polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an Fc polypeptide; and iv) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an HCV E1 polypeptide; iii) a proteolytically cleavable linker; iv) an Fc polypeptide; v) an HCV E2 polypeptide; vi) a proteolytically cleavable linker; and vii) an affinity tag polypeptide.

Where the nucleotide sequence encodes two signal peptides, in some cases, the two signal peptides are two different signal peptides. Where the nucleotide sequence encodes two affinity tag polypeptides, in some cases, the two affinity tag polypeptides are the same. Where the nucleotide sequence encodes two affinity tag polypeptides, in some cases, the two affinity tag polypeptides are two different affinity tag polypeptides.

7) Nucleic Acid Encoding Encoding an HCV E1-Affinity Tag-HCV E2-Affinity Tag Polyprotein to Produce an Affinity Tagged HCV E1/E2 Heterodimer Comprising an HCV E1-Affinity Tag Fusion Polypeptide (N-Terminal Affinity Tagged E1) and an HCV E2-Affinity Tag Fusion Polypeptide (C-Terminal Affinity Tagged E2)

In some cases, a nucleic acid of the present disclosure comprises a nucleotide sequence encoding a polyprotein comprising, in order from N-terminus to C-terminus: i) an HCV E1-affinity tag fusion polypeptide; and ii) an HCV E2-affinity tag fusion polypeptide, where the HCV E1-affinity tag fusion polypeptide comprises, in order from N-terminus to C-terminus: i) an affinity tag polypeptide; and ii) an HCV E1 polypeptide; and where the HCV E2-affinity tag fusion polypeptide comprises, in order from N-terminus to C-terminus: i) an HCV E2 polypeptide; and ii) an affinity tag polypeptide. Upon expression in a suitable host cell, an affinity tagged HCV E1/E2 heterodimer is produced, where the affinity tagged HCV E1/E2 heterodimer comprises an affinity tagged HCV E2 polypeptide and an affinity tagged HCV E2 polypeptide. The HCV E1-affinity tag fusion polypeptide so produced comprises, in order from N-terminus to C-terminus: i) an affinity tag polypeptide; and ii) an HCV E1 polypeptide. The HCV E2-affinity tag fusion polypeptide so produced comprises, in order from N-terminus to C-terminus: i) an HCV E2 polypeptide; and ii) an affinity tag polypeptide.

In some cases, a nucleic acid of the present disclosure comprises a nucleotide sequence encoding a polyprotein comprising, in order from N-terminus to C-terminus: i) an affinity tag polypeptide; ii) a proteolytically cleavable linker; iii) an HCV E1 polypeptide; iv) an HCV E2 polypeptide; v) a proteolytically cleavable linker; and vi) an affinity tag polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an affinity tag polypeptide; ii) a proteolytically cleavable linker; iii) an HCV E1 polypeptide; iv) an HCV E2 polypeptide; v) a proteolytically cleavable linker; and vi) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an affinity tag polypeptide; iii) a proteolytically cleavable linker; iv) an HCV E1 polypeptide; v) an HCV E2 polypeptide; vi) a proteolytically cleavable linker; and vii) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an affinity tag polypeptide; ii) a proteolytically cleavable linker; iii) an HCV E1 polypeptide; iv) an HCV E2 polypeptide; v) a proteolytically cleavable linker; and vi) an affinity tag polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an affinity tag polypeptide; iii) a proteolytically cleavable linker; iv) an HCV E1 polypeptide; v) an HCV E2 polypeptide; vii) a proteolytically cleavable linker; and viii) an affinity tag polypeptide.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKRGLCCVLLLCGAVFVSPS (SEQ ID NO:6).

In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) an affinity tag polypeptide; ii) a proteolytically cleavable linker; iii) an HCV E1 polypeptide; iv) an HCV E2 polypeptide; v) a proteolytically cleavable linker; and vi) an affinity tag polypeptide. In some cases, a nucleic acid of the present disclosure comprises, in order from 5' to 3' and in operable linkage: a) a CMV promoter; b) a nucleotide sequence encoding a polyprotein comprising, in order from N-terminus to C-terminus: i) a signal peptide; ii) an affinity tag polypeptide; iii) a proteolytically cleavable linker; iv) an HCV E1 polypeptide; v) an HCV E2 polypeptide; vi) a proteolytically cleavable linker; and vii) an affinity tag polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an Fc polypeptide; ii) a proteolytically cleavable linker; iii) an HCV E1 polypeptide; and iv) an HCV E2 polypeptide. In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a signal peptide; ii) an Fc polypeptide; iii) a proteolytically cleavable linker; iv) an HCV E1 polypeptide; v) an HCV E2 polypeptide; vi) a proteolytically cleavable linker; and vii) an affinity tag polypeptide.

8) Nucleic Acid Encoding an HCV E1-Affinity Tag-HCV E2-Affinity Tag Polyprotein to Produce an Affinity Tagged HCV E1/E2 Heterodimer Comprising an HCV E1-Affinity Tag Fusion Polypeptide (C-Terminal Affinity Tagged E1) and an HCV E2-Affinity Tag Fusion Polypeptide (N-Terminal Affinity Tagged E2)

In some cases, a nucleic acid of the present disclosure comprises a nucleotide sequence encoding a polyprotein comprising, in order from N-terminus to C-terminus: i) an HCV E1-affinity tag fusion polypeptide; and ii) an HCV E2-affinity tag fusion polypeptide, where the HCV E1-affinity tag fusion polypeptide comprises, in order from N-terminus to C-terminus: i) an HCV E1 polypeptide; and ii) an affinity tag polypeptide; and where the HCV E2-affinity tag fusion polypeptide comprises, in order from N-terminus to C-terminus: i) an affinity tag polypeptide; and ii) an HCV E2 polypeptide. Upon expression in a suitable host cell, an affinity tagged HCV E1/E2 heterodimer is produced, where the affinity tagged HCV E1/E2 heterodimer comprises an affinity tagged HCV E2 polypeptide and an affinity tagged HCV E2 polypeptide. The HCV E1-affinity tag fusion polypeptide so produced comprises, in order from N-terminus to C-terminus: i) an HCV E1 polypeptide; and ii) an affinity tag polypeptide. The HCV E2-affinity tag fusion polypeptide so produced comprises, in order from N-terminus to C-terminus: i) an affinity tag polypeptide; and ii) an HCV E2 polypeptide.

In some cases, a nucleic acid of the present disclosure comprises a nucleotide sequence encoding a polyprotein comprising, in order from N-terminus to C-terminus: i) an HCV E1 polypeptide; ii) a proteolytically cleavable linker; iii) an affinity tag polypeptide; iv) an affinity tag polypeptide; v) a proteolytically cleavable linker; and vi) an HCV E2 polypeptide.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) an HCV E1 polypeptide; ii) a proteolytically cleavable linker; iii) an affinity tag polypeptide; iv) an affinity tag polypeptide; v) a proteolytically cleavable linker; and vi) an HCV E2 polypeptide. In some cases, a nucleotide sequence encoding a signal peptide is interposed between the first and the second affinity tag polypeptides.

In some cases, a nucleic acid of the present disclosure comprises, in order from 5' to 3' and in operable linkage: a) a promoter that is functional in a eukaryotic cell; b) a nucleotide sequence encoding a polyprotein comprising, in order from N-terminus to C-terminus: i) a first signal peptide; ii) an HCV E1 polypeptide; iii) a proteolytically cleavable linker; iv) a first affinity tag polypeptide; v) a second signal peptide; vi) a second affinity tag polypeptide; vii) a proteolytically cleavable linker; and viii) an HCV E2 polypeptide. In some cases, the first and the second affinity tag polypeptides are two different affinity tag polypeptides. In some cases, the first and the second signal peptides are two different signal peptides.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like. (Bendtsen et al. (2004) *J. Mol. Biol.* 340 783-795; Kober et al. (2012) *Biotechnology and Bioengineering* 110(4) 1164-1173). A suitable signal peptide includes a signalase cleavage site, such that a polyprotein comprising the signal peptide is cleaved, during intracellular processing, at the signalase cleavage site. In some cases, a suitable signal peptide comprises the amino acid sequence MDAMKRGLCCVLLLCGAVFVSPSQEIHARFRRGARS (SEQ ID NO:42). In some cases, a suitable signal peptide comprises the amino acid sequence MDAMKRGLCCVLLLCGAVFVSPS (SEQ ID NO:6).

Methods of Producing an HCV E1/E2 Heterodimer

The present disclosure provides methods of producing an affinity tagged HCV E1/E2 heterodimer of the present disclosure. The two polypeptide chains of an affinity tagged HCV E1/E2 heterodimer of the present disclosure can be produced using any suitable method, e.g., recombinant and non-recombinant methods (e.g., chemical synthesis). Where the two polypeptide chains of an affinity tagged HCV E1/E2 heterodimer of the present disclosure are produced by recombinant methods, the two polypeptide chains can be produced in separate host cells, or in the same host cell. In some cases, the two polypeptide chains of an affinity tagged HCV E1/E2 heterodimer of the present disclosure is produced in the same host cell.

The present disclosure provides methods for producing an HCV E1/E2 heterodimer that is not affinity tagged. The methods generally involve producing an affinity tagged HCV E1/E2 heterodimer of the present disclosure; immobilizing the affinity tagged HCV E1/E2 heterodimer of the present disclosure on an immobilized binding partner for the affinity tag; and cleaving a linker between the affinity tag and the HCV E1 or E2 polypeptide, thereby releasing the untagged HCV E1/E2 heterodimer; and collecting the untagged HCV E1/E2 heterodimer.

Where the two polypeptide chains of an affinity tagged HCV E1/E2 heterodimer of the present disclosure are produced using recombinant techniques, the polypeptides may be produced as an intracellular protein or as an secreted protein, using any suitable construct and any suitable host cell, which can be a prokaryotic cell (e.g., a bacterial (e.g., *Escherichia coli*) cell), or a eukaryotic cell. Suitable eukaryotic cells include, e.g., a yeast host cell, an insect cell, a mammalian cell, filamentous fungi, and plant cells. Suitable yeast cells include, e.g., *Saccharomyces cerevisiae* and *Pichia* (e.g., *Pichia pastoris*).

Suitable mammalian cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCL1.3), human embryonic kidney (HEK) cells (ATCC No. CRL1573), HLHepG2 cells, MRC5 cells (ATCC No. CCL-171), and the like. Where mammalian host cells are used, such host cells may include human cells (e.g., HeLa, 293, H9 and Jurkat cells); mouse cells (e.g., NIH3T3, L cells, and C127 cells); primate cells (e.g., Cos 1, Cos 7 and CV1); MRC4 cells; and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; Ausubel et al. 1995 Current Protocols in Molecular Biology, Eds. Wiley and Sons; "Protein Expression: A Practical Approach" (1999) S. J. Higgins and B. D. James, eds., Oxford University Press; "Protein Expression in Mammalian Cells: Methods and Protocols (Methods in Molecular Biology)" (2012) James L. Hartley, ed., Humana Press; and "Production of Recombinant Proteins" (2005) Gerd Gellisen, ed., Wiley-VCH. Methods for introduction of nucleic acids into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically-integrated. A variety of appropriate vectors for use in production of a peptide of interest are available commercially.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, human immunodeficiency virus (HIV)-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as E. coli, mammalian cells, insect cells, or yeast cells).

An affinity tagged HCV E1/E2 heterodimer of the present disclosure can be produced by introducing a recombinant expression vector comprising a nucleotide sequence encoding the appropriate HCV E1 and E2 polypeptides (e.g., an E1 polypeptide and an E2-affinity tag fusion polypeptide; an E2-affinity tag fusion polypeptide and an E1 polypeptide; an E1-affinity tag fusion polypeptide and an E2-affinity tag fusion polypeptide) into an appropriate host cell, where the host cell produces the encoded polypeptides. In the expression vector, a polynucleotide comprising a nucleotide sequence(s) encoding the appropriate HCV E1 and E2 polypeptides (e.g., an E1 polypeptide and an E2-affinity tag fusion polypeptide; an E2-affinity tag fusion polypeptide and an E1 polypeptide; an E1-affinity tag fusion polypeptide and an E2-affinity tag fusion polypeptide) is linked to a regulatory sequence as appropriate to obtain the desired expression properties. These regulatory sequences can include promoters, enhancers, terminators, operators, repressors, and inducers. The promoters can be regulated or constitutive. Expression vectors generally have convenient restriction sites located near the promoter sequence to provide for the insertion of nucleic acid sequences encoding a protein of interest. A selectable marker operative in the expression host cell may be present.

In some cases, the polypeptides of an affinity tagged HCV E1/E2 heterodimer of the present disclosure (e.g., an E1 polypeptide and an E2-affinity tag fusion polypeptide; an E2-affinity tag fusion polypeptide and an E1 polypeptide; an E1-affinity tag fusion polypeptide and an E2-affinity tag fusion polypeptide) are encoded in a recombinant expression vector suitable for expression in a eukaryotic host cell (e.g., an insect cell; a yeast cell; a mammalian host cell, such as CHO cells, HeLa cells, 293 cells, MRC5 cells, etc.). In some cases, a recombinant expression vector comprises a nucleotide sequence encoding E1 and E2 polypeptides (one or both of which is a fusion polypeptide that includes an affinity tag polypeptide) as a single polypeptide chain; the recombinant expression vector is introduced into a eukaryotic host cell to generate a genetically modified host cell. In some cases, the two polypeptide chains of an HCV E1/E2 heterodimer of the present disclosure are initially produced as a single polypeptide chains, either in the same host cell or in separate host cells. Where the polypeptides of an affinity tagged HCV E1/E2 heterodimer of the present disclosure (e.g., an E1 polypeptide and an E2-affinity tag fusion polypeptide; an E2-affinity tag fusion polypeptide and an E1 polypeptide; an E1-affinity tag fusion polypeptide and an E2-affinity tag fusion polypeptide) are produced in the same host cell, the separate E1 and E2 polypeptides (one or both of which comprise an affinity tag) can form a heterodimer (e.g., a non-covalently linked heterodimer) in the endoplasmic reticulum (ER). In some cases, two polypeptide chains of an affinity tagged HCV E1/E2 heterodimer of the present disclosure are initially produced as a single polypeptide chain, which is cleaved in the ER of the genetically modified host cell to produce separate E1 and E2 polypeptides (one or both of which comprises an affinity tag). The separate E1 and E2 polypeptides (e.g., E1+E2-affinity tag; E2-affinity tag+E1; E1-affinity tag+E2-affinity tag) can form a heterodimer (e.g., a non-covalently linked heterodimer) in the ER. The affinity tagged HCV E1/E2 heterodimer can be isolated from the genetically modified host cell by, e.g., lysis using a non-ionic detergent, or using a freeze-thaw method. See, e.g., Frey et al. (2010) Vaccine 28:6367. The E1/E2 heterodimer can be purified from a cell lysate and/or cell culture medium using any of a variety of methods, including size exclusion chromatography, affinity chromatography, and the like, or combinations of such methods. In some cases, the affinity tagged HCV E1/E2 heterodimer is purified from cell lysate and/or cell culture medium using Galanthus nivalis (GNA) lectin affinity chromatography. In some cases, where the affinity tag is an Ig Fc, the affinity tagged HCV E1/E2 heterodimer is purified on an affinity column comprising an immobilized Fc-binding moiety. In some cases, where the affinity tag is a Protein A or Protein G polypeptide, the affinity tagged HCV E1/E2 heterodimer is purified on an affinity column comprising an immobilized Protein A- or Protein G-binding moiety. In some cases, where the affinity tag is an Ig light chain-containing polypeptide, the affinity tagged HCV E1/E2 heterodimer is purified on an affinity column comprising an immobilized Protein L polypeptide. In some cases, where the affinity tag is a GST polypeptide, the affinity tagged HCV E1/E2 heterodimer is purified on an affinity column comprising an immobilized GST-binding moiety. In some cases, the affinity tagged HCV E1/E2 heterodimer is purified from a cell lysate. In some cases, the affinity tagged HCV E1/E2 heterodimer is secreted from a cell and is purified from the cell culture medium. Suitable methods that can be used for purifying an affinity tagged HCV E1/E2 heterodimer of the present disclosure are described in, e.g., U.S. Pat. Nos. 6,121,020; 6,274,148; and Mazzocca et al. (2005) J. Biol. Chem. 280:11329. For example, in some cases, an affinity tagged HCV E1/E2 heterodimer can be prepared in a method comprising cell disruption and debris removal by microfiltration, followed by purification using three subsequent chromatographic steps: lectin affinity chromatography, hydroxyapatite chromatography, and ion exchange chromatography.

After production in a host cell(s), the two polypeptide chains of an affinity tagged HCV E1/E2 heterodimer of the present disclosure (e.g., as separate polypeptides or as a heterodimer) can be purified from the host cell(s). Methods of purification of recombinantly produced polypeptides from a host cell are known in the art and include, e.g., detergent lysis (e.g., with a non-ionic detergent) or freeze-thaw lysis, followed by one or more of size exclusion column chromatography, high performance liquid chromatography, affinity chromatography, and the like.

Producing an Untagged HCV E1/E2 Heterodimer

In some cases, a method of producing an untagged HCV E1/E2 heterodimer disclosure comprises: a) contacting a lysate of a genetically modified host cell (where the genetically modified host cell produces an affinity tagged HCV E1/E2 heterodimer of the present disclosure (e.g., an HCV E2 polypeptide and an HCV E1-affinity tag fusion polypeptide; an HCV E2-affinity tag fusion polypeptide and an HCV E1 polypeptide; or an HCV E1-affinity tag fusion polypeptide and an HCV E2-affinity tag fusion polypeptide) with an affinity tag-binding polypeptide immobilized on an insoluble support, where the affinity tagged HCV E1/E2 heterodimer present in the lysate binds to the immobilized affinity tag-binding polypeptide, generating an immobilized affinity tagged HCV E1/E2 heterodimer; and b) contacting the immobilized affinity tagged HCV E1/E2 heterodimer with an enzyme that cleaves between the affinity tag and the affinity-tagged HCV E1 and/or E2 polypeptides, thereby releasing an untagged HCV E1/E2 heterodimer; and collecting the released untagged HCV E1/E2 heterodimer. In some cases, the untagged HCV E1/E2 heterodimer is subjected to one or more further purification steps.

Where the affinity tag is an Ig Fc polypeptide, suitable Ig Fc binding moieties include, but are not limited to, Protein A (Graille et al. (2000) *Proc. Natl. Acad. Sci. USA* 97:5399); Protein G (Sjöbring et al. (1991) J. Biol. Chem. 266:399); and a Protein A/G fusion polypeptide (Eliasson et al. (1988) *J. Biol. Chem.* 263:4323).

The Ig Fc binding moiety can be immobilized onto a solid support, where the solid support can be of any of a variety of forms, e.g., a bead, a magnetic bead, a plate, and the like. The solid support can be made of any of a variety of materials, including, but not limited to, polystyrene, agarose, polyesters, polyethylene, and the like.

An untagged HCV E1/E2 heterodimer can be purified such that the untagged HCV E1/E2 heterodimer is at least 60% pure, at least 65% pure, at least 70% pure, at least 75% pure, at least 80% pure, at least 85% pure, at least 90% pure, at least 95% pure, at least 98% pure, at least 99% pure, or greater than 99% pure.

HCV E1/E2 Heterodimers

The present disclosure provides HCV E1/E2 heterodimers produced using a method of the present disclosure. In some cases, an HCV E1/E2 heterodimer of the present disclosure comprises a modified HCV E2 polypeptide with from 1 to 6 amino acids from the proteolytically cleavable linker on the N-terminus of the E2 polypeptide. In some cases, an HCV E1/E2 heterodimer of the present disclosure comprises a modified HCV E2 polypeptide with from 1 to 6 amino acids from the proteolytically cleavable linker on the C-terminus of the E2 polypeptide. In some cases, an HCV E1/E2 heterodimer of the present disclosure comprises a modified HCV E1 polypeptide with from 1 to 6 amino acids from the proteolytically cleavable linker on the N-terminus of the E1 polypeptide. In some cases, an HCV E1/E2 heterodimer of the present disclosure comprises a modified HCV E1 polypeptide with from 1 to 6 amino acids from the proteolytically cleavable linker on the C-terminus of the E1 polypeptide. In some cases, an HCV E1/E2 heterodimer of the present disclosure comprises a modified HCV E2 polypeptide and a modified HCV E1 polypeptide.

E2 with N-Terminal Heterologous Amino Acids

In some cases, an HCV E1/E2 heterodimer of the present disclosure comprises a modified HCV E2 polypeptide with from 1 to 6 amino acids from the proteolytically cleavable linker on the N-terminus of the E2 polypeptide. In some cases, a heterodimeric polypeptide of the present disclosure comprises: a) an HCV E1 polypeptide; and b) a modified E2 polypeptide comprising, in order from N-terminus to C-terminus: i) from 1 to 6 heterologous amino acids wherein the from 1 to 6 heterologous amino acids are C-terminal to a site of proteolytic cleavage in a proteolytically cleavable linker; and ii) an HCV E2 polypeptide.

Proteolytically cleavable linkers are described above. Following proteolytic cleavage of a precursor polypeptide, as described above, a modified E2 polypeptide is generated, which modified E2 polypeptide comprises, at its N-terminus, amino acids C-terminal to the protease cleavage site within the proteolytically cleavable linker.

For example, where the proteolytically cleavable linker comprises a PreScission cleavage site (LEVLFQGP; SEQ ID NO:1), where cleavage occurs between the glutamine and the glycine, a modified E2 polypeptide present in a heterodimeric polypeptide of the present disclosure comprises, in order from N-terminus to C-terminus: a) Gly-Pro; and b) an HCV E2 polypeptide.

As another example, where the proteolytically cleavable linker comprises a TEV cleavage site (ENLYFQS; SEQ ID NO:2), where cleavage occurs between the glutamine and the serine, a modified E2 polypeptide present in a heterodimeric polypeptide of the present disclosure comprises, in order from N-terminus to C-terminus: a) Ser; and b) an HCV E2 polypeptide.

As another example, where the proteolytically cleavable linker comprises a TEV cleavage site (ENLYFQG; SEQ ID NO:43), where cleavage occurs between the glutamine and the glycine, a modified E2 polypeptide present in a heterodimeric polypeptide of the present disclosure comprises, in order from N-terminus to C-terminus: a) Gly; and b) an HCV E2 polypeptide.

As another example, where the proteolytically cleavable linker comprises a thrombin cleavage site (LVPRGS; SEQ ID NO:5), where cleavage occurs between the arginine and the glycine, a modified E2 polypeptide present in a heterodimeric polypeptide of the present disclosure comprises, in order from N-terminus to C-terminus: a) Gly-Ser; and an HCV E2 polypeptide.

As another example, where the proteolytically cleavable linker comprises a Factor Xa cleavage site (I(E/D)GRX, where X is any amino acid except arginine or proline; SEQ ID NO:44), where cleavage occurs between the arginine and the X, a modified E2 polypeptide present in a heterodimeric polypeptide of the present disclosure comprises, in order from N-terminus to C-terminus: a) X (where X is any amino acid except arginine or proline); and an HCV E2 polypeptide.

E1 with N-Terminal Heterologous Amino Acids

In some cases, an HCV E1/E2 heterodimer of the present disclosure comprises a modified HCV E1 polypeptide with from 1 to 6 amino acids from a proteolytically cleavable linker on the N-terminus of the E1 polypeptide. In some cases, a heterodimeric polypeptide of the present disclosure comprises: a) an HCV E2 polypeptide; and b) a modified E1 polypeptide comprising, in order from N-terminus to C-terminus: i) from 1 to 6 heterologous amino acids wherein the from 1 to 6 heterologous amino acids are C-terminal to a site of proteolytic cleavage in a proteolytically cleavable linker; and ii) an HCV E1 polypeptide.

Proteolytically cleavable linkers are described above. Following proteolytic cleavage of a precursor polypeptide (e.g., a precursor polypeptide comprising, in order from N-terminus to C-terminus: a) an Fc polypeptide or an HCV E2 polypeptide; b) a proteolytically cleavable linker; and c) an HCV E1 polypeptide), a modified E1 polypeptide is generated, which modified E1 polypeptide comprises, at its N-terminus, amino acids C-terminal to the protease cleavage site within the proteolytically cleavable linker.

For example, where the proteolytically cleavable linker comprises a PreScission cleavage site (LEVLFQGP; SEQ ID NO:1), where cleavage occurs between the glutamine and the glycine, a modified E1 polypeptide present in a heterodimeric polypeptide of the present disclosure comprises, in order from N-terminus to C-terminus: a) Gly-Pro; and b) an HCV E1 polypeptide.

As another example, where the proteolytically cleavable linker comprises a TEV cleavage site (ENLYFQS; SEQ ID NO:2), where cleavage occurs between the glutamine and the serine, a modified E1 polypeptide present in a heterodimeric polypeptide of the present disclosure comprises, in order from N-terminus to C-terminus: a) Ser; and b) an HCV E1 polypeptide.

As another example, where the proteolytically cleavable linker comprises a TEV cleavage site (ENLYFQG; SEQ ID NO:43), where cleavage occurs between the glutamine and the glycine, a modified E1 polypeptide present in a heterodimeric polypeptide of the present disclosure comprises, in order from N-terminus to C-terminus: a) Gly; and b) an HCV E1 polypeptide.

As another example, where the proteolytically cleavable linker comprises a thrombin cleavage site (LVPRGS; SEQ ID NO:5), where cleavage occurs between the arginine and the glycine, a modified E1 polypeptide present in a heterodimeric polypeptide of the present disclosure comprises, in order from N-terminus to C-terminus: a) Gly-Ser; and an HCV E1 polypeptide.

As another example, where the proteolytically cleavable linker comprises a Factor Xa cleavage site (I(E/D)GRX, where X is any amino acid except arginine or proline; SEQ ID NO:44), where cleavage occurs between the arginine and the X, a modified E1 polypeptide present in a heterodimeric polypeptide of the present disclosure comprises, in order from N-terminus to C-terminus: a) X (where X is any amino acid except arginine or proline); and an HCV E1 polypeptide.

E2 with C-Terminal Heterologous Amino Acids

In some cases, an HCV E1/E2 heterodimer of the present disclosure comprises a modified HCV E2 polypeptide with from 1 to 6 amino acids from a proteolytically cleavable linker on the C-terminus of the E2 polypeptide. In some cases, a heterodimeric polypeptide of the present disclosure comprises: a) an HCV E1 polypeptide; and b) a modified E2 polypeptide comprising, in order from N-terminus to C-terminus: i) an HCV E2 polypeptide; and ii) from 1 to 6 heterologous amino acids wherein the from 1 to 6 heterologous amino acids are N-terminal to a site of proteolytic cleavage in a proteolytically cleavable linker.

Proteolytically cleavable linkers are described above. Following proteolytic cleavage of a precursor polypeptide (e.g., a precursor polypeptide comprising, in order from N-terminus to C-terminus: a) HCV E2 polypeptide; b) a proteolytically cleavable linker; and c) an Fc polypeptide or an HCV E1 polypeptide), a modified E2 polypeptide is generated, which modified E2 polypeptide comprises, at its C-terminus, amino acids N-terminal to the protease cleavage site within the proteolytically cleavable linker.

For example, where the proteolytically cleavable linker comprises a PreScission cleavage site (LEVLFQGP; SEQ ID NO:1), where cleavage occurs between the glutamine and the glycine, a modified E2 polypeptide present in a heterodimeric polypeptide of the present disclosure comprises, in order from N-terminus to C-terminus: a) an HCV E2 polypeptide; and b) LEVLFQ (SEQ ID NO:7).

As another example, where the proteolytically cleavable linker comprises an enterokinase cleavage site (DDDDK; SEQ ID NO:3), where cleavage occurs C-terminal to the Lys, a modified E2 polypeptide present in a heterodimeric polypeptide of the present disclosure comprises, in order from N-terminus to C-terminus: a) an HCV E2 polypeptide; and b) DDDDK (SEQ ID NO:3).

As another example, where the proteolytically cleavable linker comprises a TEV cleavage site (ENLYFQG; SEQ ID NO:43), where cleavage occurs between the glutamine and the glycine, a modified E2 polypeptide present in a heterodimeric polypeptide of the present disclosure comprises, in order from N-terminus to C-terminus: a) an HCV E2 polypeptide; and b) ENLYFQ (SEQ ID NO:8).

As another example, where the proteolytically cleavable linker comprises a thrombin cleavage site (LVPRGS; SEQ ID NO:5), where cleavage occurs between the arginine and the glycine, a modified E2 polypeptide present in a heterodimeric polypeptide of the present disclosure comprises, in order from N-terminus to C-terminus: a) an HCV E2 polypeptide; and LVPR (SEQ ID NO:4).

As another example, where the proteolytically cleavable linker comprises a Factor Xa cleavage site (I(E/D)GRX, where X is any amino acid except arginine or proline; SEQ ID NO:44), where cleavage occurs between the arginine and the X, a modified E2 polypeptide present in a heterodimeric polypeptide of the present disclosure comprises, in order from N-terminus to C-terminus: a) an HCV E2 polypeptide; and I(E/D)GR (SEQ ID NO:45).

E1 with C-Terminal Heterologous Amino Acids

In some cases, an HCV E1/E2 heterodimer of the present disclosure comprises a modified HCV E1 polypeptide with from 1 to 6 amino acids from a proteolytically cleavable linker on the C-terminus of the E1 polypeptide. In some cases, a heterodimeric polypeptide of the present disclosure comprises: a) an HCV E2 polypeptide; and b) a modified E1 polypeptide comprising, in order from N-terminus to C-terminus: i) an HCV E1 polypeptide; and ii) from 1 to 6 heterologous amino acids wherein the from 1 to 6 heterologous amino acids are N-terminal to a site of proteolytic cleavage in a proteolytically cleavable linker.

Proteolytically cleavable linkers are described above. Following proteolytic cleavage of a precursor polypeptide (e.g., a precursor polypeptide comprising, in order from N-terminus to C-terminus: a) HCV E1 polypeptide; b) a proteolytically cleavable linker; and c) an Fc polypeptide or an HCV E2 polypeptide), a modified E1 polypeptide is generated, which modified E1 polypeptide comprises, at its C-terminus, amino acids N-terminal to the protease cleavage site within the proteolytically cleavable linker.

For example, where the proteolytically cleavable linker comprises a PreScission cleavage site (LEVLFQGP; SEQ ID NO:1), where cleavage occurs between the glutamine and the glycine, a modified E1 polypeptide present in a heterodimeric polypeptide of the present disclosure comprises, in order from N-terminus to C-terminus: a) an HCV E1 polypeptide; and b) LEVLFQ (SEQ ID NO:7).

As another example, where the proteolytically cleavable linker comprises an enterokinase cleavage site (DDDDK; SEQ ID NO:3), where cleavage occurs C-terminal to the Lys, a modified E1 polypeptide present in a heterodimeric polypeptide of the present disclosure comprises, in order from N-terminus to C-terminus: a) an HCV E1 polypeptide; and b) DDDDK (SEQ ID NO:3).

As another example, where the proteolytically cleavable linker comprises a TEV cleavage site (ENLYFQG; SEQ ID NO:43), where cleavage occurs between the glutamine and the glycine, a modified E1 polypeptide present in a heterodimeric polypeptide of the present disclosure comprises, in order from N-terminus to C-terminus: a) an HCV E1 polypeptide; and b) ENLYFQ (SEQ ID NO:8).

As another example, where the proteolytically cleavable linker comprises a thrombin cleavage site (LVPRGS; SEQ ID NO:5), where cleavage occurs between the arginine and the glycine, a modified E1 polypeptide present in a heterodimeric polypeptide of the present disclosure comprises, in order from N-terminus to C-terminus: a) an HCV E1 polypeptide; and b) LVPR (SEQ ID NO:4).

As another example, where the proteolytically cleavable linker comprises a Factor Xa cleavage site (I(E/D)GRX, where X is any amino acid except arginine or proline; SEQ ID NO:44), where cleavage occurs between the arginine and the X, a modified E1 polypeptide present in a heterodimeric polypeptide of the present disclosure comprises, in order from N-terminus to C-terminus: a) an HCV E1 polypeptide; and I(E/D)GR (SEQ ID NO:45).

Pharmaceutical Formulations

An HCV E1/E2 heterodimeric polypeptide of the present disclosure can be formulated with a pharmaceutically acceptable excipient(s) to generate an immunogenic composition. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In some cases, a heterodimeric HCV E1/E2 polypeptide of the present disclosure is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some cases, the aqueous buffer further includes a non-ionic surfactant such as polysorbate 20 (TWEEN®20) or polysorbate 80 (TWEEN®80). For example, a formulation of E1 and variant E2 polypeptides in an aqueous buffer can include, e.g., from about 0.01% to about 0.05% polysorbate-20 (TWEEN®20) non-ionic detergent. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some cases, the aqueous buffer further includes a non-ionic surfactant. In some cases, the aqueous buffer includes the non-ionic surfactant Triton™X-100, e.g., 0.1% Triton™X-100.

An heterodimeric HCV E1/E2 polypeptide of the present disclosure can be formulated into a preparation for injection by dissolving, suspending or emulsifying the heterodimer in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An immunogenic composition of the present disclosure can include, e.g., pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of a heterodimeric HCV E1/E2 polypeptide of the present disclosure in a formulation can vary widely (e.g., from less than about 0.1% to at least about 2%, to as much as 20% to 50% or more by weight) and can be selected primarily based on fluid volumes, viscosities, and patient-based factors in accordance with the particular mode of administration selected and the patient's needs.

The HCV E1/E2 heterodimeric polypeptide-containing formulations of the present disclosure can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The HCV E1/E2 heterodimeric polypeptide polypeptide-containing formulations of the present disclosure can also be provided so as to enhance serum half-life of the heterodimer following administration. For example, where a heterodimeric HCV E1/E2 polypeptide of the present disclosure is formulated for injection, the heterodimeric HCV E1/E2 polypeptide may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Adjuvant

An immunogenic composition of the present disclosure can include, in addition to a heterodimeric HCV E1/E2 polypeptide of the present disclosure, an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN 80™ (Polysorbate 80, a nonionic surfactant), 0.5% w/v Span 85), CpG-containing nucleic acid (where the cytosine is unmethylated), QS21, MPL, 3DMPL, extracts from Aquilla, ISCOMS, LT/CT mutants, poly (D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/TWEEN 80 emulsion. Another suitable adjuvant is AS01, a suspension of liposomes comprising 3'-O-desacyl-4'-monophosphoryl lipid A (MPL) and *Quillaja saponaria* 21 (QS21). In some cases, the adjuvant is selected from MF59, AS01, AS02, AS03, AS04, alum, aluminum hydroxide, and aluminum phosphate. The effectiveness of an adjuvant may be determined by one or more of measuring the amount of antibodies directed against the immunogenic antigen or antigenic epitope thereof, measuring a cytotoxic T lymphocyte response to the antigen, and measuring a helper T cell response to the antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (see, e.g., WO 90/14837), containing 5% Squalene, 0.5% TWEEN 80, and 0.5% Span 85 (optionally containing MTP-PE) formulated into submicron particles using a microfluidizer, (b) SAF, containing 10% Squalane, 0.4% TWEEN 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions (see, e.g. EP-A-0835318, EP-A-0735898, EP-A-0761231); (7) oligonucleotides comprising a CpG motif containing at least one CG dinucleotide, where the cytosine is unmethylated (see, e.g., WO 96/02555, WO 98/16247, WO 98/18810, WO 98/40100, WO 98/55495, WO 98/37919 and WO 98/52581); (8) a polyoxyethylene ether or a polyoxyethylene ester (see, e.g. WO 99/52549); (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt (see, e.g. WO 00/23105); (12) a saponin and an oil-in-water emulsion (see e.g. WO 99/11241); (13) a saponin (e.g. QS21)+3dMPL+IM2 (optionally including a sterol) (see, e.g. WO 98/57659); (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Also suitable for use is MATRIX™; MATRIX™ is an adjuvant that comprises 40 nm nanoparticles comprising *Quillaja* saponins, cholesterol, and phospholipid. Adjuvants suitable for administration to a human are of particular interest. In some cases, the adjuvant is one that enhances a CD4+ T helper response to the immunogen.

In some instances, the adjuvant is MF59, with or without a CpG-containing oligonucleotide. In other instances, the adjuvant is alum, with or without a CpG-containing oligonucleotide. In other instances, the adjuvant is poly(D,L-lactide-co-glycolide), with or without a CpG-containing oligonucleotide. In other instances, the adjuvant is MPL, with or without a CpG-containing oligonucleotide. In some cases, the adjuvant is Matrix-M™, with or without a CpG-containing oligonucleotide. In some cases, the adjuvant is keyhole limpet hemocyanin. In some instances, the adjuvant is ASO1, a suspension of liposomes comprising 3'-O-desacyl-4'-monophosphoryl lipid A (MPL) and Quillaja *saponaria* 21 (QS21). In some cases, the adjuvant is MPL+ alum.

Methods of Inducing an Immune Response to HCV

The present disclosure provides a method of inducing an immune response (e.g., a protective immune response) to at least one HCV genotype in a mammalian subject. In some cases, the methods comprise administering to an individual in need thereof an effective amount of a heterodimeric HCV E1/E2 polypeptide of the present disclosure, or a composition (e.g., an immunogenic composition) comprising a heterodimeric HCV E1/E2 polypeptide of the present disclosure. In other cases, the methods comprise administering to an individual in need thereof an effective amount of a nucleic acid(s) (e.g., a recombinant expression vector) comprising nucleotide sequences encoding a heterodimeric polypeptide of the present disclosure.

An HCV immunogenic composition of the present disclosure, or a nucleic acid(s) comprising nucleotide sequences encoding a heterodimeric polypeptide of the present disclosure, is generally administered to a human subject who has an HCV infection or who is at risk of acquiring an HCV infection (e.g., is at greater risk than the general population of acquiring an HCV infection) so as to prevent or at least partially arrest the development of disease and its complications. An amount adequate to accomplish this is defined as a "therapeutically effective dose" or a "therapeutically effective amount." "Prophylactic" use of a subject immunogenic composition generally refers to administration to an individual who has not been infected with HCV. "Therapeutic" use of a subject immunogenic composition can refer to "prophylactic" use (administration to an individual who has not been infected with HCV) and/or to administration to an individual who has an HCV infection. A "therapeutically effective amount" of an immunogenic composition of the present disclosure, can be an amount that, when administered in one or more doses to an individual who is not infected with HCV, is effective to induce an immune response in the individual to HCV. A "therapeutically effective amount" of an immunogenic composition of the present disclosure, can be an amount that, when administered in one or more doses to an individual who is infected with HCV, is effective to enhance an immune response in the individual to HCV.

Amounts effective for therapeutic use will depend on, e.g., the immunogenic composition or the nucleic acid(s) comprising nucleotide sequences encoding a heterodimeric polypeptide of the present disclosure, the manner of administration, the weight and general state of health of the patient, and the judgment of the prescribing physician. Single or multiple doses of a subject immunogenic composition, or a nucleic acid(s) comprising nucleotide sequences encoding a heterodimeric polypeptide of the present disclosure, can be administered depending on the dosage and frequency required and tolerated by the patient, and route of administration.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) to HCV in the individual. For example, antibody to HCV (e.g., extracellular HCV), and/or to an HCV-infected cell, can be induced.

An effective amount of an HCV E1/E2 immunogenic composition of the present disclosure, or a nucleic acid(s) comprising nucleotide sequences encoding a heterodimeric polypeptide of the present disclosure, can be an amount that, when administered to an individual in one or more doses, is effective to induce a neutralizing antibody response to HCV of a variety of genotypes (e.g., genotype 1; genotype 3; etc.). A neutralizing antibody response reduces binding of HCV to one or more host receptors for HCV and inhibits entry of HCV into a cell.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce a cytotoxic T lymphocyte (CTL) response to HCV. For example, a CTL response to an HCV-infected cell can be induced.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce a helper T lymphocyte (e.g., CD4+ T cell) to HCV in an individual.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV genotype 1. In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV genotype 3. In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV genotype 1 and HCV genotype 3. In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV of any genotype.

An HCV E1/E2 immunogenic composition of the present disclosure, or a nucleic acid(s) comprising nucleotide sequences encoding a heterodimeric polypeptide of the present disclosure, is generally administered in an amount effective to elicit an immune response, e.g., a humoral immune response (e.g., an antibody response) and/or a CTL response, in the mammalian subject. Effective amounts for immunization will vary, and can generally range from about 1 µg to 100 µg per 70 kg patient, e.g., from about 5 µg/70 kg to about 50 µg/70 kg. Substantially higher dosages (e.g. 10 mg to 100 mg or more) may be suitable in oral, nasal, or topical administration routes. The initial administration can be followed by booster immunization of the same HCV E1/E2 immunogenic composition or a different HCV E1/E2 immunogenic composition. In some instances, a subject method of inducing an immune response involves an initial administration of an HCV E1/E2 immunogenic composition of the present disclosure, followed by at least one booster, and in some instances involves two or more (e.g., three, four, or five) boosters. The interval between an initial administration and a booster, or between a give booster and a subsequent booster, can be from about 1 week to about 12 weeks, e.g., from about 1 week to about 2 weeks, from about 2 weeks to about 4 weeks, from about 4 weeks to about 6 weeks, from about 6 weeks to about 8 weeks, from about 8 weeks to about 10 weeks, or from about 10 weeks to about 12 weeks.

In general, immunization can be accomplished by administration of an HCV E1/E2 immunogenic composition of the present disclosure, or a nucleic acid(s) comprising nucleotide sequences encoding a heterodimeric polypeptide of the present disclosure, by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980). In some instances, immunization is accomplished by intramuscular injection of an HCV E1/E2 immunogenic composition of the present disclosure.

In some cases, a method of the present disclosure for inducing an immune response to HCV in an individual comprises administering to the individual an effective amount of a nucleic acid(s) comprising nucleotide sequences encoding a heterodimeric polypeptide of the present disclosure. In some cases, the nucleic acid is present in an expression vector. Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623).

In some cases, a method of the present disclosure for inducing an immune response to HCV in an individual comprises administering to the individual an effective amount of a nucleic acid(s) comprising nucleotide sequences encoding a heterodimeric polypeptide of the present disclosure. In some cases, the nucleic acid is an RNA comprising nucleotide sequences encoding a heterodimeric polypeptide of the present disclosure. See, e.g., Weiner (2013) *Molec. Therapy* 21:506; and Ulmer et al. (2012) *Vaccine* 30:4414. In some cases, an RNA (e.g., a single mRNA molecule; or 2 mRNA molecules) comprising nucleotide sequences encoding a heterodimeric polypeptide of the present disclosure is formulated with a liposome. In some cases, an RNA (e.g., a single mRNA molecule; or 2 mRNA molecules) comprising nucleotide sequences encoding a heterodimeric polypeptide of the present disclosure is complexed with protamine. In some cases, an RNA (e.g., a single mRNA molecule; or 2 mRNA molecules) comprising nucleotide sequences encoding a heterodimeric polypeptide of the present disclosure is complexed with 1,2-dioleoyl-3-trimethylammonium-propane/1,2-dioleoyl-sn-glycero-3-phosphoethanolamine (DOTAP/DOPE).

Individuals Suitable for Administration

Individuals who are suitable for administration with an HCV composition of the present disclosure include immunologically naïve individuals (e.g., individuals who have not been infected with HCV and/or who have not been administered with an HCV vaccine).

Individuals who are suitable for administration with an HCV composition of the present disclosure include individuals who are at greater risk than the general population of becoming infected with HCV, where such individuals include, e.g., intravenous drug users; individuals who are the recipients, or the prospective recipients, of blood or blood products from another (donor) individual(s); individuals who are the recipients, or the prospective recipients, of non-autologous cells, tissues, or organs from another (donor) individual; health care workers; emergency medical and non-medical personnel (e.g., first responders; fire fighters; emergency medical team personnel; etc.) and the like.

Individuals who are suitable for administration with an HCV E1/E2 immunogenic composition of the present disclosure include individuals who recently became exposed to HCV or who recently became infected with HCV. For example, a subject immunogenic composition can be administered to an individual within from about 24 hours to about 48 hours, from about 48 hours to about 1 week, or from about 1 week to about 4 weeks, following possible or suspected exposure to HCV or following infection with HCV.

Individuals who are suitable for administration with an HCV E1/E2 immunogenic composition of the present disclosure include individuals who have been diagnosed as having an HCV infection, and include chronically infected individuals. In some cases, an individual who has been diagnosed as having an HCV infection is treated with an anti-viral agent and a subject HCV immunogenic composition. Suitable anti-viral agents for treating HCV infection include, e.g., ribavirin (1-β-D-ribofuranosyl-1H-1,2,4-triazole-3-carboxamide); interferon-alpha (IFN-α) (where "IFN-α" includes IFN-α2a; IFN-α2b; IFN-α that is conjugated with poly(ethylene glycol) ("pegylated IFN-α), where the pegylated IFN-α can be pegylated IFN-α2a or pegylated IFN-α2b); an HCV NS3 protease inhibitor (e.g., boceprevir; telaprevir); and an HCV NS5 protease inhibitor. In some cases, an individual who has been diagnosed as having an HCV infection is treated with, e.g.: 1) IFN-α+ ribavirin; and a subject HCV immunogenic composition; or 2) IFN-α+ ribavirin+ an HCV protease inhibitor (e.g., boceprevir or telaprevir); and a subject HCV immunogenic composition. Suitable anti-viral agents for treating HCV infection include Sovaldi (Sofosbuvir; a nucleotide analog that functions as an NS5B polymerase inhibitor), alone or in combination with pegylated IFN-α and ribavirin. Suitable anti-viral agents for treating HCV infection include Sovaldi. Suitable anti-viral agents for treating HCV infection include Harvoni® (ledipasvir 90 mg+sofosbuvir 400 mg). Ledipasvir is an HCV NS5A inhibitor. Harvoni® can be administered with or without ribavirin.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Production of Affinity Tagged HCV E1/E2 Heterodimers, and Production and Characterization of Untagged HCV E1/E2 Heterodimers FIG. 6A. Schematic representation of Fc tag insertion to E2 N-terminus in full length E1E2 polypeptide construct. The E1E2 polypeptide is expressed under the control of the CMV promoter ($P_{CMV}$) and includes the signal sequence from tissue plasminogen activator (tPA). Insertion sites are shown for representative HCV E1E2 sequences: H77 (GenBank NP_671941), JFH1 (Genbank AB047639; genotype 2A), S52 (Genbank ADF97232.1; genotype 3a), and isolate QC69 (Genbank: ABN05226.1; genotype 7A). Sizes of the polypeptide regions are shown at the top (aa=amino acids). At the N-terminus of E2, a duplication of the E2 N-terminal amino acids respective to the particular genotype (eg: ET addition for H77; GenBank NP_671941) is inserted followed by the human IgG1 Fc tag (hu IgG1 Fc) and a PreScission Protease (PP) recognition sequence (LEVLFQGP; SEQ ID NO:1). Depending on the genotype and specific isolate of E1E2, duplication of the first two amino acids of E2 may result in an undesirable amino acid created at the N-terminus of E2 following processing by signal peptidase (SP) (FIG. 6A). Such amino acids at the amino terminus include asparagine (N), glutamine (Q) or cysteine (C). Such amino acids can target the protein for proteasome-mediated degradation via the N-end rule pathway (reviewed in: Tasaki T et al. 2012. *Annu Rev Biochem* 81 261-289). In this case, an alternative amino acid could be selected according to either the consensus sequence for the particular genotype or a particular genotype subclass would be selected. Following expression of the polypeptide, signal peptidase (SP) cleavages result in the downstream E1 and E2 polypeptides shown. The E1 and E2 polypeptides interact to form a heterodimer. For purification purposes, the Fc tagged E1E2 is immobilized on Protein A or Protein G resin and digested with PreScission Protease (PP) (cleavage between Q and G in the LEVLFQGP (SEQ ID NO:1) sequence) to release the untagged E1E2 heterodimer.

Figure 6B:
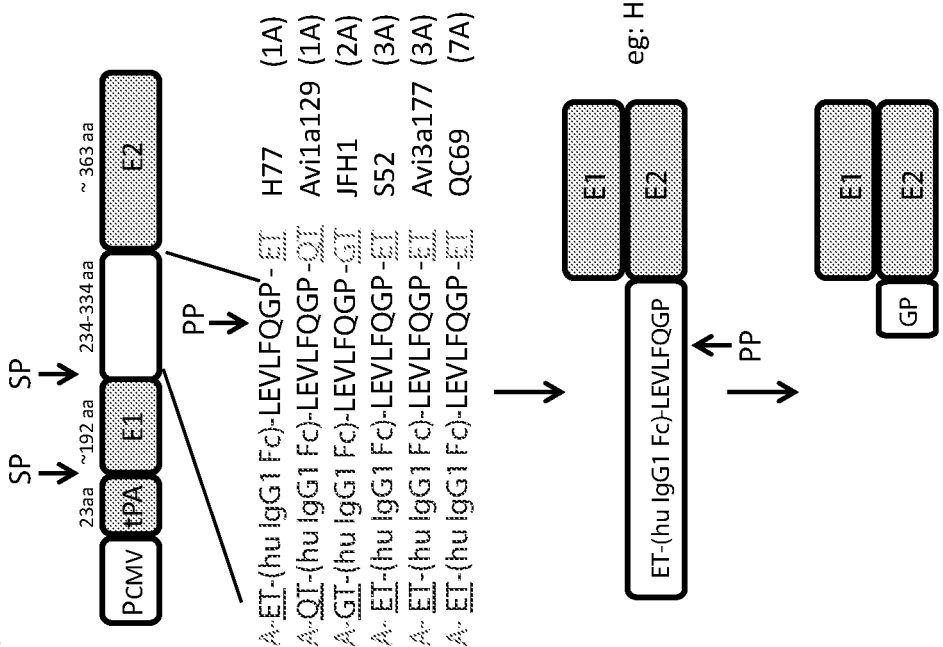
FIG. 6A-6B provide a schematic representation of Fc tagged E2 polypeptides in a full-length E1-E2 construct (FIG. 6A); and gel depicting purification of untagged HCV E1/E2 heterodimer from CHO extracts expressing Fc-tagged E1/E2 heterodimer. Sequences from top to bottom: SEQ ID NOs:110-116.
Figure 6A:
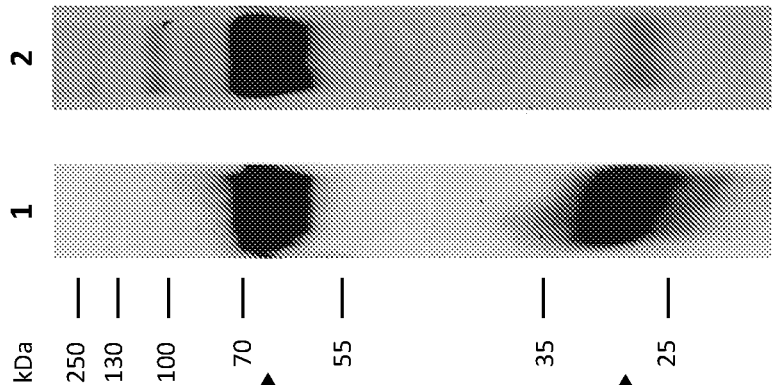

FIG. 6B. Purification of E1E2 heterodimer from CHO cell extracts expressing Fc tagged E1E2 H77. CHO cell extracts expressing an Fc-tagged E1E2 H77 construct, as diagrammed in (A), were immobilized on Protein-G Sepharose 4 Fast Flow and digested with GST-PreScission protease (GST-PP) to remove the Fc tag. Following the digestion with GST-PP and release of untagged E1E2, GST-PP was removed by Glutathione Sepharose 4B. The untagged E1E2 protein concentrate was then applied to a CHT™ ceramic hydroxyapatite ((Ca$_5$(PO$_4$)$_3$OH)$_2$) type I (HAP) column. The HAP flow through containing the final E1E2 heterodimer was collected and samples loaded onto a sodium dodecyl sulfate-polyacrylamide gel electrophoresis (SDS-PAGE) gel. After electrophoresis, the gel was stained, or blotted then probed with antibodies. (1) Western blot with anti-E1 (A4) and anti-E2 (H52) monoclonal antibodies (mAbs) (0.5 μg loaded per lane). (2) Colloidal Coomassie Brilliant Blue G250 stained gel (2 μg loaded per lane).

FIG. 7. Alignment of the Fc-tagged E1-E2 polypeptide for H77 and Alberta isolate Avila129 (genotype 1A). The amino acid sequence for the coding region of the tPa-E1-Fc-PP-E2 construct (as diagrammed in FIG. 6A) for the Alberta isolate (Avila129) and H77 (GenBank NP_671941) was aligned using Geneious software v5.6.4. Arrowhead denotes the insertion of the duplicated N-terminal E2 residues that precede the Fc-PP tag (Avila129: QT and H77: ET).

FIG. 8. Alignment of the Fc-tagged E1-E2 polypeptide for S52 (Genbank ADF97232.1) and Alberta isolate Avi3a177 (genotype 3A). The amino acid sequence for the coding region of the tPa-E1-Fc-PP-E2 construct (as diagrammed in FIG. 6A) for the Alberta isolate (Avi3a177) and S52 was aligned using Geneious software v5.6.4. Arrowhead denotes the insertion of the duplicated N-terminal E2 residues that precede the Fc-PP tag (ET for both Avi3a177 and S52).

Figure 9:
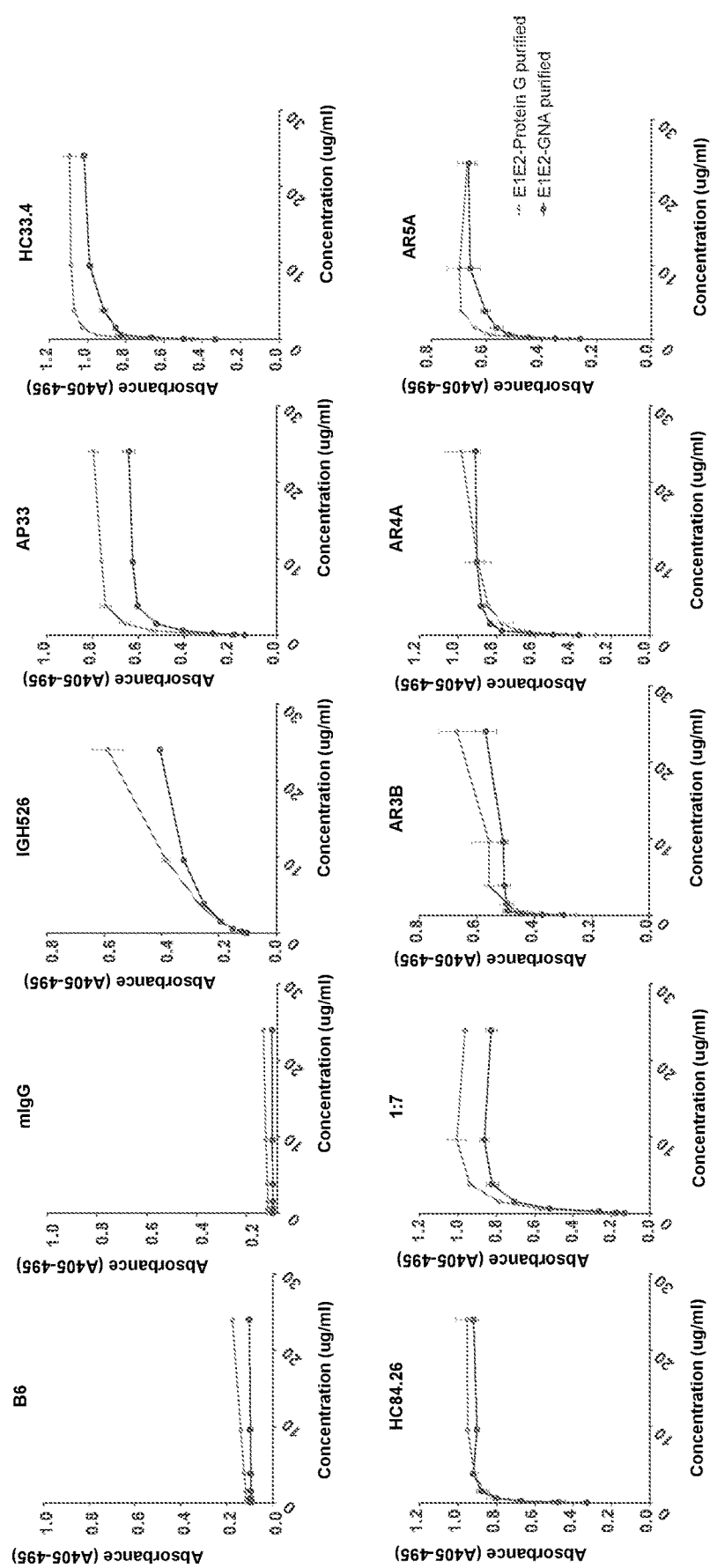
FIG. 9 depicts binding of neutralizing anti-HCV E2 monoclonal antibodies to recombinant E1/E2 antigens produced according to a method of the present disclosure.

FIG. 9. Binding of HCV neutralizing monoclonal antibodies (mAb) to recombinant E1E2 antigens. Recombinant E1E2 (H77) antigens were purified by *Galanthus nivalis* agarose (GNA agarose) (untagged E1E2; pink closed circle) or Protein G Sepharose (Fc-tagged E1E2 followed by Fc tag removal; purple open circle). To determine proper folding of the E1E2 antigens, a panel of monoclonal antibodies (mAb) established to neutralize HCV infectivity were examined by enzyme-linked immunosorbent assay (ELISA). Recombinant E1E2 antigens were coated to ELISA plates and increasing amounts of eight different neutralizing HCV mAbs directed to E1 (IGH526), E2 (AP33, HC33.4, HC84.26, 1:7, AR3B) or E1E2 (AR4A, AR5A) were used. Clone B6 (human IgG1) and mouse IgG1 were used as negative controls. Results show that E1E2 antigens isolated by both methods show equal affinity to the panel of tested mAbs.

Example 2: Characterization of Affinity Tag-Derived HCV E1/E2 Heterodimer

Materials and Methods

Cell Cultures and Antibodies

Chinese hamster ovary (CHO) cells stably expressing recombinant E1E2 constructs from the genotype 1a H77c strain (GenBank accession number AF009606) were propagated in Iscove's modified Dulbecco's medium (Thermo Fisher Scientific, Waltham, Mass., USA) containing 10% heat-inactivated fetal bovine serum (FBS) (Thermo Fisher Scientific), 0.1 mM/0.016 mM sodium hypoxanthine/thymidine (HT supplement; Thermo Fisher Scientific), 0.002 mM methotrexate, 100 units/mL penicillin, and 100 μg/mL streptomycin (PenStrep; Invitrogen, Carlsbad, Calif., USA). Huh-7.5 cells were propagated in Dulbecco's modified Eagle's medium (Thermo Fisher Scientific) containing 10% heat-inactivated fetal bovine serum (Omega Scientific, Tarzana, Calif., USA), 0.1 mM nonessential amino acids (Invitrogen), and penicillin and streptomycin (PenStrep; Invitrogen). The mAb mouse anti-cluster of differentiation 81 (CD81) clone JS-81 (BD Biosciences, Franklin Lakes, N.J., USA), mouse isotype control IgG1 (R&D Systems, Minneapolis, Minn., USA), anti-HCV mAbs (HC33.4, HC84.26, AR3B, AR4A, and AR5A), and human anti-HIV antibody B6 have been described.

Expression and Purification of Recombinant E1E2 Antigens

Figure 11A:
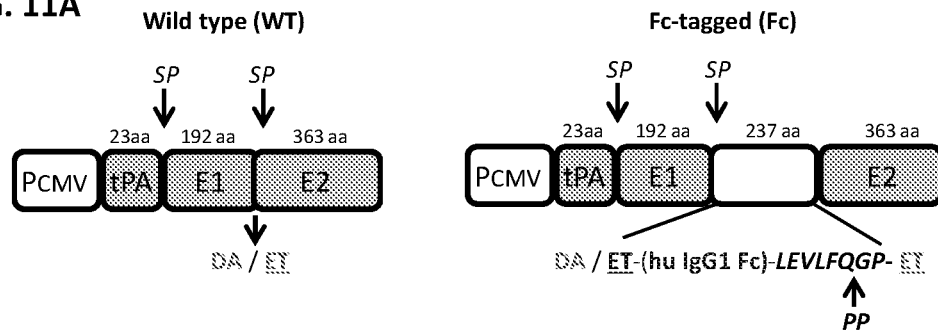
FIG. 11A-11D depict purification of E1E2 heterodimer from an Fc-tagged precursor.

The E1E2 glycoprotein coding region from H77c (genotype 1a) (Genbank AF009606; amino acids 192-746), preceded by the signal peptide sequence for tissue plasminogen activator (tPA), was inserted into the SpeI/MluI site of the pTRIP lentiviral vector bearing an IRES-AcGFP reporter. For the Fc-tagged E1E2 construct, a duplication of amino acids 384-385 (ET) was inserted at the N-terminus of E2 followed by the human IgG1 Fc tag (227 amino acids) and a PreScission Protease/human rhinovirus protease 3C (HRV3C) sequence (LEVLFQGP; SEQ ID NO:1) (FIG. 11A). Lentiviral particles were generated in HEK-293 T cells according to a previous method (Schoggins et al. (2011) *Nature* 472:481), and CHO cells were transduced with packaged lentivirus. GFP-positive CHO cells expressing WT or Fc-tagged recombinant E1E2 were sorted by flow cytometry using a BD FACSAria III cell sorter (BD Biosciences) then suspension adapted in PROCHO4 medium (Lonza, Walkersville, Md., USA) with 6% FBS in 250 ml shaker flasks (Corning, Corning, N.Y., USA) and expanded in 3 L spinner flasks (Corning, Corning, N.Y., USA).

Recombinant WT E1E2 was purified from CHO cell extracts using GNA (Vector laboratories, Burlingame, CA, USA) according to a previous study (Ralston et al. (1993) J. Virol. 67:6753). The GNA eluate fraction was loaded on to a hydroxyapatite (HAP) column (BIO-RAD™, Hercules, CA, USA; 158-8000) and the flow through concentrated with a 50,000 molecular weight cut-off centrifugal filter unit (EMD MILLIPORE™, Billerica, MA, USA). For Fc-d E1E2, the CHO cell extract was applied to Protein G Sepharose 4 Fast Flow (GE Healthcare, Piscataway, NJ, USA), washed with 10 mM sodium phosphate, 80 mM NaCl, 0.1% TX-100, pH 6.8, and the resin digested with His6-GST-HRV3C protease (Thermo Fisher Scientific) overnight at 4° C. The digested material was applied to Glutathione Sepharose 4B (GE Healthcare) to remove the protease and the flow through applied to HAP with final concentration as described for WT E1E2.

Immunization of Mice and Serum Samples

Female CB6F1 mice (Charles River Laboratories, Montreal, QC, Canada) (5-7 weeks old) used for vaccination experiments were cared for in accordance with the Canadian Council on Animal Care guidelines. Experimental methods were reviewed and approved by the University of Alberta Health Sciences Animal Welfare Committee. Recombinant E1E2 H77 antigens (2 µg) were mixed in a 1:1 ratio with 75 µg alum and 7.5 µg monophosphoryl Lipid A (MPLA Vaccigrade) (Invivogen, San Diego, Calif., USA) (30 µL final injection volume). Mice were injected intramuscularly at days 0, 14, and 28. Pre-vaccination serum was collected at day 0 and post vaccination sera (terminal bleeds) obtained at day 42. Sera were collected after centrifugation of the samples at 5000 g for 15 minutes. Sera were heat-inactivated by incubation at 56° C. for 30 minutes and stored in aliquots at −80° C. until use.

ELISA (i) E1E2 ELISA. Microtiter plates (CORNING) were coated with E1E2 antigens (100 ng/well) in carbonate buffer (15 mM sodium carbonate, 35 mM sodium bicarbonate, pH 9.6) overnight at 4° C. Plates were washed with phosphate-buffered saline containing 0.2% TWEEN 20 (PBST) and blocked for 1 h in 4% bovine serum albumin (SIGMA-ALDRICH, St. Louis, MO, USA) in PBST. E2-specific mAbs (HC33.4, HC84.26, and AR3B) (Law et al. (2008) Nat. Med. 14:25; Keck et al (2013) J. Virol. 87:37; and Keck et al. (2012) PLOS Pathogens 8: e1002653), E1E2-specific mAbs (AR4A and AR5A) (15), or control (B6) (16) mAb (50 L/well) were added for 1 h and detected by an anti-human alkaline phosphatase-conjugated secondary antibody (1:10,000; Jackson Immuno Research, West Grove, PA, USA) and p-nitrophenyl phosphate (MilliporeSigma) substrate. Absorbance (405-495 nm) was read using an Enspire plate reader (Perkin-Elmer, Waltham, MA, USA).

(ii) E2 ELISA. Microtiter plates were coated with E2 (amino acids 384-661) HCV1 (Genbank M62321.1) and blocked in 4% bovine serum albumin as described for the E1E2 ELISA. Antisera from vaccinated mice (terminal bleeds) were diluted in PBST and added to the plates for 1 h (50 µL/well). E2-specific antibodies from mouse antisera were detected by a horseradish peroxidase-conjugated goat anti-mouse secondary antibody (1:10,000; Cedarlane Laboratories, Burlington, ON, Canada) and peroxidase substrate (KPL, Gaithersburg, Md., USA). Absorbance was read at 450-570 nm. Absorbance values from three independent experiments are expressed as means±SEM.

(iii) Competition ELISA. Mouse antisera (terminal bleeds) were assessed for competition with conformation-specific E2 mAbs for E1E2 binding according to a method described previously (Wong et al. (2014) J. Virol. 88:14278). Briefly, microtiter plates (Corning) were coated with GNA purified WT E1E2 H77c in carbonate buffer overnight at 4° C. and blocked in 1% casein (Sigma-Aldrich) in PBST. Diluted mouse antisera were incubated for 1 h in E1E2-coated wells. HCV-specific (HC33.4, HC84.26, AR3B, AR4A, and AR5A) or control (B6 anti-HIV) mAbs were added at a concentration normally resulting in 70% maximal binding. Binding of HCV-specific mAbs was detected by an anti-human alkaline phosphatase-conjugated secondary antibody (1:10,000; Jackson Immuno Research) and p-nitrophenyl phosphate (MilliporeSigma) substrate. Absorbance was read at 405-495 nm. Values were calculated as the percentage of mAb binding relative to the mAb bound in the absence of antiserum. Data were plotted as means±standard error of the mean from three independent experiments.

HCV Pseudotype Virus (HCVpp) Production and Neutralization Assay

HCVpp expressing a luciferase reporter were generated as described previously (Hsu et al. (2003) Proc. Natl. Acad. Sci. USA 100:7271). For neutralization assays, human hepatoma cells (Huh7.5) were plated on poly-lysine coated 96-well plates 1 day prior to infection. HCVpp were diluted 1:10 and premixed with heat inactivated diluted sera for 1 h at 37° C. followed by addition to Huh 7.5 cells. Six h post-infection, the antibody-virus inoculum was replaced with fresh culture medium. Cells were processed 48 h post-infection using the Bright-glo luciferase assay system (Promega, Madison, Wis., USA). Luminescence was measured using an Enspire plate reader (Perkin Elmer). Neutralization activity was calculated using the following formula: % neutralization=(pre-post)/pre×100 where pre/post represent the luciferase activity done after incubating with either the pre- or post-vaccination sera. For ID50 titres, 2-fold dilutions of sera from 1:25 to 1:1600 were examined. Titres were expressed as a reciprocal of the dilution calculated to neutralize 50% of the virus. If 50% neutralization was not achieved at the highest concentration examined (1:25), then the next highest concentration was assigned to the sample (ie: 1:12.5). Similarly, if the lowest dilution examined (1:1600) resulted in >50% neutralization, we assigned the next dilution for this sample (ie: 1:3200).

Results

The results are depicted in FIGS. 11-14.

Purification of E1E2 from an Fc-Tagged Precursor

Figure 11B:
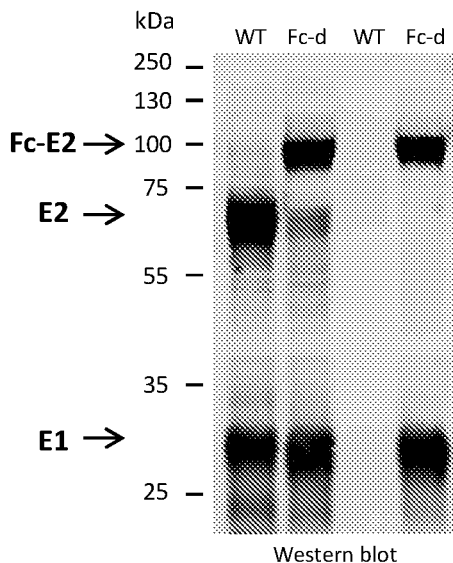

The constructs used for E1E2 expression are shown in FIG. 11A. The full length E1E2 sequence from H77c (Genbank AF009606) was inserted downstream of the tPA leader sequence and a CMV promoter. To generate an affinity tagged form of E1E2, the Fc domain from human IgG1 was inserted at the junction between E1 and E2. Both WT and Fc-E1E2 could be precipitated by GNA, whereas only the latter was precipitated by Protein G Sepharose (FIG. 11B). Importantly, the precipitated Fc-E2 protein was associated with E1, demonstrating that the Fc tag did not interfere with heterodimer formation.

Figure 11C:
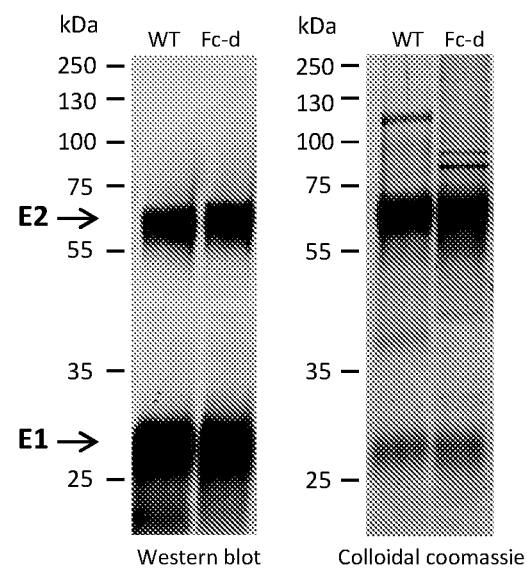
Figure 11D:
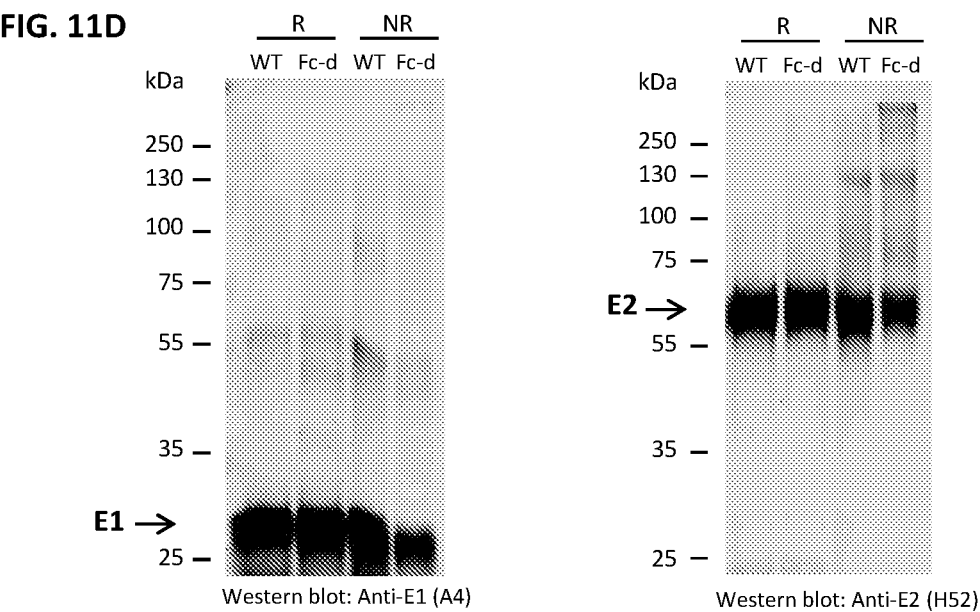

As outlined in Materials and Methods, above, Fc-d E1E2 (with the Fc tag removed) was purified and compared to WT E1E2 isolated with GNA. Both methods resulted in a highly enriched E1E2 antigen that contained a minor fraction of contaminant proteins (FIG. 11C). The yields between the two methods were similar at the scale of the isolations performed (~1 mg E1E2 per 100 g CHO cells). SDS-PAGE and western blot analyses performed with reducing vs. non-reducing Laemmli buffer supported that the vast majority of the isolated E1E2 antigens were in non-covalently linked complexes (FIG. 11D).

FIG. 11A-11D: Purification of E1E2 from an Fc-tagged precursor. (A). Schematic representation of wild type (WT) and Fc-tagged constructs and polypeptide processing. The E1E2 H77c (Genbank AF009606) polypeptide was expressed under the control of the CMV promoter ($P_{CMV}$) and preceded by the signal sequence from tissue plasminogen activator (tPA). For Fc-tagged E1E2, a duplication of the E2 N-terminal amino acids (384-385) (ET) was inserted followed by the human IgG1 Fc tag (hu IgG1 Fc) and a PreScission Protease (PP) recognition sequence (LEVLFQGP; SEQ ID NO:1). Sizes of the polypeptide regions are shown at the top (aa=amino acids) as well as cleavage sites by signal peptidase (SP). (B) Capture of wild-type (WT) or Fc tag derived (Fc-d) E1E2 from CHO cell extracts was performed with GNA and Protein G Sepharose, respectively, and proteins separated by SDS-PAGE and blotted with anti-E1 (A4) and anti-E2 (H52) monoclonal antibodies (mAbs) (C) Purified E1E2 antigens (with PP-mediated Fc tag removal step for Fc-d) were separated by SDS-PAGE. Left panel: Western blot: anti-E1 (A4) and anti-E2 (H52) mAbs (1 µg load per lane). Right panel: Coomassie Brilliant Blue G250 (2 µg load per lane). (D) Wild type (WT) and Fc tag derived (Fc-d) E1E2 antigens (1 µg/lane) were denatured at 95° C. for 5 minutes in laemelli buffer with (R) or without (NR) 1% β-mercaptoethanol. Samples were separated by SDS-PAGE and blotted with ant-E1 (A4) and anti-E2 (H52) mAbs.

Binding of HCV Cross Neutralizing Monoclonal Antibodies (mAb) to Purified E1E2 Heterodimers E1E2 antigens were coated to ELISA plates and probed using E2-specific (HC33.4, HC84.26, and AR3B) and E1E2-specific (AR4A and AR5A) cross-neutralizing mAbs. HC33.4, HC84.26, and AR3B target the disparate regions of E2 that form the CD81 receptor binding site (CD81bs) and are capable of binding soluble E2. HC33.4 recognizes a linear epitope in E2 (aa 409-423). AR3B and HC84.26 are directed to conformation-specific E2 epitopes. However, HC84.26 additionally recognizes an E2 linear synthetic peptide (aa 433-447). AR4A and AR5A recognize unique conformational epitopes outside of the CD81bs and are capable of binding native E1E2 but not E2 or E1 alone. WT and Fc-d E1E2 antigens bound E2- and E1E2-specific antibodies in a nearly identical manner. These data support that, similar to WT, Fc-d E1E2 maintains correct folding and presents conformation-specific E2 and E1E2 cross-neutralizing epitopes.

The Fc-d E1E2 Heterodimer Elicits Neutralizing Antibodies (nAbs) in Mice

Figure 12A:
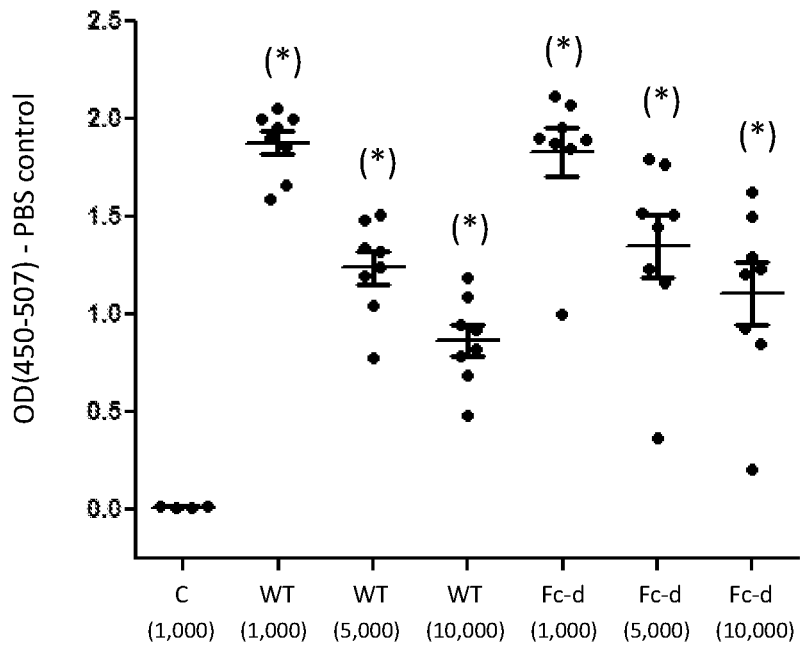
FIG. 12A-12B depict induction of neutralizing antibodies by vaccination with wild type (WT) E1/E2 heterodimer and with Fc-tag-derived (Fc-d) HCV E1/E2 heterodimer.

Eight CB6F1 mice were immunized with WT or Fc-d E1E2 (2 µg per injection) in a 1:1 ratio with adjuvant (75 µg alum and 7.5 µg MPLA). Four animals were injected with buffer containing adjuvant as controls. Animals received a total of three injections at 2 week intervals. Sera obtained from terminal bleeds were examined for homologous anti-E2 activity by ELISA plates coated with recombinant E2 HCV1 (1a). WT and Fc-d E1E2 vaccinated sera exhibited strong anti-E2 titers for E2 HCV1 at all dilutions examined (1000-, 5000-, and 10,000-fold) (FIG. 12A). For each dilution examined, sera from mice vaccinated with WT and Fc-d E1E2 were statistically elevated from controls ($p<0.05$; one-way ANOVA; Tukey's post-hoc test) (FIG. 12A). Mean absorbance values between sera from mice vaccinated with WT and Fc-d E1E2 exhibited no statistical difference at each dilution examined.

Figure 12B:
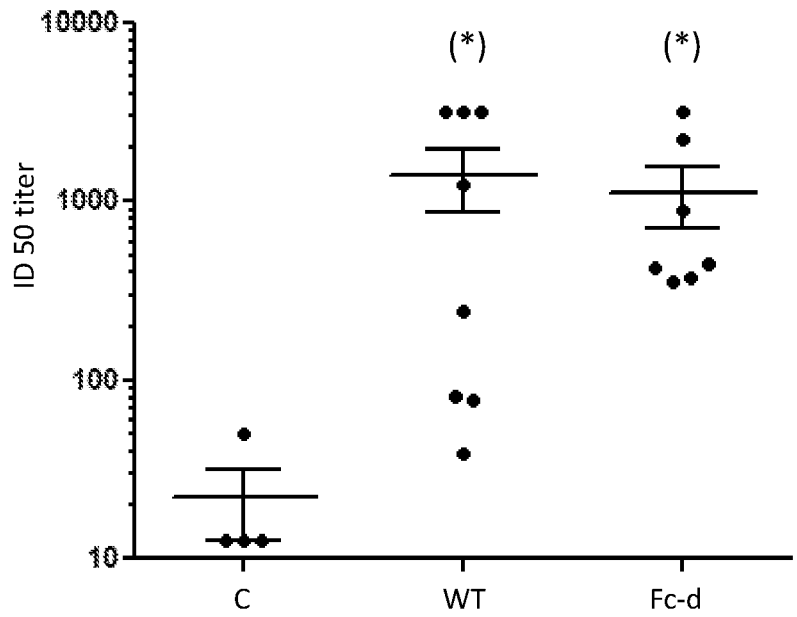
Figure 13:
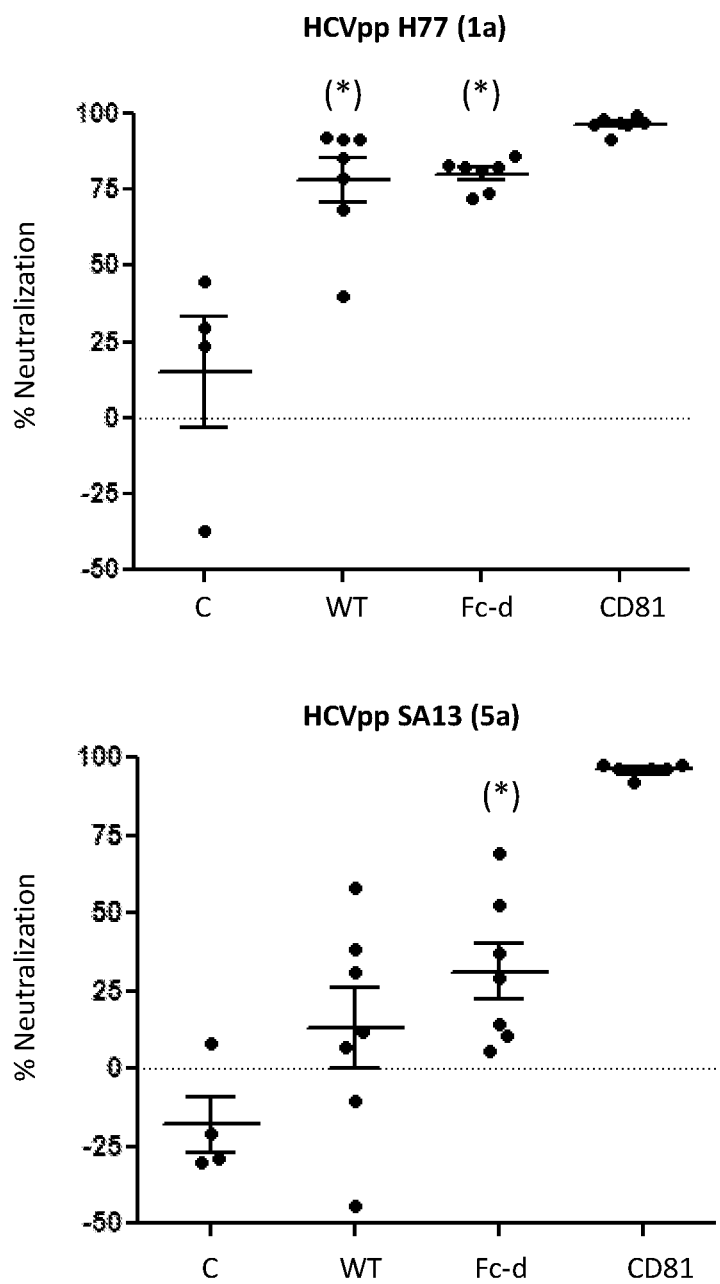
FIG. 13 depicts a comparison of neutralizing antibodies toward homologous (genotype 1a) and heterologous (genotype 5a) HCV polyprotein (HCVpp).

Pre- and post-vaccination serum samples were evaluated for their ability to inhibit the infectivity of HCVpp H77 in Huh7.5 cells. Two-fold serial dilutions (1:25 to 1:1600) of sera were examined and the inhibitory dose to achieve 50% neutralization (ID50) represented as the reciprocal value of the dilution (FIG. 12B). WT and Fc-D E1E2 exhibited similar group mean ID50 values of 1412±541 and 1134±428, respectively, that were each significant from the control group. Fc-d vaccinated mice exhibited less variability in ID50 values (min 360; max 3200) than the WT group (min 39; max 3200). The neutralization response of homologous genotype 1a (H77) to heterologous genotype 5a (SA13) HCVpp was compared. At 1:50 diluted sera WT and Fc-d groups showed very similar mean neutralizations of HCVpp H77 at 78.3±7.2% and 80.2±2.0%, respectively (FIG. 13). Fc-d vaccinated animals exhibited a significant neutralization of HCVpp SA13 (mean 31±9%) from controls. However, the WT group did not show neutralization towards SA13 that was significant from the control group (FIG. 13). No neutralization activity within the Fc-d group using further dilutions of the sera was detected.

FIG. 12A-12B: Neutralizing antibodies induced by vaccination with wild type (WT) and Fc-tag. (A) Recombinant E2 HCV1 (1a) (amino acids 384-661; Genbank M62321.1) was coated to ELISA plates in triplicate and probed with post-vaccinated mice sera. Binding of E2-specific antibodies in WT and Fc tag-derived (Fc-d) E1E2 vaccinated mice sera (1000, 5000, 10,000-fold dilutions) compared to control vaccinated sera (1000-fold dilution) were detected by anti-mouse horse radish peroxidase (HRP) conjugated secondary antibody and peroxidase substrate. The OD450-507 nm values (means and SEM) from three independent experiments are shown plotted vs serum dilution. (B) Neutralization of HCVpp H77c (1a) entry was performed using 2-fold dilutions (1:25 to 1:1600) of pre- and post-vaccinated sera and the ID50 values determined (shown as the reciprocal value of the dilution to achieve 50% neutralization). The group mean with SEM is shown from a representative of two independent experiments. Vaccinated mice groups: Control (C): buffer+alum/MPL; WT (GNA agarose-derived E1E2 H77c+alum/MPL); Fc-d (Fc tag-derived E1E2 H77c+alum/MPL). (*) designates $p<0.05$ respective to control (C) by One way ANOVA; Kruskal Wallis, Dunn's post-test.

FIG. 13: Comparison of neutralizing antibodies towards homologous (1a) and heterologous (5a) HCVpp. Neutralization of homologous HCVpp H77 (1a) and heterologous HCVpp SA13 (5a) was performed using pre- and post-vaccinated sera (1:50) and the group means with SEMs plotted from representatives of two independent experiments. Positive control: Anti-CD81 mAb (1 µg/ml). (*) designates $p<0.05$ respective to control (C) by One way ANOVA; Tukey post-test.

Antisera from E1E2-Vaccinated Mice Compete with Cross-Neutralizing HCV mAbs for Binding to E1/E2

Figure 14:
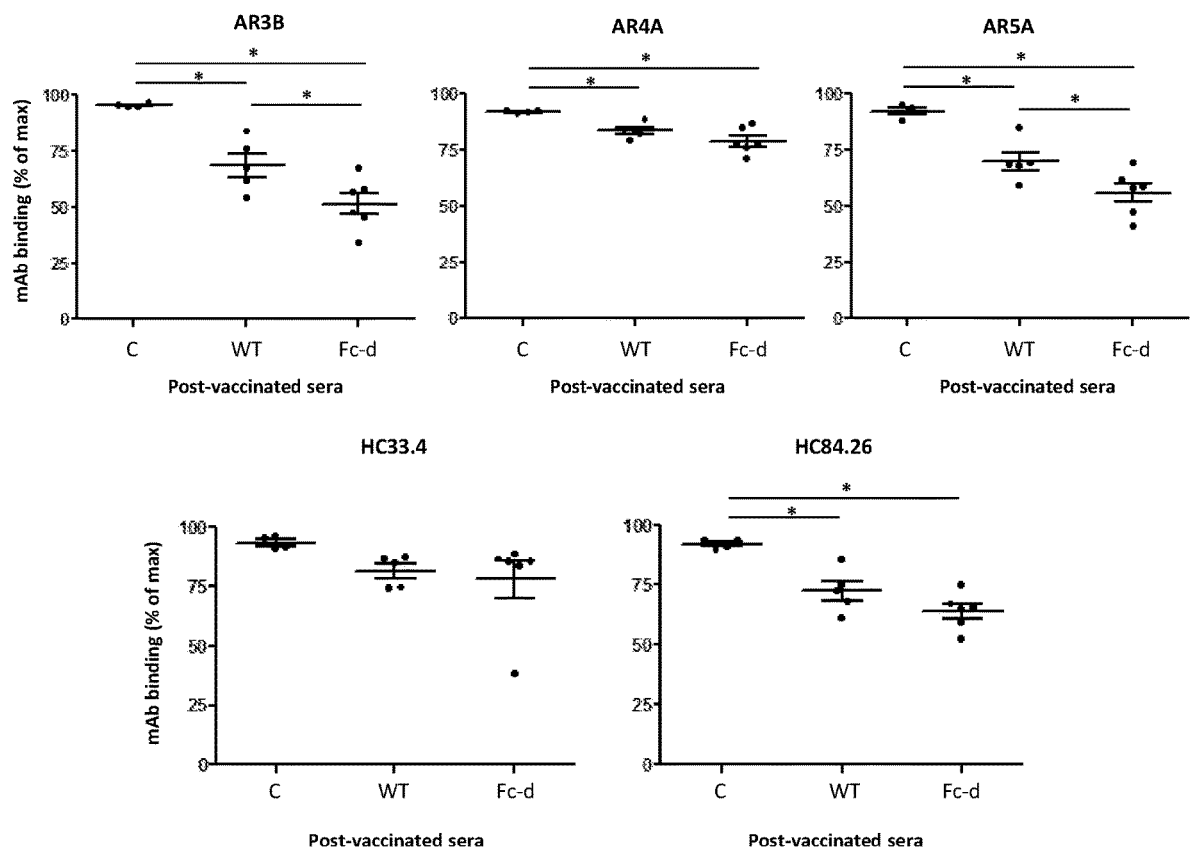
FIG. 14 depicts competition by mouse antisera with HCV cross-neutralizing monoclonal antibodies (mAb) for binding to wild-type (WT) or Fc-tag-derived (Fc-d) HCV E1/E2 heterodimer.

The observed neutralization responses of WT and Fc-d vaccinated mice for HCVpp H77 (1a) and HCVpp SA13 (5a) indicated a dominance towards homologous (1a) E1E2 epitopes. To determine if anti-E1E2 antibodies from WT and Fc-d E1E2 vaccinated animals targeted conserved epitopes to well-characterized HCV neutralizing mAbs, competition ELISA assays were performed according to Wong et al. (2014) infra. Antisera from control animals exhibited negligible competition with each of the mAbs examined: >90% mAb binding (normalized to maximum binding in the absence of any sera) (FIG. 14). Vaccination with WT and Fc-d E1E2 significantly reduced AR3B, AR4A, AR5A, and HC84.26 binding compared to control sera ($p<0.05$; one-way ANOVA; Tukey's post-hoc test). For HC33.4, neither the WT nor Fc-d E1E2 groups impaired the binding of this mAb significantly compared to controls.

For both the AR4A and HC84.26 mAbs, binding was reduced to a similar extent in WT and Fc-derived E1E2 vaccinated animals (AR4A: mean 83.4 and 78.8%; HC84.26: mean 72.3 and 63.8% for WT and Fc groups, respectively). For AR3B and AR5A, the Fc-d E1E2 vaccinated group impaired mAb binding to a greater extent than WT vaccinated animals (AR3B: mean 68.6 and 51.5%; AR5A: mean 69.8 and 55.9% for WT and Fc groups, respectively) ($p<0.05$; one-way ANOVA; Tukey's post-hoc test). These findings suggest that WT and Fc-d mice did elicit anti-HCV antibodies that target conserved neutralizing epitopes. However, it is noted that our competition ELISA likely exhibits high sensitivity since the neutralization of heterologous HCVpp SA13 (5a) was considerably lower compared to HCVpp H77 (1a) from WT and Fc-d group sera (FIG. 13).

FIG. 14. Mice antisera compete for the binding of HCV cross-neutralizing monoclonal antibodies (mAb) to E1E2. Competition studies with mouse antisera and a panel of cross-neutralizing human HCV antibodies. Microtiter wells containing GNA-purified E1E2 H77c were incubated with diluted post-vaccination antiserum (1:100) in triplicate for 1 h followed by incubation with the indicated mAb. Binding of the mAbs was detected with anti-human alkaline phosphatase-conjugated secondary antibodies. The percentages of mAb binding were calculated relative to the amount of mAb bound in the absence of antiserum. Shown are mean values for each group±range from two independent experiments. Vaccinated mice groups: Control (C): buffer+alum/MPL; WT (GNA agarose-derived E1E2 H77c+alum/MPL; Fc-d (Fc tag-derived E1E2 H77c+alum/MPL). E2-specific antibodies: HC33.4, HC84.26, AR3B. E1E2-specific antibodies: AR4A, AR5A. (*) designates p<0.05 by one-way ANOVA; Tukey's post-hoc test. With n=2 SEM is actually the same as the range.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of purifying a hepatitis C virus (HCV) E1/E2 heterodimer from a lysate, the method comprising:
   a) contacting a lysate of a genetically modified host cell with an affinity tag-binding polypeptide immobilized on an insoluble support, wherein the genetically modified host cell is genetically modified with a nucleic acid comprising a nucleotide sequence encoding a polyprotein comprising, in order from N-terminus to C-terminus:
      a) an HCV E1 polypeptide; and
      b) an HCV E2-affinity tag fusion polypeptide comprising, in order from N-terminus to C-terminus: i) an affinity tag polypeptide; ii) a proteolytically cleavable linker; and iii) an HCV E2 polypeptide
      i) a first nucleotide sequence encoding an HCV E1 polypeptide; and
      ii) a second nucleotide sequence encoding an HCV E2 polypeptide,
   wherein the polyprotein is processed in the host cell to produce the affinity tagged HCV E1/E2 heterodimer and the lysate comprises the affinity tagged HCV E1/E2 heterodimer,
   wherein the affinity tagged HCV E1/E2 heterodimer present in the lysate binds to the immobilized affinity tag-binding polypeptide, generating an immobilized affinity tagged HCV E1/E2 heterodimer;
   b) contacting the immobilized HCV E1/E2 heterodimer with a protease that cleaves the proteolytically cleavable linker present in the immobilized affinity tagged HCV E1/E2 heterodimer, thereby releasing the HCV E1/E2 heterodimer from the affinity tag; and
   c) collecting the HCV E1/E2 heterodimer.

2. The method of claim 1, wherein the affinity tag polypeptide is an Ig Fc polypeptide, and wherein the affinity tag-binding polypeptide is an immunoglobulin (Ig) Fc-binding polypeptide.

3. The method of claim 2, wherein the Ig Fc-binding polypeptide is Protein A, Protein G, or a Protein A/G fusion.

4. The method of claim 1, wherein the proteolytically cleavable linker comprises an amino acid sequence selected from the group consisting of LEVLFQGP as set forth in SEQ ID NO:1, ENLYFQS as set forth in SEQ ID NO:2, DDDDK as set forth in SEQ ID NO:3, I(E/D)GR as set forth in SEQ ID NO:45, and LVPRGS as set forth in SEQ ID NO:5.

5. The method of claim 1, wherein the proteolytically cleavable linker comprises the amino acid sequence ENLYFQS as set forth in SEQ ID NO:2, and wherein the protease is a tobacco etch virus protease.

6. The method of claim 1, wherein the proteolytically cleavable linker comprises the amino acid sequence LEVLFQGP as set forth in SEQ ID NO:1, and wherein the protease is a human rhinovirus 3C protease.

7. The method of claim 1, wherein the genetically modified host cell is a genetically modified Chinese hamster ovary (CHO) cell.

8. The method of claim 1, comprising removing the protease from a composition comprising the collected HCV E1/E2 heterodimer.

9. The method of claim 1, comprising further purifying the collected HCV E1/E2 heterodimer on a hydroxyapatite column.

10. The method of claim 1, wherein the nucleotide sequence encoding the polyprotein is operably linked to a promoter.

11. The method of claim 1, wherein the affinity tagged E1/E2 polypeptide comprises:
   a) an HCV E1 polypeptide having a length of from about 175 amino acids to about 195 amino acids; and
   b) an affinity-tagged HCV E2 polypeptide comprising, in order from N-terminus to C-terminus:
      i) an Ig Fc polypeptide;
      ii) a proteolytically cleavable linker, wherein the proteolytically cleavable linker comprises an amino acid sequence selected from the group consisting of LEVLFQGP as set forth in SEQ ID NO:1, ENLYFQS as set forth in SEQ ID NO: 2, DDDDK as set forth in SEQ ID NO:3, I(E/D)GR as set forth in SEQ ID NO: 45, and LVPRGS as set forth in SEQ ID NO:5; and
      iii) an HCV E2 polypeptide having a length of from about 350 amino acids to about 370 amino acids.

12. The method of claim 1, wherein the HCV E2 polypeptide and the HCV E1 polypeptide are of the same genotype.

13. The method of claim 1, wherein the HCV E2 polypeptide and the HCV E1 polypeptide are of different genotypes.

14. The method of claim 1, wherein the released HCV E1/E2 heterodimer is at least 50% pure.

15. The method of claim 1, wherein the released HCV E1/E2 heterodimer is at least 90% pure.

* * * * *

```
                        SEQUENCE LISTING

<160> NUMBER OF SEQ ID NOS: 123

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide.

<400> SEQUENCE: 1

Leu Glu Val Leu Phe Gln Gly Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide.

<400> SEQUENCE: 2

Glu Asn Leu Tyr Phe Gln Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 3

Asp Asp Asp Asp Lys
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide.

<400> SEQUENCE: 4

Leu Val Pro Arg
1

<210> SEQ ID NO 5
```

```
<211> LENGTH: 6
<212> TYPE: PRT
<213> ORGANISM: Artificial Sequence
<220> FEATURE:
<223> OTHER INFORMATION: Synthetic polypeptide.

<400> SEQUENCE: 5

Leu Val Pro Arg Gly Ser
1               5

<210> SEQ ID NO 6
<211> LENGTH: 23
<212> TYPE: PRT
<213> ORGANISM: Artificial Sequence
<220> FEATURE:
<223> OTHER INFORMATION: Synthetic polypeptide.

<400> SEQUENCE: 6

Met Asp Ala Met Lys Arg Gly Leu Cys Cys Val Leu Leu Leu Cys Gly
1               5                   10                  15

Ala Val Phe Val Ser Pro Ser
            20

<210> SEQ ID NO 7
<211> LENGTH: 6
<212> TYPE: PRT
<213> ORGANISM: Artificial Sequence
<220> FEATURE:
<223> OTHER INFORMATION: Synthetic polypeptide.

<400> SEQUENCE: 7

Leu Glu Val Leu Phe Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide.

<400> SEQUENCE: 8

Glu Asn Leu Tyr Phe Gln
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (1)..(5)
<223> OTHER INFORMATION: This stretch of residues may be repeated.

<400> SEQUENCE: 9

Gly Ser Gly Gly Ser
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
```

```
<222> LOCATION: (1)..(4)
<223> OTHER INFORMATION: This stretch of residues may be repeated.

<400> SEQUENCE: 10

Gly Gly Gly Ser
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide.

<400> SEQUENCE: 11

Gly Gly Ser Gly
1

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 12

Gly Gly Ser Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 13

Gly Ser Gly Ser Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 14

Gly Ser Gly Gly Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 15

Gly Gly Gly Ser Gly
1               5

<210> SEQ ID NO 16
<211> LENGTH: 5
<212> TYPE: PRT
<213> ORGANISM: Artificial Sequence
<220> FEATURE:
```

```
<223> OTHER INFORMATION: Synthetic polypeptide.

<400> SEQUENCE: 16

Gly Ser Ser Ser Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (2)..(2)
<223> OTHER INFORMATION: Xaa may be Leu or Gln.

<400> SEQUENCE: 17

Pro Xaa Gly Met Thr Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (2)..(2)
<223> OTHER INFORMATION: Xaa may be Leu or Gln.

<400> SEQUENCE: 18

Pro Xaa Gly Met Thr
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic polypeptide.

<400> SEQUENCE: 19

Cys Gly Leu Val Pro Ala Gly Ser Gly Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 20

Ser Leu Leu Lys Ser Arg Met Val Pro Asn Phe Asn
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 21

Ser Leu Leu Ile Ala Arg Arg Met Pro Asn Phe Asn
1               5                   10
```

<210> SEQ ID NO 22
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 22

Ser Lys Leu Val Gln Ala Ser Ala Ser Gly Val Asn
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 23

Ser Ser Tyr Leu Lys Ala Ser Asp Ala Pro Asp Asn
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 24

Arg Pro Lys Pro Gln Gln Phe Phe Gly Leu Met Asn
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 25

Ser Leu Arg Pro Leu Ala Leu Trp Arg Ser Phe Asn
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 26

Ser Pro Gln Gly Ile Ala Gly Gln Arg Asn Phe Asn
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic polypeptide.

<400> SEQUENCE: 27

Asp Val Asp Glu Arg Asp Val Arg Gly Phe Ala Ser Phe Leu
1               5                   10

```
<210> SEQ ID NO 28
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 28

Ser Leu Pro Leu Gly Leu Trp Ala Pro Asn Phe Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 29

Ser Leu Leu Ile Phe Arg Ser Trp Ala Asn Phe Asn
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 30

Ser Gly Val Val Ile Ala Thr Val Ile Val Ile Thr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 31

Ser Leu Gly Pro Gln Gly Ile Trp Gly Gln Phe Asn
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 32

Lys Lys Ser Pro Gly Arg Val Val Gly Gly Ser Val
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 33

Pro Gln Gly Leu Leu Gly Ala Pro Gly Ile Leu Gly
1               5                   10
```

```
<210> SEQ ID NO 34
<211> LENGTH: 31
<212> TYPE: PRT
<213> ORGANISM: Artificial Sequence
<220> FEATURE:
<223> OTHER INFORMATION: Synthetic polypeptide.

<400> SEQUENCE: 34

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 35
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 35

Gly Pro Gln Gly Leu Ala Gly Gln Arg Gly Ile Val
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 36

Gly Gly Ser Gly Gln Arg Gly Arg Lys Ala Leu Glu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 37

Ser Leu Ser Ala Leu Leu Ser Ser Asp Ile Phe Asn
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 38

Ser Leu Pro Arg Phe Lys Ile Ile Gly Gly Phe Asn
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 39

Ser Leu Leu Gly Ile Ala Val Pro Gly Asn Phe Asn
1               5                   10
```

<210> SEQ ID NO 40
<211> LENGTH: 12
<212> TYPE: PRT
<213> ORGANISM: Artificial Sequence
<220> FEATURE:
<223> OTHER INFORMATION: Synthetic polypeptide.

<400> SEQUENCE: 40

Phe Phe Lys Asn Ile Val Thr Pro Arg Thr Pro Pro
1               5                   10

<210> SEQ ID NO 41
<211> LENGTH: 22
<212> TYPE: PRT
<213> ORGANISM: Artificial Sequence
<220> FEATURE:
<223> OTHER INFORMATION: Synthetic polypeptide.

<400> SEQUENCE: 41

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 42
<211> LENGTH: 36
<212> TYPE: PRT
<213> ORGANISM: Artificial Sequence
<220> FEATURE:
<223> OTHER INFORMATION: Synthetic polypeptide.

<400> SEQUENCE: 42

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser
        35

<210> SEQ ID NO 43
<211> LENGTH: 7
<212> TYPE: PRT
<213> ORGANISM: Artificial Sequence
<220> FEATURE:
<223> OTHER INFORMATION: Synthetic polypeptide.

<400> SEQUENCE: 43

Glu Asn Leu Tyr Phe Gln Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (2)..(2)
<223> OTHER INFORMATION: Xaa may be Asp or Glu.
<220> FEATURE:
<221> NAME/KEY: MISC_FEATURE
<222> LOCATION: (5)..(5)
<223> OTHER INFORMATION: Xaa may be any amino acid except Arg or Pro.

<400> SEQUENCE: 44

```
Ile Xaa Gly Arg Xaa
1               5
```

<210> SEQ ID NO 45
<211> LENGTH: 4
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (2)..(2)
<223> OTHER INFORMATION: Xaa may be Asp or Glu.

<400> SEQUENCE: 45

```
Ile Xaa Gly Arg
1
```

<210> SEQ ID NO 46
<211> LENGTH: 746
<212> TYPE: PRT
<213> ORGANISM: Artificial Sequence
<220> FEATURE:
<223> OTHER INFORMATION: Synthetic polypeptide.
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (408)..(408)
<223> OTHER INFORMATION: Xaa can be any naturally occurring amino acid
<220> FEATURE:
<221> NAME/KEY: misc_feature
<222> LOCATION: (524)..(524)
<223> OTHER INFORMATION: Xaa can be any naturally occurring amino acid
<220> FEATURE:
<221> NAME/KEY: misc_feature
<222> LOCATION: (580)..(580)
<223> OTHER INFORMATION: Xaa can be any naturally occurring amino acid
<220> FEATURE:
<221> NAME/KEY: misc_feature
<222> LOCATION: (641)..(641)
<223> OTHER INFORMATION: Xaa can be any naturally occurring amino acid
<220> FEATURE:
<221> NAME/KEY: misc_feature
<222> LOCATION: (709)..(709)
<223> OTHER INFORMATION: Xaa can be any naturally occurring amino acid
<220> FEATURE:
<221> NAME/KEY: misc_feature
<222> LOCATION: (733)..(733)
<223> OTHER INFORMATION: Xaa can be any naturally occurring amino acid

<400> SEQUENCE: 46

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
```

```
            20                  25                  30
Gly Val Tyr Leu Leu Pro Arg Arg Gly Pro Arg Leu Gly Val Arg Ala
            35                  40                  45
Thr Arg Lys Thr Ser Glu Arg Ser Gln Pro Arg Gly Arg Arg Gln Pro
 50                  55                  60
Ile Pro Lys Ala Arg Arg Pro Glu Gly Arg Thr Trp Ala Gln Pro Gly
 65                  70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
                130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
                180                 185                 190
Gln Val Arg Asn Ser Ser Gly Leu Tyr His Val Thr Asn Asp Cys Pro
                195                 200                 205
Asn Ser Ser Ile Val Tyr Glu Thr Ala Asp Thr Ile Leu His Ser Pro
                210                 215                 220
Gly Cys Val Pro Cys Val Arg Glu Gly Asn Ala Ser Arg Cys Trp Val
225                 230                 235                 240
Ala Leu Thr Pro Thr Val Ala Xaa Arg Asp Gly Ser Leu Pro Thr Thr
                245                 250                 255
Gln Leu Arg Arg His Xaa Asp Leu Leu Val Gly Ser Ala Xaa Leu Cys
                260                 265                 270
Ser Ala Xaa Tyr Val Gly Asp Leu Cys Gly Ser Val Phe Leu Val Gly
                275                 280                 285
Gln Leu Phe Thr Phe Ser Pro Arg Arg His Trp Thr Thr Gln Asp Cys
                290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Val Ala Gln
                325                 330                 335
Leu Leu Arg Ile Pro Gln Ala Ile Leu Asp Met Ile Ala Gly Ala His
                340                 345                 350
Trp Gly Val Leu Ala Gly Ile Ala Tyr Phe Ser Met Val Gly Asn Trp
                355                 360                 365
Ala Lys Val Leu Val Val Leu Leu Phe Ala Gly Val Asp Ala Glu
                370                 375                 380
Thr His Val Thr Gly Gly Ser Ala Ala Arg Ala Thr Ser Gly Xaa Ala
385                 390                 395                 400
Ser Leu Phe Ser Pro Gly Ala Xaa Gln Asn Ile Gln Leu Ile Asn Thr
                405                 410                 415
Asn Gly Ser Trp His Ile Asn Arg Thr Ala Leu Asn Cys Asn Asp Ser
                420                 425                 430
Leu Asp Thr Gly Trp Val Ala Gly Leu Phe Tyr Tyr His Lys Phe Asn
                435                 440                 445
```

```
Ser Ser Gly Cys Pro Glu Arg Met Ala Ser Cys Arg Pro Leu Ala Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Gln Gln Val Cys Gly Pro Val Tyr Cys Phe Thr Pro Ser
            500                 505                 510

Pro Val Val Val Gly Thr Thr Asp Arg Leu Gly Xaa Pro Thr Tyr Asn
            515                 520                 525

Trp Gly Glu Asn Glu Thr Asp Val Leu Val Leu Asn Asn Thr Arg Pro
            530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Asn Ile Gly Gly Val Gly Asn
                565                 570                 575

Asn Thr Leu Xaa Cys Pro Thr Asp Cys Phe Arg Lys His Pro Glu Ala
            580                 585                 590

Thr Tyr Ser Arg Cys Gly Ser Gly Pro Trp Leu Thr Pro Arg Cys Leu
            595                 600                 605

Val Asp Tyr Pro Tyr Arg Leu Trp His Tyr Pro Cys Thr Val Asn Tyr
            610                 615                 620

Thr Ile Phe Lys Val Arg Met Tyr Val Gly Gly Val Glu His Arg Leu
625                 630                 635                 640

Xaa Ala Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Xaa Val Ser Trp Ala Ile Lys Trp Glu Tyr Val Ile
705                 710                 715                 720

Leu Leu Phe Leu Leu Leu Ala Asp Ala Arg Ile Cys Xaa Cys Leu Trp
                725                 730                 735

Met Met Leu Leu Ile Ser Gln Ala Glu Ala
            740                 745

<210> SEQ ID NO 47
<211> LENGTH: 746
<212> TYPE: PRT
<213> ORGANISM: Hepatitis C virus

<400> SEQUENCE: 47

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
```

```
            65                  70                  75                  80
Tyr Pro Trp Pro Leu Tyr Gly Asn Glu Gly Cys Gly Trp Ala Gly Trp
                    85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
                180                 185                 190
Gln Val Arg Asn Ser Thr Gly Leu Tyr His Val Thr Asn Asp Cys Pro
                195                 200                 205
Asn Ser Ser Ile Val Tyr Glu Ala Ala Asp Ala Ile Leu His Thr Pro
210                 215                 220
Gly Cys Val Pro Cys Val Arg Glu Gly Asn Thr Ser Arg Cys Trp Val
225                 230                 235                 240
Ala Met Thr Pro Thr Val Ala Thr Arg Asp Gly Lys Leu Pro Thr Thr
                245                 250                 255
Gln Leu Arg Arg His Ile Asp Leu Leu Val Gly Ser Ala Thr Leu Cys
                260                 265                 270
Ser Ala Leu Tyr Val Gly Asp Leu Cys Gly Ser Ile Phe Leu Val Gly
                275                 280                 285
Gln Met Phe Thr Phe Ser Pro Arg Arg His Trp Thr Thr Gln Asp Cys
                290                 295                 300
Asn Cys Ser Leu Tyr Pro Gly His Ile Thr Gly His Arg Met Ala Trp
305                 310                 315                 320
Asp Met Met Met Asn Trp Ser Pro Thr Ala Ala Leu Ile Thr Ala Gln
                    325                 330                 335
Leu Leu Arg Ile Pro Gln Ala Ile Leu Asp Met Ile Ala Gly Ala His
                340                 345                 350
Trp Gly Val Leu Ala Gly Ile Ala Tyr Phe Ser Met Val Gly Asn Trp
                355                 360                 365
Ala Lys Val Leu Val Val Leu Leu Leu Phe Ala Gly Val Asp Ala Gln
                370                 375                 380
Thr His Val Thr Gly Gly Arg Ala Ala His Ile Thr Ala Gly Leu Thr
385                 390                 395                 400
Ser Leu Phe Ser Pro Gly Pro Ser Gln Lys Leu Gln Leu Val Asn Thr
                405                 410                 415
Asn Gly Ser Trp His Ile Asn Ser Thr Ala Leu Asn Cys Asn Asp Ser
                420                 425                 430
Leu Lys Thr Gly Trp Ile Ala Gly Leu Leu Tyr Ser Tyr Lys Phe Asn
                435                 440                 445
Ser Ser Gly Cys Pro Glu Arg Leu Ala Ser Cys Arg Arg Leu Thr Asp
450                 455                 460
Phe Ala Gln Gly Trp Gly Pro Ile Ser His Ala Asn Gly Ser Gly Pro
465                 470                 475                 480
Asp Glu Arg Pro Tyr Cys Trp His Tyr Pro Arg Pro Cys Gly Ile
                485                 490                 495
```

Val Pro Ala Lys Ser Val Cys Gly Pro Val Tyr Cys Phe Thr Pro Ser
            500                 505                 510

Pro Val Val Val Gly Thr Thr Asp Lys Ser Gly Ala Pro Thr Tyr Asn
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu Arg Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Val Asn Tyr
    610                 615                 620

Ser Ile Phe Lys Ile Arg Met Tyr Leu Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Val Ala Ser Trp Ala Ile Lys Trp Asp Tyr Val Val
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 48
<211> LENGTH: 746
<212> TYPE: PRT
<213> ORGANISM: Hepatitis C virus

<400> SEQUENCE: 48

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys

```
            115                 120                 125
Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
            355                 360                 365

Ala Lys Val Leu Val Val Leu Leu Leu Phe Ala Gly Val Asp Ala Glu
370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
            435                 440                 445

Ser Ser Gly Cys Pro Glu Arg Leu Ala Ser Cys Arg Arg Leu Thr Asp
            450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
530                 535                 540
```

```
Pro Leu Gly Asn Trp Phe Gly Cys Thr Trp Met Asn Ser Thr Gly Phe
545                 550                 555                 560

Thr Lys Val Cys Gly Ala Pro Cys Val Ile Gly Gly Val Gly Asn
            565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala
                740                 745

<210> SEQ ID NO 49
<211> LENGTH: 746
<212> TYPE: PRT
<213> ORGANISM: Hepatitis C virus

<400> SEQUENCE: 49

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Val Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
```

```
                    165                 170                 175
Phe Leu Leu Ala Leu Leu Ser Cys Leu Thr Val Pro Ala Ser Ala Tyr
                180                 185                 190
Gln Val Arg Asn Ser Ser Gly Ile Tyr His Val Thr Asn Asp Cys Pro
                195                 200                 205
Asn Ser Ser Ile Val Tyr Glu Thr Ala Asp Thr Ile Leu His Ser Pro
210                 215                 220
Gly Cys Val Pro Cys Val Arg Glu Gly Asn Ala Ser Lys Cys Trp Val
225                 230                 235                 240
Ala Leu Ala Pro Thr Val Ala Thr Arg Asp Gly Lys Leu Pro Thr Thr
                245                 250                 255
Gln Leu Arg Arg His Ile Asp Leu Leu Val Gly Ser Ala Thr Leu Cys
                260                 265                 270
Ser Ala Leu Tyr Val Gly Asp Leu Cys Gly Ser Val Phe Leu Val Gly
            275                 280                 285
Gln Leu Phe Thr Phe Ser Pro Arg Arg His Trp Thr Thr Gln Asp Cys
            290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Val Ala Gln
                325                 330                 335
Leu Leu Arg Val Pro Gln Ala Ile Leu Asp Met Ile Ala Gly Ala His
                340                 345                 350
Trp Gly Val Leu Ala Gly Ile Ala Tyr Phe Ser Met Val Gly Asn Trp
            355                 360                 365
Ala Lys Val Leu Val Val Leu Leu Leu Phe Ala Gly Val Asp Ala Glu
            370                 375                 380
Thr Tyr Thr Thr Gly Gly Ser Val Ala Gln Ala Ala Phe Gly Leu Thr
385                 390                 395                 400
Ser Leu Phe Arg Pro Gly Pro Lys Gln Asp Ile Gln Leu Ile Asn Thr
                405                 410                 415
Asn Gly Ser Trp His Ile Asn Arg Thr Ala Leu Asn Cys Asn Ala Ser
                420                 425                 430
Leu Asp Thr Gly Trp Val Ala Gly Leu Phe Tyr Tyr His Lys Phe Asn
            435                 440                 445
Ser Ser Gly Cys Pro Glu Arg Met Ala Ser Cys Arg Ser Leu Ala Asp
            450                 455                 460
Phe Asp Gln Gly Trp Gly Pro Ile Ser Tyr Ala Asn Gly Ser Gly Pro
465                 470                 475                 480
Glu His Arg Pro Tyr Cys Trp His Tyr Pro Lys Pro Cys Gly Ile
                485                 490                 495
Val Pro Ala Gln Asn Val Cys Gly Pro Val Tyr Cys Phe Thr Pro Ser
                500                 505                 510
Pro Val Val Val Gly Thr Thr Asn Lys Leu Gly Val Pro Thr Tyr Ser
            515                 520                 525
Trp Gly Ser Asn Glu Thr Asp Val Leu Val Leu Asn Asn Thr Arg Pro
            530                 535                 540
Pro Leu Gly Asn Trp Phe Gly Cys Thr Trp Met Asn Ser Ser Gly Phe
545                 550                 555                 560
Thr Lys Val Cys Gly Ala Pro Pro Cys Val Ile Gly Gly Ala Gly Asn
                565                 570                 575
Arg Thr Leu His Cys Pro Thr Asp Cys Phe Arg Lys His Pro Glu Ala
                580                 585                 590
```

```
Thr Tyr Ser Arg Cys Gly Ser Gly Pro Trp Ile Thr Pro Arg Cys Leu
            595                 600                 605

Val His Tyr Pro Tyr Arg Leu Trp His Tyr Pro Cys Thr Val Asn Tyr
610                 615                 620

Thr Met Phe Lys Val Arg Met Tyr Val Gly Gly Val Glu His Arg Leu
625                 630                 635                 640

Glu Val Ala Cys Asn Trp Thr Arg Gly Glu Arg Cys Asp Leu Asp Asp
            645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Thr Thr Gly
            675                 680                 685

Leu Ile His Leu His Gln Asn Ile Val Asp Val Gln Tyr Leu Tyr Gly
            690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 50
<211> LENGTH: 746
<212> TYPE: PRT
<213> ORGANISM: Hepatitis C virus

<400> SEQUENCE: 50

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Phe
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
```

```
                210             215             220
Gly Cys Val Pro Cys Val Arg Glu Asp Asn Thr Ser Arg Cys Trp Val
225                 230                 235                 240

Ala Val Ala Pro Thr Val Ala Thr Arg Asp Gly Arg Leu Pro Thr Thr
                    245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                    325                 330                 335

Leu Leu Arg Val Pro Gln Ala Ile Leu Asp Met Ile Ala Gly Ala His
                340                 345                 350

Trp Gly Val Leu Ala Gly Ile Ala Tyr Phe Ser Met Val Gly Asn Trp
            355                 360                 365

Ala Lys Val Leu Val Val Leu Leu Phe Ala Ser Val Asp Ala Glu
            370                 375                 380

Thr Tyr Thr Ser Gly Gly Ser Val Ala Arg Ala Thr Ala Gly Phe Ala
385                 390                 395                 400

Gly Ile Phe Asn Pro Gly Ala Lys Gln Asp Ile Gln Leu Ile Asn Thr
                    405                 410                 415

Asn Gly Ser Trp His Ile Asn Arg Thr Ala Leu Asn Cys Asn Ala Ser
                420                 425                 430

Leu Asp Thr Gly Trp Val Ala Gly Leu Phe Tyr Tyr His Lys Phe Asn
            435                 440                 445

Ser Ser Gly Cys Pro Glu Arg Met Ala Ser Cys Lys Pro Leu Ala His
            450                 455                 460

Phe Ala Gln Gly Trp Gly Pro Ile Ser Tyr Ala Asn Gly Ser Gly Pro
465                 470                 475                 480

Asp His Arg Pro Tyr Cys Trp His Tyr Pro Pro Lys Pro Cys Gly Ile
                    485                 490                 495

Val Pro Ala Gln Asn Val Cys Gly Pro Val Tyr Cys Phe Thr Pro Ser
                500                 505                 510

Pro Val Val Val Gly Thr Thr Asn Lys Leu Gly Ala Pro Thr Tyr Asn
            515                 520                 525

Trp Gly Ser Asn Asp Thr Asp Val Phe Ile Leu Asn Asn Thr Arg Pro
            530                 535                 540

Pro Gly Gly Asn Trp Phe Gly Cys Thr Trp Met Asn Ser Ser Gly Phe
545                 550                 555                 560

Thr Lys Val Cys Gly Ala Pro Pro Cys Thr Ile Gly Gly Val Gly Asn
                    565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Val Thr Pro Arg Phe Leu
            595                 600                 605

Val His Tyr Pro Tyr Arg Leu Trp His Tyr Pro Cys Thr Val Asn Tyr
            610                 615                 620

Thr Leu Phe Lys Val Arg Met Tyr Val Gly Gly Val Glu His Arg Leu
625                 630                 635                 640
```

```
Glu Val Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
    690                 695                 700

Val Gly Ser Ser Leu Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 51
<211> LENGTH: 746
<212> TYPE: PRT
<213> ORGANISM: Hepatitis C virus

<400> SEQUENCE: 51

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
    210                 215                 220

Gly Cys Val Pro Cys Val Arg Glu Gly Asn Thr Ser Lys Cys Trp Val
225                 230                 235                 240

Ala Val Ala Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
```

```
            260                 265                 270
Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
        290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Thr Ala Gln
                325                 330                 335

Leu Leu Arg Val Pro Gln Ala Ile Leu Asp Met Ile Ala Gly Ala His
        340                 345                 350

Trp Gly Val Leu Ala Gly Ile Ala Tyr Phe Ser Met Ala Gly Asn Trp
        355                 360                 365

Ala Lys Val Leu Leu Val Leu Leu Leu Phe Ala Gly Val Asp Ala Glu
        370                 375                 380

Thr Tyr Thr Thr Gly Gly Ser Val Ala Arg Thr Thr Arg Gly Leu Ala
385                 390                 395                 400

Ser Leu Leu Gln Val Gly Pro Lys Gln Asp Ile Arg Leu Ile His Thr
        405                 410                 415

Asn Gly Ser Trp His Ile Asn Arg Thr Ala Leu Asn Cys Asn Ala Ser
        420                 425                 430

Leu Asp Thr Gly Trp Leu Ala Gly Leu Leu Tyr Tyr His Lys Phe Asn
        435                 440                 445

Ser Ser Gly Cys Pro Glu Arg Met Ala Ser Cys Arg Pro Leu Ala Asp
        450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Lys Pro Cys Gly Ile
                485                 490                 495

Val Pro Ala Gln Thr Val Cys Gly Pro Val Tyr Cys Phe Thr Pro Ser
        500                 505                 510

Pro Val Val Gly Thr Thr Asn Lys Leu Gly Val Pro Thr Tyr Thr
        515                 520                 525

Trp Gly Ser Asn Asp Thr Asp Val Phe Val Leu Asn Asn Thr Arg Pro
        530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu His Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Val Asn Tyr
        610                 615                 620

Thr Leu Phe Lys Val Arg Met Tyr Val Gly Gly Val Glu His Arg Leu
625                 630                 635                 640

Gln Ala Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Thr Thr Gly
        675                 680                 685
```

```
Leu Ile His Leu His Gln Asn Ile Val Asp Val Gln Tyr Leu Tyr Gly
            690                 695                 700
Val Gly Ser Ser Ile Val Ser Trp Ala Ile Lys Trp Glu Tyr Val Ile
705                 710                 715                 720
Leu Leu Phe Leu Leu Ala Asp Ala Arg Ile Cys Ser Cys Leu Trp
                725                 730                 735
Met Met Leu Leu Ile Ser Gln Ala Glu Ala
            740                 745

<210> SEQ ID NO 52
<211> LENGTH: 746
<212> TYPE: PRT
<213> ORGANISM: Hepatitis C virus

<400> SEQUENCE: 52

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Ile Val Tyr Glu Thr Ala Asp Thr Ile Leu His Ser Pro
210                 215                 220

Gly Cys Val Pro Cys Val Arg Glu Asp Asn Ala Ser Arg Cys Trp Val
225                 230                 235                 240

Pro Val Ala Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Ser
            275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Thr Gly His Arg Met Ala Trp
```

```
            305                 310                 315                 320
Asp Met Met Met Asn Trp Ser Pro Thr Val Ala Leu Val Met Ala Gln
                325                 330                 335
Leu Leu Arg Val Pro Gln Ala Ile Leu Asp Met Ile Ala Gly Ala His
                340                 345                 350
Trp Gly Val Leu Ala Gly Ile Ala Tyr Phe Ser Met Val Gly Asn Trp
                355                 360                 365
Ala Lys Val Leu Val Leu Leu Phe Ala Gly Val Asp Ala Gln
                370                 375             380
Thr Tyr Val Thr Gly Gly Ser Ala Ala Arg Gly Ala Ser Gly Leu Ala
385                 390                 395                 400
Asn Leu Phe Thr Pro Gly Ala Lys Gln Asp Ile Gln Leu Ile Asn Thr
                405                 410                 415
Asn Gly Ser Trp His Ile Asn Arg Thr Ala Leu Asn Cys Asn Ala Ser
                420                 425                 430
Leu Asp Thr Gly Trp Val Ala Gly Leu Phe Tyr Tyr His Lys Phe Asn
                435                 440                 445
Ser Ser Gly Cys Pro Glu Arg Met Ala Ser Cys Lys Pro Leu Ala Asp
            450                 455                 460
Phe Asp Gln Gly Trp Gly Pro Ile Arg His Ala Asn Gly Ser Gly Pro
465                 470                 475                 480
Glu His Arg Pro Tyr Cys Trp His Tyr Pro Pro Lys Pro Cys Gly Ile
                485                 490                 495
Val Ser Ala Gln Thr Val Cys Gly Pro Val Tyr Cys Phe Thr Pro Ser
                500                 505                 510
Pro Val Val Val Gly Thr Thr Asn Arg Leu Gly Val Pro Thr Tyr Ser
            515                 520                 525
Trp Gly Thr Asn Asp Thr Asp Val Phe Val Leu Asn Asn Thr Arg Pro
            530                 535                 540
Pro Leu Gly Asn Trp Phe Gly Cys Thr Trp Met Asn Ser Ser Gly Phe
545                 550                 555                 560
Thr Lys Val Cys Gly Ala Pro Pro Cys Val Ile Gly Gly Val Gly Asn
                565                 570                 575
Asn Thr Leu His Cys Pro Thr Asp Cys Phe Arg Lys His Pro Glu Ala
                580                 585                 590
Thr Tyr Ser Arg Cys Gly Ser Gly Pro Trp Ile Thr Pro Arg Cys Leu
                595                 600                 605
Val His Tyr Pro Tyr Arg Leu Trp His Tyr Pro Cys Thr Val Asn Tyr
            610                 615                 620
Thr Leu Phe Lys Val Arg Met Tyr Val Gly Gly Val Glu His Arg Leu
625                 630                 635                 640
Glu Val Ala Cys Asn Trp Thr Arg Gly Glu Arg Cys Asp Leu Asp Asp
                645                 650                 655
Arg Asp Arg Ser Glu Leu Ser Pro Leu Leu Leu Ser Thr Thr Gln Trp
                660                 665                 670
Gln Val Leu Pro Cys Ser Phe Thr Thr Leu Pro Ala Leu Thr Thr Gly
            675                 680                 685
Leu Ile His Leu His Gln Asn Ile Val Asp Val Gln Tyr Leu Tyr Gly
            690                 695                 700
Val Gly Ser Ser Ile Val Ser Trp Ala Ile Lys Trp Glu Tyr Val Ile
705                 710                 715                 720
Leu Leu Phe Leu Leu Leu Ala Asp Ala Arg Ile Cys Ser Cys Leu Trp
                725                 730                 735
```

Met Met Leu Leu Ile Ser Gln Ala Glu Ala
            740                 745

<210> SEQ ID NO 53
<211> LENGTH: 746
<212> TYPE: PRT
<213> ORGANISM: Hepatitis C virus

<400> SEQUENCE: 53

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Thr
            35                  40                  45

Thr Arg Lys Thr Ser Glu Arg Ser Glu Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Ile Val Tyr Glu Thr Lys Asp Thr Ile Leu His Ser Pro
210                 215                 220

Gly Cys Val Pro Cys Val Arg Glu Gly Asn Val Ser Lys Cys Trp Val
225                 230                 235                 240

Pro Val Ala Leu Thr Val Ala Thr Arg Asp Gly Asn Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
    290                 295                 300

Asn Cys Ser Met Tyr Pro Gly His Ile Thr Gly His Arg Met Ala Trp
305                 310                 315                 320

Asp Met Met Met Asn Trp Ser Pro Thr Ser Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Leu Ala Tyr Phe Ser Met Val Gly Asn Trp

```
                355                 360                 365
Ala Lys Val Leu Val Leu Leu Phe Ala Ser Val Asp Ala Gly
        370                 375                 380

Thr His Val Thr Gly Gly Ser Ala Ala His Asp Val Ser Ala Leu Ala
385                 390                 395                 400

Gly Phe Phe Arg Arg Gly Ala Lys Gln Asn Ile Gln Leu Ile Asn Thr
                405                 410                 415

Asn Gly Ser Trp His Val Asn Arg Thr Ala Leu Asn Cys Asn Ala Ser
                420                 425                 430

Leu Asp Thr Gly Trp Val Ala Gly Leu Leu Tyr Tyr His Arg Phe Asn
            435                 440                 445

Ser Ser Gly Cys Pro Glu Arg Met Ala Ser Cys Arg Pro Leu Ala Asp
        450                 455                 460

Phe Asp Gln Gly Trp Gly Pro Ile Thr Asn Val Asp Gly Gly Ser
465                 470                 475                 480

Glu Tyr Arg Pro Tyr Cys Trp His Tyr Pro Lys Pro Cys Gly Ile
                485                 490                 495

Glu Pro Ala Gln Asn Val Cys Gly Pro Val Tyr Cys Phe Thr Pro Ser
            500                 505                 510

Pro Val Val Gly Thr Thr Asp Lys Val Gly Val Pro Thr Tyr Asn
        515                 520                 525

Trp Gly Glu Asn Asp Thr Asp Val Phe Val Leu Asn Asn Thr Arg Pro
530                 535                 540

Pro Leu Gly Asn Trp Phe Gly Cys Thr Trp Met Asn Ser Ser Gly Phe
545                 550                 555                 560

Val Lys Val Cys Gly Ala Pro Pro Cys Ile Ile Gly Gly Ala Gly Asn
                565                 570                 575

Lys Thr Leu His Cys Pro Thr Asp Cys Phe Arg Lys His Pro Asp Ala
            580                 585                 590

Thr Tyr Ser Arg Cys Gly Ser Gly Pro Trp Leu Thr Pro Arg Cys Leu
        595                 600                 605

Val Asp Tyr Pro Tyr Arg Leu Trp His Tyr Pro Cys Thr Val Asn Tyr
610                 615                 620

Thr Leu Phe Lys Ile Arg Met Tyr Val Gly Gly Val Glu His Arg Leu
625                 630                 635                 640

Val Ala Ala Cys Asn Trp Thr Tyr Gly Glu Arg Cys Asn Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
690                 695                 700

Val Gly Ser Ser Ile Val Ser Trp Ala Ile Lys Trp Glu Tyr Val Ile
                705                 710                 715                 720

Leu Leu Phe Leu Leu Leu Ala Asp Ala Arg Ile Cys Ser Cys Leu Trp
            725                 730                 735

Met Met Leu Leu Ile Ser Gln Ala Glu Ala
                740                 745

<210> SEQ ID NO 54
<211> LENGTH: 746
<212> TYPE: PRT
<213> ORGANISM: Hepatitis C virus
```

<400> SEQUENCE: 54

```
Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gln Ile Val Gly
            20                  25                  30
Gly Val Tyr Leu Leu Pro Arg Arg Gly Pro Arg Leu Gly Val Arg Ala
            35                  40                  45
Thr Arg Lys Thr Ser Glu Arg Ser Gln Pro Arg Gly Arg Gln Pro
50                  55                  60
Ile Pro Lys Ala Arg Arg Pro Glu Gly Arg Thr Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Leu
130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
                180                 185                 190
Gln Val Arg Asn Ser Ser Gly Leu Tyr His Val Thr Asn Asp Cys Pro
            195                 200                 205
Asn Ser Ser Ile Val Tyr Glu Thr Ala Asp Thr Ile Leu His Ser Pro
210                 215                 220
Gly Cys Val Pro Cys Val Arg Glu Gly Asn Ala Ser Lys Cys Trp Val
225                 230                 235                 240
Ala Val Ala Pro Thr Val Ala Thr Arg Asp Gly Thr Leu Pro Thr Thr
                245                 250                 255
Gln Leu Arg Arg His Ile Asp Leu Leu Val Gly Gly Ala Thr Leu Cys
            260                 265                 270
Ser Ala Leu Tyr Val Gly Asp Leu Cys Gly Ser Val Phe Leu Val Gly
            275                 280                 285
Gln Leu Phe Thr Phe Ser Pro Arg Arg His Trp Thr Thr Gln Asp Cys
            290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Ile Val Ala Gln
                325                 330                 335
Leu Leu Arg Val Pro Gln Ala Ile Leu Asp Met Ile Ala Gly Ala His
            340                 345                 350
Trp Gly Val Leu Ala Gly Ile Ala Tyr Phe Ser Met Val Gly Asn Trp
            355                 360                 365
Ala Lys Val Leu Val Val Leu Leu Phe Ala Gly Val Asp Ala Glu
            370                 375                 380
Thr His Val Thr Gly Gly Ser Ala Ala Gln Val Thr Ser Arg Val Ala
385                 390                 395                 400
Gly Phe Phe Asn Pro Gly Pro Lys Gln Asn Val Gln Leu Ile Asn Thr
```

```
                    405                 410                 415
Asn Gly Ser Trp His Ile Asn Arg Thr Ala Leu Asn Cys Asn Ala Ser
            420                 425                 430

Leu Asp Thr Gly Trp Val Ala Gly Leu Phe Tyr His Tyr Asn Phe Asn
        435                 440                 445

Ser Ser Gly Cys Pro Glu Arg Met Ala Ser Cys Arg Pro Leu Ala Asp
    450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Pro Lys Pro Cys Gly Ile
                485                 490                 495

Val Pro Ala Gln Asn Val Cys Gly Pro Val Tyr Cys Phe Thr Pro Ser
            500                 505                 510

Pro Val Val Val Gly Thr Thr Asn Arg Leu Gly Val Pro Thr Tyr Asn
        515                 520                 525

Trp Gly Ser Asn Asp Thr Asp Val Phe Val Leu Asn Asn Thr Arg Pro
530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Val Gly Asn
                565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val His Tyr Pro Tyr Arg Leu Trp His Tyr Pro Cys Thr Val Asn Tyr
    610                 615                 620

Thr Leu Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
    690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 55
<211> LENGTH: 746
<212> TYPE: PRT
<213> ORGANISM: Hepatitis C virus

<400> SEQUENCE: 55

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

```
Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Gln Pro
 50                  55                  60

Ile Pro Lys Ala Arg Arg Pro Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Ile Tyr His Val Thr Asn Asp Cys Pro
            195                 200                 205

Asn Ser Ser Ile Val Tyr Glu Thr Ala Asp Thr Ile Leu His Ser Pro
210                 215                 220

Gly Cys Val Pro Cys Val Arg Glu Gly Asn Ala Ser Lys Cys Trp Val
225                 230                 235                 240

Ala Leu Ala Pro Thr Val Ala Thr Arg Asp Gly Arg Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
            355                 360                 365

Ala Lys Val Leu Val Val Leu Leu Leu Phe Ala Gly Val Asp Ala His
370                 375                 380

Thr Arg Val Thr Gly Gly Ser Ala Ala Arg Ala Thr Ala Arg Leu Thr
385                 390                 395                 400

Thr Leu Phe Ser Pro Gly Ala Lys Gln Asp Ile Gln Leu Ile Asn Thr
                405                 410                 415

Asn Gly Ser Trp His Ile Asn Arg Thr Ala Leu Asn Cys Asn Ala Ser
                420                 425                 430

Leu Asp Thr Gly Trp Val Ala Gly Leu Phe Tyr Tyr His Lys Phe Asn
            435                 440                 445

Ser Ser Gly Cys Pro Glu Arg Met Ala Ser Cys Arg Pro Leu Ala Asp
```

```
              450                 455                 460
    Phe Asp Gln Gly Trp Gly Pro Ile Ser Tyr Ala Asn Gly Ser Gly Pro
    465                 470                 475                 480

Glu His Arg Pro Tyr Cys Trp His Tyr Pro Lys Pro Cys Gly Ile
                        485                 490                 495

Ile Pro Ala Lys Thr Val Cys Gly Pro Val Tyr Cys Phe Thr Pro Ser
                    500                 505                 510

Pro Val Val Gly Thr Thr Asp Arg Ser Gly Ala Pro Thr Phe Asn
                515                 520                 525

Trp Gly Asp Asn Asp Thr Asp Val Leu Val Leu Asn Asn Thr Arg Pro
                530                 535                 540

Pro Leu Gly Asn Trp Phe Gly Cys Thr Trp Met Asn Ser Ser Gly Tyr
    545                 550                 555                 560

Thr Lys Val Cys Gly Ala Pro Pro Cys Ile Ile Gly Gly Val Gly Asn
                        565                 570                 575

Asn Thr Leu His Cys Pro Thr Asp Cys Phe Arg Lys His Pro Glu Ala
                    580                 585                 590

Thr Tyr Ser Arg Cys Gly Ser Gly Pro Trp Ile Thr Pro Arg Cys Leu
                    595                 600                 605

Val His Tyr Pro Tyr Arg Leu Trp His Tyr Pro Cys Thr Val Asn Tyr
                    610                 615                 620

Thr Leu Phe Lys Val Arg Met Tyr Val Gly Gly Val Glu His Arg Leu
    625                 630                 635                 640

Glu Ala Ala Cys Asn Trp Thr Arg Gly Glu Arg Cys Asn Leu Asp Asp
                        645                 650                 655

Arg Asp Arg Ser Glu Leu Ser Pro Leu Leu Leu Ser Thr Thr Gln Trp
                    660                 665                 670

Gln Val Leu Pro Cys Ser Phe Thr Thr Leu Pro Ala Leu Thr Thr Gly
                    675                 680                 685

Leu Ile His Leu His Gln Asn Ile Val Asp Val Gln Tyr Leu Tyr Gly
                    690                 695                 700

Val Gly Ser Ser Ile Val Ser Trp Ala Ile Lys Trp Glu Tyr Val Ile
    705                 710                 715                 720

Leu Leu Phe Leu Leu Leu Ala Asp Ala Arg Val Cys Ser Cys Leu Trp
                        725                 730                 735

Met Met Leu Leu Ile Ser Gln Val Glu Ala
                    740                 745

<210> SEQ ID NO 56
<211> LENGTH: 746
<212> TYPE: PRT
<213> ORGANISM: Hepatitis C virus

<400> SEQUENCE: 56

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80
```

-continued

```
Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
    210                 215                 220

Gly Cys Val Pro Cys Val Arg Glu Gly Asn Ala Ser Lys Cys Trp Val
225                 230                 235                 240

Ala Val Thr Pro Thr Val Ala Thr Arg Asp Gly Arg Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Ile Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Gly
    370                 375                 380

Thr His Val Thr Gly Gly Ser Ala Ala Lys Asp Thr Ser Gly Phe Thr
385                 390                 395                 400

Ser Leu Phe Arg Ile Gly Ala Arg Gln Asn Ile Gln Leu Ile Asn Ser
                405                 410                 415

Asn Gly Ser Trp His Ile Asn Arg Thr Ala Leu Asn Cys Asn Glu Ser
            420                 425                 430

Leu Asp Thr Gly Trp Val Ala Gly Leu Leu Tyr Tyr His Lys Phe Asn
        435                 440                 445

Ser Ser Gly Cys Pro Glu Arg Met Ala Ser Cys Arg Ser Leu Ala Asp
    450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Lys Pro Cys Gly Ile
                485                 490                 495

Val Pro Ala Gln Ser Val Cys Gly Pro Val Tyr Cys Phe Thr Pro Ser
```

```
                500                 505                 510
Pro Val Val Gly Thr Thr Asp Lys Ser Gly Ala Pro Thr Tyr Asn
            515                 520                 525

Trp Gly Cys Asn Glu Thr Asp Val Phe Val Leu Asn Asn Thr Arg Pro
        530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Gly Val Gly Asn
                565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val His Tyr Ala Tyr Arg Leu Trp His Tyr Pro Cys Thr Val Asn Tyr
            610                 615                 620

Thr Leu Phe Lys Val Arg Met Tyr Val Gly Gly Val Glu His Arg Leu
625                 630                 635                 640

Asp Val Ala Cys Asn Trp Thr Arg Gly Glu Arg Cys Asn Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
            690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 57
<211> LENGTH: 746
<212> TYPE: PRT
<213> ORGANISM: Hepatitis C virus

<400> SEQUENCE: 57

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

```
Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
210                 215                 220

Gly Cys Val Pro Cys Val Arg Glu Gly Asn Ala Ser Lys Cys Trp Val
225                 230                 235                 240

Ala Val Thr Pro Thr Val Ala Thr Arg Asp Gly Arg Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Ile Phe Leu Val Gly
        275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Gly Thr
370                 375                 380

Thr His Val Thr Gly Gly Ser Ala Ala Lys Asp Thr Ser Gly Phe Thr
385                 390                 395                 400

Ser Leu Phe Arg Ile Gly Ala Arg Gln Asn Ile Gln Leu Ile Asn Ser
                405                 410                 415

Asn Gly Ser Trp His Ile Asn Arg Thr Ala Leu Asn Cys Asn Glu Ser
            420                 425                 430

Leu Asp Thr Gly Trp Val Ala Gly Leu Leu Tyr Tyr His Lys Phe Asn
        435                 440                 445

Ser Ser Gly Cys Pro Glu Arg Met Ala Ser Cys Arg Ser Leu Ala Asp
450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Lys Pro Cys Gly Ile
                485                 490                 495

Val Pro Ala Gln Ser Val Cys Gly Pro Val Tyr Cys Phe Thr Pro Ser
            500                 505                 510

Pro Val Val Val Gly Thr Thr Asp Lys Ser Gly Ala Pro Thr Tyr Asn
        515                 520                 525

Trp Gly Cys Asn Glu Thr Asp Val Phe Val Leu Asn Asn Thr Arg Pro
530                 535                 540

Pro Leu Gly Asn Trp Phe Gly Cys Thr Trp Met Asn Ser Ser Gly Phe
```

```
                545                 550                 555                 560
            Thr Lys Val Cys Gly Ala Pro Pro Cys Val Ile Gly Gly Val Gly Asn
                            565                 570                 575

Asn Thr Leu His Cys Pro Thr Asp Cys Phe Arg Lys His Pro Glu Ala
                            580                 585                 590

Thr Tyr Ser Arg Cys Gly Ser Gly Pro Trp Ile Thr Pro Arg Cys Leu
                            595                 600                 605

Val His Tyr Ala Tyr Arg Leu Trp His Tyr Pro Cys Thr Val Asn Tyr
                            610                 615                 620

Thr Leu Phe Lys Val Arg Met Tyr Val Gly Gly Val Glu His Arg Leu
            625                 630                 635                 640

Asp Val Ala Cys Asn Trp Thr Arg Gly Glu Arg Cys Asn Leu Asp Asp
                            645                 650                 655

Arg Asp Arg Ser Glu Leu Ser Pro Leu Leu Leu Ser Thr Thr Gln Trp
                            660                 665                 670

Gln Val Leu Pro Cys Ser Phe Thr Thr Leu Pro Ala Leu Ser Thr Gly
                            675                 680                 685

Leu Ile His Leu His Gln Asn Ile Val Asp Val Gln Tyr Leu Tyr Gly
                            690                 695                 700

Val Gly Ser Ser Ile Val Ser Trp Ala Ile Lys Trp Glu Tyr Val Ile
            705                 710                 715                 720

Leu Leu Phe Leu Leu Leu Ala Asp Ala Arg Ile Cys Ser Cys Leu Trp
                            725                 730                 735

Met Met Leu Leu Ile Ser Gln Ala Glu Ala
                            740                 745

<210> SEQ ID NO 58
<211> LENGTH: 746
<212> TYPE: PRT
<213> ORGANISM: Hepatitis C virus

<400> SEQUENCE: 58

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
            50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

```
Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
            195                 200                 205

Asn Ser Ser Ile Val Tyr Glu Thr Ala Asp Thr Ile Leu His Ser Pro
        210                 215                 220

Gly Cys Val Pro Cys Val Arg Glu Gly Asn Ala Ser Lys Cys Trp Val
225                 230                 235                 240

Ala Val Thr Pro Thr Val Ala Thr Arg Asp Gly Arg Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Ile Phe Leu Val Gly
        275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Gly
        370                 375                 380

Thr His Val Thr Gly Gly Ser Ala Ala Lys Thr Ser Gly Phe Thr
385                 390                 395                 400

Ser Leu Phe Arg Ile Gly Ala Arg Gln Asn Ile Gln Leu Ile Asn Ser
                405                 410                 415

Asn Gly Ser Trp His Ile Asn Arg Thr Ala Leu Asn Cys Asn Glu Ser
            420                 425                 430

Leu Asp Thr Gly Trp Val Ala Gly Leu Leu Tyr Tyr His Lys Phe Asn
        435                 440                 445

Ser Ser Gly Cys Pro Glu Arg Met Ala Ser Cys Arg Ser Leu Ala Asp
450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Pro Lys Pro Cys Gly Ile
                485                 490                 495

Val Pro Ala Gln Ser Val Cys Gly Pro Val Tyr Cys Phe Thr Pro Ser
            500                 505                 510

Pro Val Val Val Gly Thr Thr Asp Lys Ser Gly Ala Pro Thr Tyr Asn
        515                 520                 525

Trp Gly Cys Asn Glu Thr Asp Val Phe Val Leu Asn Asn Thr Arg Pro
530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Gly Val Gly Asn
                565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
```

```
                595                 600                 605
Val His Tyr Ala Tyr Arg Leu Trp His Tyr Pro Cys Thr Val Asn Tyr
    610                 615                 620

Thr Leu Phe Lys Val Arg Met Tyr Val Gly Gly Val Glu His Arg Leu
625                 630                 635                 640

Asp Val Ala Cys Asn Trp Thr Arg Gly Glu Arg Cys Asn Leu Asp Asp
                    645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
                740                 745

<210> SEQ ID NO 59
<211> LENGTH: 746
<212> TYPE: PRT
<213> ORGANISM: Hepatitis C virus

<400> SEQUENCE: 59

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Ser Ile Leu His Ser Pro
    210                 215                 220
```

```
Gly Cys Val Pro Cys Val Arg Glu Gly Asn Ala Ser Lys Cys Trp Val
225                 230                 235                 240

Ala Val Ala Pro Thr Val Ala Thr Arg Asp Gly Lys Leu Pro Ala Thr
            245                 250                 255

Gln Leu Arg Arg His Ile Asp Leu Leu Val Gly Ser Ala Thr Leu Cys
        260                 265                 270

Ser Ala Leu Tyr Val Gly Asp Leu Cys Gly Ser Val Phe Leu Val Ser
    275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Val Pro Gln Ala Ile Leu Asp Met Ile Ala Gly Ala His
        340                 345                 350

Trp Gly Val Leu Ala Gly Ile Ala Tyr Phe Ser Met Val Gly Asn Trp
    355                 360                 365

Ala Lys Val Leu Val Val Leu Leu Leu Phe Ala Gly Val Asp Ala Glu
370                 375                 380

Thr His Thr Thr Gly Gly Ser Ala Ala Tyr Ala Thr Ser Gly Phe Val
385                 390                 395                 400

Gly Leu Phe Arg Gln Gly Ala Lys Gln Asn Ile Gln Leu Ile Asn Thr
                405                 410                 415

Asn Gly Ser Trp His Val Asn Arg Thr Ala Leu Asn Cys Asn Ala Ser
                420                 425                 430

Leu Asp Thr Gly Trp Val Ala Gly Leu Phe Tyr Tyr His Lys Phe Asn
        435                 440                 445

Ser Ser Gly Cys Pro Glu Arg Leu Ala Ser Cys Lys Pro Leu Ala Asn
450                 455                 460

Phe Asp Gln Gly Trp Gly Ser Ile Ser Tyr Thr Asn Gly Ser Gly Pro
465                 470                 475                 480

Glu His Arg Pro Tyr Cys Trp His Tyr Pro Pro Lys Pro Cys Gly Ile
                485                 490                 495

Val Pro Ala Gln Asn Val Cys Gly Pro Val Tyr Cys Phe Thr Pro Ser
                500                 505                 510

Pro Val Val Val Gly Thr Thr Asp Arg Leu Gly Ala Pro Thr Phe Asn
        515                 520                 525

Trp Gly Glu Asn Glu Ser Asp Val Phe Val Leu Asn Asn Thr Arg Pro
530                 535                 540

Pro Ser Gly Asn Trp Phe Gly Cys Thr Trp Met Asn Ser Ser Gly Phe
545                 550                 555                 560

Thr Lys Val Cys Gly Ala Pro Pro Cys Asn Ile Gly Gly Val Gly Asn
                565                 570                 575

Asn Thr Leu His Cys Pro Thr Asp Cys Phe Arg Lys His Pro Glu Ala
        580                 585                 590

Thr Tyr Ser Arg Cys Gly Ser Gly Pro Trp Val Thr Pro Arg Cys Leu
    595                 600                 605

Val His Tyr Pro Tyr Arg Leu Trp His Tyr Pro Cys Thr Leu Asn Tyr
    610                 615                 620

Ser Leu Phe Lys Val Arg Met Tyr Val Gly Gly Ile Glu His Arg Leu
625                 630                 635                 640

Glu Val Ala Cys Asn Trp Thr Arg Gly Glu Arg Cys Asn Leu Asp Asp
```

-continued

```
                      645                 650                 655
Arg Asp Arg Ser Glu Leu Ser Pro Leu Leu Thr Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Val Val Asp Val Gln Tyr Leu Tyr Gly
        690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
                740                 745

<210> SEQ ID NO 60
<211> LENGTH: 746
<212> TYPE: PRT
<213> ORGANISM: Hepatitis C virus

<400> SEQUENCE: 60

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
    210                 215                 220

Gly Cys Val Pro Cys Val Arg Glu Gly Asn Ala Ser Lys Cys Trp Val
225                 230                 235                 240

Ala Val Ala Pro Thr Val Ala Thr Arg Asp Gly Arg Leu Pro Thr Thr
                245                 250                 255

Gln Leu Arg Arg His Ile Asp Leu Leu Val Gly Ser Ala Thr Leu Cys
            260                 265                 270
```

-continued

```
Ser Ala Leu Tyr Val Gly Asp Leu Cys Gly Ser Val Phe Val Gly
            275                 280                 285

Gln Leu Phe Thr Phe Ser Pro Arg His His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Thr
    370                 375                 380

Thr His Thr Thr Gly Gly Ala Val Ala His Asn Thr Arg Met Phe Thr
385                 390                 395                 400

Ser Ile Phe Ser Leu Gly Pro Arg Gln Glu Ile Gln Leu Val Asn Thr
            405                 410                 415

Asn Gly Ser Trp His Ile Asn Arg Thr Ala Leu Asn Cys Asn Ala Ser
        420                 425                 430

Leu Glu Thr Gly Trp Ile Ala Gly Leu Leu Tyr Ala Asn Arg Phe Asn
    435                 440                 445

Ser Ser Gly Cys Pro Glu Arg Met Ala Ser Cys Lys Pro Leu Ala Asp
450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Pro Lys Pro Cys Gly Ile
            485                 490                 495

Val Pro Ala Gln Asn Val Cys Gly Pro Val Tyr Cys Phe Thr Pro Ser
        500                 505                 510

Pro Val Val Val Gly Thr Thr Asp Arg Leu Gly Thr Pro Thr Tyr Asp
    515                 520                 525

Trp Gly Ser Asn Asp Thr Asp Val Phe Val Leu Asn Asn Thr Arg Pro
530                 535                 540

Pro Ala Gly Asn Trp Phe Gly Cys Thr Trp Met Asn Ser Ser Gly Tyr
545                 550                 555                 560

Thr Lys Val Cys Gly Ala Pro Pro Cys Val Ile Gly Val Ser Asn
            565                 570                 575

Asn Thr Leu His Cys Pro Thr Asp Cys Phe Arg Lys His Pro Glu Ala
        580                 585                 590

Thr Tyr Ser Arg Cys Gly Ser Gly Pro Trp Ile Thr Pro Arg Cys Leu
    595                 600                 605

Val His Tyr Ala Tyr Arg Leu Trp His Tyr Pro Cys Thr Val Asn Tyr
610                 615                 620

Thr Leu Phe Lys Val Arg Met Tyr Val Gly Gly Val Glu His Arg Leu
625                 630                 635                 640

Glu Val Ala Cys Asn Trp Thr Arg Gly Glu Arg Cys Asn Leu Asp Asp
            645                 650                 655

Arg Asp Arg Ser Glu Leu Ser Pro Leu Leu Leu Ser Thr Thr Gln Trp
        660                 665                 670

Gln Val Leu Pro Cys Ser Phe Thr Thr Leu Pro Ala Leu Thr Thr Gly
    675                 680                 685

Leu Ile His Leu His Gln Asn Ile Val Asp Val Gln Tyr Leu Tyr Gly
```

```
            690              695             700
Val Gly Ser Ser Ile Val Ser Trp Ala Val Lys Trp Glu Tyr Val Ile
705                 710             715                 720

Leu Leu Phe Leu Leu Leu Ala Asp Ala Arg Ile Cys Ser Cys Leu Trp
                725             730             735

Met Met Leu Leu Ile Ser Gln Ala Glu Ala
                740             745
```

<210> SEQ ID NO 61
<211> LENGTH: 746
<212> TYPE: PRT
<213> ORGANISM: Hepatitis C virus

<400> SEQUENCE: 61

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ala Ser Ile Val Tyr Glu Ala Ala Asp Met Ile Met His Thr Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ala
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Thr Gly His Arg Met Ala Trp
305                 310                 315                 320
```

```
Asp Met Met Met Asn Trp Ser Pro Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Thr Met Ala Lys Asn Thr Leu Gly Ile Thr
385                 390                 395                 400

Ser Leu Phe Ser Pro Gly Ser Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Val His Lys Phe Asn
        435                 440                 445

Ser Ser Gly Cys Pro Glu Arg Met Ala Ser Cys Ser Pro Ile Asp Ala
    450                 455                 460

Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
            500                 505                 510

Pro Val Val Val Gly Thr Thr Asp Arg Phe Gly Val Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ile Gly Asn
                565                 570                 575

Lys Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val His Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
        675                 680                 685

Leu Ile His Leu His Gln Asn Val Val Asp Val Gln Tyr Leu Tyr Gly
    690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
```

<210> SEQ ID NO 62
<211> LENGTH: 746
<212> TYPE: PRT
<213> ORGANISM: Hepatitis C virus

<400> SEQUENCE: 62

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Val Ala Arg Ala Leu Ala His Gly Val Arg Val Val Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Met Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Ala Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Ile Gln Asp Cys
290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
        355                 360                 365
```

```
Ala Lys Val Leu Ile Val Met Leu Leu Phe Ala Gly Val Asp Gly Glu
        370                 375                 380
Thr Arg Val Thr Gly Gly Gln Ile Ala Arg Asn Ala Tyr Ser Leu Thr
385                 390                 395                 400
Thr Leu Phe Ser Ser Gly Ser Ala Gln Asn Ile Gln Leu Ile Asn Thr
                    405                 410                 415
Asn Gly Ser Trp His Ile Asn Arg Thr Ala Leu Asn Cys Asn Asp Ser
                420                 425                 430
Leu Asn Thr Gly Phe Leu Ala Ala Leu Phe Tyr Thr His Lys Phe Asn
            435                 440                 445
Ala Ser Gly Cys Pro Glu Arg Leu Ala Ser Cys Arg Pro Ile Asp Lys
450                 455                 460
Phe Asp Gln Gly Trp Gly Pro Ile Thr Tyr Ala Glu Gln Gly Gly Gln
465                 470                 475                 480
Asp Gln Arg Pro Tyr Cys Trp His Tyr Ala Pro Lys Pro Cys Gly Ile
                485                 490                 495
Val Ser Ala Ser Lys Val Cys Gly Pro Val Tyr Cys Phe Thr Pro Ser
                500                 505                 510
Pro Val Val Val Gly Thr Thr Asp Arg Phe Gly Val Pro Thr Tyr Ser
            515                 520                 525
Trp Gly Glu Asn Glu Thr Asp Val Leu Leu Leu Asn Asn Thr Arg Pro
530                 535                 540
Pro Gln Gly Asn Trp Phe Gly Cys Thr Trp Met Asn Gly Thr Gly Phe
545                 550                 555                 560
Thr Lys Thr Cys Gly Gly Pro Pro Cys Asn Ile Gly Gly Gly Gly Asn
                565                 570                 575
Asn Thr Leu Thr Cys Pro Thr Asp Cys Phe Arg Lys His Pro Ala Ala
                580                 585                 590
Thr Tyr Thr Lys Cys Gly Ser Gly Pro Trp Leu Thr Pro Arg Cys Leu
            595                 600                 605
Val Asp Tyr Pro Tyr Arg Leu Trp His Tyr Pro Cys Thr Ala Asn Phe
610                 615                 620
Thr Ile Phe Lys Val Arg Met Tyr Val Gly Gly Val Glu His Arg Leu
625                 630                 635                 640
Asp Ala Ala Cys Asn Trp Thr Arg Gly Glu Arg Cys Asn Leu Glu Asp
                645                 650                 655
Arg Asp Arg Leu Glu Leu Ser Pro Leu Leu Leu Ser Thr Thr Glu Trp
                660                 665                 670
Gln Val Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
            690                 695                 700
Ile Gly Ser Ala Val Val Ser Phe Ala Ile Lys Trp Asp Tyr Ile Val
705                 710                 715                 720
Ile Leu Phe Leu Leu Leu Ala Asp Ala Arg Val Cys Ala Cys Leu Trp
                725                 730                 735
Met Met Leu Leu Ile Ala Gln Ala Glu Ala
            740                 745

<210> SEQ ID NO 63
<211> LENGTH: 747
<212> TYPE: PRT
<213> ORGANISM: Hepatitis C virus

<400> SEQUENCE: 63
```

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
        20                  25                  30

Gly Val Tyr Leu Leu Pro Arg Arg Gly Pro Arg Leu Gly Val Arg Ala
            35                  40                  45

Ile Arg Lys Thr Ser Glu Arg Ser Gln Pro Arg Gly Arg Arg Gln Pro
50                      55                  60

Ile Pro Lys Ala Arg Arg Pro Glu Gly Arg Ala Trp Ala Gln Pro Gly
65                      70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Gly Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala His
                180                 185                 190

Glu Val Arg Asn Ala Ser Gly Val Tyr His Val Thr Asn Asp Cys Ser
        195                 200                 205

Asn Ser Ser Ile Val Phe Glu Ala Ala Asp Leu Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Thr Ile Pro Thr Thr
                245                 250                 255

Thr Ile Arg His His Val Asp Leu Leu Val Gly Ala Ala Ala Leu Cys
        260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Ala Thr Leu Gln Asp Cys
        290                 295                 300

Asn Cys Ser Ile Tyr Pro Gly His Ala Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Ile Asp Met Val Ala Gly Ala His
                340                 345                 350

Trp Gly Val Leu Ala Gly Leu Ala Tyr Tyr Ser Met Ala Gly Asn Trp
        355                 360                 365

Ala Lys Val Leu Ile Val Met Leu Leu Phe Ala Gly Val Asp Gly His
        370                 375                 380

Thr Leu Thr Thr Gly Gly His Ala Ala Arg Leu Thr Ser Gly Phe Ala
385                 390                 395                 400

Gly Leu Phe Thr Pro Gly Pro Ser Gln Arg Ile Gln Leu Ile Asn Thr
                405                 410                 415
```

```
Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Ala His Arg Phe Asn
        435                 440                 445

Ser Ser Gly Cys Pro Glu Arg Met Ala Ser Cys Arg Ser Ile Asp Lys
    450                 455                 460

Phe Asp Gln Gly Trp Gly Pro Ile Thr Tyr Ala Glu Pro Thr Lys Asp
465                 470                 475                 480

Pro Asp Gln Arg Pro Tyr Cys Trp His Tyr Pro Pro Gln Gln Cys Gly
                485                 490                 495

Ile Val Pro Ala Ser Gln Val Cys Gly Pro Val Tyr Cys Phe Thr Pro
            500                 505                 510

Ser Pro Val Val Val Gly Thr Thr Asp Arg Leu Gly Asn Pro Thr Tyr
        515                 520                 525

Ser Trp Gly Glu Asn Asp Thr Asp Val Leu Leu Asn Asn Thr Arg
        530                 535                 540

Pro Pro Gln Gly Asn Trp Phe Gly Cys Thr Trp Met Asn Ser Thr Gly
545                 550                 555                 560

Phe Thr Lys Thr Cys Gly Ala Pro Pro Cys Asn Ile Gly Gly Val Gly
                565                 570                 575

Asn Asn Thr Leu Thr Cys Pro Thr Asp Cys Phe Arg Lys His Pro Glu
            580                 585                 590

Ala Thr Tyr Ser Lys Cys Gly Ser Gly Pro Trp Leu Thr Pro Arg Cys
        595                 600                 605

Met Val Asp Tyr Pro Tyr Arg Leu Trp His Tyr Pro Cys Thr Val Asn
        610                 615                 620

Phe Ser Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Asp
                645                 650                 655

Asp Arg Asp Arg Ser Glu Leu Ser Pro Leu Leu Leu Ser Thr Thr Glu
            660                 665                 670

Trp Gln Val Leu Pro Cys Ser Phe Thr Thr Leu Pro Ala Leu Ser Thr
        675                 680                 685

Gly Leu Ile His Leu His Gln Asn Ile Val Asp Val Gln Tyr Leu Tyr
        690                 695                 700

Gly Ile Gly Ser Ala Val Ser Phe Ala Ile Lys Trp Glu Tyr Val
705                 710                 715                 720

Val Leu Leu Phe Leu Leu Leu Ala Asp Ala Arg Val Cys Ala Cys Leu
                725                 730                 735

Trp Met Met Leu Leu Ile Ala Gln Ala Glu Ala
            740                 745

<210> SEQ ID NO 64
<211> LENGTH: 746
<212> TYPE: PRT
<213> ORGANISM: Hepatitis C virus

<400> SEQUENCE: 64

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

```
Thr Arg Lys Thr Ser Glu Arg Ser Gln Pro Arg Gly Arg Gln Pro
     50                  55                  60

Ile Pro Lys Ala Arg His Pro Glu Gly Arg Thr Trp Ala Gln Pro Gly
 65              70                  75                      80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
            195                 200                 205

Asn Ser Ser Ile Val Tyr Glu Ala Ala Asp Val Ile Met His Thr Pro
210                 215                 220

Gly Cys Val Pro Cys Val Gln Asp Gly Asn Thr Ser Arg Cys Trp Val
225                 230                 235                 240

Ala Leu Thr Pro Thr Leu Ala Ala Arg Asn Ala Ser Val Pro Val Thr
                245                 250                 255

Ala Ile Arg Arg His Val Asp Leu Leu Val Gly Thr Ala Ala Phe Cys
            260                 265                 270

Ser Ala Met Tyr Val Gly Asp Leu Cys Gly Ser Val Phe Pro Val Ser
        275                 280                 285

Gln Leu Phe Thr Phe Ser Pro Arg Arg His Gln Thr Val Gln Asp Cys
    290                 295                 300

Asn Cys Ser Ile Tyr Pro Gly His Ile Ser Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Met Ile Val Leu Leu Leu Phe Ala Gly Val Asp Gly Thr
    370                 375                 380

Thr His Thr Thr Gly Gly Ala Ala Ala Arg Ala Thr Gln Gly Phe Thr
385                 390                 395                 400

Ser Phe Phe Ser Leu Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Thr Tyr Arg Phe Asn
        435                 440                 445

Ala Ser Gly Cys Pro Glu Arg Met Ala Ser Cys Arg Pro Ile Asp Lys
    450                 455                 460
```

```
Phe Asp Gln Gly Trp Gly Pro Ile Thr Tyr Ala Glu Pro Asp Ser Ser
465                 470                 475                 480

Asp Gln Arg Pro Tyr Cys Trp His Tyr Ala Pro Arg Pro Cys Gly Ile
            485                 490                 495

Val Pro Ala Ser Gln Val Cys Gly Pro Val Tyr Cys Phe Thr Pro Ser
        500                 505                 510

Pro Val Val Gly Thr Thr Asp Arg Phe Gly Val Pro Thr Tyr Thr
        515                 520                 525

Trp Gly Glu Asn Glu Thr Asp Val Leu Leu Leu Asn Thr Arg Pro
    530                 535                 540

Pro Leu Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ala Gly Asn
            565                 570                 575

Thr Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Ala Val Asn Phe
610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Glu Trp
        660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Ile Gly Ser Ala Val Ile Pro Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 65
<211> LENGTH: 746
<212> TYPE: PRT
<213> ORGANISM: Hepatitis C virus

<400> SEQUENCE: 65

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95
```

```
Leu Leu Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Ile Ile Met His Thr Pro
    210                 215                 220

Gly Cys Val Pro Cys Val Arg Glu Lys Asn Ile Ser Arg Cys Trp Val
225                 230                 235                 240

Ala Leu Thr Pro Thr Leu Ala Ala Arg Asn Ile Ser Val Pro Thr Ala
                245                 250                 255

Thr Ile Arg Arg His Val Asp Leu Leu Val Gly Thr Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Trp His Glu Thr Val Gln Asp Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ile Gly Asn Trp
        355                 360                 365

Ala Lys Val Leu Ile Val Met Leu Leu Phe Ala Gly Ala Asp Gly Thr
    370                 375                 380

Thr His Val Thr Gly Gly Val Gln Ala His Gly Ala Tyr Gly Leu Ala
385                 390                 395                 400

Ser Leu Phe Asn Val Gly Pro His Gln Lys Ile Gln Leu Val Asn Thr
                405                 410                 415

Asn Gly Ser Trp His Ile Asn Arg Thr Ala Leu Asn Cys Asn Asp Thr
            420                 425                 430

Leu Gln Thr Gly Phe Leu Ala Ala Leu Phe Tyr Lys His Arg Phe Asn
        435                 440                 445

Ala Ser Gly Cys Pro Glu Arg Met Ala Ser Cys Arg Pro Ile Asp Lys
    450                 455                 460

Phe Ala Gln Gly Trp Gly Pro Ile Thr Tyr Ala Glu Pro Asp Arg Leu
465                 470                 475                 480

Asp Gln Arg Pro Tyr Cys Trp His Tyr Pro Arg Pro Cys Gly Ile
                485                 490                 495

Val Pro Ala Leu Glu Val Cys Gly Pro Val Tyr Cys Phe Thr Pro Ser
            500                 505                 510
```

```
Pro Val Val Gly Thr Thr Asp Arg Phe Gly Val Pro Thr Tyr Ser
            515                 520                 525

Trp Gly Glu Asn Glu Thr Asp Val Leu Leu Asn Asn Thr Arg Pro
    530                 535                 540

Pro Gln Gly Asn Trp Phe Gly Cys Thr Trp Met Asn Ser Thr Gly Tyr
545                 550                 555                 560

Thr Lys Thr Cys Gly Pro Pro Cys Asn Ile Gly Gly Val Gly Asn
            565                 570                 575

Asn Thr Leu Thr Cys Pro Thr Asp Cys Phe Arg Lys His Pro Glu Ala
                580                 585                 590

Thr Tyr Thr Lys Cys Gly Ser Gly Pro Trp Leu Thr Pro Arg Cys Leu
            595                 600                 605

Val His Tyr Pro Tyr Arg Leu Trp His Tyr Pro Cys Thr Val Asn Phe
    610                 615                 620

Thr Ile Phe Lys Val Arg Met Tyr Val Gly Gly Ile Glu His Arg Leu
625                 630                 635                 640

Asp Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
                675                 680                 685

Leu Ile His Leu His Arg Asn Ile Val Asp Val Gln Tyr Leu Tyr Gly
            690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 66
<211> LENGTH: 746
<212> TYPE: PRT
<213> ORGANISM: Hepatitis C virus

<400> SEQUENCE: 66

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140
```

```
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
            195                 200                 205

Asn Ser Ser Ile Val Tyr Glu Ala Ala Asp Val Ile Met His Ala Pro
        210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Leu Arg Arg His Val Asp Leu Leu Val Gly Thr Ala Ala Phe Cys
            260                 265                 270

Ser Ala Met Tyr Val Gly Asp Leu Cys Gly Ser Val Phe Leu Ile Ser
            275                 280                 285

Gln Leu Phe Thr Phe Ser Pro Arg Arg His Glu Thr Val Gln Asp Cys
        290                 295                 300

Asn Cys Ser Ile Tyr Pro Gly His Val Ser Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Val Met Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly His
        370                 375                 380

Thr Arg Val Thr Gly Gly Val Gln Gly His Val Thr Ser Thr Leu Thr
385                 390                 395                 400

Ser Leu Phe Arg Pro Gly Ala Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Lys Thr Gly Phe Leu Ala Ala Leu Phe Tyr Thr His Lys Phe Asn
        435                 440                 445

Ala Ser Gly Cys Pro Glu Arg Met Ala Ser Cys Arg Ser Ile Asp Lys
450                 455                 460

Phe Asp Gln Gly Trp Gly Pro Ile Thr Tyr Ala Gln Pro Asp Asn Ser
465                 470                 475                 480

Asp Gln Arg Pro Tyr Cys Trp His Tyr Ala Pro Arg Gln Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Ala Pro Thr Tyr Asn
        515                 520                 525

Trp Gly Asp Asn Glu Thr Asp Val Leu Leu Asn Asn Thr Arg Pro
        530                 535                 540

Pro His Gly Asn Trp Phe Gly Cys Thr Trp Met Asn Ser Thr Gly Phe
545                 550                 555                 560
```

```
Thr Lys Thr Cys Gly Gly Pro Pro Cys Asn Ile Arg Gly Val Gly Asn
                565                 570                 575

Asn Thr Leu Thr Cys Pro Thr Asp Cys Phe Arg Lys His Pro Asp Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Val Glu His Arg Leu
625                 630                 635                 640

Asp Ala Ala Cys Asn Trp Thr Arg Gly Glu Arg Cys Asp Leu Glu Asp
                645                 650                 655

Arg Asp Arg Ala Glu Leu Ser Pro Leu Leu Leu Ser Thr Thr Glu Trp
            660                 665                 670

Gln Ile Leu Pro Cys Ser Tyr Thr Thr Leu Pro Ala Leu Ser Thr Gly
        675                 680                 685

Leu Ile His Leu His Gln Asn Ile Val Asp Ile Gln Tyr Leu Tyr Gly
    690                 695                 700

Ile Gly Ser Ala Val Val Ser Ile Ala Ile Lys Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 67
<211> LENGTH: 746
<212> TYPE: PRT
<213> ORGANISM: Hepatitis C virus

<400> SEQUENCE: 67

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asp Glu Gly Met Gly Trp Ala Gly Trp
                85                  90                  95

Leu Leu Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190
```

-continued

```
Glu Val Arg Asn Val Ser Gly Ile Tyr His Val Thr Asn Asp Cys Ser
            195                 200                 205

Asn Ser Ser Ile Val Tyr Glu Ala Ala Asp Ile Ile Met His Thr Pro
210                 215                 220

Gly Cys Val Pro Cys Val Arg Glu Lys Asn Thr Ser Arg Cys Trp Val
225                 230                 235                 240

Ala Leu Thr Pro Thr Leu Ala Ala Arg Asn Ile Ser Val Pro Thr Thr
                245                 250                 255

Thr Ile Arg Arg His Val Asp Leu Leu Val Gly Thr Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Val Gln Asp Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Ala Asp Gly Thr
    370                 375                 380

Thr His Val Thr Gly Gly Val Gln Ala His Gly Ala Tyr Gly Leu Ala
385                 390                 395                 400

Ser Leu Phe Asn Val Gly Pro His Gln Lys Ile Gln Leu Val Asn Thr
                405                 410                 415

Asn Gly Ser Trp His Ile Asn Arg Thr Ala Leu Asn Cys Asn Asp Thr
            420                 425                 430

Leu Gln Thr Gly Phe Leu Ala Ala Leu Phe Tyr Lys His Arg Phe Asn
        435                 440                 445

Ala Ser Gly Cys Pro Glu Arg Met Ala Ser Cys Arg Pro Ile Asp Lys
    450                 455                 460

Phe Ala Gln Gly Trp Gly Pro Ile Thr Tyr Ala Glu Pro Asp Arg Leu
465                 470                 475                 480

Asp Gln Arg Pro Tyr Cys Trp His Tyr Pro Pro Arg Pro Cys Gly Ile
                485                 490                 495

Val Pro Ala Leu Glu Val Cys Gly Pro Val Tyr Cys Phe Thr Pro Ser
            500                 505                 510

Pro Val Val Val Gly Thr Thr Asp Arg Phe Gly Val Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Asn Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605
```

```
Val Asp Tyr Pro Tyr Arg Leu Trp His Tyr Pro Cys Thr Val Asn Phe
610                 615                 620

Thr Val Phe Lys Val Arg Met Tyr Val Gly Gly Ile Glu His Arg Leu
625                 630                 635                 640

Asp Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
                660                 665                 670

Gln Ile Leu Pro Cys Ser Phe Thr Thr Leu Pro Ala Leu Ser Thr Gly
            675                 680                 685

Leu Ile His Leu His Arg Asn Ile Val Asp Val Gln Tyr Leu Tyr Gly
        690                 695                 700

Ile Gly Ser Ala Val Val Ser Phe Ala Ile Lys Trp Glu Tyr Ile Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
                740                 745

<210> SEQ ID NO 68
<211> LENGTH: 746
<212> TYPE: PRT
<213> ORGANISM: Hepatitis C virus

<400> SEQUENCE: 68

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65              70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Val Tyr His Val Thr Asn Asp Cys Ser
            195                 200                 205

Asn Ser Ser Ile Val Tyr Glu Ala Ala Asp Met Ile Met His Thr Pro
    210                 215                 220

Gly Cys Val Pro Cys Val Arg Glu Asp Asn Ser Ser Arg Cys Trp Val
225                 230                 235                 240
```

-continued

```
Ala Leu Thr Pro Thr Leu Ala Ala Arg Asn Ser Ser Val Pro Thr Thr
            245                 250                 255

Thr Ile Arg Arg His Val Asp Leu Leu Val Gly Ala Ala Phe Cys
            260                 265                 270

Ser Ala Met Tyr Val Gly Asp Leu Cys Gly Ser Val Phe Leu Ile Ser
        275                 280                 285

Gln Leu Phe Thr Phe Ser Pro Arg Arg Tyr Glu Thr Val Gln Asp Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Asn
    370                 375                 380

Thr Arg Val Ser Gly Gly Glu Ala Ala Lys Asn Thr Met Gly Phe Ala
385                 390                 395                 400

Ser Leu Phe Val Ser Gly Pro Ser Gln Lys Ile Gln Leu Ile Asn Thr
                405                 410                 415

Asn Gly Ser Trp His Ile Asn Arg Thr Ala Leu Asn Cys Asp Asp Ser
            420                 425                 430

Leu His Thr Gly Phe Leu Ala Ala Leu Phe Tyr Ala His Lys Phe Asn
        435                 440                 445

Ser Ser Gly Cys Ser Gly Arg Met Ala Ser Cys Arg Pro Ile Asp Glu
    450                 455                 460

Phe Ala Gln Gly Trp Gly Pro Ile Thr His Gly Val Pro Asp Asn Leu
465                 470                 475                 480

Asp Gln Arg Pro Tyr Cys Trp His Tyr Ala Pro Arg Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Ala Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Asp Ala Ala Cys Asn Trp Thr Arg Gly Glu Arg Cys Asn Val Glu Asp
                645                 650                 655
```

```
Arg Asp Arg Ser Glu Leu Ser Pro Leu Leu Ser Thr Thr Glu Trp
            660                 665                 670

Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Val Val Ser Val Val Ile Arg Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 69
<211> LENGTH: 746
<212> TYPE: PRT
<213> ORGANISM: Hepatitis C virus

<400> SEQUENCE: 69

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Met Tyr His Val Thr Asn Asp Cys Ser
        195                 200                 205

Asn Ser Ser Ile Val Tyr Glu Ala Ala Asp Met Ile Leu His Ala Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Ala Ile Arg Arg His Val Asp Leu Leu Val Gly Ala Ala Ala Phe Cys
            260                 265                 270

Ser Ala Met Tyr Val Gly Asp Leu Cys Gly Ser Val Leu Leu Val Ser
        275                 280                 285
```

```
Gln Ile Phe Thr Phe Ser Pro Arg Arg His Glu Thr Met Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Glu Ala Gly Arg Arg Thr Ser Gly Phe Ala
385                 390                 395                 400

Ser Ile Phe Thr Pro Gly Ala Ser Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ala Leu Phe Tyr His His Lys Phe Asn
        435                 440                 445

Ala Ser Gly Cys Pro Glu Arg Met Ala Ser Cys Arg Pro Ile Gly Glu
    450                 455                 460

Phe Ala Gln Gly Trp Gly Pro Ile Ser Tyr Thr Glu Pro Pro Ser Ser
465                 470                 475                 480

Asp Gln Arg Pro Tyr Cys Trp His Tyr Pro Pro Arg Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Leu Gly Ala Pro Thr Tyr Asn
        515                 520                 525

Trp Gly Asp Asn Asp Thr Asp Val Leu Leu Leu Asn Asn Thr Arg Pro
    530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Ile
        595                 600                 605

Val Asp Tyr Pro Tyr Arg Leu Trp His Tyr Pro Cys Thr Val Asn Phe
    610                 615                 620

Thr Ile Thr Lys Ile Arg Met Tyr Val Gly Gly Val Glu His Arg Leu
625                 630                 635                 640

Thr Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Met Pro Cys Ser Phe Thr Thr Leu Pro Ala Leu Ser Thr Gly
        675                 680                 685

Leu Ile His Leu His Gln Asn Ile Val Asp Ile Gln Tyr Leu Tyr Gly
    690                 695                 700
```

```
Ile Gly Ser Ala Ala Val Ser Phe Ala Ile Arg Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 70
<211> LENGTH: 746
<212> TYPE: PRT
<213> ORGANISM: Hepatitis C virus

<400> SEQUENCE: 70

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Met Tyr His Val Thr Asn Asp Cys Ser
        195                 200                 205

Asn Ser Ser Ile Val Tyr Glu Ala Ala Asp Met Ile Leu His Ala Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Ala Ile Arg Arg His Val Asp Leu Leu Val Gly Ala Ala Phe Cys
            260                 265                 270

Ser Ala Met Tyr Val Gly Asp Leu Cys Gly Ser Val Leu Leu Val Ser
        275                 280                 285

Gln Ile Phe Thr Phe Ser Pro Arg Arg His Glu Thr Met Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ser Gln
                325                 330                 335
```

```
Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly Gly
370                 375                 380

Thr Tyr Val Thr Gly Gly Glu Ala Gly Arg Arg Thr Ser Gly Phe Ala
385                 390                 395                 400

Ser Ile Phe Thr Pro Gly Ala Ser Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ala Leu Phe Tyr His His Lys Phe Asn
            435                 440                 445

Ala Ser Gly Cys Pro Glu Arg Met Ala Ser Cys Arg Pro Ile Gly Glu
            450                 455                 460

Phe Ala Gln Gly Trp Gly Pro Ile Ser Tyr Thr Glu Pro Pro Ser Ser
465                 470                 475                 480

Asp Gln Arg Pro Tyr Cys Trp His Tyr Pro Pro Arg Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Leu Gly Ala Pro Thr Tyr Asn
            515                 520                 525

Trp Gly Asp Asn Asp Thr Asp Val Leu Leu Leu Asn Asn Thr Arg Pro
530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Ile
            595                 600                 605

Val Asp Tyr Pro Tyr Arg Leu Trp His Tyr Pro Cys Thr Val Asn Phe
610                 615                 620

Thr Ile Thr Lys Ile Arg Met Tyr Val Gly Gly Val Glu His Arg Leu
625                 630                 635                 640

Thr Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Met Pro Cys Ser Phe Thr Thr Leu Pro Ala Leu Ser Thr Gly
            675                 680                 685

Leu Ile His Leu His Gln Asn Ile Val Asp Ile Gln Tyr Leu Tyr Gly
            690                 695                 700

Ile Gly Ser Ala Ala Val Ser Phe Ala Ile Arg Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745
```

```
<210> SEQ ID NO 71
<211> LENGTH: 746
<212> TYPE: PRT
<213> ORGANISM: Hepatitis C virus

<400> SEQUENCE: 71

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Thr Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ser Ser Ile Val Tyr Glu Thr Ala Asp Met Ile Met His Thr Pro
210                 215                 220

Gly Cys Val Pro Cys Val Arg Glu Asp Asn Phe Thr Arg Cys Trp Val
225                 230                 235                 240

Ala Leu Thr Pro Thr Leu Ala Ala Arg Asn Gly Ser Val Pro Thr Thr
                245                 250                 255

Ala Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Trp His Glu Thr Val Gln Glu Cys
290                 295                 300

Asn Cys Ser Ile Tyr Pro Gly His Val Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Thr Leu Leu Phe Ala Gly Val Asp Gly Asn
370                 375                 380
```

```
Thr His Thr Ile Gly Gly Lys Gln Ala Gln Ala Thr Gly Gly Phe Val
385                 390                 395                 400

Ala Trp Leu Ala Arg Gly Pro Ser Gln Glu Ile Gln Leu Ile Asn Thr
            405                 410                 415

Asn Gly Ser Trp His Ile Asn Arg Thr Ala Leu Asn Cys Asn Asp Ser
        420                 425                 430

Leu Lys Thr Gly Phe Ile Ala Ala Leu Phe Tyr Ala His Arg Phe Asn
    435                 440                 445

Ser Ser Gly Cys Pro Glu Arg Met Ala Ser Cys Arg Pro Ile Asp Lys
450                 455                 460

Phe Ala Gln Gly Trp Gly Pro Ile Thr Tyr Ala Lys Pro Asp Ser Leu
465                 470                 475                 480

Asp Gln Arg Pro Tyr Cys Trp His Tyr Ala Pro Gln Pro Cys Gly Ile
                485                 490                 495

Val Pro Ala Ser Glu Val Cys Gly Pro Val Tyr Cys Phe Thr Pro Ser
            500                 505                 510

Pro Val Val Val Gly Thr Thr Asp Arg Ser Gly Val Pro Thr Tyr Arg
        515                 520                 525

Trp Gly Glu Asn Glu Thr Asp Val Leu Leu Leu Asn Asn Thr Arg Pro
530                 535                 540

Pro Gln Gly Asn Trp Phe Gly Cys Thr Trp Met Asn Ala Thr Gly Phe
545                 550                 555                 560

Thr Lys Thr Cys Gly Gly Pro Pro Cys Lys Ile Gly Gly Leu Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Ile
        595                 600                 605

Val Asp Tyr Pro Tyr Arg Leu Trp His Tyr Pro Cys Thr Val Asn Phe
610                 615                 620

Thr Ile Phe Lys Val Arg Met Tyr Val Gly Gly Ile Glu His Arg Leu
625                 630                 635                 640

Ser Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Thr Val Asp Val Gln Tyr Leu Tyr Gly
690                 695                 700

Val Gly Ser Val Leu Val Ser Phe Ala Ile Lys Trp Glu Tyr Ile Leu
705                 710                 715                 720

Leu Phe Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 72
<211> LENGTH: 746
<212> TYPE: PRT
<213> ORGANISM: Hepatitis C virus

<400> SEQUENCE: 72

Met Ser Thr Asn Pro Lys Pro Gln Arg Lys Thr Lys Arg Asn Thr Asn
```

-continued

```
1               5                   10                  15
Arg Arg Pro Gln Asn Val Lys Phe Pro Gly Gly Gln Ile Val Gly
            20                  25                  30
Gly Val Cys Leu Leu Pro Arg Arg Gly Pro Arg Val Gly Val Arg Ala
            35                  40                  45
Thr Arg Lys Thr Ser Glu Arg Ser Gln Pro Arg Gly Arg Arg Gln Pro
            50                  55                  60
Ile Pro Lys Ala Arg Arg Pro Glu Gly Arg Ser Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Arg Gly Pro Ser Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
                130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Val
                180                 185                 190
Glu Val Arg Asn Ser Ser Gly Ile Tyr His Val Thr Asn Asp Cys Pro
                195                 200                 205
Asn Ala Ser Val Val Tyr Glu Thr Asp Ser Leu Ile Ile His Leu Pro
210                 215                 220
Gly Cys Val Pro Cys Val Arg Glu Gly Asn Ala Ser Arg Cys Trp Val
225                 230                 235                 240
Ser Leu Ser Pro Thr Val Ala Ala Lys Asp Pro Gly Val Pro Val Asn
                245                 250                 255
Glu Ile Arg Arg His Val Asp Leu Ile Val Gly Ala Ala Ala Phe Cys
                260                 265                 270
Ser Ala Met Tyr Val Gly Asp Leu Cys Gly Ser Ile Phe Leu Val Gly
            275                 280                 285
Gln Leu Phe Thr Leu Ser Pro Arg Arg His Trp Thr Thr Gln Asp Cys
            290                 295                 300
Asn Cys Ser Ile Tyr Pro Gly His Val Thr Gly His Arg Met Ala Trp
305                 310                 315                 320
Asp Met Met Met Asn Trp Ser Pro Thr Gly Ala Leu Val Val Ala Gln
                325                 330                 335
Leu Leu Arg Ile Pro Gln Ala Val Leu Asp Met Ile Ala Gly Ala His
                340                 345                 350
Trp Gly Val Leu Ala Gly Pro Ala Tyr Tyr Ser Met Val Gly Asn Trp
                355                 360                 365
Ala Lys Val Leu Val Val Leu Leu Leu Phe Ala Gly Val Asp Ala Thr
            370                 375                 380
Thr Gln Val Thr Gly Gly Thr Ala Gly Arg Asn Ala Tyr Arg Leu Ala
385                 390                 395                 400
Ser Leu Phe Ser Thr Gly Pro Ser Gln Asn Ile Gln Leu Ile Asn Ser
                405                 410                 415
Asn Gly Ser Trp His Ile Asn Arg Thr Ala Leu Asn Cys Asn Asp Ser
                420                 425                 430
```

```
Leu His Thr Gly Trp Val Ala Ala Leu Phe Tyr Ser His Lys Phe Asn
        435                 440                 445

Ser Ser Gly Arg Pro Glu Arg Met Ala Ser Cys Arg Pro Leu Thr Ala
    450                 455                 460

Phe Asp Gln Gly Trp Gly Pro Ile Thr Tyr Gly Gly Lys Ala Ser Asn
465                 470                 475                 480

Asp Gln Arg Pro Tyr Cys Trp His Tyr Ala Pro Arg Pro Cys Gly Ile
                485                 490                 495

Val Pro Ala Lys Glu Val Cys Gly Pro Val Tyr Cys Phe Thr Pro Ser
                500                 505                 510

Pro Val Val Val Gly Thr Thr Asp Lys Tyr Gly Val Pro Thr Tyr Thr
                515                 520                 525

Trp Gly Glu Asn Glu Thr Asp Val Leu Leu Leu Asn Asn Ser Arg Pro
    530                 535                 540

Pro Ile Gly Asn Trp Phe Gly Cys Thr Trp Met Asn Ser Thr Gly Phe
545                 550                 555                 560

Thr Lys Thr Cys Gly Ala Pro Ala Cys Asn Val Gly Gly Ser Glu Thr
                565                 570                 575

Asn Thr Leu Ser Cys Pro Thr Asp Cys Phe Arg Arg His Pro Asp Ala
                580                 585                 590

Thr Tyr Ala Lys Cys Gly Ser Gly Pro Trp Leu Asn Pro Arg Cys Met
                595                 600                 605

Val Asp Tyr Pro Tyr Arg Leu Trp His Tyr Pro Cys Thr Val Asn Tyr
                610                 615                 620

Thr Ile Phe Lys Ile Arg Met Phe Val Gly Ile Glu His Arg Leu
625                 630                 635                 640

Thr Ala Ala Cys Asn Trp Thr Arg Gly Glu Arg Cys Asp Leu Asp Asp
                645                 650                 655

Arg Asp Arg Ala Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
                690                 695                 700

Leu Ser Ser Val Val Thr Ser Trp Ala Ile Arg Trp Glu Tyr Val Val
705                 710                 715                 720

Leu Leu Phe Leu Leu Leu Ala Asp Ala Arg Ile Cys Ala Cys Leu Trp
                725                 730                 735

Met Met Leu Leu Ile Ser Gln Val Glu Ala
                740                 745

<210> SEQ ID NO 73
<211> LENGTH: 746
<212> TYPE: PRT
<213> ORGANISM: Hepatitis C virus

<400> SEQUENCE: 73

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
```

```
                50              55              60
Ile Pro Lys Ala Arg Arg Pro Glu Gly Arg Thr Trp Ala Gln Pro Gly
 65              70              75              80

Tyr Pro Trp Pro Leu Tyr Gly Asn Glu Gly Cys Gly Trp Ala Gly Trp
                 85              90              95

Leu Leu Ser Pro Arg Gly Ser Arg Pro Ser Trp Gly Pro Thr Asp Pro
                100             105             110

Arg Arg Arg Ser Arg Asn Leu Gly Lys Val Ile Asp Thr Leu Thr Tyr
                115             120             125

Gly Phe Ala Asp Leu Met Gly Tyr Ile Pro Leu Val Gly Ala Pro Leu
130             135             140

Gly Gly Ala Ala Arg Ala Leu Ala His Gly Val Arg Val Leu Glu Asp
145             150             155             160

Gly Val Asn Tyr Ala Thr Gly Asn Leu Pro Gly Cys Ser Phe Ser Ile
                165             170             175

Phe Leu Leu Ala Leu Leu Ser Cys Leu Thr Val Pro Ala Ser Ala Val
                180             185             190

Gly Val Arg Asn Ser Ser Gly Val Tyr His Val Thr Asn Asp Cys Pro
                195             200             205

Asn Ala Ser Val Val Tyr Glu Thr Asp Ser Leu Ile Ile His Leu Pro
210             215             220

Gly Cys Val Pro Cys Val Arg Glu Gly Asn Gly Ser Arg Cys Trp Val
225             230             235             240

Ser Leu Ser Pro Thr Val Ala Ala Lys Asp Pro Gly Val Pro Val Asn
                245             250             255

Glu Ile Arg Arg His Val Asp Leu Ile Ala Gly Ala Ala Ala Phe Cys
                260             265             270

Ser Ala Met Tyr Val Gly His Leu Cys Gly Ser Ile Phe Leu Val Gly
                275             280             285

Gln Leu Phe Thr Leu Ser Pro Arg Arg His Trp Thr Thr Gln Asp Cys
290             295             300

Asn Cys Ser Ile Tyr Pro Gly His Val Thr Gly His Arg Met Ala Trp
305             310             315             320

Asp Met Met Met Asn Trp Ser Pro Thr Thr Ala Leu Val Val Ala Gln
                325             330             335

Leu Leu Arg Ile Pro Gln Ala Ile Leu Asp Met Ile Ala Gly Ala His
                340             345             350

Trp Gly Val Leu Ala Gly Ile Ala Tyr Phe Ser Met Val Gly Asn Trp
                355             360             365

Thr Lys Val Leu Val Val Leu Leu Leu Phe Ala Gly Val Asp Ala Thr
370             375             380

Thr Ile Val Ser Gly Gly Ser Ala Gly Arg Thr Ala Gly Leu Val
385             390             395             400

Gly Leu Phe Ser Pro Gly Ala Arg Gln Asn Ile Gln Leu Ile Asn Thr
                405             410             415

Asn Gly Ser Trp His Ile Asn Arg Thr Ala Leu Asn Cys Asn Asp Thr
                420             425             430

Leu Gln Thr Gly Trp Val Ala Gly Leu Phe Tyr Thr Asn Lys Phe Asn
                435             440             445

Ser Ser Gly Cys Pro Glu Arg Leu Ala Ser Cys Arg Pro Leu Ala Asp
                450             455             460

Phe Asp Gln Gly Trp Gly Pro Ile Ser Tyr Thr Asn Gly Ser Gly Pro
465             470             475             480
```

```
Asp Gln Arg Pro Tyr Cys Trp His Tyr Pro Lys Pro Cys Gly Ile
                485                 490                 495
Val Pro Ala Glu Ser Val Cys Gly Pro Val Tyr Cys Phe Thr Pro Ser
            500                 505                 510
Pro Val Val Gly Thr Thr Asp Arg Ser Gly Ala Pro Thr Tyr Asn
        515                 520                 525
Trp Gly Glu Asn Glu Thr Asp Val Phe Val Leu Asn Asn Thr Arg Pro
    530                 535                 540
Arg Leu Gly Asn Trp Phe Gly Thr Trp Met Asn Ser Thr Gly Phe
545                 550                 555                 560
Thr Lys Val Cys Gly Ala Pro Cys Ala Ile Gly Val Gly Asn
            565                 570                 575
Asn Thr Leu Tyr Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Leu
        595                 600                 605
Ile His Tyr Pro Tyr Arg Leu Trp His Tyr Pro Cys Thr Ile Asn Tyr
        610                 615                 620
Thr Ile Phe Lys Ile Arg Met Phe Val Gly Gly Val Glu His Arg Leu
625                 630                 635                 640
Asp Ala Ala Cys Asn Trp Thr Arg Gly Glu Arg Cys Asp Leu Asp Asp
            645                 650                 655
Arg Asp Arg Ala Glu Leu Ser Pro Leu Leu Leu Ser Thr Thr Gln Trp
            660                 665                 670
Gln Val Leu Pro Cys Ser Phe Thr Thr Leu Pro Ala Leu Ser Thr Gly
        675                 680                 685
Leu Ile His Leu His Gln Asn Ile Val Asp Val Gln Tyr Leu Tyr Gly
        690                 695                 700
Leu Ser Ser Ala Val Thr Ser Trp Val Ile Lys Trp Glu Tyr Val Val
705                 710                 715                 720
Leu Leu Phe Leu Leu Leu Ala Asp Ala Arg Ile Cys Ala Cys Leu Trp
                725                 730                 735
Met Met Leu Leu Ile Ser Gln Val Glu Ala
                740                 745

<210> SEQ ID NO 74
<211> LENGTH: 746
<212> TYPE: PRT
<213> ORGANISM: Hepatitis C virus

<400> SEQUENCE: 74

Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gly Gln Ile Val Gly
            20                  25                  30
Gly Val Tyr Leu Leu Pro Arg Arg Gly Pro Arg Val Gly Val Arg Ala
        35                  40                  45
Thr Arg Lys Thr Ser Glu Arg Ser Gln Pro Arg Gly Arg Arg Gln Pro
    50                  55                  60
Ile Pro Lys Ala Arg Arg Pro Glu Gly Arg Ser Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Ser Asp Pro
```

```
                100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Leu
            130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Val
                180                 185                 190
Gly Val Arg Asn Ser Ser Gly Val Tyr His Val Thr Asn Asp Cys Pro
            195                 200                 205
Asn Ala Ser Val Val Tyr Glu Thr Glu Asn Leu Ile Met His Leu Pro
            210                 215                 220
Gly Cys Val Pro Tyr Val Arg Glu Gly Asn Ala Ser Arg Cys Trp Val
225                 230                 235                 240
Ser Leu Ser Pro Thr Val Ala Ala Arg Asp Ser Arg Val Pro Val Ser
                245                 250                 255
Glu Val Arg Arg Arg Val Asp Ser Ile Val Gly Ala Ala Phe Cys
                260                 265                 270
Ser Ala Met Tyr Val Gly Asp Leu Cys Gly Ser Ile Phe Leu Val Gly
            275                 280                 285
Gln Ile Phe Thr Phe Ser Pro Arg His His Trp Thr Thr Gln Asp Cys
            290                 295                 300
Asn Cys Ser Ile Tyr Pro Gly His Val Thr Gly His Arg Met Ala Trp
305                 310                 315                 320
Asp Met Met Met Asn Trp Ser Pro Thr Gly Ala Leu Val Val Ala Gln
                325                 330                 335
Leu Leu Arg Ile Pro Gln Ala Ile Val Asp Met Ile Ala Gly Ala His
                340                 345                 350
Trp Gly Val Leu Ala Gly Leu Ala Tyr Tyr Ser Met Val Gly Asn Trp
            355                 360                 365
Ala Lys Val Val Val Val Leu Leu Leu Phe Ala Gly Val Asp Ala Glu
            370                 375                 380
Thr Arg Val Thr Gly Gly Ala Ala Gly His Thr Ala Phe Gly Phe Ala
385                 390                 395                 400
Ser Phe Leu Ala Pro Gly Ala Lys Gln Lys Ile Gln Leu Ile Asn Thr
                405                 410                 415
Asn Gly Ser Trp His Ile Asn Arg Thr Ala Leu Asn Cys Asn Glu Ser
            420                 425                 430
Leu Asp Thr Gly Trp Leu Ala Gly Leu Leu Tyr Tyr His Lys Phe Asn
            435                 440                 445
Ser Ser Gly Cys Pro Glu Arg Met Ala Ser Cys Gln Pro Leu Thr Ala
            450                 455                 460
Phe Asp Gln Gly Trp Gly Pro Ile Thr His Glu Gly Asn Ala Ser Asp
465                 470                 475                 480
Asp Gln Arg Pro Tyr Cys Trp His Tyr Ala Leu Arg Pro Cys Gly Ile
                485                 490                 495
Val Pro Ala Lys Lys Val Cys Gly Pro Val Tyr Cys Phe Thr Pro Ser
            500                 505                 510
Pro Val Val Val Gly Thr Thr Asp Arg Ala Gly Val Pro Thr Tyr Arg
            515                 520                 525
```

```
Trp Gly Ala Asn Glu Thr Asp Val Leu Leu Asn Ser Arg Pro
        530                 535                 540

Pro Met Gly Asn Trp Phe Gly Cys Thr Trp Met Asn Ser Ser Gly Phe
545                 550                 555                 560

Thr Lys Thr Cys Gly Ala Pro Ala Cys Asn Ile Gly Gly Ser Gly Asn
            565                 570                 575

Asn Thr Leu Leu Cys Pro Thr Asp Cys Phe Arg Lys His Pro Asp Ala
            580                 585                 590

Thr Tyr Ser Arg Cys Gly Ser Gly Pro Trp Leu Thr Pro Arg Cys Leu
            595                 600                 605

Val Asp Tyr Pro Tyr Arg Leu Trp His Tyr Pro Cys Thr Val Asn Tyr
        610                 615                 620

Thr Ile Phe Lys Ile Arg Met Phe Val Gly Gly Val Glu His Arg Leu
625                 630                 635                 640

Asp Ala Ala Cys Asn Trp Thr Arg Gly Glu Arg Cys Asp Leu Asp Asp
            645                 650                 655

Arg Asp Arg Ala Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Leu Ser Ser Ala Val Thr Ser Trp Val Ile Lys Trp Glu Tyr Val Val
705                 710                 715                 720

Leu Leu Phe Leu Leu Leu Ala Asp Ala Arg Ile Cys Ala Cys Leu Trp
                725                 730                 735

Met Met Leu Leu Ile Ser Gln Val Glu Ala
            740                 745

<210> SEQ ID NO 75
<211> LENGTH: 749
<212> TYPE: PRT
<213> ORGANISM: Artificial Sequence
<220> FEATURE:
<223> OTHER INFORMATION: Synthetic polypeptide.
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (249)..(250)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
```

```
<221> NAME/KEY: misc_feature
<222> LOCATION: (495)..(495)
<223> OTHER INFORMATION: Xaa can be any naturally occurring amino acid
<220> FEATURE:
<221> NAME/KEY: misc_feature
<222> LOCATION: (627)..(627)
<223> OTHER INFORMATION: Xaa can be any naturally occurring amino acid
<220> FEATURE:
<221> NAME/KEY: misc_feature
<222> LOCATION: (663)..(663)
<223> OTHER INFORMATION: Xaa can be any naturally occurring amino acid
<220> FEATURE:
<221> NAME/KEY: misc_feature
<222> LOCATION: (682)..(682)
<223> OTHER INFORMATION: Xaa can be any naturally occurring amino acid

<400> SEQUENCE: 75

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Lys Asn Ile Ser Thr Ser Tyr Met Val Thr Asn Asp Cys Ser
        195                 200                 205

Asn Asp Ser Ile Thr Trp Gln Leu Gln Ala Ala Val Leu His Val Pro
210                 215                 220

Gly Cys Val Pro Cys Glu Asn Asp Xaa Asn Thr Ser Arg Cys Trp Ile
225                 230                 235                 240

Pro Val Ser Pro Asn Val Ala Val Xaa Xaa Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Xaa Phe Ile Val Ser Pro Gln Arg His Trp Phe Val Gln Glu Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
```

-continued

```
                325                 330                 335
Ala Met Arg Val Pro Glu Val Ile Ile Asp Ile Ile Phe Gly Ala His
                340                 345                 350
Trp Gly Val Met Phe Gly Leu Ala Tyr Phe Ser Met Gln Gly Ala Trp
                355                 360                 365
Ala Lys Val Ile Val Ile Leu Leu Xaa Ala Gly Val Asp Ala Arg
            370                 375                 380
Thr His Thr Val Gly Gly Ser Xaa Gly Arg Thr Thr Ser Gly Xaa Ala
385                 390                 395                 400
Gly Leu Phe Ser Ser Gly Pro Lys Gln Asn Ile Gln Leu Ile Asn Thr
                405                 410                 415
Asn Gly Ser Trp His Ile Asn Arg Thr Ala Leu Asn Cys Asn Asp Ser
                420                 425                 430
Leu Gln Thr Gly Phe Ile Ala Ser Leu Phe Tyr Thr Xaa Asn Phe Asn
                435                 440                 445
Ser Ser Gly Cys Pro Glu Arg Leu Ser Ala Cys Arg Gly Ile Glu Ala
                450                 455                 460
Phe Arg Ile Gly Trp Gly Thr Leu Gln Tyr Glu Asp Asn Val Thr Asn
465                 470                 475                 480
Pro Glu Asp Met Arg Pro Tyr Cys Trp His Tyr Pro Pro Lys Xaa Cys
                485                 490                 495
Gly Ile Val Pro Ala Arg Ser Val Cys Gly Pro Val Tyr Cys Phe Thr
                500                 505                 510
Pro Ser Pro Val Val Gly Thr Thr Asp Arg Leu Gly Val Pro Thr
                515                 520                 525
Tyr Thr Trp Gly Glu Asn Glu Thr Asp Val Phe Leu Leu Asn Ser Thr
                530                 535                 540
Arg Pro Pro Arg Gly Ser Trp Phe Gly Cys Thr Trp Met Asn Ser Thr
545                 550                 555                 560
Gly Phe Thr Lys Thr Cys Gly Ala Pro Pro Cys Arg Ile Arg Ala Asp
                565                 570                 575
Phe Asn Ala Ser Thr Asp Leu Leu Cys Pro Thr Asp Cys Phe Arg Lys
                580                 585                 590
His Pro Asp Ala Thr Tyr Lys Cys Gly Ser Gly Pro Trp Leu Thr Pro
                595                 600                 605
Arg Cys Leu Val Asp Tyr Pro Tyr Arg Leu Trp His Tyr Pro Cys Thr
                610                 615                 620
Val Asn Xaa Thr Ile Phe Lys Ile Arg Met Tyr Val Gly Gly Val Glu
625                 630                 635                 640
His Arg Leu Thr Ala Ala Cys Asn Phe Thr Arg Gly Asp Arg Cys Asn
                645                 650                 655
Leu Glu Asp Arg Asp Arg Xaa Gln Leu Ser Pro Leu Leu His Ser Thr
                660                 665                 670
Thr Glu Trp Ala Ile Leu Pro Cys Ser Xaa Ser Asp Leu Pro Ala Leu
                675                 680                 685
Ser Thr Gly Leu Leu His Leu His Gln Asn Ile Val Asp Val Gln Tyr
                690                 695                 700
Met Tyr Gly Leu Ser Pro Ala Leu Thr Lys Tyr Ile Val Arg Trp Glu
705                 710                 715                 720
Trp Val Val Leu Leu Phe Leu Leu Ala Asp Ala Arg Val Cys Ala
                725                 730                 735
Cys Leu Trp Met Leu Ile Leu Leu Gly Gln Ala Glu Ala
                740                 745
```

<210> SEQ ID NO 76
<211> LENGTH: 750
<212> TYPE: PRT
<213> ORGANISM: Hepatitis C virus

<400> SEQUENCE: 76

```
Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
130                 135                 140

Ser Gly Ala Ala Arg Ala Val Ala His Gly Val Arg Val Leu Glu Asp
145                 150                 155                 160

Gly Val Asn Tyr Ala Thr Gly Asn Leu Pro Gly Phe Pro Phe Ser Ile
                165                 170                 175

Phe Leu Leu Ala Leu Leu Ser Cys Ile Thr Val Pro Val Ser Ala Ala
            180                 185                 190

Gln Val Lys Asn Thr Ser Ser Ser Tyr Met Val Thr Asn Asp Cys Ser
        195                 200                 205

Asn Asp Ser Ile Thr Trp Gln Leu Glu Ala Ala Val Leu His Val Pro
210                 215                 220

Gly Cys Val Pro Cys Glu Arg Val Gly Asn Thr Ser Arg Cys Trp Val
225                 230                 235                 240

Pro Val Ser Pro Asn Met Ala Val Arg Gln Pro Gly Ala Leu Thr Gln
                245                 250                 255

Gly Leu Arg Thr His Ile Asp Met Val Val Met Ser Ala Thr Phe Cys
            260                 265                 270

Ser Ala Leu Tyr Val Gly Asp Leu Cys Gly Gly Val Met Leu Ala Ala
        275                 280                 285

Gln Val Phe Ile Val Ser Pro Gln Tyr His Trp Phe Val Gln Glu Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Val Met Arg Val Pro Glu Val Ile Ile Asp Ile Val Ser Gly Ala His
            340                 345                 350

Trp Gly Val Met Phe Gly Leu Ala Tyr Phe Ser Met Gln Gly Ala Trp
        355                 360                 365

Ala Lys Val Ile Val Ile Leu Leu Leu Ala Ala Gly Val Asp Ala Gly
```

```
              370                 375                 380
Thr Thr Thr Val Gly Gly Ala Val Ala Arg Ser Thr Asn Val Ile Ala
385                 390                 395                 400

Gly Val Phe Ser His Gly Pro Gln Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Thr Asn Arg Phe Asn
                435                 440                 445

Ser Ser Gly Cys Pro Gly Arg Leu Ser Ala Cys Arg Asn Ile Glu Ala
            450                 455                 460

Phe Arg Ile Gly Trp Gly Thr Leu Gln Tyr Glu Asp Asn Val Thr Asn
465                 470                 475                 480

Pro Glu Asp Met Arg Pro Tyr Cys Trp His Tyr Pro Pro Lys Pro Cys
                485                 490                 495

Gly Val Val Pro Ala Arg Ser Val Cys Gly Pro Val Tyr Cys Phe Thr
                500                 505                 510

Pro Ser Pro Val Val Val Gly Thr Thr Asp Arg Arg Gly Val Pro Thr
            515                 520                 525

Tyr Thr Trp Gly Glu Asn Glu Thr Asp Val Phe Leu Leu Asn Ser Thr
            530                 535                 540

Arg Pro Pro Gln Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Ala Thr Tyr Ile Lys Cys Gly Ser Gly Pro Trp Leu Thr
            595                 600                 605

Pro Lys Cys Leu Val His Tyr Pro Tyr Arg Leu Trp His Tyr Pro Cys
            610                 615                 620

Thr Val Asn Phe Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asp Leu Glu Asp Arg Asp Arg Ser Gln Leu Ser Pro Leu Leu His Ser
                660                 665                 670

Thr Thr Glu Trp Ala Ile Leu Pro Cys Thr Tyr Ser Asp Leu Pro Ala
            675                 680                 685

Leu Ser Thr Gly Leu Leu His Leu His Gln Asn Ile Val Asp Val Gln
            690                 695                 700

Tyr Met Tyr Gly Leu Ser Pro Ala Ile Thr Lys Tyr Val Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala
                740                 745                 750

<210> SEQ ID NO 77
<211> LENGTH: 749
<212> TYPE: PRT
<213> ORGANISM: Hepatitis C virus

<400> SEQUENCE: 77
```

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
                180                 185                 190

Gln Val Lys Asn Thr Ser Asp Ile Tyr Met Val Thr Asn Asp Cys Ser
                195                 200                 205

Asn Asp Ser Ile Thr Trp Gln Leu Gln Ala Ala Ala Leu His Val Pro
210                 215                 220

Gly Cys Val Pro Cys Glu Arg Val Gly Asn Thr Ser Arg Cys Trp Ile
225                 230                 235                 240

Pro Val Ser Pro Asn Val Ala Val Arg Gln Pro Gly Ala Leu Thr Gln
                245                 250                 255

Gly Leu Arg Thr His Ile Asp Met Val Val Met Ser Ala Thr Leu Cys
                260                 265                 270

Ser Ala Leu Tyr Val Gly Asp Leu Cys Gly Gly Val Met Leu Ala Ala
                275                 280                 285

Gln Met Phe Ile Ile Ser Pro Gln His His Trp Phe Val Gln Glu Cys
                290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Thr Thr Met Ile Leu Ala Tyr
                325                 330                 335

Val Met Arg Val Pro Glu Val Ile Ile Asp Ile Ile Gly Gly Ala His
                340                 345                 350

Trp Gly Val Met Phe Gly Leu Ala Tyr Phe Ser Met Gln Gly Ala Trp
                355                 360                 365

Ala Lys Val Val Val Ile Leu Leu Leu Ala Ala Gly Val Asp Ala His
                370                 375                 380

Thr Arg Thr Gly Ser Ser Val Gly Tyr Ala Thr Ser Gly Ile Val Gly
385                 390                 395                 400

Leu Phe Thr Ser Gly Pro Lys Gln Asn Ile Gln Leu Ile Asn Thr Asn
                405                 410                 415

Gly Ser Trp His Ile Asn Arg Thr Ala Leu Asn Cys Asn Asp Ser Leu
```

```
                420             425             430
Asn Thr Gly Phe Ile Val Ser Leu Phe Tyr Ala Arg Asn Phe Asn Ser
            435                 440                 445

Thr Gly Cys Pro Glu Arg Leu Ser Ala Cys Arg Gly Ile Glu Gly Phe
450                 455                 460

Arg Ile Gly Trp Gly Thr Leu Gln Tyr Glu Asp Asn Val Thr Asn Pro
465                 470                 475                 480

Glu Asp Met Arg Pro Tyr Cys Trp His Tyr Pro Pro Lys Gln Cys Gly
                485                 490                 495

Ile Val Pro Ala Gly Ser Val Cys Gly Pro Val Tyr Cys Phe Thr Pro
            500                 505                 510

Ser Pro Val Val Gly Thr Thr Asp Arg Leu Gly Val Pro Thr Tyr
            515                 520                 525

Thr Trp Gly Glu Asn Glu Thr Asp Val Phe Leu Leu Asn Ser Thr Arg
        530                 535                 540

Pro Pro Val Gly Ser Trp Phe Gly Cys Thr Trp Met Asn Ser Thr Gly
545                 550                 555                 560

Phe Thr Lys Thr Cys Gly Ala Pro Pro Cys Arg Ile Arg Ala Asp Phe
                565                 570                 575

Asn Ala Ser Thr Asp Leu Leu Cys Pro Thr Asp Cys Phe Arg Lys His
            580                 585                 590

Pro Glu Ala Thr Tyr Ile Lys Cys Gly Ser Gly Pro Trp Leu Thr Pro
        595                 600                 605

Arg Cys Leu Val Asp Tyr Pro Tyr Arg Leu Trp His Tyr Pro Cys Thr
        610                 615                 620

Val Asn Tyr Ser Ile Phe Lys Ile Arg Met Tyr Val Gly Gly Val Glu
625                 630                 635                 640

His Arg Leu Thr Ala Ala Cys Asn Phe Thr Arg Gly Asp Arg Cys Asn
                645                 650                 655

Leu Glu Asp Arg Asp Arg Ser Gln Leu Thr Pro Leu Leu His Ser Thr
            660                 665                 670

Thr Glu Trp Ala Ile Leu Pro Cys Thr Tyr Ser Asp Leu Pro Ala Leu
        675                 680                 685

Ser Thr Gly Leu Leu His Leu His Gln Asn Ile Val Asp Val Gln Tyr
        690                 695                 700

Met Tyr Gly Leu Ser Pro Ala Leu Thr Lys Tyr Val Val Arg Trp Glu
705                 710                 715                 720

Trp Val Val Leu Leu Phe Leu Leu Leu Ala Asp Ala Arg Val Cys Ala
                725                 730                 735

Cys Val Trp Met Leu Ile Leu Leu Gly Gln Ala Glu Ala
                740                 745

<210> SEQ ID NO 78
<211> LENGTH: 750
<212> TYPE: PRT
<213> ORGANISM: Hepatitis C virus
<220> FEATURE:
<221> NAME/KEY: misc_feature
<222> LOCATION: (458)..(458)
<223> OTHER INFORMATION: Xaa can be any naturally occurring amino acid

<400> SEQUENCE: 78

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

```
Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
                130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
                180                 185                 190

Gln Val Lys Asn Thr Ser Glu Thr Tyr Met Val Thr Asn Asp Cys Ser
                195                 200                 205

Asn Asp Ser Ile Thr Trp Gln Leu Gln Ala Ala Val Leu His Val Pro
                210                 215                 220

Gly Cys Val Pro Cys Glu Arg Thr Gly Asn Thr Ser Arg Cys Trp Ile
225                 230                 235                 240

Pro Val Ser Pro Asn Val Ala Val Gln Gln Pro Gly Ala Leu Thr Gln
                245                 250                 255

Gly Leu Arg Thr His Ile Asp Met Val Val Met Ser Ala Thr Leu Cys
                260                 265                 270

Ser Ala Leu Tyr Val Gly Asp Leu Cys Gly Gly Val Val Leu Ala Ala
                275                 280                 285

Gln Leu Phe Ile Val Ser Pro Arg Arg His Trp Phe Val Gln Glu Cys
                290                 295                 300

Asn Cys Ser Ile Tyr Pro Gly Ala Ile Thr Gly His Arg Met Ala Trp
305                 310                 315                 320

Asp Met Met Met Asn Trp Ser Pro Thr Thr Thr Met Val Leu Ala Tyr
                325                 330                 335

Ala Met Arg Val Pro Glu Val Ile Ile Asp Ile Ile Ser Gly Ala His
                340                 345                 350

Trp Gly Val Met Phe Gly Leu Ala Tyr Phe Ser Met Gln Gly Ala Trp
                355                 360                 365

Ala Lys Val Ala Val Ile Leu Leu Leu Thr Ala Gly Val Glu Ala Arg
                370                 375                 380

Thr His Thr Thr Gly Ser Val Ala Gly Arg Thr Thr Ser Gly Phe Ala
385                 390                 395                 400

Gly Ile Phe Thr Ser Gly Pro Lys Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Met Ala Ala Leu Phe Tyr Thr Lys Asn Phe Asn
                435                 440                 445
```

Ser Ser Gly Cys Pro Glu Arg Leu Ser Xaa Cys Arg Asn Ile Glu Ala
450                 455                 460

Phe Arg Ile Gly Trp Gly Thr Leu Gln Tyr Glu Asp Asp Val Thr Asn
465                 470                 475                 480

Pro Glu Asp Met Arg Pro Tyr Cys Trp His Tyr Pro Pro Lys Gln Cys
            485                 490                 495

Gly Ile Phe Pro Ala Gly Ser Val Cys Gly Pro Val Tyr Cys Phe Thr
            500                 505                 510

Pro Ser Pro Val Val Val Gly Thr Thr Asn Lys Leu Gly Val Pro Thr
            515                 520                 525

Tyr Thr Trp Gly Glu Asn Glu Thr Asp Val Phe Ile Leu Asn Ser Thr
530                 535                 540

Arg Pro Pro Arg Gly Ser Trp Phe Gly Cys Thr Trp Met Asn Ser Thr
545                 550                 555                 560

Gly Phe Thr Lys Thr Cys Gly Ala Pro Pro Cys Arg Ile Arg Ala Asp
                565                 570                 575

Phe Asn Ala Ser Thr Asp Leu Leu Cys Pro Thr Asp Cys Phe Arg Lys
            580                 585                 590

His Pro Glu Ala Thr Tyr Ile Lys Cys Gly Ser Gly Pro Trp Leu Thr
            595                 600                 605

Pro Arg Cys Leu Val Asp Tyr Pro Tyr Arg Leu Trp His Tyr Pro Cys
610                 615                 620

Thr Val Asn Tyr Ser Ile Phe Lys Ile Arg Met Tyr Val Gly Gly Val
625                 630                 635                 640

Glu His Arg Leu Thr Ala Ala Cys Asn Phe Ser Arg Gly Asp Arg Cys
                645                 650                 655

Asn Leu Glu Asp Arg Asp Arg Ser Gln Leu Thr Pro Leu Leu His Ser
            660                 665                 670

Thr Thr Glu Trp Ala Ile Leu Pro Cys Ser Tyr Ser Asp Leu Pro Ala
            675                 680                 685

Leu Ser Thr Gly Leu Leu His Leu His Gln Asn Ile Val Asp Val Gln
690                 695                 700

Tyr Met Tyr Gly Leu Thr Pro Ala Leu Thr Lys Tyr Val Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala
            740                 745                 750

<210> SEQ ID NO 79
<211> LENGTH: 750
<212> TYPE: PRT
<213> ORGANISM: Hepatitis C virus

<400> SEQUENCE: 79

Met Ser Thr Asn Pro Lys Pro Gln Arg Lys Thr Lys Arg Asn Thr Ser
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Gly Arg Arg Gln Pro
50                  55                  60

Ile Pro Lys Asp Arg Arg Ser Thr Gly Lys Ser Trp Gly Lys Pro Gly
65                  70                  75                  80

-continued

Tyr Pro Trp Pro Leu Tyr Gly Asn Glu Gly Leu Gly Trp Ala Gly Trp
            85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Ile Thr Val Pro Val Ser Ala Val
        180                 185                 190

Gln Val Lys Asn Ile Ser Asp Ser Tyr Met Val Thr Asn Asp Cys Ser
        195                 200                 205

Asn Asp Ser Ile Thr Trp Gln Leu Gln Ala Ala Val Leu His Val Pro
210                 215                 220

Gly Cys Val Pro Cys Glu Lys Met Gly Asn Ile Ser Arg Cys Trp Ile
225                 230                 235                 240

Pro Val Ser Pro Asn Val Ala Val Gln Arg Pro Gly Ala Leu Thr Gln
            245                 250                 255

Gly Leu Arg Ala His Ile Asp Met Val Val Met Ser Ala Thr Leu Cys
            260                 265                 270

Ser Ala Leu Tyr Val Gly Asp Leu Cys Gly Val Met Leu Ala Ala
            275                 280                 285

Gln Met Phe Ile Val Ser Pro Gln His His His Phe Val Gln Glu Cys
        290                 295                 300

Asn Cys Ser Ile Tyr Pro Gly Ala Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
            355                 360                 365

Ala Lys Val Val Ile Leu Leu Leu Thr Ala Gly Val Asp Ala His
370                 375                 380

Thr Arg Ser Ile Ala Gly Ser Val Ala His Ala Thr Ser Gly Leu Ala
385                 390                 395                 400

Gly Leu Phe Thr Ser Gly Ala Lys Gln Asn Ile Gln Leu Ile Asn Thr
            405                 410                 415

Asn Gly Ser Trp His Ile Asn Arg Thr Ala Leu Asn Cys Asn Asp Ser
            420                 425                 430

Leu Asn Thr Gly Phe Ile Ala Ser Leu Phe Tyr Thr Tyr Arg Phe Asn
        435                 440                 445

Ser Ser Gly Cys Pro Glu Arg Leu Ser Ala Cys Arg Gly Ile Gln Ala
450                 455                 460

Phe Arg Ile Gly Trp Gly Thr Leu Arg Tyr Glu Asp Asn Val Thr Asn
465                 470                 475                 480

Pro Glu Asp Met Arg Pro Tyr Cys Trp His Tyr Pro Pro Lys Gln Cys
            485                 490                 495

Gly Ile Val Ser Ala Arg Ser Val Cys Gly Pro Val Tyr Cys Phe Thr
                500                 505                 510

Pro Ser Pro Val Val Gly Thr Thr Asp Arg Leu Gly Val Pro Thr
    515                 520                 525

Tyr Thr Trp Gly Glu Asn Glu Thr Asp Val Phe Ile Leu Asn Ser Thr
    530                 535                 540

Arg Pro Pro Gly Gly Ser Trp Phe Gly Cys Thr Trp Met Asn Ser Thr
545                 550                 555                 560

Gly Phe Thr Lys Thr Cys Gly Ala Pro Pro Cys Arg Ile Arg Ala Asp
                565                 570                 575

Phe Asn Ala Ser Met Asp Leu Leu Cys Pro Thr Asp Cys Phe Arg Lys
                580                 585                 590

His Pro Asp Ala Thr Tyr Ile Lys Cys Gly Ser Gly Pro Trp Leu Thr
                595                 600                 605

Pro Arg Cys Leu Val Asp Tyr Pro Tyr Arg Leu Trp His Tyr Pro Cys
                610                 615                 620

Thr Ile Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Pro Cys
                645                 650                 655

Asn Leu Glu Asp Arg Asp Arg Ser Gln Leu Ser Pro Leu Leu His Ser
                660                 665                 670

Thr Thr Glu Trp Ala Ile Leu Pro Cys Ser Tyr Ser Asp Leu Pro Ala
                675                 680                 685

Leu Ser Thr Gly Leu Leu His Leu His Gln Asn Ile Val Asp Val Gln
                690                 695                 700

Tyr Met Tyr Gly Leu Ser Pro Ala Leu Thr Lys Tyr Ile Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala
                740                 745                 750

<210> SEQ ID NO 80
<211> LENGTH: 751
<212> TYPE: PRT
<213> ORGANISM: Hepatitis C virus

<400> SEQUENCE: 80

Met Ser Thr Asn Pro Lys Pro Gln Arg Lys Thr Gln Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Thr
                35                  40                  45

Ala Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
            115                 120                 125

```
Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Ile Pro Ala Ser Ala Val
                180                 185                 190

Glu Val Lys Asn Thr Ser Thr Gly Tyr Met Val Thr Asn Asp Cys Ala
        195                 200                 205

Asn Ser Ser Ile Thr Trp Gln Leu His Ala Ala Val Leu His Val Pro
210                 215                 220

Gly Cys Val Pro Cys Glu Arg Val Asp Asn Asn Thr Ser Arg Cys Trp
225                 230                 235                 240

Ile Pro Val Ser Pro Asn Ile Ala Val Gln Arg Pro Gly Ala Leu Thr
                245                 250                 255

Gln Gly Leu Arg Ser His Ile Asp Ile Val Val Met Ser Ala Thr Leu
                260                 265                 270

Cys Ser Ala Leu Tyr Val Gly Asp Leu Cys Gly Gly Val Met Leu Ala
        275                 280                 285

Ala Gln Met Phe Val Val Ser Pro Glu His His Trp Phe Val Gln Glu
290                 295                 300

Cys Asn Cys Ser Ile Tyr Pro Gly Thr Ile Thr Gly His Arg Met Ala
305                 310                 315                 320

Trp Asp Met Met Met Asn Trp Ser Pro Thr Ala Thr Met Ile Leu Ala
                325                 330                 335

Tyr Ala Met Arg Val Pro Glu Val Ile Ile Asp Ile Ile Gly Gly Ala
                340                 345                 350

His Trp Gly Val Met Phe Gly Leu Ala Tyr Phe Ser Met Gln Gly Ala
        355                 360                 365

Trp Ala Lys Val Val Val Ile Leu Leu Leu Ala Ala Gly Val Asp Ala
370                 375                 380

Tyr Thr His Thr Val Gly Gly Ala Ala Ala Ser Thr Ala Asn Ser Ile
385                 390                 395                 400

Ala Gly Leu Leu Ser Arg Gly Pro Arg Gln Asn Leu Gln Leu Ile Asn
                405                 410                 415

Ser Asn Gly Ser Trp His Ile Asn Arg Thr Ala Leu Asn Cys His Asp
                420                 425                 430

Ser Leu Gln Thr Gly Phe Ile Thr Ala Leu Phe Tyr Ala Arg His Phe
        435                 440                 445

Asn Ser Ser Gly Cys Pro Glu Arg Leu Ala Ala Cys Arg Asn Ile Glu
450                 455                 460

Ala Phe Arg Val Gly Trp Gly Ala Leu Gln Tyr Glu Asp Asn Val Thr
465                 470                 475                 480

Asn Pro Glu Asp Met Arg Pro Tyr Cys Trp His Tyr Pro Pro Lys Gln
                485                 490                 495

Cys Gly Ile Val Pro Ala Arg Ser Val Cys Gly Pro Val Tyr Cys Phe
                500                 505                 510

Thr Pro Ser Pro Val Val Gly Thr Thr Asp Lys Leu Gly Val Pro
        515                 520                 525

Thr Tyr Thr Trp Gly Glu Asn Glu Thr Asp Val Phe Leu Leu Asn Ser
530                 535                 540
```

```
Thr Arg Pro Pro Gln Gly Pro Trp Phe Gly Cys Thr Trp Met Asn Ser
545                 550                 555                 560

Thr Gly Phe Thr Lys Thr Cys Gly Ala Pro Pro Cys Arg Thr Arg Ala
                565                 570                 575

Asp Phe Asn Ala Ser Thr Asp Leu Leu Cys Pro Thr Asp Cys Phe Arg
            580                 585                 590

Lys His Pro Asp Ala Thr Tyr Asn Lys Cys Gly Ser Gly Pro Trp Leu
        595                 600                 605

Thr Pro Arg Cys Leu Ile Asp Tyr Pro Tyr Arg Leu Trp His Tyr Pro
    610                 615                 620

Cys Thr Val Asn Tyr Thr Thr Phe Lys Ile Arg Met Tyr Val Gly Gly
625                 630                 635                 640

Val Glu His Arg Leu Met Ala Ala Cys Asn Phe Thr Arg Gly Asp Ser
                645                 650                 655

Cys Asp Leu Ser Gln Arg Asp Arg Gly Gln Leu Ser Pro Leu Leu His
            660                 665                 670

Ser Thr Thr Glu Trp Ala Ile Leu Pro Cys Ser Phe Ser Asp Leu Pro
        675                 680                 685

Ala Leu Ser Thr Gly Leu Leu His Leu His Gln Asn Ile Val Asp Val
    690                 695                 700

Gln Tyr Met Tyr Gly Leu Ser Pro Ala Leu Thr Lys Tyr Ile Val Arg
705                 710                 715                 720

Trp Glu Trp Val Val Leu Leu Phe Leu Leu Leu Ala Asp Ala Arg Val
                725                 730                 735

Cys Ala Cys Ile Trp Met Leu Ile Leu Leu Gly Gln Ala Glu Ala
            740                 745                 750

<210> SEQ ID NO 81
<211> LENGTH: 750
<212> TYPE: PRT
<213> ORGANISM: Hepatitis C virus

<400> SEQUENCE: 81

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175
```

```
Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
    210                 215                 220

Gly Cys Val Pro Cys Glu Lys Val Gly Asn Thr Ser Arg Cys Trp Ile
225                 230                 235                 240

Pro Val Ser Pro Asn Val Ala Val Gln Gln Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Gly Gly Ala His
            340                 345                 350

Trp Gly Val Met Phe Gly Leu Ala Tyr Phe Ser Met Gln Gly Ala Trp
        355                 360                 365

Ala Lys Val Val Val Ile Leu Leu Ala Ala Gly Val Asp Ala Gln
    370                 375                 380

Thr His Thr Val Gly Gly Ser Thr Ala His Asn Ala Arg Thr Leu Thr
385                 390                 395                 400

Gly Met Phe Ser Leu Gly Ala Arg Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Leu Ala Ser Leu Phe Tyr Thr His Ser Phe Asn
        435                 440                 445

Ser Ser Gly Cys Pro Glu Arg Met Ser Ala Cys Arg Ser Ile Glu Ala
    450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
                485                 490                 495

Gly Val Val Ser Ala Ser Ser Val Cys Gly Pro Val Tyr Cys Phe Thr
            500                 505                 510

Pro Ser Pro Val Val Val Gly Thr Thr Asp Arg Leu Gly Ala Pro Thr
        515                 520                 525

Tyr Thr Trp Gly Glu Asn Glu Thr Asp Val Phe Leu Leu Asn Ser Thr
    530                 535                 540

Arg Pro Pro Gln Gly Ser Trp Phe Gly Cys Thr Trp Met Asn Ser Thr
545                 550                 555                 560

Gly Tyr Thr Lys Thr Cys Gly Ala Pro Pro Cys Arg Ile Arg Ala Asp
                565                 570                 575

Phe Asn Ala Ser Met Asp Leu Leu Cys Pro Thr Asp Cys Phe Arg Lys
            580                 585                 590
```

```
His Pro Asp Thr Thr Tyr Ile Lys Cys Gly Ser Gly Pro Trp Leu Thr
            595                 600                 605

Pro Arg Cys Leu Ile Asp Tyr Pro Tyr Arg Leu Trp His Tyr Pro Cys
610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
            645                 650                 655

Asn Leu Glu Asp Arg Asp Arg Ser Gln Leu Ser Pro Leu Leu His Ser
            660                 665                 670

Thr Thr Glu Trp Ala Ile Leu Pro Cys Thr Tyr Ser Asp Leu Pro Ala
            675                 680                 685

Leu Ser Thr Gly Leu Leu His Leu His Gln Asn Ile Val Asp Val Gln
            690                 695                 700

Phe Met Tyr Gly Leu Ser Pro Ala Leu Thr Lys Tyr Ile Val Arg Trp
705                 710                 715                 720

Glu Trp Val Val Leu Leu Phe Leu Leu Ala Asp Ala Arg Val Cys
            725                 730                 735

Ala Cys Leu Trp Met Leu Ile Leu Leu Gly Gln Ala Glu Ala
            740                 745                 750

<210> SEQ ID NO 82
<211> LENGTH: 750
<212> TYPE: PRT
<213> ORGANISM: Hepatitis C virus

<400> SEQUENCE: 82

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
            195                 200                 205

Asn Asp Ser Ile Thr Trp Gln Leu Gln Ala Ala Val Leu His Val Pro
210                 215                 220
```

```
Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
            245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Val Met Leu Ala Ala
        275                 280                 285

Gln Met Phe Ile Val Ser Pro Gln His His Trp Phe Val Gln Asp Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
            355                 360                 365

Ala Lys Val Val Val Ile Leu Leu Leu Ala Ala Gly Val Asp Ala Arg
370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
            435                 440                 445

Ser Ser Gly Cys Pro Glu Arg Met Ser Ala Cys Arg Ser Ile Glu Ala
        450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Arg Gln Cys
                485                 490                 495

Gly Val Val Ser Ala Lys Thr Val Cys Gly Pro Val Tyr Cys Phe Thr
            500                 505                 510

Pro Ser Pro Val Val Val Gly Thr Thr Asp Arg Leu Gly Ala Pro Thr
        515                 520                 525

Tyr Thr Trp Gly Glu Asn Glu Thr Asp Val Phe Leu Leu Asn Ser Thr
        530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
        595                 600                 605

Pro Arg Cys Leu Ile Asp Tyr Pro Tyr Arg Leu Trp His Tyr Pro Cys
        610                 615                 620

Thr Val Asn Tyr Thr Ile Phe Lys Ile Arg Met Tyr Val Gly Gly Val
625                 630                 635                 640
```

```
Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
            660                 665                 670

Thr Thr Glu Trp Ala Ile Leu Pro Cys Ser Tyr Ser Asp Leu Pro Ala
        675                 680                 685

Leu Ser Thr Gly Leu Leu His Leu His Gln Asn Ile Val Asp Val Gln
690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
                725                 730                 735

Ala Cys Leu Trp Met Leu Ile Leu Leu Gly Gln Ala Glu Ala
            740                 745                 750

<210> SEQ ID NO 83
<211> LENGTH: 750
<212> TYPE: PRT
<213> ORGANISM: Hepatitis C virus

<400> SEQUENCE: 83

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270
```

```
Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
        290                 295                 300

Asn Cys Ser Ile Tyr Gln Gly His Ile Thr Gly His Arg Met Ala Trp
305                 310                 315                 320

Asp Met Met Leu Ser Trp Ser Pro Thr Leu Thr Met Ile Leu Ala Tyr
                325                 330                 335

Ala Ala Arg Val Pro Glu Leu Val Leu Glu Ile Ile Phe Gly Gly His
                340                 345                 350

Trp Gly Val Val Phe Gly Leu Ala Tyr Phe Ser Met Gln Gly Ala Trp
                355                 360                 365

Ala Lys Val Ile Ala Ile Leu Leu Leu Val Ala Gly Val Asp Ala Thr
        370                 375                 380

Thr Tyr Ser Ser Gly Gln Glu Ala Gly Arg Thr Val Ala Gly Phe Ala
385                 390                 395                 400

Gly Leu Phe Thr Thr Gly Ala Lys Gln Asn Leu Tyr Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Leu Ala Ser Leu Phe Tyr Thr His Lys Phe Asn
        435                 440                 445

Ser Ser Gly Cys Pro Glu Arg Leu Ser Ser Cys Arg Gly Leu Asp Asp
        450                 455                 460

Phe Arg Ile Gly Trp Gly Thr Leu Glu Tyr Glu Thr Asn Val Thr Asn
465                 470                 475                 480

Asp Gly Asp Met Arg Pro Tyr Cys Trp His Tyr Pro Arg Pro Cys
                485                 490                 495

Gly Ile Val Pro Ala Arg Thr Val Cys Gly Pro Val Tyr Cys Phe Thr
                500                 505                 510

Pro Ser Pro Val Val Gly Thr Thr Asp Lys Gln Gly Val Pro Thr
        515                 520                 525

Tyr Thr Trp Gly Glu Asn Glu Thr Asp Val Phe Leu Leu Asn Ser Thr
        530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Tyr Asn Ser Thr Ile Asp Leu Leu Cys Pro Thr Asp Cys Phe Arg Lys
                580                 585                 590

His Pro Asp Ala Thr Tyr Leu Lys Cys Gly Ala Gly Pro Trp Leu Thr
        595                 600                 605

Pro Arg Cys Leu Val Asp Tyr Pro Tyr Arg Leu Trp His Tyr Pro Cys
610                 615                 620

Thr Val Asn Phe Thr Ile Phe Lys Ala Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
                660                 665                 670

Thr Thr Glu Trp Ala Val Leu Pro Cys Ser Phe Ser Asp Leu Pro Ala
                675                 680                 685
```

```
Leu Ser Thr Gly Leu Leu His Leu His Gln Asn Ile Val Asp Val Gln
    690                 695                 700

Tyr Leu Tyr Gly Leu Ser Pro Ala Leu Thr Arg Tyr Ile Val Lys Trp
705                 710                 715                 720

Glu Trp Val Ile Leu Phe Leu Leu Leu Ala Asp Ala Arg Ile Cys
                725                 730                 735

Ala Cys Leu Trp Met Leu Ile Ile Leu Gly Gln Ala Glu Ala
                740                 745                 750

<210> SEQ ID NO 84
<211> LENGTH: 750
<212> TYPE: PRT
<213> ORGANISM: Hepatitis C virus

<400> SEQUENCE: 84

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro His Trp Gly Pro Thr Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Ile Gly Ala Pro Val
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Glu Asn Ala Val Leu His Leu Pro
210                 215                 220

Gly Cys Val Pro Cys Glu Asn Asp Asn Gly Thr Leu Arg Cys Trp Thr
225                 230                 235                 240

Gln Val Thr Pro Asn Val Ala Val Lys His Arg Gly Ala Leu Thr Gln
                245                 250                 255

Asn Leu Arg Thr His Val Asp Val Ile Val Val Ala Ala Thr Val Cys
            260                 265                 270

Ser Ala Leu Tyr Val Gly Asp Val Cys Gly Ala Val Met Ile Ala Ser
        275                 280                 285

Gln Ala Leu Ile Val Ser Pro Ala Arg His Asn Phe Thr Gln Glu Cys
290                 295                 300

Asn Cys Ser Ile Tyr Gln Gly Arg Ile Thr Gly His His Met Ala Trp
305                 310                 315                 320
```

```
Asp Met Met Leu Asn Trp Ser Pro Thr Ile Thr Met Ile Leu Ala Tyr
                325                 330                 335

Ala Ala Arg Ile Pro Glu Leu Val Leu Glu Val Ile Phe Gly Gly His
            340                 345                 350

Trp Gly Val Met Phe Gly Leu Ala Tyr Phe Ser Met Gln Gly Ala Trp
        355                 360                 365

Ala Lys Val Ile Val Ile Leu Leu Val Ala Gly Val Asp Ala Arg
    370                 375                 380

His His Thr Thr Gly Leu Gln Ala Gly Lys Thr Leu Ala Arg Val Thr
385                 390                 395                 400

Ser Leu Phe Ser Ile Gly Ala Lys Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ser Leu Phe Tyr Val Asn Asn Ile Asn
        435                 440                 445

Ser Ser Gly Cys Pro Glu Arg Met Ser Ser Cys Arg Glu Leu Asp Asp
    450                 455                 460

Phe Arg Ile Gly Trp Gly Thr Leu Glu Tyr Glu Thr Asn Val Thr Asn
465                 470                 475                 480

Asp Glu Asp Met Arg Pro Tyr Cys Trp His Tyr Pro Pro Lys Pro Cys
                485                 490                 495

Gly Ile Val Pro Ala Arg Thr Val Cys Gly Pro Val Tyr Cys Phe Thr
            500                 505                 510

Pro Ser Pro Ile Val Val Gly Thr Thr Asp Lys Gln Gly Val Pro Thr
        515                 520                 525

Tyr Ser Trp Gly Glu Asn Glu Thr Asp Val Phe Leu Leu Asn Ser Thr
    530                 535                 540

Arg Pro Pro Arg Gly Ser Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

Tyr Asn Ser Thr Leu Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
        595                 600                 605

Pro Lys Cys Leu Val Glu Tyr Pro Tyr Arg Leu Trp His Tyr Pro Cys
    610                 615                 620

Thr Val Asn Phe Thr Ile Phe Lys Val Arg Met Tyr Val Gly Ala Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
    690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735
```

```
Ala Cys Leu Trp Met Leu Ile Ile Leu Gly Gln Ala Glu Ala
            740                 745                 750

<210> SEQ ID NO 85
<211> LENGTH: 750
<212> TYPE: PRT
<213> ORGANISM: Hepatitis C virus

<400> SEQUENCE: 85

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Cys Thr Val Pro Val Ser Ala Val
            180                 185                 190

Glu Val Arg Asn Ile Ser Thr Ser Tyr Tyr Ala Thr Asn Asp Cys Ser
        195                 200                 205

Asn Thr Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Thr His Val Asp Val Ile Val Met Ala Ala Thr Val Cys
            260                 265                 270

Ser Ala Leu Tyr Val Gly Asp Ile Cys Gly Ala Val Met Ile Val Ser
        275                 280                 285

Gln Ala Phe Ile Ile Ser Pro Glu Arg His Asn Phe Thr Gln Glu Cys
    290                 295                 300

Asn Cys Ser Met Tyr Gln Gly His Ile Thr Gly His Arg Met Ala Trp
305                 310                 315                 320

Asp Met Met Leu Asn Trp Ser Pro Thr Leu Thr Met Ile Leu Ala Tyr
                325                 330                 335

Ala Ala Arg Val Pro Glu Leu Val Leu Glu Val Ile Phe Gly Gly His
            340                 345                 350

Trp Gly Val Val Phe Gly Leu Ala Tyr Phe Ser Met Gln Gly Ala Trp
        355                 360                 365
```

Ala Lys Val Ile Ala Ile Leu Leu Leu Val Ala Gly Val Asp Ala Asn
    370                 375                 380

Thr Tyr Ser Ser Gly

<400> SEQUENCE: 86

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Ser Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Arg Asn Leu Pro Gly Cys Ser Phe Ser Ile
                165                 170                 175

Phe Leu Leu Ala Leu Leu Ser Cys Val Thr Val Pro Val Ser Ser Val
            180                 185                 190

Glu Ile Arg Asn Ile Ser Thr Ser Tyr Tyr Ala Thr Asn Asp Cys Ser
        195                 200                 205

Asn Asn Ser Ile Thr Trp Gln Leu Thr Asn Ala Val Leu His Leu Pro
210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Ala His Val Asp Val Ile Val Met Ala Ala Thr Val Cys
            260                 265                 270

Ser Ala Leu Tyr Val Gly Asp Val Cys Gly Ala Val Met Ile Val Ser
        275                 280                 285

Gln Ala Leu Ile Val Ser Pro Glu Arg His Asn Phe Thr Gln Glu Cys
290                 295                 300

Asn Cys Ser Ile Tyr Gln Gly His Ile Thr Gly Gln Arg Met Ala Trp
305                 310                 315                 320

Asp Met Met Leu Asn Trp Ser Pro Thr Leu Thr Met Ile Leu Ala Tyr
                325                 330                 335

Ala Ala Arg Val Pro Glu Leu Val Leu Glu Ile Val Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Thr
370                 375                 380

Thr Tyr Ser Thr Gly Ala Thr Val Gly Arg Thr Val Gly Ser Phe Ala
385                 390                 395                 400

Gly Leu Phe Lys Leu Gly Ala Gln Gln Asn Val Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Met Ala Ala Leu Phe Tyr Ala Asn Lys Phe Asn
            435                 440                 445

Ser Ser Gly Cys Pro Glu Arg Leu Ser Ser Cys Arg Gly Leu Asp Asp
450                 455                 460

Phe Arg Ile Gly Trp Gly Thr Leu Glu Tyr Glu Thr Asn Val Thr Asn
465                 470                 475                 480

Val Glu Asp Met Arg Pro Tyr Cys Trp His Tyr Pro Pro Lys Pro Cys
                485                 490                 495

Gly Ile Val Pro Ala Gln Ser Val Cys Gly Pro Val Tyr Cys Phe Thr
            500                 505                 510

Pro Ser Pro Val Val Val Gly Thr Thr Asp Arg Gln Gly Val Pro Thr
            515                 520                 525

Tyr Asn Trp Gly Asp Asn Glu Thr Asp Val Phe Leu Leu Asn Ser Thr
530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Phe Asn Ser Thr Leu Asp Leu Leu Cys Pro Thr Asp Cys Phe Arg Lys
            580                 585                 590

His Pro Asp Ala Thr Tyr Val Lys Cys Gly Ala Gly Pro Trp Leu Thr
            595                 600                 605

Pro Arg Cys Leu Ile Asp Tyr Pro Tyr Arg Leu Trp His Tyr Pro Cys
610                 615                 620

Thr Val Asn Phe Thr Ile Phe Lys Val Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
690                 695                 700

Tyr Leu Tyr Gly Leu Ser Pro Ala Val Thr Lys Tyr Ile Val Lys Trp
705                 710                 715                 720

Glu Trp Val Val Leu Leu Phe Leu Leu Leu Ala Asp Ala Arg Ile Cys
                725                 730                 735

Ala Cys Leu Trp Met Leu Ile Ile Leu Gly Gln Ala Glu Ala
            740                 745                 750

<210> SEQ ID NO 87
<211> LENGTH: 750
<212> TYPE: PRT
<213> ORGANISM: Hepatitis C virus
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature

```
<222> LOCATION: (343)..(343)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid

<400> SEQUENCE: 87

Met Ser Thr Asp Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Thr Ser Glu Arg Ser Gln Pro Arg Gly Arg Arg Gln Pro
    50                  55                  60

Ile Pro Lys Asp Arg Arg Ser Pro Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Glu Val Arg Asn Ile Ser Ser Gly Tyr Tyr Xaa Thr Asn Asp Cys Ser
        195                 200                 205

Asn Ser Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys Tyr Arg Gly Ala Leu Thr His
                245                 250                 255

Asn Leu Arg Thr His Val Asp Met Ile Val Met Ala Ala Thr Val Cys
            260                 265                 270

Ser Ala Leu Tyr Val Gly Asp Val Cys Gly Ala Val Met Ile Val Ser
        275                 280                 285

Gln Ala Phe Ile Met Ser Xaa Glu Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Gly Trp Ser Pro Thr Leu Thr Met Ile Leu Ala Tyr
                325                 330                 335
```

```
Ala Ala Arg Val Pro Glu Xaa Val Leu Glu Val Val Phe Gly Gly His
            340                 345                 350

Trp Gly Val Val Phe Gly Leu Ala Tyr Phe Ser Met Gln Gly Ala Trp
            355                 360                 365

Ala Lys Val Ile Ala Ile Leu Leu Val Ala Gly Val Asp Ala Gly
    370                 375                 380

Thr Tyr Ser Ser Gly Ala Thr Ile Gly Gln Gly Thr Arg Gly Leu Val
385                 390                 395                 400

Xaa Leu Phe Ser Ala Gly Pro Ser Gln Lys Ile Ser Leu Ile Asn Thr
                405                 410                 415

Asn Gly Ser Trp His Ile Asn Arg Thr Xaa Leu Asn Cys Asn Asp Ser
            420                 425                 430

Leu Gln Thr Gly Phe Ile Ala Ser Leu Phe Tyr Ala Lys Ser Phe Asn
            435                 440                 445

Ser Ser Gly Cys Pro Glu Arg Leu Ser Ser Cys Arg Gly Leu Asp Asp
    450                 455                 460

Phe Arg Ile Gly Trp Gly Thr Leu Glu Tyr Glu Asn Asn Val Thr Asn
465                 470                 475                 480

Asp Glu Asp Met Arg Pro Tyr Cys Trp His Tyr Pro Pro Lys Pro Cys
                485                 490                 495

Gly Ile Val Pro Ala Arg Thr Val Cys Gly Pro Val Tyr Cys Phe Thr
            500                 505                 510

Pro Ser Pro Val Val Val Gly Thr Thr Asp Lys Gln Gly Val Pro Thr
            515                 520                 525

Tyr Ser Trp Gly Glu Asn Glu Thr Asp Val Phe Leu Leu Asn Ser Thr
            530                 535                 540

Arg Pro Pro Gln Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

His Thr Ser Thr Leu Asp Leu Leu Cys Pro Thr Asp Cys Phe Arg Lys
            580                 585                 590

His Pro Asp Thr Thr Tyr Leu Lys Cys Gly Ala Gly Pro Trp Leu Thr
            595                 600                 605

Pro Lys Cys Leu Val Asp Tyr Pro Tyr Arg Leu Trp His Tyr Pro Cys
    610                 615                 620

Thr Xaa Asn Phe Thr Ile Phe Lys Val Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
            690                 695                 700

Tyr Leu Tyr Gly Leu Ser Pro Ala Ile Thr Lys Tyr Ile Val Lys Trp
705                 710                 715                 720

Glu Trp Val Ile Leu Leu Phe Leu Leu Leu Ala Asp Ala Arg Val Cys
                725                 730                 735

Ala Cys Leu Trp Met Leu Ile Ile Leu Gly Gln Ala Glu Ala
            740                 745                 750
```

```
<210> SEQ ID NO 88
<211> LENGTH: 752
<212> TYPE: PRT
<213> ORGANISM: Artificial Sequence
<220> FEATURE:
<223> OTHER INFORMATION: Synthetic polypeptide.
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (466)..(466)
<223> OTHER INFORMATION: Xaa can be any naturally occurring amino acid

<400> SEQUENCE: 88

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Val Ile Leu His Thr Pro
    210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Leu Ser Gly His Arg Met Ala Trp
305                 310                 315                 320

Asp Met Met Met Asn Trp Ser Pro Ala Val Gly Met Val Val Ala His
```

```
                    325                 330                 335
Val Leu Arg Leu Pro Gln Thr Leu Phe Asp Ile Ile Ala Gly Ala His
                340                 345                 350
Trp Gly Ile Leu Ala Gly Leu Ala Tyr Tyr Ser Met Gln Gly Asn Trp
                355                 360                 365
Ala Lys Val Ala Ile Ile Met Val Met Phe Ser Gly Val Asp Ala Thr
            370                 375                 380
Thr Tyr Thr Thr Gly Gly Ser Ala Ala Arg Gly Ala Arg Gly Leu Thr
385                 390                 395                 400
Ser Leu Phe Ser Val Gly Ala Lys Gln Lys Leu Gln Leu Val Asn Thr
                405                 410                 415
Asn Gly Ser Trp His Ile Asn Ser Thr Ala Leu Asn Cys Asn Xaa Ser
            420                 425                 430
Ile Asn Thr Gly Phe Ile Ala Gly Leu Phe Tyr Tyr His Lys Phe Asn
                435                 440                 445
Ser Thr Gly Cys Pro Gln Arg Leu Ser Ser Cys Lys Pro Ile Thr Phe
            450                 455                 460
Phe Xaa Gln Gly Trp Gly Pro Leu Thr Asp Ala Asn Ile Thr Gly Pro
465                 470                 475                 480
Ser Asp Asp Lys Pro Tyr Cys Trp His Tyr Ala Pro Arg Pro Cys Asp
                485                 490                 495
Val Val Pro Ala Ser Ser Val Cys Gly Pro Val Tyr Cys Phe Thr Pro
            500                 505                 510
Ser Pro Val Val Gly Thr Thr Asp Ala Lys Gly Val Pro Thr Tyr
                515                 520                 525
Thr Trp Gly Glu Asn Glu Thr Asp Val Phe Leu Leu Glu Ser Leu Arg
            530                 535                 540
Pro Pro Ser Gly Arg Trp Phe Gly Cys Thr Trp Met Asn Ser Thr Gly
545                 550                 555                 560
Phe Val Lys Thr Cys Gly Ala Pro Pro Cys Asn Ile Tyr Gly Gly Gly
                565                 570                 575
Gly Asn Pro His Asn Glu Ser Asp Leu Phe Cys Pro Thr Asp Cys Phe
            580                 585                 590
Arg Lys His Pro Glu Ala Thr Tyr Ser Arg Cys Gly Ala Gly Pro Trp
                595                 600                 605
Leu Thr Pro Arg Cys Met Val Asp Tyr Pro Tyr Arg Leu Trp His Tyr
            610                 615                 620
Pro Cys Thr Val Asn Phe Thr Leu Phe Lys Val Arg Met Phe Val Gly
625                 630                 635                 640
Gly Phe Glu His Arg Phe Thr Ala Ala Cys Asn Trp Thr Arg Gly Glu
                645                 650                 655
Arg Cys Asp Ile Glu Asp Arg Asp Arg Ser Glu Gln His Pro Leu Leu
            660                 665                 670
His Ser Thr Thr Glu Leu Ala Ile Leu Pro Cys Ser Phe Thr Pro Met
                675                 680                 685
Pro Ala Leu Ser Thr Gly Leu Ile His Leu His Gln Asn Ile Val Asp
            690                 695                 700
Val Gln Tyr Leu Tyr Gly Val Gly Ser Gly Met Val Gly Trp Ala Leu
705                 710                 715                 720
Lys Trp Glu Phe Val Ile Leu Val Phe Leu Leu Leu Ala Asp Ala Arg
                725                 730                 735
Val Cys Val Ala Leu Trp Leu Met Leu Met Ile Ser Gln Ala Glu Ala
            740                 745                 750
```

<210> SEQ ID NO 89
<211> LENGTH: 752
<212> TYPE: PRT
<213> ORGANISM: Hepatitis C virus

<400> SEQUENCE: 89

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Glu Arg Arg Gln Pro
    50                  55                  60

Ile Pro Lys Ala Arg Arg Ser Asp Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Ile Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Leu Ser Cys Leu Ile His Pro Ala Ala Ser Leu
            180                 185                 190

Glu Trp Arg Asn Thr Ser Gly Leu Tyr Ile Leu Thr Asn Asp Cys Pro
        195                 200                 205

Asn Ser Ser Ile Val Tyr Glu Ala Asp Asp Val Ile Leu His Thr Pro
    210                 215                 220

Gly Cys Ile Pro Cys Val Gln Asp Gly Asn Thr Ser Thr Cys Trp Thr
225                 230                 235                 240

Ser Val Ser Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Leu Thr Gly His Arg Met Ala Trp
305                 310                 315                 320

Asp Met Met Met Asn Trp Ser Pro Ala Val Gly Met Val Val Ala His
                325                 330                 335

Val Leu Arg Met Pro Gln Thr Val Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Ile Met Val Met Phe Ser Gly Val Asp Ala Glu
```

```
                370             375             380
Thr His Thr Thr Gly Gly Thr Ala Ala Arg Asn Ala Phe Thr Leu Thr
385                 390                 395                 400

Gly Leu Phe Thr Gln Gly Ala Arg Gln Lys Leu Glu Leu Ile Asn Thr
                405                 410                 415

Asn Gly Ser Trp His Ile Asn Arg Thr Ala Leu Asn Cys Asn Glu Ser
            420                 425                 430

Leu Asn Thr Gly Phe Ile Ala Gly Leu Phe Tyr Leu His Lys Phe Asn
        435                 440                 445

Ser Thr Gly Cys Pro Glu Arg Leu Ser Ser Cys Lys Pro Ile Thr Phe
    450                 455                 460

Phe Arg Gln Gly Trp Gly Ser Leu Thr Asp Ala Asn Ile Thr Gly Pro
465                 470                 475                 480

Ser Asp Asp Lys Pro Tyr Cys Trp His Tyr Ala Pro Arg Pro Cys Glu
                485                 490                 495

Val Val Pro Ala Leu Asn Val Cys Gly Pro Val Tyr Cys Phe Thr Pro
            500                 505                 510

Ser Pro Val Val Gly Thr Thr Asp Arg Gln Gly Val Pro Thr Tyr
        515                 520                 525

Thr Trp Gly Glu Asn Glu Thr Asp Val Phe Leu Leu Arg Ser Leu Arg
    530                 535                 540

Pro Pro Ser Gly Gln Trp Phe Gly Cys Thr Trp Met Asn Ser Thr Gly
545                 550                 555                 560

Phe Val Lys Thr Cys Gly Ala Pro Pro Cys Asp Ile Tyr Gly Gly Gly
                565                 570                 575

Gly Asn Arg Cys Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Leu Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Gly Val Val Gly Trp Ala Leu
705                 710                 715                 720

Arg Trp Glu Phe Val Val Leu Val Phe Leu Leu Leu Ala Asp Ala Arg
                725                 730                 735

Val Cys Val Ala Leu Trp Leu Met Leu Met Ile Ser Gln Ala Glu Ala
            740                 745                 750
```

<210> SEQ ID NO 90
<211> LENGTH: 752
<212> TYPE: PRT
<213> ORGANISM: Hepatitis C virus

<400> SEQUENCE: 90

-continued

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Gly Arg Arg Gln Pro
50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
            195                 200                 205

Asn Ser Ser Ile Val Tyr Glu Ala Asp Asp Val Ile Leu His Thr Pro
210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Glu
370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
```

```
            420             425             430
Ile Asn Thr Gly Phe Ile Ala Gly Leu Phe Tyr Tyr His Lys Phe Asn
            435             440             445

Ser Thr Gly Cys Pro Gln Arg Leu Ser Ser Cys Lys Pro Ile Ile Ser
450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
                500                 505                 510

Ser Pro Val Val Gly Thr Thr Asp Ile Lys Gly Lys Pro Thr Tyr
        515                 520                 525

Asn Trp Gly Glu Asn Glu Thr Asp Val Phe Leu Leu Glu Ser Leu Arg
        530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
                580                 585                 590

Arg Lys His Pro Glu Ala Thr Tyr Ser Arg Cys Gly Ala Gly Pro Trp
                595                 600                 605

Leu Thr Pro Arg Cys Met Val Asp Tyr Pro Tyr Arg Leu Trp His Tyr
        610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
                660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
                740                 745                 750

<210> SEQ ID NO 91
<211> LENGTH: 752
<212> TYPE: PRT
<213> ORGANISM: Hepatitis C virus

<400> SEQUENCE: 91

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45
```

-continued

```
Thr Arg Lys Thr Ser Glu Arg Ser Gln Pro Arg Gly Arg Gln Pro
     50                  55                  60
Ile Pro Lys Ala Arg Arg Ser Glu Gly Arg Ser Trp Ala Gln Pro Gly
 65              70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro Ser Trp Gly Pro Asn Asp Pro
                100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Val
    130                 135                 140
Gly Gly Val Ala Arg Ala Leu Ala His Gly Val Arg Ala Leu Glu Asp
145                 150                 155                 160
Gly Ile Asn Phe Ala Thr Gly Asn Leu Pro Gly Cys Ser Phe Ser Ile
                165                 170                 175
Phe Leu Leu Ala Leu Phe Ser Cys Leu Ile His Pro Ala Ala Ser Leu
                180                 185                 190
Glu Trp Arg Asn Thr Ser Gly Leu Tyr Val Leu Thr Asn Asp Cys Ser
            195                 200                 205
Asn Ser Ser Ile Val Tyr Glu Ala Asp Asp Val Ile Leu His Thr Pro
    210                 215                 220
Gly Cys Val Pro Cys Val Gln Asp Gly Asn Thr Ser Thr Cys Trp Thr
225                 230                 235                 240
Pro Val Thr Pro Thr Val Ala Val Arg Tyr Val Gly Ala Thr Thr Ala
                245                 250                 255
Ser Ile Arg Ser His Val Asp Leu Leu Val Gly Ala Ala Thr Met Cys
                260                 265                 270
Ser Ala Leu Tyr Val Gly Asp Met Cys Gly Ala Val Phe Leu Val Gly
            275                 280                 285
Gln Ala Phe Thr Phe Arg Pro Arg Arg His Gln Thr Val Gln Thr Cys
    290                 295                 300
Asn Cys Ser Leu Tyr Pro Gly His Leu Ser Gly His Arg Met Ala Trp
305                 310                 315                 320
Asp Met Met Met Asn Trp Ser Pro Ala Val Gly Met Val Val Ala His
                325                 330                 335
Val Leu Arg Leu Pro Gln Thr Leu Phe Asp Ile Met Ala Gly Ala His
                340                 345                 350
Trp Gly Ile Leu Ala Gly Leu Ala Tyr Tyr Ser Met Gln Gly Asn Trp
            355                 360                 365
Ala Lys Val Ala Ile Ile Met Val Met Phe Ser Gly Val Asp Ala His
    370                 375                 380
Thr Tyr Thr Thr Gly Gly Thr Ala Ser Arg His Thr Gln Ala Phe Ala
385                 390                 395                 400
Gly Leu Phe Asp Ile Gly Pro Gln Gln Lys Leu Gln Leu Val Asn Thr
                405                 410                 415
Asn Gly Ser Trp His Ile Asn Ser Thr Ala Leu Asn Cys Asn Glu Ser
                420                 425                 430
Ile Asn Thr Gly Phe Ile Ala Gly Leu Phe Tyr Tyr His Lys Phe Asn
            435                 440                 445
Ser Thr Gly Cys Pro Gln Arg Leu Ser Ser Cys Lys Pro Ile Thr Phe
    450                 455                 460
Phe Arg Gln Gly Trp Gly Pro Leu Thr Asp Ala Asn Ile Thr Gly Pro
```

```
                465                 470                 475                 480
        Ser Asp Asp Arg Pro Tyr Cys Trp His Tyr Ala Pro Arg Pro Cys Asp
                        485                 490                 495

Ile Val Pro Ala Ser Ser Val Cys Gly Pro Val Tyr Cys Phe Thr Pro
                        500                 505                 510

Ser Pro Val Val Val Gly Thr Thr Asp Ala Arg Gly Val Pro Thr Tyr
                        515                 520                 525

Thr Trp Gly Glu Asn Glu Lys Asp Val Phe Leu Leu Lys Ser Gln Arg
                        530                 535                 540

Pro Pro Ser Gly Arg Trp Phe Gly Cys Ser Trp Met Asn Ser Thr Gly
        545                 550                 555                 560

Phe Leu Lys Thr Cys Gly Ala Pro Pro Cys Asn Ile Tyr Gly Gly Glu
                        565                 570                 575

Gly Asn Pro His Asn Glu Ser Asp Leu Phe Cys Pro Thr Asp Cys Phe
                        580                 585                 590

Arg Lys His Pro Glu Thr Thr Tyr Ser Arg Cys Gly Ala Gly Pro Trp
                        595                 600                 605

Leu Thr Pro Arg Cys Met Val Asp Tyr Pro Tyr Arg Leu Trp His Tyr
                        610                 615                 620

Pro Cys Thr Val Asp Phe Arg Leu Phe Lys Val Arg Met Phe Val Gly
        625                 630                 635                 640

Gly Phe Glu His Arg Phe Thr Ala Ala Cys Asn Trp Thr Arg Gly Glu
                        645                 650                 655

Arg Cys Asp Ile Glu Asp Arg Asp Arg Ser Glu Gln His Pro Leu Leu
                        660                 665                 670

His Ser Thr Thr Glu Leu Ala Ile Leu Pro Cys Ser Phe Thr Pro Met
                        675                 680                 685

Pro Ala Leu Ser Thr Gly Leu Ile His Leu His Gln Asn Ile Val Asp
                        690                 695                 700

Val Gln Tyr Leu Tyr Gly Val Gly Ser Gly Met Val Gly Trp Ala Leu
        705                 710                 715                 720

Lys Trp Glu Phe Val Ile Leu Val Phe Leu Leu Leu Ala Asp Ala Arg
                        725                 730                 735

Val Cys Val Ala Leu Trp Leu Met Leu Met Ile Ser Gln Thr Glu Ala
                        740                 745                 750

<210> SEQ ID NO 92
<211> LENGTH: 752
<212> TYPE: PRT
<213> ORGANISM: Hepatitis C virus

<400> SEQUENCE: 92

Met Ser Thr Leu Pro Lys Pro Gln Arg Lys Thr Lys Arg Asn Thr Ile
        1               5                   10                  15

Arg Arg Pro Gln Asp Val Lys Phe Pro Gly Gly Gly Gln Ile Val Gly
                        20                  25                  30

Gly Val Tyr Val Leu Pro Arg Arg Gly Pro Arg Leu Gly Val Arg Ala
                        35                  40                  45

Thr Arg Lys Thr Ser Glu Arg Ser Gln Pro Arg Gly Arg Arg Gln Pro
                        50                  55                  60

Ile Pro Lys Ala Arg Arg Ser Glu Gly Arg Ser Trp Ala Gln Pro Gly
        65                  70                  75                  80

Tyr Pro Trp Pro Leu Tyr Gly Asn Glu Gly Cys Gly Trp Ala Gly Trp
                        85                  90                  95
```

```
Leu Leu Ser Pro Arg Gly Ser Arg Pro Ser Trp Gly Gln Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Val Ile Leu His Thr Pro
    210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
                260                 265                 270

Ser Ala Leu Tyr Val Gly Asp Met Cys Gly Ala Val Phe Leu Val Gly
            275                 280                 285

Gln Ala Phe Thr Phe Arg Pro Arg Arg His Gln Thr Val Gln Thr Cys
290                 295                 300

Asn Cys Ser Leu Tyr Pro Gly His Leu Ser Gly His Arg Met Ala Trp
305                 310                 315                 320

Asp Met Met Met Asn Trp Ser Pro Ala Val Gly Met Val Val Ser His
                325                 330                 335

Val Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Val Ile Met Val Met Phe Ser Gly Val Asp Ala Glu
370                 375                 380

Thr Tyr Ile Thr Gly Gly Ser Ala Ala His Gly Val Ser Thr Leu Thr
385                 390                 395                 400

Ser Leu Phe Ser Ser Gly Pro Gln Gln Lys Leu Gln Leu Val Lys Thr
                405                 410                 415

Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
            435                 440                 445

Ser Thr Gly Cys Pro Gln Arg Leu Ser Ser Cys Lys Pro Ile Thr Phe
        450                 455                 460

Phe Arg Gln Gly Trp Gly Ser Leu Thr Asp Ala Asn Val Thr Gly Ala
465                 470                 475                 480

Ser Ala Asp Lys Pro Tyr Cys Trp His Tyr Ala Pro Arg Pro Cys Asp
                485                 490                 495

Val Val Pro Ala Leu Asn Val Cys Gly Pro Val Tyr Cys Phe Thr Pro
            500                 505                 510

Ser Pro Val Val Val Gly Thr Thr Asp Arg Lys Gly Val Pro Thr Tyr
```

```
            515                 520                 525
Asn Trp Gly Glu Asn Glu Ser Asp Val Phe Leu Leu Glu Ser Leu Arg
530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Gly
                565                 570                 575

Gly Asn Pro Asn Asn Glu Ser His Leu Phe Cys Pro Thr Asp Cys Phe
            580                 585                 590

Arg Lys His Pro Asp Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Gly Met Val Gly Trp Ala Leu
705                 710                 715                 720

Lys Trp Glu Phe Val Ile Leu Ile Phe Leu Leu Leu Ala Asp Ala Arg
                725                 730                 735

Val Cys Val Ala Leu Trp Leu Met Leu Met Ile Ser Gln Ala Glu Ala
            740                 745                 750

<210> SEQ ID NO 93
<211> LENGTH: 752
<212> TYPE: PRT
<213> ORGANISM: Hepatitis C virus

<400> SEQUENCE: 93

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Cys Ala
        35                  40                  45

Thr Arg Lys Thr Ser Glu Arg Ser Gln Pro Arg Arg Arg Arg Gln Pro
    50                  55                  60

Ile Pro Lys Ala Arg Gln Ser Gly Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140
```

```
Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
            165                 170                 175

Phe Leu Leu Ala Leu Phe Ser Cys Leu Ile His Pro Ala Ala Ser Leu
        180                 185                 190

Glu Trp Arg Asn Thr Ser Gly Leu Tyr Val Leu Thr Asn Asp Cys Ser
    195                 200                 205

Asn Ser Ser Ile Val Tyr Glu Ala Asp Val Ile Leu His Thr Pro
210                 215                 220

Gly Cys Val Pro Cys Val Gln Asn Asp Asn Ile Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg His Gln Thr Val Gln Thr Cys
290                 295                 300

Asn Cys Ser Leu Tyr Pro Gly His Leu Ser Gly His Arg Met Ala Trp
305                 310                 315                 320

Asp Met Met Met Asn Trp Phe Pro Ala Leu Gly Met Ala Val Ala His
                325                 330                 335

Val Leu Arg Val Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Ile Met Val Met Phe Ser Gly Val Asp Ala Val
370                 375                 380

Thr Tyr Thr Thr Gly Gly Ser Ala Ala His Ala Thr Arg Gly Leu Thr
385                 390                 395                 400

Ser Leu Phe Ser Val Gly Ala Gln Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr His Arg Phe Asn
        435                 440                 445

Ser Thr Gly Cys Pro Gln Arg Leu Ser Ser Cys Lys Pro Ile Thr Phe
450                 455                 460

Phe Lys Gln Gly Trp Gly Pro Leu Thr Asp Ala Asn Ile Ser Gly Pro
465                 470                 475                 480

Ser Asp Asp Lys Pro Tyr Cys Trp His Tyr Ala Pro Arg Pro Cys Lys
                485                 490                 495

Val Val Pro Ala Ser Gly Val Cys Gly Pro Val Tyr Cys Phe Thr Pro
            500                 505                 510

Ser Pro Val Val Val Gly Thr Thr Asp Ala Lys Gly Val Pro Thr Tyr
        515                 520                 525

Thr Trp Gly Ala Asn Asp Thr Asp Val Phe Leu Leu Glu Ser Leu Arg
530                 535                 540

Pro Pro Gly Gly Arg Trp Phe Gly Cys Thr Trp Met Asn Ser Thr Gly
545                 550                 555                 560

Phe Val Lys Thr Cys Gly Ala Ser Pro Cys Asp Ile Tyr Gly Gly Gly
```

```
                    565                 570                 575
Gly Asn Ser Gly Asn Glu Ser Asp Leu Phe Cys Pro Thr Asp Cys Phe
                580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
        610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Gly Met Val Gly Trp Ala Leu
705                 710                 715                 720

Lys Trp Glu Phe Val Ile Leu Ile Phe Leu Leu Ala Asp Arg Arg
                725                 730                 735

Val Cys Val Ala Leu Trp Leu Met Leu Met Ile Thr Gln Ala Glu Ala
            740                 745                 750
```

<210> SEQ ID NO 94
<211> LENGTH: 752
<212> TYPE: PRT
<213> ORGANISM: Hepatitis C virus

<400> SEQUENCE: 94

```
Met Ser Thr Leu Pro Lys Pro Gln Arg Lys Thr Lys Arg Asn Thr Val
1               5                   10                  15

Cys Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190
```

-continued

Glu Trp Arg Asn Val Ser Gly Leu Tyr Ile Leu Thr Asn Asp Cys Pro
                195                 200                 205

Asn Ser Ser Ile Val Tyr Glu Ala Asp Asp Val Ile Leu His Thr Pro
            210                 215                 220

Gly Cys Ile Pro Cys Val Gln Asp Gly Asn Thr Ser Thr Cys Trp Thr
225                 230                 235                 240

Ala Leu Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
            275                 280                 285

Gln Ala Phe Thr Phe Arg Pro Arg His Gln Thr Val Gln Thr Cys
            290                 295                 300

Asn Cys Ser Leu Tyr Pro Gly His Leu Thr Gly His Arg Met Ala Trp
305                 310                 315                 320

Asp Met Met Met Asn Trp Ser Pro Ala Val Gly Met Val Ala His
                325                 330                 335

Val Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
            355                 360                 365

Ala Lys Val Ile Ile Met Val Met Phe Ser Gly Val Asp Ala Thr
            370                 375                 380

Thr His Val Thr Gly Gly Thr Ala Gly Leu Thr Ala Phe Arg Leu Thr
385                 390                 395                 400

Gly Leu Phe Thr Val Gly Pro Gln Gln Lys Leu Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Ile Ala Gly Leu Phe Arg Phe His Lys Phe Asn
            435                 440                 445

Ser Thr Gly Cys Pro Glu Met Leu Ser Ser Cys Lys Pro Ile Thr Ser
450                 455                 460

Phe Lys Gln Gly Trp Gly Pro Leu Thr Asp Ala Asn Ile Thr Ile Pro
465                 470                 475                 480

Ser Asp Asp Arg Pro Tyr Cys Trp His Tyr Pro Pro Arg Ser Cys Glu
                485                 490                 495

Val Val Pro Ala Leu Ser Val Cys Gly Pro Val Tyr Cys Phe Thr Pro
            500                 505                 510

Ser Pro Val Val Gly Thr Thr Asp Ala Lys Gly Val Pro Thr Tyr
            515                 520                 525

Thr Trp Gly Glu Asn Glu Thr Asp Val Phe Leu Leu Lys Ser Leu Arg
530                 535                 540

Pro Pro Gly Gly Arg Trp Phe Gly Cys Thr Trp Met Asn Ser Thr Gly
545                 550                 555                 560

Phe Val Gln Thr Cys Gly Ala Pro Pro Cys Asn Ile Tyr Gly Gly Gly
                565                 570                 575

Gly Asp Leu Lys Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr

```
                    610             615             620
Pro Cys Thr Val Asn Phe Thr Leu Phe Lys Val Arg Met Phe Val Gly
625             630             635             640

Gly Phe Glu His Arg Phe Thr Ala Ala Cys Asn Trp Thr Arg Gly Glu
                645             650             655

Arg Cys Asp Ile Glu Asp Arg Asp Arg Ser Glu Leu His Pro Leu Leu
            660             665             670

His Ser Thr Thr Glu Leu Ala Ile Leu Pro Cys Ser Phe Thr Pro Met
        675             680             685

Pro Ala Leu Ser Thr Gly Leu Ile His Leu His Gln Asn Ile Val Asp
690             695             700

Val Gln Tyr Leu Tyr Gly Val Gly Ser Gly Met Val Gly Trp Ala Val
705             710             715             720

Lys Trp Glu Phe Val Ile Leu Val Phe Leu Leu Leu Ala Asp Ala Arg
                725             730             735

Val Cys Val Ala Leu Trp Leu Met Leu Met Ile Ser Gln Ala Glu Ala
            740             745             750

<210> SEQ ID NO 95
<211> LENGTH: 752
<212> TYPE: PRT
<213> ORGANISM: Hepatitis C virus

<400> SEQUENCE: 95

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Gln Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
210                 215                 220

Gly Cys Val Pro Cys Val Gln Asp Gly Asn Thr Ser Thr Cys Trp Thr
225                 230                 235                 240
```

-continued

```
Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg His Gln Thr Val Gln Thr Cys
    290                 295                 300

Asn Cys Ser Leu Tyr Pro Gly His Leu Ser His Arg Met Ala Trp
305                 310                 315                 320

Asp Met Met Met Asn Trp Ser Pro Ala Ala Gly Met Val Val Ala His
                325                 330                 335

Ile Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Ile Met Val Met Phe Ser Gly Val Asp Ala Thr
    370                 375                 380

Thr Tyr Thr Ser Gly Gly Ser Val Ala Gln Gln Ala Arg Gly Leu Ala
385                 390                 395                 400

Asp Leu Phe Ser Val Gly Ala Lys Gln Asn Leu Gln Leu Val Asn Thr
                405                 410                 415

Asn Gly Ser Trp His Ile Asn Ser Thr Ala Leu Asn Cys Asp Asp Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Asp Cys Lys Pro Ile Thr Phe
    450                 455                 460

Phe Lys Gln Gly Trp Gly Pro Leu Thr Asp Ala Asn Ile Thr Gly Pro
465                 470                 475                 480

Ser Asp Asp Lys Pro Tyr Cys Trp His Tyr Ala Pro Arg Arg Cys Gly
                485                 490                 495

Val Val Pro Ala Ser Ser Val Cys Gly Pro Val Tyr Cys Phe Thr Pro
            500                 505                 510

Ser Pro Val Val Gly Thr Thr Asp Ala Lys Gly Val Pro Thr Tyr
        515                 520                 525

Thr Trp Gly Ala Asn Glu Thr Asp Val Phe Leu Leu Glu Ser Leu Arg
    530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Gly
                565                 570                 575

Gly Asn Pro His Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Met Arg Thr Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
```

```
            660                 665                 670
His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
            690                 695                 700

Val Gln Tyr Leu Tyr Gly Val Gly Ser Gly Met Val Gly Trp Ala Leu
705                 710                 715                 720

Lys Trp Glu Phe Val Ile Leu Val Phe Leu Leu Leu Ala Asp Ala Arg
                    725                 730                 735

Val Cys Val Ala Leu Trp Leu Met Leu Met Ile Ser Gln Ala Glu Ala
                    740                 745                 750

<210> SEQ ID NO 96
<211> LENGTH: 752
<212> TYPE: PRT
<213> ORGANISM: Hepatitis C virus

<400> SEQUENCE: 96

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Gln Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285
```

-continued

```
Gln Ala Phe Thr Phe Arg Pro Arg Arg His Gln Thr Val Gln Thr Cys
    290                 295                 300
Asn Cys Ser Leu Tyr Pro Gly His Leu Ser Gly His Arg Met Ala Trp
305                 310                 315                 320
Asp Met Met Asn Trp Ser Pro Ala Ala Gly Met Val Val Ala His
                325                 330                 335
Ile Leu Arg Leu Pro Gln Thr Leu Phe Asp Ile Ile Ala Gly Ala His
            340                 345                 350
Trp Gly Ile Leu Ala Gly Leu Ala Tyr Tyr Ser Met Gln Gly Asn Trp
        355                 360                 365
Ala Lys Val Ala Ile Ile Met Val Met Phe Ser Gly Val Asp Ala Thr
    370                 375                 380
Thr Tyr Thr Ser Gly Gly Ser Val Ala Gln Gln Ala Arg Gly Leu Ala
385                 390                 395                 400
Asp Leu Phe Ser Val Gly Ala Lys Gln Asn Leu Gln Leu Val Asn Thr
                405                 410                 415
Asn Gly Ser Trp His Ile Asn Ser Thr Ala Leu Asn Cys Asp Asp Ser
            420                 425                 430
Ile Asn Thr Gly Phe Ile Ala Gly Leu Phe Tyr Tyr His Lys Phe Asn
        435                 440                 445
Ser Thr Gly Cys Pro Gln Arg Leu Ser Asp Cys Lys Pro Ile Thr Phe
    450                 455                 460
Phe Lys Gln Gly Trp Gly Pro Leu Thr Asp Ala Asn Ile Thr Gly Pro
465                 470                 475                 480
Ser Asp Asp Lys Pro Tyr Cys Trp His Tyr Ala Pro Arg Arg Cys Gly
                485                 490                 495
Val Val Pro Ala Ser Ser Val Cys Gly Pro Val Tyr Cys Phe Thr Pro
            500                 505                 510
Ser Pro Val Val Gly Thr Thr Asp Ala Lys Gly Val Pro Thr Tyr
    515                 520                 525
Thr Trp Gly Ala Asn Glu Thr Asp Val Phe Leu Leu Glu Ser Leu Arg
530                 535                 540
Pro Pro Ser Gly Arg Trp Phe Gly Cys Ala Trp Met Asn Ser Thr Gly
545                 550                 555                 560
Phe Leu Lys Thr Cys Gly Ala Pro Pro Cys Asn Ile Tyr Gly Gly Gly
                565                 570                 575
Gly Asn Pro His Asn Glu Ser Asp Leu Phe Cys Pro Thr Asp Cys Phe
            580                 585                 590
Arg Lys His Pro Glu Ala Thr Tyr Ser Arg Cys Gly Ala Gly Pro Trp
        595                 600                 605
Leu Thr Pro Arg Cys Met Val Asp Tyr Pro Tyr Arg Leu Trp His Tyr
    610                 615                 620
Pro Cys Thr Val Asn Phe Thr Leu Phe Lys Met Arg Thr Phe Val Gly
625                 630                 635                 640
Gly Phe Glu His Arg Phe Thr Ala Ala Cys Asn Trp Thr Arg Gly Glu
                645                 650                 655
Arg Cys Asp Ile Glu Asp Arg Asp Arg Ser Glu Gln His Pro Leu Leu
            660                 665                 670
His Ser Thr Thr Glu Leu Ala Ile Leu Pro Cys Ser Phe Thr Pro Met
        675                 680                 685
Pro Ala Leu Ser Thr Gly Leu Ile His Leu His Gln Asn Ile Val Asp
    690                 695                 700
Val Gln Tyr Leu Tyr Gly Val Gly Ser Gly Met Val Gly Trp Ala Leu
```

```
                        705                 710                 715                 720
Lys Trp Glu Phe Val Ile Leu Val Phe Leu Leu Ala Asp Ala Arg
                725                 730                 735
Val Cys Val Ala Leu Trp Leu Met Leu Met Ile Ser Gln Ala Glu Ala
            740                 745                 750

<210> SEQ ID NO 97
<211> LENGTH: 752
<212> TYPE: PRT
<213> ORGANISM: Hepatitis C virus

<400> SEQUENCE: 97

Met Ser Thr Leu Pro Lys Pro Gln Arg Lys Thr Lys Arg Asn Thr Ile
1               5                   10                  15
Arg Arg Pro Gln Asp Val Lys Phe Pro Gly Gly Gly Gln Ile Val Gly
                20                  25                  30
Gly Val Tyr Val Leu Pro Arg Arg Gly Pro Arg Leu Gly Val Cys Ala
            35                  40                  45
Thr Arg Lys Thr Ser Glu Arg Ser Gln Pro Arg Gly Arg Arg Gln Pro
50              55                  60
Ile Pro Lys Ala Arg Arg Ser Glu Gly Arg Ser Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Asn Asp Pro
            100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Val
130                 135                 140
Gly Gly Val Ala Arg Ala Leu Ala His Gly Val Arg Ala Leu Glu Asp
145                 150                 155                 160
Gly Ile Asn Phe Ala Thr Gly Asn Leu Pro Gly Cys Ser Phe Ser Ile
                165                 170                 175
Phe Leu Leu Ala Leu Phe Ser Cys Leu Val His Pro Ala Ala Ser Leu
            180                 185                 190
Glu Trp Arg Asn Thr Ser Gly Leu Tyr Val Leu Thr Asn Asp Cys Pro
        195                 200                 205
Asn Ser Ser Ile Val Tyr Glu Ala Asp Asp Val Ile Leu His Thr Pro
210                 215                 220
Gly Cys Ile Pro Cys Val Gln Asp Gly Asn Lys Ser Thr Cys Trp Thr
225                 230                 235                 240
Ser Val Thr Pro Thr Val Ala Val Lys Tyr Val Gly Ala Thr Thr Ala
                245                 250                 255
Ser Ile Arg Ser His Val Asp Leu Leu Val Gly Ala Ala Thr Met Cys
            260                 265                 270
Ser Ala Leu Tyr Val Gly Asp Met Cys Gly Ala Val Phe Leu Val Gly
        275                 280                 285
Gln Ala Phe Thr Phe Arg Pro Arg Arg His Gln Thr Val Gln Thr Cys
    290                 295                 300
Asn Cys Ser Leu Tyr Pro Gly His Leu Ser Gly His Arg Met Ala Trp
305                 310                 315                 320
Asp Met Met Met Asn Trp Ser Pro Ala Val Gly Met Val Val Ala His
                325                 330                 335
```

-continued

Val Leu Arg Leu Pro Gln Thr Leu Phe Asp Ile Ala Gly Ala His
            340                 345                 350

Trp Gly Ile Leu Ala Gly Leu Ala Tyr Tyr Ser Met Gln Gly Asn Trp
            355                 360                 365

Ala Lys Val Ala Ile Ile Met Val Met Phe Ser Gly Val Asp Ala Thr
    370                 375                 380

Thr Tyr Thr Thr Gly Gly Asn Ala Ala Arg Gly Ala Ser Gly Ile Val
385                 390                 395                 400

Ser Leu Phe Thr Pro Gly Ala Lys Gln Asn Leu Gln Leu Val Asn Thr
                405                 410                 415

Asn Gly Ser Trp His Ile Asn Arg Thr Ala Leu Asn Cys Asn Asp Ser
            420                 425                 430

Ile Asn Thr Gly Phe Ile Ala Gly Leu Ile Tyr Tyr His Lys Phe Asn
        435                 440                 445

Ser Thr Gly Cys Pro Gln Arg Leu Ser Ser Cys Lys Pro Ile Thr Phe
    450                 455                 460

Phe Arg Gln Gly Trp Gly Ser Leu Thr Asp Ala Asn Ile Thr Gly Pro
465                 470                 475                 480

Ser Asp Asp Lys Pro Tyr Cys Trp His Tyr Pro Arg Pro Cys Asp
                485                 490                 495

Thr Ile Arg Ala Ser Ser Val Cys Gly Pro Val Tyr Cys Phe Thr Pro
            500                 505                 510

Ser Pro Val Val Gly Thr Thr Asp Ala Lys Gly Ala Pro Thr Tyr
        515                 520                 525

Asn Trp Gly Ala Asn Glu Thr Asp Met Phe Leu Leu Gln Ser Leu Arg
    530                 535                 540

Pro Pro Ser Gly Arg Trp Phe Gly Cys Thr Trp Met Asn Ser Thr Gly
545                 550                 555                 560

Phe Thr Lys Thr Cys Gly Ala Pro Pro Cys Asn Ile Tyr Gly Gly Gly
                565                 570                 575

Gly Asn Leu Asn Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Leu Val Asp Tyr Pro Tyr Arg Leu Trp His Tyr
    610                 615                 620

Pro Cys Thr Val Asn Phe Thr Leu Phe Arg Met Arg Thr Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Ile Gly Ser Gly Val Val Gly Trp Ala Leu
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Ile Ser Gln Ala Glu Ala
            740                 745                 750

<210> SEQ ID NO 98
<211> LENGTH: 752
<212> TYPE: PRT
<213> ORGANISM: Hepatitis C virus

<400> SEQUENCE: 98

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Val Ile Tyr Val
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Lys Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asn Trp Ala Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Val Ile Leu His Thr Pro
    210                 215                 220

Gly Cys Ile Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Gly Thr Met Cys
            260                 265                 270

Ser Ala Leu Tyr Val Gly Asp Met Cys Gly Pro Val Phe Leu Val Gly
        275                 280                 285

Gln Ala Phe Thr Phe Arg Pro Arg Arg His Arg Thr Val Gln Thr Cys
    290                 295                 300

Asn Cys Ser Leu Tyr Pro Gly His Leu Ser Gly Gln Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Val Val Ala Gly Ala His
            340                 345                 350

Trp Gly Ile Ile Ala Gly Leu Ala Tyr Tyr Ser Met Gln Gly Asn Trp
        355                 360                 365

Ala Lys Val Ala Ile Ile Met Val Met Phe Ser Gly Val Asp Ala Ser
    370                 375                 380
```

```
Thr His Val Thr Ala Gly Gln Ala Ala Arg Asn Ala Tyr Gly Ile Thr
385                 390                 395                 400

Ser Leu Phe Ser Val Gly Ala Lys Gln Asn Leu Gln Leu Ile Asn Thr
            405                 410                 415

Asn Gly Ser Trp His Ile Asn Arg Thr Ala Leu Asn Cys Asn Glu Ser
        420                 425                 430

Ile Asn Thr Gly Phe Ile Ala Gly Leu Phe Tyr Tyr His Lys Phe Asn
    435                 440                 445

Ser Thr Gly Cys Pro Gln Arg Leu Ser Ser Cys Lys Pro Ile Thr Phe
450                 455                 460

Phe Lys Gln Gly Trp Gly Pro Leu Thr Asp Ala Asn Ile Thr Gly Pro
465                 470                 475                 480

Ser Asp Asp Lys Pro Tyr Cys Trp His Tyr Ala Pro Arg Pro Cys Gly
            485                 490                 495

Ile Val Pro Ala Leu Asn Val Cys Gly Pro Val Tyr Cys Phe Thr Pro
        500                 505                 510

Ser Pro Val Val Val Gly Thr Thr Asp Ala Lys Gly Ala Pro Thr Tyr
    515                 520                 525

Thr Trp Gly Ala Asn Lys Thr Asp Val Phe Leu Leu Glu Ser Leu Arg
530                 535                 540

Pro Pro Ser Gly Arg Trp Phe Gly Cys Thr Trp Met Asn Ser Thr Gly
545                 550                 555                 560

Phe Val Lys Thr Cys Gly Ala Pro Pro Cys Asn Ile Tyr Gly Asp Gly
            565                 570                 575

Arg Asp Ala Gln Asn Glu Ser Asp Leu Phe Cys Pro Thr Asp Cys Phe
        580                 585                 590

Arg Lys His Pro Glu Ala Thr Tyr Ser Arg Cys Gly Ala Gly Pro Trp
    595                 600                 605

Leu Thr Pro Arg Cys Leu Val Asp Tyr Pro Tyr Arg Leu Trp His Tyr
610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
            645                 650                 655

Arg Cys Asp Ile Glu Asp Arg Asp Arg Ser Glu Gln His Pro Leu Leu
        660                 665                 670

His Ser Thr Thr Glu Leu Ala Ile Leu Pro Cys Ser Phe Thr Pro Met
    675                 680                 685

Pro Ala Leu Ser Thr Gly Leu Ile His Leu His Gln Asn Ile Val Asp
690                 695                 700

Val Gln Tyr Leu Tyr Gly Ile Gly Ser Gly Met Val Gly Trp Ala Leu
705                 710                 715                 720

Lys Trp Glu Phe Val Ile Leu Ile Phe Leu Leu Leu Ala Asp Ala Arg
            725                 730                 735

Val Cys Val Ala Leu Trp Leu Ile Leu Thr Ile Ser Gln Ala Glu Ala
        740                 745                 750

<210> SEQ ID NO 99
<211> LENGTH: 754
<212> TYPE: PRT
<213> ORGANISM: Hepatitis C virus

<400> SEQUENCE: 99

Met Ser Thr Leu Pro Lys Pro Lys Arg Gln Thr Lys Arg Asn Thr Leu
1               5                   10                  15
```

-continued

Arg Arg Pro Lys Asn Val Lys Phe Pro Ala Gly Gly Gln Ile Val Gly
            20                  25                  30

Glu Val Tyr Val Leu Pro Arg Arg Gly Pro Gln Leu Gly Val Arg Glu
            35                  40                  45

Val Arg Lys Thr Ser Glu Arg Ser Gln Pro Arg Gly Arg Arg Gln Pro
50                  55                  60

Thr Pro Lys Ala Arg Pro Arg Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Pro Pro Arg Gly Ser Arg Pro Ser Trp Gly Gln Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Ile Gly Ala Pro Val
130                 135                 140

Gly Gly Val Ala Arg Ala Leu Ala His Gly Val Arg Ala Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Phe Ser Cys Leu Thr Cys Pro Ala Ser Ser Leu
            180                 185                 190

Glu Tyr Arg Asn Ala Ser Gly Leu Tyr Leu Leu Thr Asn Asp Cys Ser
            195                 200                 205

Asn Arg Ser Ile Val Tyr Glu Ala Asp Asp Val Ile Leu His Leu Pro
            210                 215                 220

Gly Cys Val Pro Cys Val Glu Thr Asp Asn Asn Asn Thr Ser Cys Trp
225                 230                 235                 240

Thr Pro Ile Ser Pro Thr Val Ala Val Lys His Pro Gly Val Thr Thr
            245                 250                 255

Ala Ser Ile Arg Asn His Val Asn Met Leu Val Ala Pro Pro Thr Leu
            260                 265                 270

Cys Ser Ala Leu Tyr Val Glu Asp Ala Phe Gly Ala Val Ser Leu Val
            275                 280                 285

Gly Gln Ala Phe Thr Phe Arg Pro Arg Gln His Lys Thr Val Gln Thr
290                 295                 300

Cys Asn Cys Ser Ile Tyr Pro Gly His Val Ser Gly His Arg Met Ala
305                 310                 315                 320

Trp Asp Met Met Met Asn Trp Ser Pro Ala Ile Gly Leu Val Ile Ser
                325                 330                 335

His Leu Met Arg Leu Pro Gln Thr Phe Phe Asp Leu Val Val Gly Ala
            340                 345                 350

His Trp Gly Val Met Ala Gly Leu Ala Tyr Phe Ser Met Gln Gly Asn
            355                 360                 365

Trp Ala Lys Val Val Ile Val Leu Ile Met Phe Ser Gly Val Asp Ala
            370                 375                 380

Thr Thr His Thr Thr Gly Gly Ser Ala Ala Gln Ala Thr Ala Gly Phe
385                 390                 395                 400

Thr Ser Phe Phe Thr Arg Gly Pro Ser Gln Asn Leu Gln Leu Val Asn
            405                 410                 415

Ser Asn Gly Ser Trp His Ile Asn Ser Thr Ala Leu Asn Cys Asn Asp
            420                 425                 430

```
Ser Leu Asn Thr Gly Phe Ile Ala Gly Leu Phe Tyr Tyr His Lys Phe
        435                 440                 445

Asn Ser Ser Gly Cys Pro Glu Arg Met Ser Ser Cys Lys Pro Ile Thr
450                 455                 460

Tyr Phe Asn Gln Gly Trp Gly Pro Leu Thr Asp Ala Asn Ile Asn Gly
465                 470                 475                 480

Pro Ser Glu Asp Arg Pro Tyr Cys Trp His Tyr Pro Arg Pro Cys
                485                 490                 495

Asn Ile Thr Lys Pro Leu Asn Val Cys Gly Pro Val Tyr Cys Phe Thr
            500                 505                 510

Pro Ser Pro Val Val Gly Thr Thr Asp Ile Lys Gly Leu Pro Thr
            515                 520                 525

Tyr Arg Phe Gly Val Asn Glu Ser Asp Val Phe Leu Leu Thr Ser Leu
        530                 535                 540

Arg Pro Pro Gln Gly Arg Trp Phe Gly Cys Val Trp Met Asn Ser Thr
545                 550                 555                 560

Gly Phe Val Lys Thr Cys Gly Ala Pro Pro Cys Asn Ile Tyr Gly Gly
                565                 570                 575

Met Lys Asp Ile Glu Ala Asn Gln Thr His Leu Lys Cys Pro Thr Asp
            580                 585                 590

Cys Phe Arg Lys His His Asp Ala Thr Phe Thr Arg Cys Gly Ser Gly
            595                 600                 605

Pro Trp Leu Thr Pro Arg Cys Leu Val Asp Tyr Pro Tyr Arg Leu Trp
        610                 615                 620

His Tyr Pro Cys Thr Val Asn Phe Ser Ile Phe Lys Val Arg Met Phe
625                 630                 635                 640

Val Gly Gly His Glu His Arg Phe Ser Ala Ala Cys Asn Trp Thr Arg
                645                 650                 655

Gly Glu Arg Cys Asp Leu Glu Asp Arg Asp Arg Ser Glu Gln Gln Pro
            660                 665                 670

Leu Leu His Ser Thr Thr Asp Ser Leu Ile Leu Pro Cys Ser Phe Thr
            675                 680                 685

Pro Met Arg Arg Leu Ser Thr Gly Leu Ile His Leu His Gln Asn Ile
690                 695                 700

Val Asp Val Gln Tyr Leu Tyr Gly Val Gly Ser Ala Val Val Gly Trp
705                 710                 715                 720

Ala Leu Lys Trp Glu Phe Val Val Leu Phe Leu Leu Leu Ala Asp
                725                 730                 735

Ala Arg Val Cys Val Ala Leu Trp Met Met Leu Leu Ile Ser Gln Ala
            740                 745                 750

Glu Ala

<210> SEQ ID NO 100
<211> LENGTH: 751
<212> TYPE: PRT
<213> ORGANISM: Hepatitis C virus

<400> SEQUENCE: 100

Met Ser Thr Leu Pro Lys Pro Gln Arg Ile Thr Lys Arg Asn Ile Asn
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Lys Leu Gly Val Arg Ala
            35                  40                  45
```

```
Val Arg Lys Thr Ser Glu Arg Ser Gln Pro Arg Ser Arg Gln Pro
 50                  55                  60

Ile Pro Arg Ala Arg Arg Thr Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Leu Ser Cys Leu Leu Thr Pro Thr Ala Gly Leu
                180                 185                 190

Glu Tyr Arg Asn Ala Ser Gly Leu Tyr Thr Val Thr Asn Asp Cys Ser
                195                 200                 205

Asn Gly Ser Ile Val Tyr Glu Ala Gly Asp Val Ile Leu His Leu Pro
210                 215                 220

Gly Cys Ile Pro Cys Val Arg Leu Asn Asn Ala Ser Lys Cys Trp Thr
225                 230                 235                 240

Pro Val Ser Pro Thr Val Ala Val Ser Arg Pro Gly Ala Ala Thr Ala
                245                 250                 255

Ser Leu Arg Thr His Val Asp Met Met Val Gly Ala Ala Thr Leu Cys
                260                 265                 270

Ser Ala Leu Tyr Val Gly Asp Leu Cys Gly Ala Leu Phe Leu Val Gly
                275                 280                 285

Gln Gly Phe Ser Trp Arg His Arg Gln His Trp Thr Val Gln Asp Cys
290                 295                 300

Asn Cys Ser Ile Tyr Pro Gly His Leu Thr Gly His Arg Met Ala Trp
305                 310                 315                 320

Asp Met Met Met Asn Trp Ser Pro Ala Met Thr Leu Ile Val Ser Gln
                325                 330                 335

Val Leu Arg Leu Pro Gln Thr Met Phe Asp Leu Val Ile Gly Ala His
                340                 345                 350

Trp Gly Val Met Ala Gly Val Ala Tyr Tyr Ser Met Gln Gly Asn Trp
                355                 360                 365

Ala Lys Val Phe Leu Val Leu Cys Leu Phe Ser Gly Val Asp Ala Ser
370                 375                 380

Thr Thr Ile Thr Gly Gly Val Ala Ala Ser Gly Ala Phe Thr Ile Thr
385                 390                 395                 400

Ser Leu Phe Ser Thr Gly Ala Lys Gln Pro Leu His Leu Val Asn Thr
                405                 410                 415

Asn Gly Ser Trp His Ile Asn Arg Thr Ala Leu Asn Cys Asn Asp Ser
                420                 425                 430

Leu Asn Thr Gly Phe Ile Ala Gly Leu Leu Tyr Tyr His Lys Phe Asn
                435                 440                 445

Ser Ser Gly Cys Val Glu Arg Met Ser Ala Cys Ser Pro Leu Asp Arg
450                 455                 460

Phe Ala Gln Gly Trp Gly Pro Leu Gly Pro Ala Asn Ile Ser Gly Pro
```

```
            465                 470                 475                 480
        Ser Ser Glu Lys Pro Tyr Cys Trp His Tyr Ala Pro Arg Pro Cys Asp
                        485                 490                 495

Thr Val Pro Ala Gln Ser Val Cys Gly Pro Val Tyr Cys Phe Thr Pro
                        500                 505                 510

Ser Pro Val Val Val Gly Ala Thr Asp Lys Arg Gly Ala Pro Thr Tyr
                        515                 520                 525

Thr Trp Gly Glu Asn Glu Ser Asp Val Phe Leu Leu Glu Ser Ala Arg
                    530                 535                 540

Pro Pro Thr Glu Pro Trp Phe Gly Cys Thr Trp Met Asn Gly Ser Gly
        545                 550                 555                 560

Tyr Val Lys Thr Cys Gly Ala Pro Pro Cys His Ile Tyr Gly Gly Arg
                        565                 570                 575

Glu Gly Lys Ser Asn Asn Ser Leu Val Cys Pro Thr Cys Phe Arg
                    580                 585                 590

Lys His Pro Asp Ala Thr Tyr Asn Arg Cys Gly Ala Gly Pro Trp Leu
                        595                 600                 605

Thr Pro Arg Cys Leu Val Asp Tyr Pro Tyr Arg Leu Trp His Tyr Pro
                    610                 615                 620

Cys Thr Val Asn Tyr Thr Ile Phe Lys Val Arg Met Phe Val Gly Gly
        625                 630                 635                 640

Leu Glu His Arg Phe Asn Ala Ala Cys Asn Trp Thr Arg Gly Glu Arg
                        645                 650                 655

Cys Asn Leu Glu Asp Arg Asp Arg Ser Glu Met Tyr Pro Leu Leu His
                    660                 665                 670

Ser Thr Thr Glu Gln Ala Ile Leu Pro Cys Ser Phe Val Pro Ile Pro
                    675                 680                 685

Ala Leu Ser Thr Gly Leu Ile His Leu His Gln Asn Ile Val Asp Val
                    690                 695                 700

Gln Tyr Leu Tyr Gly Ile Ser Ser Gly Leu Val Gly Trp Ala Ile Lys
        705                 710                 715                 720

Trp Glu Phe Val Ile Leu Ile Phe Leu Leu Leu Ala Asp Ala Arg Val
                        725                 730                 735

Cys Val Val Leu Trp Met Met Met Leu Ile Ser Gln Ala Glu Ala
                    740                 745                 750

<210> SEQ ID NO 101
<211> LENGTH: 750
<212> TYPE: PRT
<213> ORGANISM: Hepatitis C virus

<400> SEQUENCE: 101

Met Ser Thr Asn Pro Lys Pro Gln Arg Leu Thr Lys Arg Asn Thr Val
        1               5                   10                  15

Arg Arg Pro Gln Asn Val Lys Phe Pro Gly Gly Gly Gln Ile Val Gly
                        20                  25                  30

Gly Val Tyr Leu Leu Pro Arg Arg Gly Pro Arg Leu Gly Val Arg Gly
                    35                  40                  45

Thr Arg Lys Ser Ser Glu Arg Ser Gln Pro Arg Gly Arg Arg Gln
                50                  55                  60

Ile Pro Lys Ala Ala Ser Ser Gln Gly Lys Ala Trp Gly Lys Pro Gly
        65                  70                  75                  80

Tyr Pro Trp Pro Leu Tyr Gly Asn Glu Gly Cys Gly Trp Ala Gly Trp
                        85                  90                  95
```

```
Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
            115                 120                 125

Gly Phe Ala Asp Leu Met Gly Tyr Ile Pro Val Leu Gly Ala Pro Leu
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Val Pro Ala Ser Ala Tyr
        180                 185                 190

Glu Val Arg Asn Ser Ser Gly Val Tyr His Leu Thr Asn Asp Cys Pro
            195                 200                 205

Asn Ala Ser Ile Val Tyr Glu Thr Asp Asn Ala Ile Leu His Glu Pro
        210                 215                 220

Gly Cys Val Pro Cys Val Arg Glu Gly Asn Thr Ser Arg Cys Trp Glu
225                 230                 235                 240

Pro Val Ala Pro Thr Leu Ala Val Arg Tyr Arg Gly Ala Leu Thr Asp
            245                 250                 255

Asp Leu Arg Thr His Ile Asp Leu Val Val Ala Ser Ala Thr Leu Cys
        260                 265                 270

Ser Ala Leu Tyr Val Gly Asp Ile Cys Gly Ala Ile Phe Ile Ala Ser
            275                 280                 285

Gln Ala Val Leu Trp Lys Pro Gly Gly Gly Arg Ile Val Gln Asp Cys
        290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
            325                 330                 335

Ala Val Arg Val Pro Gly Val Ile Ile Thr Thr Val Ala Gly Gly His
        340                 345                 350

Trp Gly Val Leu Phe Gly Leu Ala Tyr Phe Gly Met Ala Gly Asn Trp
            355                 360                 365

Ala Lys Val Ile Leu Ile Met Leu Leu Met Ser Gly Val Asp Ala Glu
        370                 375                 380

Thr Met Ala Val Gly Ala Arg Ala Ala His Thr Thr Gly Ala Leu Val
385                 390                 395                 400

Ser Leu Leu Asn Pro Gly Pro Ser Gln Arg Leu Gln Leu Ile Asn Thr
            405                 410                 415

Asn Gly Ser Trp His Ile Asn Arg Thr Ala Leu Asn Cys Asn Asp Ser
        420                 425                 430

Leu Gln Thr Gly Phe Ile Ala Ala Leu Phe Tyr Thr His Arg Phe Asn
            435                 440                 445

Ser Ser Gly Cys Pro Glu Arg Met Ala Ser Cys Lys Pro Leu Ser Asp
        450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
            485                 490                 495

Ile Val Pro Ala Lys Asp Val Cys Gly Pro Val Tyr Cys Phe Thr Pro
        500                 505                 510

Ser Pro Val Val Val Gly Thr Thr Asp Arg Arg Gly Val Pro Thr Tyr
```

```
               515                 520                 525

Thr Trp Gly Glu Asn Glu Ser Asp Val Phe Leu Leu Asn Ser Thr Arg
530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
                565                 570                 575

Ala Gln Ser Asn Thr Ser Leu Thr Cys Pro Thr Asp Cys Phe Arg Lys
                580                 585                 590

His Pro Arg Ala Thr Tyr Ser Ala Cys Gly Ser Gly Pro Trp Leu Thr
                595                 600                 605

Pro Arg Cys Met Val His Tyr Pro Tyr Arg Leu Trp His Tyr Pro Cys
610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
                660                 665                 670

Thr Thr Glu Leu Ala Ile Leu Pro Cys Ser Phe Val Pro Leu Pro Ala
                675                 680                 685

Leu Ser Thr Gly Leu Ile His Leu His Gln Asn Ile Val Asp Ala Gln
690                 695                 700

Tyr Leu Tyr Gly Leu Ser Pro Ala Ile Ser Trp Ala Ile Arg Trp
705                 710                 715                 720

Glu Trp Val Val Leu Val Phe Leu Leu Leu Ala Asp Ala Arg Ile Cys
                725                 730                 735

Ala Cys Leu Trp Met Met Met Leu Met Ala Gln Ala Glu Ala
                740                 745                 750

<210> SEQ ID NO 102
<211> LENGTH: 227
<212> TYPE: PRT
<213> ORGANISM: Homo sapiens

<400> SEQUENCE: 102

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
                130                 135                 140
```

-continued

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 103
<211> LENGTH: 325
<212> TYPE: PRT
<213> ORGANISM: Homo sapiens

<400> SEQUENCE: 103

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285
```

```
Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 104
<211> LENGTH: 246
<212> TYPE: PRT
<213> ORGANISM: Homo sapiens

<400> SEQUENCE: 104

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 105
<211> LENGTH: 383
<212> TYPE: PRT
<213> ORGANISM: Homo sapiens

<400> SEQUENCE: 105

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30
```

-continued

His Pro Thr Ser Val Thr Val Thr Trp Tyr Met Gly Thr Gln Ser Gln
         35                      40                  45

Pro Gln Arg Thr Phe Pro Glu Ile Gln Arg Arg Asp Ser Tyr Tyr Met
 50                  55                  60

Thr Ser Ser Gln Leu Ser Thr Pro Leu Gln Gln Trp Arg Gln Gly Glu
 65                  70                  75                  80

Tyr Lys Cys Val Val Gln His Thr Ala Ser Lys Ser Lys Glu Ile
                 85                  90                  95

Phe Arg Trp Pro Glu Ser Pro Lys Ala Gln Ala Ser Ser Val Pro Thr
                100                 105                 110

Ala Gln Pro Gln Ala Glu Gly Ser Leu Ala Lys Ala Thr Thr Ala Pro
            115                 120                 125

Ala Thr Thr Arg Asn Thr Gly Arg Gly Gly Glu Glu Lys Lys Lys Glu
        130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
    370                 375                 380

<210> SEQ ID NO 106
<211> LENGTH: 270
<212> TYPE: PRT
<213> ORGANISM: Homo sapiens

<400> SEQUENCE: 106

Val Thr Ser Thr Leu Thr Ile Lys Ser Asp Trp Leu Gly Glu Ser Met
1                5                  10                  15

Phe Thr Cys Arg Val Asp His Arg Gly Leu Thr Phe Gln Gln Asn Ala

```
            20                  25                  30
Ser Ser Met Cys Val Pro Asp Gln Asp Thr Ala Ile Arg Val Phe Ala
        35                  40                  45
Ile Pro Pro Ser Phe Ala Ser Ile Phe Leu Thr Lys Ser Thr Lys Leu
 50                  55                  60
Thr Cys Leu Val Thr Asp Leu Thr Thr Tyr Ser Val Thr Ile Ser Trp
 65                  70                  75                  80
Thr Arg Glu Glu Asn Gly Ala Val Lys Thr His Thr Asn Ile Ser Glu
                85                  90                  95
Ser His Pro Asn Ala Thr Phe Ser Ala Val Gly Glu Ala Ser Ile Cys
            100                 105                 110
Glu Asp Asp Trp Ser Gly Glu Arg Phe Thr Cys Thr Val Thr His Thr
            115                 120                 125
Asp Leu Pro Ser Pro Leu Lys Gln Thr Ile Ser Arg Pro Lys Gly Val
        130                 135                 140
Ala Leu His Arg Pro Val Tyr Leu Leu Pro Pro Ala Arg Leu Asn Leu
145                 150                 155                 160
Arg Glu Ser Ala Thr Ile Thr Cys Leu Val Thr Gly Phe Ser Pro Ala
                165                 170                 175
Asp Val Phe Val Glu Trp Met Gln Arg Gly Glu Pro Leu Ser Pro Gln
            180                 185                 190
Lys Tyr Val Thr Ser Ala Pro Met Pro Glu Pro Gln Ala Pro Gly Arg
        195                 200                 205
Tyr Phe Ala His Ser Ile Leu Thr Val Ser Glu Glu Glu Trp Asn Thr
            210                 215                 220
Gly Gly Thr Tyr Thr Cys Val Val Ala His Glu Ala Leu Pro Asn Arg
225                 230                 235                 240
Val Thr Glu Arg Thr Val Asp Lys Ser Thr Gly Lys Pro Thr Leu Tyr
                245                 250                 255
Asn Val Ser Leu Val Met Ser Asp Thr Ala Gly Thr Cys Tyr
            260                 265                 270

<210> SEQ ID NO 107
<211> LENGTH: 353
<212> TYPE: PRT
<213> ORGANISM: Homo sapiens

<400> SEQUENCE: 107

Ala Ser Pro Thr Ser Pro Lys Val Phe Pro Leu Ser Leu Cys Ser Thr
 1                   5                  10                  15
Gln Pro Asp Gly Asn Val Val Ile Ala Cys Leu Val Gln Gly Phe Phe
                20                  25                  30
Pro Gln Glu Pro Leu Ser Val Thr Trp Ser Glu Ser Gly Gln Gly Val
            35                  40                  45
Thr Ala Arg Asn Phe Pro Pro Ser Gln Asp Ala Ser Gly Asp Leu Tyr
        50                  55                  60
Thr Thr Ser Ser Gln Leu Thr Leu Pro Ala Thr Gln Cys Leu Ala Gly
 65                  70                  75                  80
Lys Ser Val Thr Cys His Val Lys His Tyr Thr Asn Pro Ser Gln Asp
                85                  90                  95
Val Thr Val Pro Cys Pro Val Pro Ser Thr Pro Pro Thr Pro Ser Pro
            100                 105                 110
Ser Thr Pro Pro Thr Pro Ser Pro Ser Cys Cys His Pro Arg Leu Ser
        115                 120                 125
```

Leu His Arg Pro Ala Leu Glu Asp Leu Leu Leu Gly Ser Glu Ala Asn
130 135 140

Leu Thr Cys Thr Leu Thr Gly Leu Arg Asp Ala Ser Gly Val Thr Phe
145 150 155 160

Thr Trp Thr Pro Ser Ser Gly Lys Ser Ala Val Gln Gly Pro Pro Glu
165 170 175

Arg Asp Leu Cys Gly Cys Tyr Ser Val Ser Ser Val Leu Pro Gly Cys
180 185 190

Ala Glu Pro Trp Asn His Gly Lys Thr Phe Thr Cys Thr Ala Ala Tyr
195 200 205

Pro Glu Ser Lys Thr Pro Leu Thr Ala Thr Leu Ser Lys Ser Gly Asn
210 215 220

Thr Phe Arg Pro Glu Val His Leu Leu Pro Pro Ser Glu Glu Leu
225 230 235 240

Ala Leu Asn Glu Leu Val Thr Leu Thr Cys Leu Ala Arg Gly Phe Ser
245 250 255

Pro Lys Asp Val Leu Val Arg Trp Leu Gln Gly Ser Gln Glu Leu Pro
260 265 270

Arg Glu Lys Tyr Leu Thr Trp Ala Ser Arg Gln Glu Pro Ser Gln Gly
275 280 285

Thr Thr Thr Phe Ala Val Thr Ser Ile Leu Arg Val Ala Ala Glu Asp
290 295 300

Trp Lys Lys Gly Asp Thr Phe Ser Cys Met Val Gly His Glu Ala Leu
305 310 315 320

Pro Leu Ala Phe Thr Gln Lys Thr Ile Asp Arg Leu Ala Gly Lys Pro
325 330 335

Thr His Val Asn Val Ser Val Val Met Ala Glu Val Asp Gly Thr Cys
340 345 350

Tyr

<210> SEQ ID NO 108
<211> LENGTH: 222
<212> TYPE: PRT
<213> ORGANISM: Homo sapiens

<400> SEQUENCE: 108

Ala Asp Pro Cys Asp Ser Asn Pro Arg Gly Val Ser Ala Tyr Leu Ser
1 5 10 15

Arg Pro Ser Pro Phe Asp Leu Phe Ile Arg Lys Ser Pro Thr Ile Thr
20 25 30

Cys Leu Val Val Asp Leu Ala Pro Ser Lys Gly Thr Val Asn Leu Thr
35 40 45

Trp Ser Arg Ala Ser Gly Lys Pro Val Asn His Ser Thr Arg Lys Glu
50 55 60

Glu Lys Gln Arg Asn Gly Thr Leu Thr Val Thr Ser Thr Leu Pro Val
65 70 75 80

Gly Thr Arg Asp Trp Ile Glu Gly Glu Thr Tyr Gln Cys Arg Val Thr
85 90 95

His Pro His Leu Pro Arg Ala Leu Met Arg Ser Thr Thr Lys Thr Ser
100 105 110

Gly Pro Arg Ala Ala Pro Glu Val Tyr Ala Phe Ala Thr Pro Glu Trp
115 120 125

Pro Gly Ser Arg Asp Lys Arg Thr Leu Ala Cys Leu Ile Gln Asn Phe
130 135 140

```
Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
    210                 215                 220

<210> SEQ ID NO 109
<211> LENGTH: 327
<212> TYPE: PRT
<213> ORGANISM: Homo sapiens

<400> SEQUENCE: 109

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 110
<211> LENGTH: 14
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (4)..(5)
<223> OTHER INFORMATION: Hu IgG1 Fc may be between residues 4 and 5.

<400> SEQUENCE: 110

Asp Ala Glu Thr Leu Glu Val Leu Phe Gln Gly Pro Glu Thr
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (4)..(5)
<223> OTHER INFORMATION: Hu IgG1 Fc may be between residues 4 and 5.

<400> SEQUENCE: 111

Asp Ala Gln Thr Leu Glu Val Leu Phe Gln Gly Pro Gln Thr
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (4)..(5)
<223> OTHER INFORMATION: Hu IgG1 Fc may be between residues 4 and 5.

<400> SEQUENCE: 112

Asp Ala Gly Thr Leu Glu Val Leu Phe Gln Gly Pro Gly Thr
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (4)..(5)
<223> OTHER INFORMATION: Hu IgG1 Fc may be between residues 4 and 5.

<400> SEQUENCE: 113

Asp Ala Glu Thr Leu Glu Val Leu Phe Gln Gly Pro Glu Thr
1               5                   10

<210> SEQ ID NO 114
<211> LENGTH: 14
<212> TYPE: PRT
```

```
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (4)..(5)
<223> OTHER INFORMATION: Hu IgG1 Fc may be between residues 4 and 5.

<400> SEQUENCE: 114

Asp Ala Glu Thr Leu Glu Val Leu Phe Gln Gly Pro Glu Thr
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (4)..(5)
<223> OTHER INFORMATION: Hu IgG1 Fc may be between residues 4 and 5.

<400> SEQUENCE: 115

Asp Ala Glu Thr Leu Glu Val Leu Phe Gln Gly Pro Glu Thr
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (2)..(3)
<223> OTHER INFORMATION: Hu IgG1 Fc may be between residues 2 and 3.

<400> SEQUENCE: 116

Glu Thr Leu Glu Val Leu Phe Gln Gly Pro
1               5                   10

<210> SEQ ID NO 117
<211> LENGTH: 815
<212> TYPE: PRT
<213> ORGANISM: Artificial Sequence
<220> FEATURE:
<223> OTHER INFORMATION: Synthetic polypeptide.

<400> SEQUENCE: 117

Met Asp Ala Met Lys Arg Gly Leu Cys Cys Val Leu Leu Cys Gly
1               5                   10                  15

Ala Val Phe Val Ser Pro Ser Tyr Gln Val Arg Asn Ser Thr Gly Leu
            20                  25                  30

Tyr His Val Thr Asn Asp Cys Pro Asn Ser Ser Ile Val Tyr Glu Ala
        35                  40                  45

Ala Asp Ala Ile Leu His Thr Pro Gly Cys Val Pro Cys Val Arg Glu
    50                  55                  60

Gly Asn Thr Ser Arg Cys Trp Val Ala Met Thr Pro Thr Val Ala Thr
65                  70                  75                  80

Arg Asp Gly Lys Leu Pro Thr Thr Gln Leu Arg Arg His Ile Asp Leu
                85                  90                  95

Leu Val Gly Ser Ala Thr Leu Cys Ser Ala Leu Tyr Val Gly Asp Leu
            100                 105                 110

Cys Gly Ser Ile Phe Leu Val Gly Gln Met Phe Thr Phe Ser Pro Arg
```

-continued

```
            115                 120                 125
Arg His Trp Thr Thr Gln Asp Cys Asn Cys Ser Leu Tyr Pro Gly His
        130                 135                 140
Ile Thr Gly His Arg Met Ala Trp Asp Met Met Asn Trp Ser Pro
145                 150                 155                 160
Thr Ala Ala Leu Ile Thr Ala Gln Leu Leu Arg Ile Pro Gln Ala Ile
                165                 170                 175
Leu Asp Met Ile Ala Gly Ala His Trp Gly Val Leu Ala Gly Ile Ala
                180                 185                 190
Tyr Phe Ser Met Val Gly Asn Trp Ala Lys Val Leu Val Val Leu Leu
            195                 200                 205
Leu Phe Ala Gly Val Asp Ala Gln Thr Asp Lys Thr His Thr Cys Pro
        210                 215                 220
Pro Cys Pro Ala Pro Glu Ala Glu Gly Ala Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys Leu Glu Val Leu
        435                 440                 445
Phe Gln Gly Pro Gln Thr His Val Thr Gly Gly Arg Ala Ala His Ile
    450                 455                 460
Thr Ala Gly Leu Thr Ser Leu Phe Ser Pro Gly Pro Ser Gln Lys Leu
465                 470                 475                 480
Gln Leu Val Asn Thr Asn Gly Ser Trp His Ile Asn Ser Thr Ala Leu
                485                 490                 495
Asn Cys Asn Asp Ser Leu Lys Thr Gly Trp Ile Ala Gly Leu Leu Tyr
            500                 505                 510
Ser Tyr Lys Phe Asn Ser Ser Gly Cys Pro Glu Arg Leu Ala Ser Cys
        515                 520                 525
Arg Arg Leu Thr Asp Phe Ala Gln Gly Trp Gly Pro Ile Ser His Ala
    530                 535                 540
```

```
Asn Gly Ser Gly Pro Asp Glu Arg Pro Tyr Cys Trp His Tyr Pro Pro
545                 550                 555                 560

Arg Pro Cys Gly Ile Val Pro Ala Lys Ser Val Cys Gly Pro Val Tyr
                565                 570                 575

Cys Phe Thr Pro Ser Pro Val Val Gly Thr Thr Asp Lys Ser Gly
            580                 585                 590

Ala Pro Thr Tyr Asn Trp Gly Glu Asn Asp Trp Asp Val Phe Val Leu
            595                 600                 605

Asn Asn Thr Arg Pro Pro Leu Gly Asn Trp Phe Gly Cys Thr Trp Met
610                 615                 620

Asn Ser Thr Gly Phe Thr Lys Val Cys Gly Ala Pro Pro Cys Val Ile
625                 630                 635                 640

Gly Gly Ala Gly Asn Asn Thr Leu Arg Cys Pro Thr Asp Cys Phe Arg
                645                 650                 655

Lys His Pro Asp Ala Thr Tyr Ser Arg Cys Gly Ser Gly Pro Trp Ile
            660                 665                 670

Thr Pro Arg Cys Leu Val Asp Tyr Pro Tyr Arg Leu Trp His Tyr Pro
        675                 680                 685

Cys Thr Val Asn Tyr Ser Ile Phe Lys Ile Arg Met Tyr Leu Gly Gly
            690                 695                 700

Val Glu His Arg Leu Glu Ala Ala Cys Asn Trp Thr Arg Gly Glu Arg
705                 710                 715                 720

Cys Asp Leu Glu Asp Arg Asp Arg Ser Glu Leu Ser Pro Leu Leu Leu
                725                 730                 735

Ser Thr Thr Gln Trp Gln Val Leu Pro Cys Ser Phe Thr Thr Leu Pro
            740                 745                 750

Ala Leu Ser Thr Gly Leu Ile His Leu His Gln Asn Ile Val Asp Val
        755                 760                 765

Gln Tyr Leu Tyr Gly Val Gly Ser Ser Val Ala Ser Trp Ala Ile Lys
    770                 775                 780

Trp Asp Tyr Val Val Leu Leu Phe Leu Leu Leu Ala Asp Ala Arg Ile
785                 790                 795                 800

Cys Ser Cys Leu Trp Met Met Leu Leu Ile Ser Gln Ala Glu Ala
                805                 810                 815

<210> SEQ ID NO 118
<211> LENGTH: 815
<212> TYPE: PRT
<213> ORGANISM: Artificial Sequence
<220> FEATURE:
<223> OTHER INFORMATION: Synthetic polypeptide.

<400> SEQUENCE: 118

Met Asp Ala Met Lys Arg Gly Leu Cys Cys Val Leu Leu Leu Cys Gly
1               5                   10                  15

Ala Val Phe Val Ser Pro Ser Tyr Gln Val Arg Asn Ser Ser Gly Leu
                20                  25                  30

Tyr His Val Thr Asn Asp Cys Pro Asn Ser Ser Ile Val Tyr Glu Ala
            35                  40                  45

Ala Asp Ala Ile Leu His Thr Pro Gly Cys Val Pro Cys Val Arg Glu
        50                  55                  60

Gly Asn Ala Ser Arg Cys Trp Val Ala Val Thr Pro Thr Val Ala Thr
65                  70                  75                  80

Arg Asp Gly Lys Leu Pro Thr Thr Gln Leu Arg Arg His Ile Asp Leu
                85                  90                  95
```

```
Leu Val Gly Ser Ala Thr Leu Cys Ser Ala Leu Tyr Val Gly Asp Leu
                100                 105                 110

Cys Gly Ser Val Phe Leu Val Gly Gln Leu Phe Thr Phe Ser Pro Arg
            115                 120                 125

Arg His Trp Thr Thr Gln Asp Cys Asn Cys Ser Ile Tyr Pro Gly His
        130                 135                 140

Ile Thr Gly His Arg Met Ala Trp Asp Met Met Asn Trp Ser Pro
145                 150                 155                 160

Thr Ala Ala Leu Val Val Ala Gln Leu Leu Arg Ile Pro Gln Ala Ile
                165                 170                 175

Met Asp Met Ile Ala Gly Ala His Trp Gly Val Leu Ala Gly Ile Ala
            180                 185                 190

Tyr Phe Ser Met Val Gly Asn Trp Ala Lys Val Leu Val Val Leu Leu
        195                 200                 205

Leu Phe Ala Gly Val Asp Ala Glu Thr Asp Lys Thr His Thr Cys Pro
    210                 215                 220

Pro Cys Pro Ala Pro Glu Ala Glu Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys Leu Glu Val Leu
        435                 440                 445

Phe Gln Gly Pro Glu Thr His Val Thr Gly Gly Ser Ala Gly Arg Thr
    450                 455                 460

Thr Ala Gly Leu Val Gly Leu Leu Thr Pro Gly Ala Lys Gln Asn Ile
465                 470                 475                 480

Gln Leu Ile Asn Thr Asn Gly Ser Trp His Ile Asn Ser Thr Ala Leu
                485                 490                 495

Asn Cys Asn Glu Ser Leu Asn Thr Gly Trp Leu Ala Gly Leu Phe Tyr
            500                 505                 510
```

Gln His Lys Phe Asn Ser Ser Gly Cys Pro Glu Arg Leu Ala Ser Cys
            515                 520                 525

Arg Arg Leu Thr Asp Phe Ala Gln Gly Trp Gly Pro Ile Ser Tyr Ala
530                 535                 540

Asn Gly Ser Gly Leu Asp Glu Arg Pro Tyr Cys Trp His Tyr Pro Pro
545                 550                 555                 560

Arg Pro Cys Gly Ile Val Pro Ala Lys Ser Val Cys Gly Pro Val Tyr
                565                 570                 575

Cys Phe Thr Pro Ser Pro Val Val Gly Thr Thr Asp Arg Ser Gly
                580                 585                 590

Ala Pro Thr Tyr Ser Trp Gly Ala Asn Asp Thr Asp Val Phe Val Leu
                595                 600                 605

Asn Asn Thr Arg Pro Pro Leu Gly Asn Trp Phe Gly Cys Thr Trp Met
            610                 615                 620

Asn Ser Thr Gly Phe Thr Lys Val Cys Gly Ala Pro Pro Cys Val Ile
625                 630                 635                 640

Gly Gly Val Gly Asn Asn Thr Leu Leu Cys Pro Thr Asp Cys Phe Arg
                645                 650                 655

Lys His Pro Glu Ala Thr Tyr Ser Arg Cys Gly Ser Gly Pro Trp Ile
                660                 665                 670

Thr Pro Arg Cys Met Val Asp Tyr Pro Tyr Arg Leu Trp His Tyr Pro
            675                 680                 685

Cys Thr Ile Asn Tyr Thr Ile Phe Lys Val Arg Met Tyr Val Gly Gly
            690                 695                 700

Val Glu His Arg Leu Glu Ala Ala Cys Asn Trp Thr Arg Gly Glu Arg
705                 710                 715                 720

Cys Asp Leu Glu Asp Arg Asp Arg Ser Glu Leu Ser Pro Leu Leu Leu
                725                 730                 735

Ser Thr Thr Gln Trp Gln Val Leu Pro Cys Ser Phe Thr Thr Leu Pro
                740                 745                 750

Ala Leu Ser Thr Gly Leu Ile His Leu His Gln Asn Ile Val Asp Val
            755                 760                 765

Gln Tyr Leu Tyr Gly Val Gly Ser Ser Ile Ala Ser Trp Ala Ile Lys
            770                 775                 780

Trp Glu Tyr Val Val Leu Leu Phe Leu Leu Leu Ala Asp Ala Arg Val
785                 790                 795                 800

Cys Ser Cys Leu Trp Met Met Leu Leu Ile Ser Gln Ala Glu Ala
                805                 810                 815

<210> SEQ ID NO 119
<211> LENGTH: 821
<212> TYPE: PRT
<213> ORGANISM: Artificial Sequence
<220> FEATURE:
<223> OTHER INFORMATION: Synthetic polypeptide.

<400> SEQUENCE: 119

Met Asp Ala Met Lys Arg Gly Leu Cys Cys Val Leu Leu Leu Cys Gly
1               5                   10                  15

Ala Val Phe Val Ser Pro Ser Leu Glu Trp Arg Asn Thr Ser Gly Leu
                20                  25                  30

Tyr Val Leu Thr Asn Asp Cys Ser Asn Ser Ser Ile Val Tyr Glu Ala
            35                  40                  45

Asp Asp Val Ile Leu His Thr Pro Gly Cys Val Pro Cys Val Gln Asp
        50                  55                  60

-continued

```
Asp Asn Thr Ser Thr Cys Trp Thr Pro Val Thr Pro Thr Val Ala Val
 65                  70                  75                  80

Arg Tyr Val Gly Ala Thr Thr Ala Ser Ile Arg Ser His Val Asp Leu
                 85                  90                  95

Leu Val Gly Ala Ala Thr Leu Cys Ser Ala Leu Tyr Val Gly Asp Met
                100                 105                 110

Cys Gly Ala Val Phe Leu Val Gly Gln Ala Phe Thr Phe Arg Pro Arg
                115                 120                 125

Arg His Gln Thr Val Gln Thr Cys Asn Cys Ser Leu Tyr Pro Gly His
            130                 135                 140

Val Ser Gly His Arg Met Ala Trp Asp Met Met Asn Trp Ser Pro
145                 150                 155                 160

Ala Val Gly Met Val Val Ala His Ile Leu Arg Leu Pro Gln Thr Leu
                165                 170                 175

Phe Asp Ile Leu Ala Gly Ala His Trp Gly Ile Leu Ala Gly Leu Ala
                180                 185                 190

Tyr Tyr Ser Met Gln Gly Asn Trp Ala Lys Val Ala Ile Val Met Ile
            195                 200                 205

Met Phe Ser Gly Val Asp Ala Glu Thr Asp Lys Thr His Thr Cys Pro
210                 215                 220

Pro Cys Pro Ala Pro Glu Ala Glu Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys Leu Glu Val Leu
            435                 440                 445

Phe Gln Gly Pro Glu Thr Tyr Val Thr Gly Gly Ser Val Ala His Ser
            450                 455                 460

Ala Arg Gly Leu Thr Ser Leu Phe Ser Met Gly Ala Lys Gln Lys Leu
465                 470                 475                 480

Gln Leu Val Asn Thr Asn Gly Ser Trp His Ile Asn Ser Thr Ala Leu
```

```
            485                 490                 495
Asn Cys Asn Glu Ser Ile Asn Thr Gly Phe Ile Ala Gly Leu Phe Tyr
            500                 505                 510

Tyr His Lys Phe Asn Ser Thr Gly Cys Pro Gln Arg Leu Ser Ser Cys
            515                 520                 525

Lys Pro Ile Ile Ser Phe Arg Gln Gly Trp Gly Pro Leu Thr Asp Ala
            530                 535                 540

Asn Ile Thr Gly Pro Ser Asp Asp Arg Pro Tyr Cys Trp His Tyr Ala
545                 550                 555                 560

Pro Arg Pro Cys Ser Val Val Pro Ala Ser Ser Val Cys Gly Pro Val
            565                 570                 575

Tyr Cys Phe Thr Pro Ser Pro Val Val Val Gly Thr Thr Asp Ile Lys
            580                 585                 590

Gly Lys Pro Thr Tyr Asn Trp Gly Glu Asn Glu Thr Asp Val Phe Leu
            595                 600                 605

Leu Glu Ser Leu Arg Pro Pro Ser Gly Arg Trp Phe Gly Cys Ala Trp
            610                 615                 620

Met Asn Ser Thr Gly Phe Leu Lys Thr Cys Gly Ala Pro Pro Cys Asn
625                 630                 635                 640

Ile Tyr Gly Gly Glu Gly Asp Pro Glu Asn Glu Thr Asp Leu Phe Cys
                        645                 650                 655

Pro Thr Asp Cys Phe Arg Lys His Pro Glu Ala Thr Tyr Ser Arg Cys
                        660                 665                 670

Gly Ala Gly Pro Trp Leu Thr Pro Arg Cys Met Val Asp Tyr Pro Tyr
                        675                 680                 685

Arg Leu Trp His Tyr Pro Cys Thr Val Asn Phe Thr Leu Phe Lys Val
            690                 695                 700

Arg Met Phe Val Gly Gly Phe Glu His Arg Phe Thr Ala Ala Cys Asn
705                 710                 715                 720

Trp Thr Arg Gly Glu Arg Cys Asn Ile Glu Asp Arg Asp Arg Ser Glu
                        725                 730                 735

Gln His Pro Leu Leu His Ser Thr Thr Glu Leu Ala Ile Leu Pro Cys
                        740                 745                 750

Ser Phe Thr Pro Met Pro Ala Leu Ser Thr Gly Leu Ile His Leu His
            755                 760                 765

Gln Asn Ile Val Asp Val Gln Tyr Leu Tyr Gly Val Gly Ser Asp Met
            770                 775                 780

Val Gly Trp Ala Leu Lys Trp Glu Phe Val Ile Leu Val Phe Leu Leu
785                 790                 795                 800

Leu Ala Asp Ala Arg Val Cys Val Ala Leu Trp Leu Met Leu Met Val
                        805                 810                 815

Ser Gln Ala Glu Ala
            820

<210> SEQ ID NO 120
<211> LENGTH: 821
<212> TYPE: PRT
<213> ORGANISM: Artificial Sequence
<220> FEATURE:
<223> OTHER INFORMATION: Synthetic polypeptide.

<400> SEQUENCE: 120

Met Asp Ala Met Lys Arg Gly Leu Cys Cys Val Leu Leu Leu Cys Gly
1               5                   10                  15

Ala Val Phe Val Ser Pro Ser Leu Glu Trp Arg Asn Thr Ser Gly Leu
```

-continued

```
               20                  25                  30
Tyr Ile Leu Thr Asn Asp Cys Pro Asn Ser Ser Ile Val Tyr Glu Ala
            35                  40                  45
Asp Asp Val Ile Leu His Thr Pro Gly Cys Ile Pro Cys Val Gln Asp
 50                  55                  60
Gly Asn Thr Ser Thr Cys Trp Thr Ser Val Ser Pro Thr Val Ala Val
 65                  70                  75                  80
Arg Tyr Val Gly Ala Thr Thr Ala Ser Ile Arg Ser His Val Asp Leu
                85                  90                  95
Leu Val Gly Ala Ala Thr Leu Cys Ser Ala Leu Tyr Val Gly Asp Met
                100                 105                 110
Cys Gly Ala Val Phe Leu Val Gly Gln Ala Phe Thr Phe Arg Pro Arg
                115                 120                 125
Arg His Gln Thr Val Gln Thr Cys Asn Cys Ser Leu Tyr Pro Gly His
                130                 135                 140
Leu Thr Gly His Arg Met Ala Trp Asp Met Met Met Asn Trp Ser Pro
145                 150                 155                 160
Ala Val Gly Met Val Val Ala His Val Leu Arg Met Pro Gln Thr Val
                165                 170                 175
Phe Asp Ile Ile Ala Gly Ala His Trp Gly Ile Leu Ala Gly Leu Ala
                180                 185                 190
Tyr Tyr Ser Met Gln Gly Asn Trp Ala Lys Val Ala Ile Ile Met Val
                195                 200                 205
Met Phe Ser Gly Val Asp Ala Glu Thr Asp Lys Thr His Thr Cys Pro
                210                 215                 220
Pro Cys Pro Ala Pro Glu Ala Glu Gly Ala Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
                260                 265                 270
Asn Trp Tyr Val Asp Gly Val Glu Val His Asn Ala Lys Thr Lys Pro
                275                 280                 285
Arg Glu Glu Gln Tyr Asn Ser Thr Tyr Arg Val Val Ser Val Leu Thr
                290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
                370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys Leu Glu Val Leu
                435                 440                 445
```

Phe Gln Gly Pro Glu Thr His Thr Gly Gly Thr Ala Ala Arg Asn
            450                 455                 460

Ala Phe Thr Leu Thr Gly Leu Phe Thr Gln Gly Ala Arg Gln Lys Leu
465                 470                 475                 480

Glu Leu Ile Asn Thr Asn Gly Ser Trp His Ile Asn Arg Thr Ala Leu
                485                 490                 495

Asn Cys Asn Glu Ser Leu Asn Thr Gly Phe Ile Ala Gly Leu Phe Tyr
            500                 505                 510

Leu His Lys Phe Asn Ser Thr Gly Cys Pro Glu Arg Leu Ser Ser Cys
        515                 520                 525

Lys Pro Ile Thr Phe Phe Arg Gln Gly Trp Gly Ser Leu Thr Asp Ala
530                 535                 540

Asn Ile Thr Gly Pro Ser Asp Asp Lys Pro Tyr Cys Trp His Tyr Ala
545                 550                 555                 560

Pro Arg Pro Cys Glu Val Val Pro Ala Leu Asn Val Cys Gly Pro Val
                565                 570                 575

Tyr Cys Phe Thr Pro Ser Pro Val Val Val Gly Thr Thr Asp Arg Gln
            580                 585                 590

Gly Val Pro Thr Tyr Thr Trp Gly Glu Asn Glu Thr Asp Val Phe Leu
        595                 600                 605

Leu Arg Ser Leu Arg Pro Pro Ser Gly Gln Trp Phe Gly Cys Thr Trp
610                 615                 620

Met Asn Ser Thr Gly Phe Val Lys Thr Cys Gly Ala Pro Pro Cys Asp
625                 630                 635                 640

Ile Tyr Gly Gly Gly Gly Asn Arg Cys Asn Glu Ser Asp Leu Phe Cys
                645                 650                 655

Pro Thr Asp Cys Phe Arg Lys His Pro Glu Ala Thr Tyr Ser Arg Cys
            660                 665                 670

Gly Ala Gly Pro Trp Leu Thr Pro Arg Cys Leu Val Asp Tyr Pro Tyr
        675                 680                 685

Arg Leu Trp His Tyr Pro Cys Thr Val Asn Phe Thr Leu Phe Lys Val
690                 695                 700

Arg Met Phe Val Gly Gly Phe Glu His Arg Phe Thr Ala Ala Cys Asn
705                 710                 715                 720

Trp Thr Arg Gly Glu Arg Cys Asn Ile Glu Asp Arg Asp Arg Ser Glu
                725                 730                 735

Gln His Pro Leu Leu His Ser Thr Thr Glu Leu Ala Ile Leu Pro Cys
            740                 745                 750

Ser Phe Thr Pro Met Pro Ala Leu Ser Thr Gly Leu Ile His Leu His
        755                 760                 765

Gln Asn Ile Val Asp Val Gln Tyr Leu Tyr Gly Val Gly Ser Gly Val
770                 775                 780

Val Gly Trp Ala Leu Arg Trp Glu Phe Val Val Leu Val Phe Leu Leu
785                 790                 795                 800

Leu Ala Asp Ala Arg Val Cys Val Ala Leu Trp Leu Met Leu Met Ile
                805                 810                 815

Ser Gln Ala Glu Ala
            820

<210> SEQ ID NO 121
<211> LENGTH: 227
<212> TYPE: PRT
<213> ORGANISM: Staphylococcus aureus

<400> SEQUENCE: 121

```
Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
        50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile
225
```

<210> SEQ ID NO 122
<211> LENGTH: 448
<212> TYPE: PRT
<213> ORGANISM: Streptococcus dysgalactiae

<400> SEQUENCE: 122

```
Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
            35                  40                  45

Glu Leu Thr Asn Leu Leu Gly Asn Ser Glu Thr Thr Leu Ala Leu Arg
        50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Tyr Lys Asn Leu Ile
        115                 120                 125
```

```
Asn Asn Ala Lys Thr Val Glu Gly Val Lys Asp Leu Gln Ala Gln Val
    130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
            180                 185                 190

Tyr Gly Val Ser Asp Tyr Tyr Lys Asn Leu Ile Asn Asn Ala Lys Thr
                195                 200                 205

Val Glu Gly Val Lys Ala Leu Ile Asp Glu Ile Leu Ala Ala Leu Pro
210                 215                 220

Lys Thr Asp Thr Tyr Lys Leu Ile Leu Asn Gly Lys Thr Leu Lys Gly
225                 230                 235                 240

Gln Thr Thr Thr Glu Ala Val Asp Ala Ala Thr Ala Glu Lys Val Phe
                245                 250                 255

Lys Gln Tyr Ala Asn Asp Asn Gly Val Asp Gly Glu Trp Thr Tyr Asp
            260                 265                 270

Asp Ala Thr Lys Thr Phe Thr Val Thr Glu Lys Pro Glu Val Ile Asp
            275                 280                 285

Ala Pro Glu Leu Thr Pro Ala Val Thr Thr Tyr Lys Leu Val Ile Asn
290                 295                 300

Gly Lys Thr Leu Lys Gly Glu Thr Thr Thr Lys Ala Val Asp Ala Glu
305                 310                 315                 320

Thr Ala Glu Lys Ala Phe Lys Gln Tyr Ala Asn Asp Asn Gly Val Asp
                325                 330                 335

Gly Val Trp Thr Tyr Asp Asp Ala Thr Lys Thr Phe Thr Val Thr Glu
            340                 345                 350

Met Val Thr Glu Val Pro Gly Asp Ala Pro Thr Glu Pro Glu Lys Pro
            355                 360                 365

Glu Ala Ser Ile Pro Leu Val Pro Leu Thr Pro Ala Thr Pro Ile Ala
370                 375                 380

Lys Asp Asp Ala Lys Lys Asp Thr Lys Lys Glu Asp Ala Lys Lys
385                 390                 395                 400

Pro Glu Ala Lys Lys Glu Asp Ala Lys Lys Ala Glu Thr Leu Pro Thr
                405                 410                 415

Thr Gly Glu Gly Ser Asn Pro Phe Phe Thr Ala Ala Ala Leu Ala Val
            420                 425                 430

Met Ala Gly Ala Gly Ala Leu Ala Val Ala Ser Lys Arg Lys Glu Asp
435                 440                 445

<210> SEQ ID NO 123
<211> LENGTH: 992
<212> TYPE: PRT
<213> ORGANISM: Finegoldia magna

<400> SEQUENCE: 123

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
                20                  25                  30

Asp Asn Asn Leu Ser Met Asp Glu Ile Ser Asp Ala Tyr Phe Asp Tyr
            35                  40                  45

His Gly Asp Val Ser Asp Ser Val Asp Pro Val Glu Glu Glu Ile Asp
        50                  55                  60
```

```
Glu Ala Leu Ala Lys Ala Leu Ala Glu Ala Lys Thr Ala Lys Lys
65                  70                  75                  80

His Ile Asp Ser Leu Asn His Leu Ser Glu Thr Ala Lys Lys Leu Ala
                85                  90                  95

Lys Asn Asp Ile Asp Ser Ala Thr Thr Ile Asn Ala Ile Asn Asp Ile
            100                 105                 110

Val Ala Arg Ala Asp Val Met Glu Arg Lys Thr Ala Glu Lys Glu Glu
            115                 120                 125

Ala Glu Lys Leu Ala Ala Ala Lys Glu Thr Ala Lys Lys His Ile Asp
130                 135                 140

Glu Leu Lys His Leu Ala Asp Lys Thr Lys Glu Leu Ala Lys Arg Asp
145                 150                 155                 160

Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Glu Ala Glu Lys
            180                 185                 190

Leu Ala Ala Ala Lys Glu Thr Ala Lys Lys His Ile Asp Glu Leu Lys
            195                 200                 205

His Leu Ala Asp Lys Thr Lys Glu Leu Ala Lys Arg Asp Ile Asp Ser
210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
                245                 250                 255

Val Thr Ile Lys Ala Asn Leu Ile Phe Ala Asp Gly Ser Thr Gln Asn
            260                 265                 270

Ala Glu Phe Lys Gly Thr Phe Ala Lys Ala Val Ser Asp Ala Tyr Ala
            275                 280                 285

Tyr Ala Asp Ala Leu Lys Lys Asp Asn Gly Glu Tyr Thr Val Asp Val
290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Glu Val Thr Ile Lys Val Asn Leu Ile
                325                 330                 335

Phe Ala Asp Gly Lys Thr Gln Thr Ala Glu Phe Lys Gly Thr Phe Glu
            340                 345                 350

Glu Ala Thr Ala Lys Ala Tyr Ala Tyr Ala Asp Leu Leu Ala Lys Glu
            355                 360                 365

Asn Gly Glu Tyr Thr Ala Asp Leu Glu Asp Gly Gly Asn Thr Ile Asn
            370                 375                 380

Ile Lys Phe Ala Gly Lys Glu Thr Pro Glu Thr Pro Glu Glu Pro Lys
385                 390                 395                 400

Glu Glu Val Thr Ile Lys Val Asn Leu Ile Phe Ala Asp Gly Lys Ile
                405                 410                 415

Gln Thr Ala Glu Phe Lys Gly Thr Phe Glu Glu Ala Thr Ala Lys Ala
            420                 425                 430

Tyr Ala Tyr Ala Asn Leu Leu Ala Lys Glu Asn Gly Glu Tyr Thr Ala
            435                 440                 445

Asp Leu Glu Asp Gly Gly Asn Thr Ile Asn Ile Lys Phe Ala Gly Lys
            450                 455                 460

Glu Thr Pro Glu Thr Pro Glu Glu Pro Lys Glu Glu Val Thr Ile Lys
465                 470                 475                 480
```

-continued

```
Val Asn Leu Ile Phe Ala Asp Gly Lys Thr Gln Thr Ala Glu Phe Lys
                485                 490                 495
Gly Thr Phe Glu Glu Ala Thr Ala Glu Ala Tyr Arg Tyr Ala Asp Leu
            500                 505                 510
Leu Ala Lys Val Asn Gly Glu Tyr Thr Ala Asp Leu Glu Asp Gly Gly
        515                 520                 525
Tyr Thr Ile Asn Ile Lys Phe Ala Gly Lys Glu Gln Pro Gly Glu Asn
    530                 535                 540
Pro Gly Ile Thr Ile Asp Glu Trp Leu Leu Lys Asn Ala Lys Glu Glu
545                 550                 555                 560
Ala Ile Lys Glu Leu Lys Glu Ala Gly Ile Thr Ser Asp Leu Tyr Phe
                565                 570                 575
Ser Leu Ile Asn Lys Ala Lys Thr Val Glu Gly Val Glu Ala Leu Lys
            580                 585                 590
Asn Glu Ile Leu Lys Ala His Ala Gly Glu Glu Thr Pro Glu Leu Lys
        595                 600                 605
Asp Gly Tyr Ala Thr Tyr Glu Glu Ala Glu Ala Ala Lys Glu Ala
    610                 615                 620
Leu Lys Asn Asp Asp Val Asn Asn Ala Tyr Glu Ile Val Gln Gly Ala
625                 630                 635                 640
Asp Gly Arg Tyr Tyr Tyr Val Leu Lys Ile Glu Val Ala Asp Glu Glu
                645                 650                 655
Glu Pro Gly Glu Asp Thr Pro Glu Val Gln Glu Gly Tyr Ala Thr Tyr
            660                 665                 670
Glu Glu Ala Glu Ala Ala Lys Glu Ala Leu Lys Glu Asp Lys Val
        675                 680                 685
Asn Asn Ala Tyr Glu Val Val Gln Gly Ala Asp Gly Arg Tyr Tyr Tyr
    690                 695                 700
Val Leu Lys Ile Glu Asp Lys Glu Asp Glu Gln Pro Gly Glu Glu Pro
705                 710                 715                 720
Gly Glu Asn Pro Gly Ile Thr Ile Asp Glu Trp Leu Leu Lys Asn Ala
                725                 730                 735
Lys Glu Asp Ala Ile Lys Glu Leu Lys Glu Ala Gly Ile Ser Ser Asp
            740                 745                 750
Ile Tyr Phe Asp Ala Ile Asn Lys Ala Lys Thr Val Glu Gly Val Glu
    755                 760                 765
Ala Leu Lys Asn Glu Ile Leu Lys Ala His Ala Glu Lys Pro Gly Glu
        770                 775                 780
Asn Pro Gly Ile Thr Ile Asp Glu Trp Leu Leu Lys Asn Ala Lys Glu
785                 790                 795                 800
Ala Ala Ile Lys Glu Leu Lys Glu Ala Gly Ile Thr Ala Glu Tyr Leu
                805                 810                 815
Phe Asn Leu Ile Asn Lys Ala Lys Thr Val Glu Gly Val Glu Ser Leu
            820                 825                 830
Lys Asn Glu Ile Leu Lys Ala His Ala Glu Lys Pro Gly Glu Asn Pro
        835                 840                 845
Gly Ile Thr Ile Asp Glu Trp Leu Leu Lys Asn Ala Lys Glu Asp Ala
    850                 855                 860
Ile Lys Glu Leu Lys Glu Ala Gly Ile Thr Ser Asp Ile Tyr Phe Asp
865                 870                 875                 880
Ala Ile Asn Lys Ala Lys Thr Ile Glu Gly Val Glu Ala Leu Lys Asn
                885                 890                 895
Glu Ile Leu Lys Ala His Lys Lys Asp Glu Glu Pro Gly Lys Lys Pro
```

-continued

```
                900                 905                 910
Gly Glu Asp Lys Lys Pro Glu Asp Lys Lys Pro Gly Glu Asp Lys Lys
            915                 920                 925

Pro Glu Asp Lys Lys Pro Gly Glu Asp Lys Lys Pro Glu Asp Lys Lys
        930                 935                 940

Pro Gly Lys Thr Asp Lys Asp Ser Pro Asn Lys Lys Lys Ala Lys
945                 950                 955                 960

Leu Pro Lys Ala Gly Ser Glu Ala Glu Ile Leu Thr Leu Ala Ala Ala
                965                 970                 975

Ala Leu Ser Thr Ala Ala Gly Ala Tyr Val Ser Leu Lys Lys Arg Lys
            980                 985                 990
```